US012774306B2

(12) United States Patent
Stoddard et al.

(10) Patent No.: US 12,774,306 B2
(45) Date of Patent: Oct. 27, 2026

(54) SELF-ASSEMBLING CIRCULAR TANDEM REPEAT PROTEINS WITH INCREASED STABILITY

(71) Applicant: Fred Hutchinson Cancer Center, Seattle, WA (US)

(72) Inventors: Barry L. Stoddard, Seattle, WA (US); Philip Bradley, Seattle, WA (US); Colin E. Correnti, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 1310 days.

(21) Appl. No.: 17/624,208

(22) PCT Filed: Jul. 2, 2020

(86) PCT No.: PCT/US2020/040733

§ 371 (c)(1),
(2) Date: Dec. 30, 2021

(87) PCT Pub. No.: WO2021/003413

PCT Pub. Date: Jan. 7, 2021

(65) Prior Publication Data

US 2022/0411472 A1 Dec. 29, 2022

Related U.S. Application Data

(60) Provisional application No. 62/984,706, filed on Mar. 3, 2020, provisional application No. 62/870,005, filed on Jul. 2, 2019.

(51) Int. Cl.
*C07K 14/00* (2006.01)
*C07K 7/08* (2006.01)

(52) U.S. Cl.
CPC .............. *C07K 14/001* (2013.01); *C07K 7/08* (2013.01); *C07K 2319/60* (2013.01)

(58) Field of Classification Search
CPC ....... C07K 7/08; C07K 2319/00; A61K 38/00
See application file for complete search history.

(56) References Cited

U.S. PATENT DOCUMENTS 10,597,466 B2 * 3/2020 Bradley ................. C12N 15/62
11,078,300 B2 * 8/2021 Bradley ................. C12N 15/62
11,879,018 B2 * 1/2024 Bradley ................. C07K 14/00

FOREIGN PATENT DOCUMENTS

WO WO2015161820 A1 10/2015
WO WO2017096236 A1 6/2017

OTHER PUBLICATIONS

Mejias et al. Nanoscale, 2014, 6, 10982-10988 (Year: 2014).*
Li et al. Curr Top Med Chem. Mar. 2002;2(3):325-41. (Year: 2002).*
Invitation to Pay Additional Fees Dated Oct. 27, 2020 for International Application No. PCT/US20/40733, 3 pages.
Search Report and Written Opinion Dated Jan. 21, 2021 for International Application No. PCT/US2020/040733, 14 pages.
Bandaranayake, et al., "Daedalus: a robust, turnkey platform for rapid production of decigram quantities of active recombinant proteins in human cell lines using novel lentiviral vectors," Nucleic Acids Res., vol. 39, No. 21, 2011, 11 pages.
Barkan, et al., "A combinatorial amino acid code for RNA recognition by pentatricopeptide repeat proteins," PLoS Genet., vol. 8, No. 8, 2012, 9 pages.
Chen and Flies, "Molecular mechanisms of T cell co-stimulation and co-inhibition," Nat. Rev. Immunol., vol. 13, No. 4, 2013, pp. 227-242.
Deng, et al., "Structural basis for sequence-specific recognition of DNA by TAL effectors," Science, vol. 335, No. 6069, 2012, pp. 720-723.
Dou, et al., "De novo design of a fluorescence-activating ß-barrel," Nature, vol. 561, No. 7724, 2018, pp. 485-491.
Dyer, et al., "High-throughput SAXS for the characterization of biomolecules in solution: a practical approach," Methods. Mol. Biol., vol. 1091, 2014, pp. 245-258.
Frese, et al., "The phosphotyrosine peptide binding specificity of Nck1 and Nck2 Src homology 2 domains," J. Biol. Chem., vol. 281, No. 26, 2006, pp. 18236-1845.
Itzhaki and Lowe, "From artificial antibodies to nanosprings: the biophysical properties of repeat proteins," Adv. Exp. Med. Biol., vol. 747, 2012, pp. 153-166.
Javadi and Itzhaki, "Tandem-repeat proteins: regularity plus modularity equals design-ability," Curr. Opin. Struct Biol., vol. 23, No. 4, 2013, pp. 622-631.
Kobe and Kajava, "When protein folding is simplified to protein coiling: the continuum of solenoid protein structures," Trends. Biochem. Sci., vol. 25, No. 10, 2000, pp. 509-515.
Main, et al., "Design of stable alpha-helical arrays from an idealized TPR motif," Structure, vol. 11, No. 5, 2003, pp. 497-508.
Mak, et al., "Folding, DNA recognition, and function of GIY-YIG endonucleases: crystal structures of R.Eco29kl," Structure, vol. 18, No. 10, 2010, pp. 1321-1331.
Mak, et al., "The crystal structure of TAL effector PthXo1 bound to its DNA target," Science, vol. 335, No. 6069, 2012, pp. 716-719.
Matsushima, et al., "Non-globular structures of tandem repeats in proteins," Protein. Pept. Lett., vol. 16, No. 11, 2009, pp. 1297-12322.
International Preliminary Report on Patentability for PCT Application No. PCT/US2020/040733, mailed Jan. 13, 2022.

(Continued)

*Primary Examiner* — Jeffrey Stucker
*Assistant Examiner* — Sarah Cooper Patterson
(74) *Attorney, Agent, or Firm* — C. Rachal Winger; Lee & Hayes PC

(57) ABSTRACT

Circular handed alpha-helical repeat proteins are described. The repeat proteins have a number of uses as scaffolds for geometrically precise, arrayed presentation of cell-signaling or immune-related protein and peptide epitopes, as well as numerous other therapeutic, diagnostic, and nanotechnological uses.

10 Claims, 49 Drawing Sheets

Specification includes a Sequence Listing.

(56) References Cited

OTHER PUBLICATIONS

Reichen, et al., "Modular peptide binding: from a comparison of natural binders to designed armadillo repeat proteins," J. Struct. Biol., vol. 185, No. 2, 2014, pp. 147-162.
Scarff, et al., "Variations on Negative Stain Electron Microscopy Methods: Tools for Tackling Challenging Systems," J. Vis. Exp., vol. 132, 2018, 8 pages.
Warren, et al., "Cytotoxic T-lymphocyte-defined human minor histocompatibility antigens with a restricted tissue distribution," Blood, vol. 91, No. 6, 1998, pp. 2197-2207.
Wierenga, et al., "The TIM-barrel fold: a versatile framework for e ¤cient enzymes," FEBS. Lett., vol. 492, pp. 193-198.
Yu, et al., "Cutting edge: single-chain trimers of MHC class I molecules form stable structures that potently stimulate antigen-specific T cells and B cells," J. Immunol., vol. 168, No. 7, 2002, pp. 3145-3149.
Zakeri, et al., "Peptide tag forming a rapid covalent bond to a protein, through engineering a bacterial adhesin," PNAS, vol. 109, No. 12, 2012, pp. 690-697.

* cited by examiner

| CMV:PBMC | cTRP24$_6$SS-scMHC | SA-Tetramer |
|---|---|---|
| CMV Only | 87.1% | 98.7% |
| 1:4 | 9.3% | 10.1% |
| 1:20 | 1.6% | 2.0% |
| 1:100 | 0.6% | 0.5% |

FIG. 14

Group I.

SEEILELLRAAHEL (SEQ ID NO: 2);
SEEILELLRAAHVL (SEQ ID NO: 3);
SEEILELLVAAHLL (SEQ ID NO: 4);
SIEILELLRAAHEL (SEQ ID NO: 5);
SEEIKELLRAAHEL (SEQ ID NO: 6);
SEEILELLRAAHEK (SEQ ID NO: 7);
PEAEKAAAELGKA (SEQ ID NO: 8);
PEAIKKAAELGKA (SEQ ID NO: 9);
PEAIKAAAELGKA (SEQ ID NO: 10);
PECIKAAAELGKA (SEQ ID NO: 11);
PTEVLLELIAEAS (SEQ ID NO: 12);
PELEYALAYAKKV (SEQ ID NO: 13);
SEEILELLRAAHAL (SEQ ID NO: 14);
SAEILELLMAAHEL (SEQ ID NO: 15);
SEEILELLRAAHGL (SEQ ID NO: 16);
SEEILELLRAAHGG (SEQ ID NO: 17);
REEVKEKFLKELRK (SEQ ID NO: 18);
KEEVKEKFLKELSF (SEQ ID NO: 19);
KEEVKKKFWKELSL (SEQ ID NO: 20);

Group II.

SELAARILIILFQQLVELARLAIES (SEQ ID NO: 21);
EELLRRVSEWLEEVIKDMRRVVEQALRE (SEQ ID NO: 22);
ELLRRVSEWLEEVIKDMRRVVEQALRE (SEQ ID NO: 23);
ELALKALQILVNAAYVLAEIARDR (SEQ ID NO: 24);
ELLEKAARLAEEAARQAEEIARQARKE (SEQ ID NO: 25);
LELALKALQILVNAAYVLAEIARDR (SEQ ID NO: 26);

Group III.

CEAIKAAAELGKA (SEQ ID NO: 27);
SELAARCLIILFQQLVELARLAIES (SEQ ID NO: 28);
CEAEKAAAELGKA (SEQ ID NO: 29);
CEAIKKAAELGKA (SEQ ID NO: 30);
CECIKAAAELGKA (SEQ ID NO: 31);
CTEVLLELIAEAS (SEQ ID NO: 32);
CELEYALAYAKKV (SEQ ID NO: 33);

Group IV.

PECIKAAAELGKA (SEQ ID NO: 11);
SELACRILIILFQQLVELARLAIES (SEQ ID NO: 35);
PECEKAAAELGKA (SEQ ID NO: 36);
PECIKKAAELGKA (SEQ ID NO: 37);
CECIKAAAELGKA (SEQ ID NO: 31);

FIG. 14 cont'd

Group V.

GLDPEAIKAAAELGKA (SEQ ID NO: 39);
GNSELAARILIILFQQLVELARLAIES (SEQ ID NO: 40);
GDEPELEYALAYAKKV (SEQ ID NO: 41);
GLNPEAIKAAAELGKA (SEQ ID NO: 42);

Group VI.

GLDCEAIKAAAELGKA (SEQ ID NO: 43);
GNSELAARCLIILFQQLVELARLAIES (SEQ ID NO: 44);
GDECELEYALAYAKKV (SEQ ID NO: 45);
GLNCEAIKAAAELGKA (SEQ ID NO: 46);
GLNCEAEKAAAELGKA (SEQ ID NO: 187),
GLDCEAEKAAAELGKA (SEQ ID NO: 188),
GLDCEAIKKAAELGKA (SEQ ID NO: 191),
GLNCEAIKKAAELGKA (SEQ ID NO: 192),

Group VII.

GLDPECIKAAAELGKA (SEQ ID NO: 47);
GNSELACRILIILFQQLVELARLAIES (SEQ ID NO: 48);
GLNPECIKAAAELGKA (SEQ ID NO: 49);
GLNELCARILIILFQQLVELARLAIES (SEQ ID NO: 50);
GLNELCLKALQILVNAAYVLAEIARDR (SEQ ID NO: 51);

Group VIII.

GLDPEAIKAAAELGKAGIS (SEQ ID NO: 52);
GNSELAARILIILFQQLVELARLAIESGD (SEQ ID NO: 53);
GKSPTEVLLELIAEASGTT (SEQ ID NO: 54);
GLNPEAIKAAAELGKAGIS (SEQ ID NO: 55);

Group IX.

GLDCEAIKAAAELGKAGIS (SEQ ID NO: 56);
GNSELAARCLIILFQQLVELARLAIESGD (SEQ ID NO: 57);
GKSCTEVLLELIAEASGTT (SEQ ID NO: 58);
GLNCEAIKAAAELGKAGIS (SEQ ID NO: 59);
GLNCEAEKAAAELGKAGTT (SEQ ID NO: 189),
GLDCEAEKAAAELGKAGIS (SEQ ID NO: 190)
GLDCEAIKKAAELGKAGTT (SEQ ID NO: 193),
GLDCEAIKKAAELGKAGIS (SEQ ID NO: 194)

Group X.

GLDPECIKAAAELGKAGIS (SEQ ID NO: 60);
GNSELACRILIILFQQLVELARLAIESGD (SEQ ID NO: 61);
GLNPECIKAAAELGKAGIS (SEQ ID NO: 62);

FIG. 14 cont'd

Group XI.

GLDPEAIKAAAELGKAGISSEEILELLRAAHEL (SEQ ID NO: 1);
GLDPEAIKAAAELGKAGISSEEILELLRAAHVL (SEQ ID NO: 63);
GLDPEAIKAAAELGKAGISSEEILELLVAAHLL (SEQ ID NO: 64);
GLDPEAIKAAAELGKAGISSIEILELLRAAHEL (SEQ ID NO: 65);
GNSELAARILIILFQQLVELARLAIESGDEELLRRVSEWLEEVIKDMRRVVEQALRE (SEQ ID NO: 66);
GKSPTEVLLELIAEASGTTREEVKEKFLKELRK (SEQ ID NO: 67);
GKSPTEVLLELIAEASGTTKEEVKEKFLKELSF (SEQ ID NO: 68);
GKSPTEVLLELIAEASGTTKEEVKKKFWKELSL (SEQ ID NO: 69);
GLNPEAIKAAAELGKAGISSEEILELLRAAHEL (SEQ ID NO: 70);
GLNPEAIKAAAELGKAGISSEEILELLRAAHAL (SEQ ID NO: 71);
GLNPEAIKAAAELGKAGISSAEILELLMAAHEL (SEQ ID NO: 72);
GLNPEAIKAAAELGKAGISSEEILELLRAAHGL (SEQ ID NO: 73);
GLNPEAIKAAAELGKAGISSEEILELLRAAHGG (SEQ ID NO: 74);

Group XII.

GLDCEAIKAAAELGKAGISSEEILELLRAAHEL (SEQ ID NO: 75);
GNSELAARCLIILFQQLVELARLAIESGDEELLRRVSEWLEEVIKDMRRVVEQALRE (SEQ ID NO: 76);
GKSCTEVLLELIAEASGTTREEVKEKFLKELRK (SEQ ID NO: 77);
GKSCTEVLLELIAEASGTTKEEVKEKFLKELSF (SEQ ID NO: 78);
GKSCTEVLLELIAEASGTTKEEVKKKFWKELSL (SEQ ID NO: 79);
GLDCEAIKAAAELGKAGISSEEILELLRAAHVL (SEQ ID NO: 80);
GLDCEAIKAAAELGKAGISSEEILELLVAAHLL (SEQ ID NO: 81);
GLDCEAIKAAAELGKAGISSIEILELLRAAHEL (SEQ ID NO: 82);
GLNCEAIKAAAELGKAGISSEEILELLRAAHEL (SEQ ID NO: 83);
GLNCEAIKAAAELGKAGISSEEILELLRAAHAL (SEQ ID NO: 84);
GLNCEAIKAAAELGKAGISSAEILELLMAAHEL (SEQ ID NO: 85);
GLNCEAIKAAAELGKAGISSEEILELLRAAHGL (SEQ ID NO: 86);
GLNCEAIKAAAELGKAGISSEEILELLRAAHGG (SEQ ID NO: 87);

Group XIII.

GLDPECIKAAAELGKAGISSEEILELLRAAHEL (SEQ ID NO: 88);
GNSELACRILIILFQQLVELARLAIESGDEELLRRVSEWLEEVIKDMRRVVEQALRE (SEQ ID NO: 89);
GLDPECIKAAAELGKAGISSEEILELLRAAHVL (SEQ ID NO: 90);
GLDPECIKAAAELGKAGISSEEILELLVAAHLL (SEQ ID NO: 91);
GLDPECIKAAAELGKAGISSIEILELLRAAHEL (SEQ ID NO: 92);
GLNPECIKAAAELGKAGISSEEILELLRAAHEL (SEQ ID NO: 93);
GLNPECIKAAAELGKAGISSEEILELLRAAHAL (SEQ ID NO: 94);
GLNPECIKAAAELGKAGISSAEILELLMAAHEL (SEQ ID NO: 95);
GLNPECIKAAAELGKAGISSEEILELLRAAHGL (SEQ ID NO: 96);
GLNPECIKAAAELGKAGISSEEILELLRAAHGG (SEQ ID NO: 97);

FIG. 14 cont'd

>cTRP24 (Single chain cTRP with 24 repeats)
ATGGCTAGCAGCCATCATCATCATCATCATAGCAGCGGCCTGGTGCCGCGCGGCAGCTCC
ATGGGCCTGGACCCGGAAGCGATCAAAGCGGCTGCGGAACTGGGCAAAGCTGGTATCTC
GTCAGAAGAAATCCTGGAACTGCTGCGTGCGGCGCATGAACTGGGCCTGGATCCGGAAG
CCATTAAAGCCGCGGCGGAACTGGGCAAAGCGGGTATCAGCAGCGAAGAAATCCTGGAA
CTGCTGCGCGCGGCCCATGAACTGGGTCTGGATCCGGAAGCCATCAAAGCCGCGGCGGA
ACTGGGCAAAGCGGGCATCAGCAGCGAAGAAATCCTGGAACTGCTGCGCGCCGCGCATG
AACTGGGTCTGGATCCGGAAGCGATTAAAGCCGCCGCCGAACTGGGTAAAGCGGGTATTA
GCAGCGAAGAAATCCTGGAACTGCTGCGTGCGGCGCATGAACTGGGCCTGGATCCGGAA
GCCATCAAAGCCGCCGCCGAACTGGGTAAAGCCGGTATCAGCAGCGAAGAAATTCTGGAA
CTGCTGCGTGCCGCCCATGAACTGGGCCTGGATCCGGAAGCGATTAAAGCCGCCGCGGA
ACTGGGTAAAGCCGGTATTAGCAGCGAAGAAATCCTGGAACTGCTGCGTGCCGCGCATGA
ACTGGGTCTGGATCCGGAAGCCATCAAAGCGGCGGCCGAACTGGGTAAAGCCGGCATCA
GCAGCGAAGAAATCCTGGAACTGCTGCGTGCCGCCCATGAACTGGGCCTGGATCCGGAA
GCGATCAAAGCCGCCGCGGAACTGGGTAAAGCCGGCATTAGCAGCGAAGAAATCCTGGA
ACTGCTGCGTGCCGCGCATGAACTGGGTCTGGATCCGGAAGCGATTAAAGCGGCGGCCG
AACTGGGCAAAGCCGGTATTAGCAGCGAAGAAATCCTGGAACTGCTGCGTGCGGCCCATG
AACTGGGCCTGGATCCGGAAGCGATCAAAGCGGCGGCCGAACTGGGTAAAGCGGGTATC
AGCAGCGAAGAAATCCTGGAACTGCTGCGTGCCGCCCATGAACTGGGTCTGGATCCGGAA
GCCATTAAAGCGGCGGCGGAACTGGGTAAAGCGGGCATCAGCAGCGAAGAAATTCTGGA
ACTGCTGCGCGCGGCGCATGAACTGGGTCTGGATCCGGAAGCCATTAAAGCCGCCGCGG
AACTGGGCAAAGCGGGTATTAGCAGCGAAGAAATTCTGGAACTGCTGCGCGCGGCGCATG
AACTGGGCCTGGATCCGGAAGCGATTAAAGCCGCCGCCGAACTGGGCAAAGCCGGCATC
AGCAGCGAAGAAATTCTGGAACTGCTGCGCGCCGCCCATGAACTGGGCCTGGATCCGGA
AGCGATCAAAGCCGCCGCGGAACTGGGCAAAGCGGGCATCAGCAGCGAAGAAATCCTGG
AACTGCTGCGTGCGGCGCATGAACTGGGTCTGGATCCGGAAGCCATTAAAGCCGCGGCG
GAACTGGGCAAAGCCGGCATTAGCAGCGAAGAAATTCTGGAACTGCTGCGTGCGGCGCAT
GAACTGGGTCTGGATCCGGAAGCCATCAAAGCCGCGGCGGAACTGGGTAAAGCGGGTAT
TAGCAGCGAAGAAATTCTGGAACTGCTGCGCGCGGCCCATGAACTGGGCCTGGATCCGG
AAGCGATTAAAGCGGCGGCCGAACTGGGCAAAGCGGGCATTAGCAGCGAAGAAATCCTG
GAACTGCTGCGCGCGGCGCATGAACTGGGTCTGGATCCGGAAGCCATTAAAGCCGCCGC
CGAACTGGGCAAAGCCGGTATCAGCAGCGAAGAAATTCTGGAACTGCTGCGCGCGGCCC
ATGAACTGGGTCTGGATCCGGAAGCCATCAAAGCCGCCGCGGAACTGGGTAAAGCCGGT
ATCAGCAGCGAAGAAATCCTGGAACTGCTGCGCGCCGCCCATGAACTGGGCCTGGATCC
GGAAGCGATCAAAGCCGCGGCGGAACTGGGTAAAGCGGGCATTAGCAGCGAAGAAATTC
TGGAACTGCTGCGTGCGGCCCATGAACTGGGTCTGGATCCGGAAGCGATCAAAGCCGCG
GCCGAACTGGGTAAAGCGGGCATCAGCAGCGAAGAAATTCTGGAACTGCTGCGTGCCGC
GCATGAACTGGGCCTGGATCCGGAAGCGATTAAAGCCGCGGCCGAACTGGGCAAAGCGG
GCATTAGCAGCGAAGAAATTCTGGAACTGCTGCGCGCGGCGCATGAACTGGGCCTGGATC
CGGAAGCGATTAAAGCGGCGGCCGAACTGGGCAAAGCGGGTATCAGCAGCGAAGAAATC
CTGGAACTGCTGCGCGCCGCGCATGAACTGGGCCTGGATCCGGAAGCGATTAAAGCCGC
GGCCGAACTGGGCAAAGCGGGTATCTCGTCTGAAGAAATCCTGGAACTGCTGCGTGCTGC
CCATGAACTGGGTGGTTGGTAATAA (SEQ ID NO: 98)

FIG. 14 cont'd

MASSHHHHHHSSGLVPRGSSMGLDPEAIKAAAELGKAGISSEEILELLRAAHELGLDPEAIKA AAELGKAGISSEEILELLRAAHELGLDPEAIKAAAELGKAGISSEEILELLRAAHELGLDPEAIK AAAELGKAGISSEEILELLRAAHELGLDPEAIKAAAELGKAGISSEEILELLRAAHELGLDPEAI KAAAELGKAGISSEEILELLRAAHELGLDPEAIKAAAELGKAGISSEEILELLRAAHELGLDPE AIKAAAELGKAGISSEEILELLRAAHELGLDPEAIKAAAELGKAGISSEEILELLRAAHELGLDP EAIKAAAELGKAGISSEEILELLRAAHELGLDPEAIKAAAELGKAGISSEEILELLRAAHELGLD PEAIKAAAELGKAGISSEEILELLRAAHELGLDPEAIKAAAELGKAGISSEEILELLRAAHELGL DPEAIKAAAELGKAGISSEEILELLRAAHELGLDPEAIKAAAELGKAGISSEEILELLRAAHELG LDPEAIKAAAELGKAGISSEEILELLRAAHELGLDPEAIKAAAELGKAGISSEEILELLRAAHEL GLDPEAIKAAAELGKAGISSEEILELLRAAHELGLDPEAIKAAAELGKAGISSEEILELLRAAHE LGLDPEAIKAAAELGKAGISSEEILELLRAAHELGLDPEAIKAAAELGKAGISSEEILELLRAAH ELGLDPEAIKAAAELGKAGISSEEILELLRAAHELGLDPEAIKAAAELGKAGISSEEILELLRAA HELGLDPEAIKAAAELGKAGISSEEILELLRAAHELGGW (SEQ ID NO: 99)

>cTRP24_Sub3 ('Sub3' cTRP construct containing 3 repeats)
ATGGCTAGCAGCCATCATCATCATCATCATAGCAGCGGCCTGGTGCCGCGCGGCAGCTCC ATGGGCCTGGATCCGGAAGCTATTAAAGCGGCGGCAGAACTGGGCAAAGCCGGTATTAGC TCTGAAGAAATCCTGGAACTGCTGCGTGCTGCGCATGAACTGGGTCTGGACCCGGAAGCA ATCAAAGCCGCAGCTGAACTGGGCAAAGCGGGTATTAGTTCCGAAGAAATTCTGGAACTG CTGCGTGCCGCACATGAACTGGGTCTGGATCCGGAAGCCATTAAAGCAGCTGCGGAACTG GGTAAAGCCGGTATTAGCAGCGAGGAGATTCTGGAACTGCTGCGCGCCGCACATGAACTG GGCGGTTGGTAA (SEQ ID NO: 100)

MASSHHHHHHSSGLVPRGSSMGLDPEAIKAAAELGKAGISSEEILELLRAAHELGLDPEAIKA AAELGKAGISSEEILELLRAAHELGLDPEAIKAAAELGKAGISSEEILELLRAAHELGGW (SEQ ID NO: 101)

>cTRP24_Sub4 ('Sub4' cTRP construct containing 4 repeats)
ATGGCTAGCAGCCATCATCATCATCATCATAGCAGCGGCCTGGTGCCGCGCGGCAGCTCC ATGGGCCTGGATCCGGAAGCGATTAAAGCGGCGGCAGAACTGGGCAAAGCCGGTATTAG CTCTGAAGAAATCCTGGAACTGCTGCGTGCTGCGCATGAACTGGGTCTGGACCCGGAAGC AATCAAAGCCGCAGCTGAACTGGGCAAAGCTGGTATTAGTTCCGAAGAAATTCTGGAACTG CTGCGTGCCGCACATGAACTGGGTCTGGATCCGGAAGCCATCAAAGCAGCTGCGGAACTG GGTAAAGCGGGTATTTCATCGGAGGAGATCCTGGAACTGCTGCGCGCGGCCCACGAACT GGGCCTGGATCCGGAAGCTATCAAAGCTGCGGCCGAACTGGGTAAAGCTGGTATTAGCAG CGAGGAGATTCTGGAACTGCTGCGCGCAGCTCACGAACTGGGCGGTTGGTAA (SEQ ID NO: 102)

MASSHHHHHHSSGLVPRGSSMGLDPEAIKAAAELGKAGISSEEILELLRAAHELGLDPEAIKA AAELGKAGISSEEILELLRAAHELGLDPEAIKAAAELGKAGISSEEILELLRAAHELGLDPEAIK AAAELGKAGISSEEILELLRAAHELGGW (SEQ ID NO: 103)

FIG. 14 cont'd

>cTRP24_Sub6 ('Sub6' cTRP construct containing 6 repeats)
ATGGCTAGCAGCCATCATCATCATCATCATAGCAGCGGCCTGGTGCCGCGCGGCAGCTCC
ATGGGCCTGGATCCGGAAGCAATTAAAGCGGCGGCAGAACTGGGCAAAGCTGGTATTAGC
TCTGAAGAAATCCTGGAACTGCTGCGTGCTGCGCATGAACTGGGTCTGGACCCGGAAGCA
ATCAAAGCCGCAGCTGAACTGGGCAAAGCGGGTATTAGTTCCGAAGAAATTCTGGAACTG
CTGCGTGCCGCACATGAACTGGGTCTGGATCCGGAAGCCATTAAAGCAGCTGCGGAACTG
GGCAAAGCAGGTATTTCATCGGAGGAGATCCTGGAACTGCTGCGCGCGGCCCACGAACT
GGGCCTGGACCCGGAAGCGATCAAAGCTGCGGCCGAACTGGGCAAAGCCGGCATCTCTA
GCGAGGAGATTCTGGAACTGCTGCGCGCAGCTCACGAACTGGGCCTGGATCCGGAAGCG
ATCAAGGCGGCGGCAGAGCTGGGCAAAGCCGGTATTAGTTCAGAGGAGATACTGGAACTG
CTGCGCGCCGCCCACGAGTTAGGTCTGGATCCGGAAGCGATTAAGGCCGCAGCTGAGCT
GGGTAAAGCCGGTATTAGCTCCGAGGAGATATTAGAACTGCTGCGTGCCGCGCATGAACT
GGGCGGTTGGTAA (SEQ ID NO: 104)

**MASSHHHHHHSSGLVPRGSSMGLDPEAIKAAAELGKAGISSEEILELLRAAHELGLDPEAIKA
AAELGKAGISSEEILELLRAAHELGLDPEAIKAAAELGKAGISSEEILELLRAAHELGLDPEAIK
AAAELGKAGISSEEILELLRAAHELGLDPEAIKAAAELGKAGISSEEILELLRAAHELGLDPEAI
KAAAELGKAGISSEEILELLRAAHELGGW** (SEQ ID NO: 105)

Secreted cTRP24$_6$SS protein sequence (naked tetramer)

METDTLLLWVLLLWVPGSTGDYKDEGGGSCEAIKAAAELGKAGISSEEILELLRAAHELGLDPE
AIKAAAELGKAGISSEEILELLRAAHELGLDPEAIKAAAELGKAGISSEEILELLRAAHELGLDPEAI
KAAAELGKAGISSEEILELLRAAHELGLDPEAIKAAAELGKAGISSEEILELLRAAHELGLDPECIK
AAAELGKAGISSEEILELLRAAHELGL*GGGSENLYFQGSHHHHHHGSGLNDIFEAQKIEWHE**
(SEQ ID NO: 253)

Signal Peptide (underlined); Short FLAG Tag (bolded); cTRP subunit (plain text); TEV-His-Avi Tag (italicized)

>cTRP24_Sub8 ('Sub8' cTRP construct containing 8 repeats)
ATGGCTAGCAGCCATCATCATCATCATCATAGCAGCGGCCTGGTGCCGCGCGGCAGCTCC
ATGGGCCTGGATCCGGAAGCGATTAAAGCGGCGGCAGAACTGGGCAAAGCCGGTATTAG
CTCTGAAGAAATCCTGGAACTGCTGCGTGCTGCGCATGAACTGGGTCTGGACCCGGAAGC
AATCAAAGCCGCAGCTGAACTGGGCAAAGCTGGTATTAGTTCCGAAGAAATTCTGGAACTG
CTGCGTGCCGCACATGAACTGGGTCTGGATCCGGAAGCAATTAAAGCAGCTGCGGAACTG
GGCAAAGCGGGTATTTCATCGGAGGAGATCCTGGAACTGCTGCGCGCCGCACATGTGCTG
GGCCTGGATCCGGAAGCCATCAAAGCTGCGGCCGAACTGGGCAAAGCAGGCATCTCTAG
CGAGGAGATTCTGGAACTGCTGGTTGCAGCTCACCTGCTGGGTTTAGACCCTGAAGCCAT
CAAGGCGGCGGCAGAGCTGGGTAAAGCGGGCATCAGTTCCGAGGAGATACTGGAACTGC
TGCGCGCGGCCCACGAACTGGGCCTGGACCCGGAAGCGATTAAGGCCGCAGCTGAGCTG
GGTAAAGCGGGTATCAGCTCGGAGGAGATATTAGAACTGCTGCGCGCCGCCCATGAGTTA
GGCCTGGACCCGGAAGCCATCAAGGCAGCTGCGGAGCTGGGTAAAGCTGGCATCTCTAG
CGAGGAAATTTTAGAGCTGCTGCGTGCGGCCCACGAGTTAGGTCTGGACCCGGAAGCCAT
TAAGGCTGCGGCCGAGCTGGGCAAAGCGGGTATCTCATCCATTGAGATATTGGAGCTGCT
GCGTGCAGCTCACGAACTGGGCGGTTGGTAA (SEQ ID NO: 106)

FIG. 14 cont'd

MASSHHHHHHSSGLVPRGSSMGLDPEAIKAAAELGKAGISSEEILELLRAAHELGLDPEAIKA AAELGKAGISSEEILELLRAAHELGLDPEAIKAAAELGKAGISSEEILELLRAAHVLGLDPEAIK AAAELGKAGISSEEILELLVAAHLLGLDPEAIKAAAELGKAGISSEEILELLRAAHELGLDPEAI KAAAELGKAGISSEEILELLRAAHELGLDPEAIKAAAELGKAGISSEEILELLRAAHELGLDPE AIKAAAELGKAGISSIEILELLRAAHELGGW (SEQ ID NO: 107)

Secreted cTRP24$_8$SS protein sequence (naked trimer)

<u>METDTLLLWVLLLWVPGSTG</u>DYKDEGGGSCEAIKAAAELGKAGISSEEILELLRAAHELGLDPE AIKAAAELGKAGISSEEILELLRAAHELGLDPEAIKAAAELGKAGISSEEILELLRAAHELGLDPEAI KAAAELGKAGISSEEILELLRAAHELGLDPEAIKAAAELGKAGISSEEILELLRAAHELGLDPEAIK AAAELGKAGISSEEILELLRAAHELGLDPEAIKAAAELGKAGISSEEILELLRAAHELGLDPECIKA AAELGKAGISSEEILELLRAAHELGL*GGGSENLYFQGSHHHHHHGSGLNDIFEAQKIEWHE**
(SEQ ID NO: 254)

Signal Peptide (underlined); Short FLAG Tag (bolded); cTRP subunit (plain text); TEV-His-Avi Tag (italicized)

>cTRP24_Sub12 (cTRP construct containing 12 repeats)
ATGGCTAGCAGCCATCATCATCATCATCATAGCAGCGGCCTGGTGCCGCGCGGCAGCTCC
ATGGGCCTGGACCCGGAGGCGATCAAGGCTGCGGCGGAACTGGGTAAAGCGGGCATCAG
CAGCGAGGAAATTCTGGAGCTGCTGCGTGCGGCGCATGAGCTGGGTCTGGACCCGGAAG
CGATTAAGGCTGCGGCGGAGCTGGGCAAGGCGGGTATCAGCAGCGAAGAAATTCTGGAA
CTGCTGCGCGCGGCGCATGAGCTGGGCCTGGACCCGGAAGCGATCAAAGCTGCGGCGG
AGCTGGGTAAGGCTGGTATCAGCAGCGAGGAGATTCTGGAATTATTACGCGCGGCGCATG
AACTGGGTCTGGACCCGGAGGCGATTAAAGCTGCGGCGGAACTGGGCAAGGCGGGCATC
AGCAGCGAAGAGATTCTGGAATTACTTCGTGCTGCGCATGAACTGGGCCTGGACCCGGAG
GCTATTAAGGCTGCGGCGGAATTAGGCAAAGCTGGCATCAGCAGCGAAGAAATTCTGGAA
TTACTGCGTGCCGCTCATGAATTAGGTCTGGACCCGGAAGCTATCAAAGCTGCGGCGGAA
TTAGGTAAGGCCGGTATCAGCAGCGAGGAAATTCTGGAATTGTTACGAGCTGCTCATGAAT
TAGGCCTGGACCCGGAGGCCATTAAGGCTGCGGCGGAGTTAGGCAAAGCGGGTATCAGC
AGCGAGGAAATTCTGGAACTTTTACGAGCTGCTCATGAGTTAGGTCTGGACCCGGAGGCT
ATCAAGGCTGCGGCGGAGTTGGGCAAAGCCGGCATCAGCAGCGAGGAGATTCTGGAACT
TTTACGGGCTGCTCATGAACTTGGCCTGGACCCGGAGGCAATTAAGGCTGCGGCGGAGCT
AGGCAAGGCTGGTATCAGCAGCGAGGAAATTCTGGAACTACTGCGTGCCGCCCATGAATT
GGGTCTGGACCCGGAAGCAATCAAGGCTGCGGCGGAGCTTGGCAAGGCCGGTATCAGCA
GCGAGGAAATTCTGGAACTGTTACGAGCTGCCCATGAACTTGGTCTGGACCCGGAAGCCA
TAAAAGCTGCGGCGGAGTTAGGTAAGGCAGGTATCAGCAGCGAGGAAATTCTGGAACTCC
TGCGTGCCGCACATGAACTCGGTCTGGACCCGGAGGCCATTAAAGCTGCGGCGGAGTTG
GGTAAGGCGGGTATCAGCAGCGAGGAAATTCTGGAGTTACTGCGTGCCGCGCATGAGCT
GGGTGGCTGGTAATAA (SEQ ID NO: 108)

FIG. 14 cont'd

**MASSHHHHHHSSGLVPRGSSMGLDPEAIKAAAELGKAGISSEEILELLRAAHELGLDPEAIKA
AAELGKAGISSEEILELLRAAHELGLDPEAIKAAAELGKAGISSEEILELLRAAHELGLDPEAIK
AAAELGKAGISSEEILELLRAAHELGLDPEAIKAAAELGKAGISSEEILELLRAAHELGLDPEAI
KAAAELGKAGISSEEILELLRAAHELGLDPEAIKAAAELGKAGISSEEILELLRAAHELGLDPE
AIKAAAELGKAGISSEEILELLRAAHELGLDPEAIKAAAELGKAGISSEEILELLRAAHELGLDP
EAIKAAAELGKAGISSEEILELLRAAHELGLDPEAIKAAAELGKAGISSEEILELLRAAHELGLD
PEAIKAAAELGKAGISSEEILELLRAAHELGGW** (SEQ ID NO: 109)

>cTRP24_Sub12SS (cTRP construct containing 12 repeats and disulfide staples)
ATGGCTAGCAGCCATCATCATCATCATCATAGCAGCGGCCTGGTGCCGCGCGGCAGCTCC
ATGGGCCTGGACTGCGAGGCGATCAAGGCTGCGGCGGAACTGGGTAAAGCGGGCATCAG
CAGCGAGGAAATTCTGGAGCTGCTGCGTGCGGCGCATGAGCTGGGTCTGGACCCGGAAG
CGATTAAGGCTGCGGCGGAGCTGGGCAAGGCGGGTATCAGCAGCGAAGAAATTCTGGAA
CTGCTGCGCGCGGCGCATGAGCTGGGCCTGGACCCGGAAGCGATCAAAGCTGCGGCGG
AGCTGGGTAAGGCTGGTATCAGCAGCGAGGAGATTCTGGAATTATTACGCGCGGCGCATG
AACTGGGTCTGGACCCGGAGGCGATTAAAGCTGCGGCGGAACTGGGCAAGGCGGGCATC
AGCAGCGAAGAGATTCTGGAATTACTTCGTGCTGCGCATGAACTGGGCCTGGACCCGGAG
GCTATTAAGGCTGCGGCGGAATTAGGCAAAGCTGGCATCAGCAGCGAAGAAATTCTGGAA
TTACTGCGTGCCGCTCATGAATTAGGTCTGGACCCGGAAGCTATCAAAGCTGCGGCGGAA
TTAGGTAAGGCCGGTATCAGCAGCGAGGAAATTCTGGAATTGTTACGAGCTGCTCATGAAT
TAGGCCTGGACCCGGAGGCCATTAAGGCTGCGGCGGAGTTAGGCAAAGCGGGTATCAGC
AGCGAGGAAATTCTGGAACTTTTACGAGCTGCTCATGAGTTAGGTCTGGACCCGGAGGCT
ATCAAGGCTGCGGCGGAGTTGGGCAAAGCCGGCATCAGCAGCGAGGAGATTCTGGAACT
TTTACGGGCTGCTCATGAACTTGGCCTGGACCCGGAGGCAATTAAGGCTGCGGCGGAGCT
AGGCAAGGCTGGTATCAGCAGCGAGGAAATTCTGGAACTACTGCGTGCCGCCCATGAATT
GGGTCTGGACCCGGAAGCAATCAAGGCTGCGGCGGAGCTTGGCAAGGCCGGTATCAGCA
GCGAGGAAATTCTGGAACTGTTACGAGCTGCCCATGAACTTGGTCTGGACCCGGAAGCCA
TAAAAGCTGCGGCGGAGTTAGGTAAGGCAGGTATCAGCAGCGAGGAAATTCTGGAACTCC
TGCGTGCCGCACATGAACTCGGTCTGGACCCGGAATGCATAAAGGCTGCGGCGGAATTG
GGCAAAGCTGGTATCAGCAGCGAGGAAATTCTGGAGTTACTGCGTGCCGCGCATGAGCTG
GGTGGCTGGTAATAA (SEQ ID NO: 110)

**MASSHHHHHHSSGLVPRGSSMGLDCEAIKAAAELGKAGISSEEILELLRAAHELGLDPEAIKA
AAELGKAGISSEEILELLRAAHELGLDPEAIKAAAELGKAGISSEEILELLRAAHELGLDPEAIK
AAAELGKAGISSEEILELLRAAHELGLDPEAIKAAAELGKAGISSEEILELLRAAHELGLDPEAI
KAAAELGKAGISSEEILELLRAAHELGLDPEAIKAAAELGKAGISSEEILELLRAAHELGLDPE
AIKAAAELGKAGISSEEILELLRAAHELGLDPEAIKAAAELGKAGISSEEILELLRAAHELGLDP
EAIKAAAELGKAGISSEEILELLRAAHELGLDPEAIKAAAELGKAGISSEEILELLRAAHELGLD
PECIKAAAELGKAGISSEEILELLRAAHELGGW** (SEQ ID NO: 111)

FIG. 14 cont'd

>cTRP24_Sub12_capped (cTRP construct containing 12 repeats and mutations blocking dimerization)

ATGGCTAGCAGCCATCATCATCATCATCATAGCAGCGGCCTGGTGCCGCGCGGCAGCTCC
ATGGGCCTGGACCCGGAGGCGGAAAAGGCTGCGGCGGAGCTGGGTAAAGCGGGCATCA
GCAGCGAGGAAATTAAAGAACTGCTGCGTGCGGCGCATGAGCTGGGTCTGGACCCGGAA
GCGATCAAAGCTGCGGCGGAACTGGGCAAGGCGGGTATCAGCAGCGAAGAAATTCTGGA
ACTGCTGCGCGCGGCGCATGAGCTGGGCCTGGACCCGGAAGCGATTAAAGCTGCGGCGG
AGCTGGGCAAGGCGGGCATCAGCAGCGAAGAGATTCTGGAATTATTACGCGCGGCGCAT
GAACTGGGTCTGGACCCGGAGGCGATCAAGGCTGCGGCGGAACTGGGTAAGGCTGGTAT
CAGCAGCGAGGAGATTCTGGAATTACTTCGTGCTGCGCATGAACTGGGCCTGGACCCGGA
GGCGATTAAGGCTGCGGCGGAGTTAGGCAAAGCTGGCATCAGCAGCGAAGAAATTCTGGA
ATTACTGCGTGCCGCTCATGAATTAGGTCTGGACCCGGAAGCTATCAAGGCTGCGGCGGA
GTTGGGCAAAGCCGGCATCAGCAGCGAGGAGATTCTGGAACTTTTACGAGCTGCTCATGA
ATTAGGCCTGGACCCGGAAGCTATTAAAGCTGCGGCGGAATTAGGTAAGGCCGGTATCAG
CAGCGAGGAAATTCTGGAATTGTTACGAGCTGCTCATGAGTTAGGTCTGGACCCGGAGGC
TATCAAAGCTGCGGCGGAGTTAGGTAAGGCAGGTATCAGCAGCGAGGAAATTCTGGAACT
TTTACGGGCTGCTCATGAACTTGGCCTGGACCCGGAAGCCATCAAAGCTGCGGCGGAATT
AGGGAAAGCTGGAATCAGCAGCGAAGAGATTCTGGAACTTCTTCGTGCCGCTCATGAACTT
GGTCTGGACCCGGAGGCCATTAAAGCTGCGGCGGAACTTGGTAAGGCGGGTATCAGCAG
CGAGGAAATTCTGGAACTACTGCGTGCCGCCCATGAATTGGGTCTGGACCCGGAAGCAAT
CAAGGCTGCGGCGGAGCTTGGCAAAGCAGGTATCAGCAGCGAGGAAATTCTGGAGTTATT
GCGTGCCGCTCATGAACTCGGTCTGGACCCGGAAGCCATCAAGAAAGCGGCGGAACTGG
GCAAAGCAGGCATCAGCAGCGAAGAGATTCTGGAGCTGCTGCGTGCGGCGCACGAAAAA
GGTGGCTGGTAATAA (SEQ ID NO: 112)

**MASSHHHHHHSSGLVPRGSSMGLDPEAEKAAAELGKAGISSEEIKELLRAAHELGLDPEAIK
AAAELGKAGISSEEILELLRAAHELGLDPEAIKAAAELGKAGISSEEILELLRAAHELGLDPEAI
KAAAELGKAGISSEEILELLRAAHELGLDPEAIKAAAELGKAGISSEEILELLRAAHELGLDPE
AIKAAAELGKAGISSEEILELLRAAHELGLDPEAIKAAAELGKAGISSEEILELLRAAHELGLDP
EAIKAAAELGKAGISSEEILELLRAAHELGLDPEAIKAAAELGKAGISSEEILELLRAAHELGLD
PEAIKAAAELGKAGISSEEILELLRAAHELGLDPEAIKAAAELGKAGISSEEILELLRAAHELGL
DPEAIKKAAELGKAGISSEEILELLRAAHEKGGW** (SEQ ID NO: 113)

FIG. 14 cont'd

>cTRP24_Sub6SS ('Sub6SS' cTRP construct containing 6 repeats and disulfide staples)
ATGGCTAGCAGCCATCATCATCATCATCATAGCAGCGGCCTGGTGCCGCGCGGCAGCTCC
ATGGGCCTGGACtgcGAGGCCATTAAGGCTGCGGCGGAGTTAGGCAAAGCGGGTATCAGC
AGCGAGGAAATTCTGGAACTTTTACGAGCTGCTCATGAGTTAGGTCTGGACCCGGAGGCT
ATCAAGGCTGCGGCGGAGTTGGGCAAAGCCGGCATCAGCAGCGAGGAGATTCTGGAACT
TTTACGGGCTGCTCATGAACTTGGCCTGGACCCGGAGGCAATTAAGGCTGCGGCGGAGCT
AGGCAAGGCTGGTATCAGCAGCGAGGAAATTCTGGAACTACTGCGTGCCGCCCATGAATT
GGGTCTGGACCCGGAAGCAATCAAGGCTGCGGCGGAGCTTGGCAAGGCCGGTATCAGCA
GCGAGGAAATTCTGGAACTGTTACGAGCTGCCCATGAACTTGGTCTGGACCCGGAAGCCA
TAAAAGCTGCGGCGGAGTTAGGTAAGGCAGGTATCAGCAGCGAGGAAATTCTGGAACTCC
TGCGTGCCGCACATGAACTCGGTCTGGACCCGGAGtgcATTAAAGCTGCGGCGGAGTTGG
GTAAGGCGGGTATCAGCAGCGAGGAAATTCTGGAGTTACTGCGTGCCGCGCATGAGCTG
GGTGGCTGGTAA (SEQ ID NO: 114)

**MASSHHHHHHSSGLVPRGSSMGLDCEAIKAAAELGKAGISSEEILELLRAAHELGLDPEAIKA
AAELGKAGISSEEILELLRAAHELGLDPEAIKAAAELGKAGISSEEILELLRAAHELGLDPEAIK
AAAELGKAGISSEEILELLRAAHELGLDPEAIKAAAELGKAGISSEEILELLRAAHELGLDPECI
KAAAELGKAGISSEEILELLRAAHELGGW** (SEQ ID NO: 115)

>thick cTRP sub3
GNLELALKALQILVNAAYVLAEIARDRGNEELLEKAARLAEEAARQAEEIARQARKEGNLELALK
ALQILVNAAYVLAEIARDRGNEELLEKAARLAEEAARQAEEIARQARKEGNLELALKALQILVNAA
YVLAEIARDRGNEELLEKAARLAEEAARQAEEIARQARKEG (SEQ ID NO: 116)

>thick cTRP sub6
GNSELAARILIILFQQLVELARLAIESGDEELLRRVSEWLEEVIKDMRRVVEQALREGNSELAARI
LIILFQQLVELARLAIESGDEELLRRVSEWLEEVIKDMRRVVEQALREGNSELAARILIILFQQLVE
LARLAIESGDEELLRRVSEWLEEVIKDMRRVVEQALREGNSELAARILIILFQQLVELARLAIESG
DEELLRRVSEWLEEVIKDMRRVVEQALREGNSELAARILIILFQQLVELARLAIESGDEELLRRVS
EWLEEVIKDMRRVVEQALREGNSELAARILIILFQQLVELARLAIESGDEELLRRVSEWLEEVIKD
MRRVVEQALRE (SEQ ID NO: 117)

>thick cTRP sub8
GNSELAARILIILFQQLVELARLAIESGDEELLRRVSEWLEEVIKDMRRVVEQALREGNSELAARI
LIILFQQLVELARLAIESGDEELLRRVSEWLEEVIKDMRRVVEQALREGNSELAARILIILFQQLVE
LARLAIESGDEELLRRVSEWLEEVIKDMRRVVEQALREGNSELAARILIILFQQLVELARLAIESG
DEELLRRVSEWLEEVIKDMRRVVEQALREGNSELAARILIILFQQLVELARLAIESGDEELLRRVS
EWLEEVIKDMRRVVEQALREGNSELAARILIILFQQLVELARLAIESGDEELLRRVSEWLEEVIKD
MRRVVEQALREGNSELAARILIILFQQLVELARLAIESGDEELLRRVSEWLEEVIKDMRRVVEQA
LREGNSELAARILIILFQQLVELARLAIESGDEELLRRVSEWLEEVIKDMRRVVEQALREG (SEQ
ID NO: 118)

FIG. 14 cont'd

>thick cTRP sub8 w/ 2 cysteine modifications underlined
GNSELAARCLIILFQQLVELARLAIESGDEELLRRVSEWLEEVIKDMRRVVEQALREGNSELAARILIILFQQLVELARLAIESGDEELLRRVSEWLEEVIKDMRRVVEQALREGNSELAARILIILFQQLVELARLAIESGDEELLRRVSEWLEEVIKDMRRVVEQALREGNSELAARILIILFQQLVELARLAIESGDEELLRRVSEWLEEVIKDMRRVVEQALREGNSELAARILIILFQQLVELARLAIESGDEELLRRVSEWLEEVIKDMRRVVEQALREGNSELAARILIILFQQLVELARLAIESGDEELLRRVSEWLEEVIKDMRRVVEQALREGNSELAARILIILFQQLVELARLAIESGDEELLRRVSEWLEEVIKDMRRVVEQALREGNSELACRILIILFQQLVELARLAIESGDEELLRRVSEWLEEVIKDMRRVVEQALREG (SEQ ID NO: 119)

>cTRP24_Sub12_Spy (cTRP Construct containing 12 repeats and inserted fusions of spycatcher domains)
ATGGCTAGCAGCCATCATCATCATCATCATAGCAGCGGCCTGGTGCCGCGCGGCAGCTCCATGGGCCTGGACCCGGAAGCGATTAAGGCGGCGGCGGAACTGGGCAAGGCGGGCATTAGCAGCGAGGAGATTCTGGAACTGCTGCGTGCGGCGCATGAGTTGGGTCTGGACCCGGAAGCCATTAAGGCAGCGGCCGAGCTGGGCAAGGCCGGTATTTCCAGCGAGGAGATCTTGGAACTGTTGCGTGCTGCACACGAGCTGGGCCTGGACCCGGAAGCTATTAAAGCGGCTGCGGAGCTGGGTAAAGCTGGTATCTCCAGCGAAGAAATTTTGGAGTTGCTGCGTGCGGCACACGAACTGGGTGGTTCCGACGGTCAAGACAAAGGTTCCGATGGCCAAGACAAGGGTGGTGACTCCGCGACCCATATTAAATTTTCTAAGCGCGACGAGGATGGCAAGGAATTGGCAGGCGCGACGATGGAACTGCGCGATTCCAGCGGCAAGACCATCTCCACCTGGATCTCTGACGGTCAGGTGAAAGATTTTTATCTGTACCCGGGTAAGTACACGTTCGTGGAGACGGCAGCCCCGGATGGTTATGAGGTGGCCACCGCGATCACCTTCACGGTTAATGAGCAGGGCCAGGTCACCGTTAATGGTGGCTCCGATGGTCAGGATAAGGGTTCCGACGGTCAAGATAAGGGTGGTTTGGATCCGGAGGCCATCAAGGCGGCAGCAGAGCTGGGCAAAGCGGGCATTTCCAGCGAAGAAATCCTGGAGCTGCTGCGCGCTGCTCACGAACTGGGCTTGGACCCGGAGGCGATCAAAGCAGCAGCGGAATTGGGCAAAGCGGGTATTAGCTCTGAGGAAATCCTGGAATTGTTGCGTGCAGCGCACGAGCTGGGTTTGGACCCGGAAGCGATTAAAGCGGCGGCGGAGTTGGGTAAAGCAGGCATTAGCAGCGAAGAGATTCTGGAACTGTTGCGTGCGGCACATGAACTGGGTTTGGATCCGGAGGCAATTAAGGCCGCTGCAGAACTGGGCAAGGCAGGTATTAGCTCCGAAGAGATTCTGGAATTGCTGCGCGCGGCGCACGAACTGGGTCTGGATCCGGAAGCAATTAAGGCGGCAGCAGAGCTGGGTAAGGCGGGTATCTCTTCTGAGGAGATCCTGGAGTTGCTGCGTGCGGCACACGAATTGGGTCTGGATCCGGAGGCAATTAAGGCTGCGGCGGAGCTGGGCAAGGCGGGTATTTCCTCCGAGGAAATCTTGGAACTGCTGCGCGCAGCACACGAACTGGGCGGCTCTGACGGTCAGGATAAAGGCTCCGACGGCCAGGATAAAGGCGGCGATTCCGCGACCCACATTAAATTTAGCAAACGTGACGAAGATGGTAAAGAGCTGGCAGGTGCGACGATGGAGCTGCGCGATAGCTCCGGTAAAACCATCAGCACCTGGATCAGCGACGGTCAAGTTAAGGACTTCTATCTGTATCCGGGCAAGTATACGTTCGTGGAAACCGCAGCCCCGGACGGTTACGAAGTGGCTACCGCGATTACCTTCACCGTGAACGAACAGGGCCAGGTGACCGTCAACGGCGGCTCTGACGGCCAAGATAAAGGCTCTGATGGCCAGGACAAGGGCGGCTTGGACCCGGAGGCGATCAAAGCAGCCGCGGAGTTGGGTAAAGCGGGCATCTCTAGCGAAGAGATTTTGGAGCTGTTGCGTGCTGCGCACGAGCTGGGCTTGGACCCGGAGGCCATTAAGGCGGCAGCTGAACTGGGTAAAGCTGGCATTAGCTCCGAAGAGATCTTGGAGCTGCTGCGTGCCGCGCACGAATTGGGCCTGGATCCGGAAGCAATCAAGGCAGCTGCTGAGTTGGGTAAGGCAGGCATCAGCAGCGAAGAAATCCTGGAACTGCTGCGTGCGGCGCATGAACTGGGTTAA (SEQ ID NO: 120)

FIG. 14 cont'd

MASSHHHHHHSSGLVPRGSSMGLDCEAIKAAAELGKAGISSEEILELLRAAHELGLDPEAIKAAAELGKAGISSEEILELLRAAHELGLDPEAIKAAAELGKAGISSEEILELLRAAHELGGSDGQDKGSDGQDKGGDSATHIKFSKRDEDGKELAGATMELRDSSGKTISTWISDGQVKDFYLYPGKYTFVETAAPDGYEVATAITFTVNEQGQVTVNGGSDGQDKGSDGQDKGGLDPEAIKAAAELGKAGISSEEILELLRAAHELGLDPEAIKAAAELGKAGISSEEILELLRAAHELGLDPEAIKAAAELGKAGISSEEILELLRAAHELGLDPEAIKAAAELGKAGISSEEILELLRAAHELGLDPEAIKAAAELGKAGISSEEILELLRAAHELGLDPEAIKAAAELGKAGISSEEILELLRAAHELGGSDGQDKGSDGQDKGGDSATHIKFSKRDEDGKELAGATMELRDSSGKTISTWISDGQVKDFYLYPGKYTFVETAAPDGYEVATAITFTVNEQGQVTVNGGSDGQDKGSDGQDKGGLDPEAIKAAAELGKAGISSEEILELLRAAHELGLDPEAIKAAAELGKAGISSEEILELLRAAHELGLDPECIKAAAELGKAGISSEEILELLRAAHELG (SEQ ID NO: 121)

>cTRP24_Sub12SS_SH2 (cTRP Construct containing 12 repeats and inserted fusions of SH2 domains)

ATGGCTAGCAGCCATCATCATCATCATCATAGCAGCGGCCTGGTGCCGCGCGGCAGCTCCATGGGCCTGGATTGCGAGGCGATCAAAGCGGCGGCGGAACTGGGTAAAGCGGGTATTAGCAGCGAGGAGATTCTGGAACTGCTGCGTGCGGCGCACGAGTTGGGTTTGGATCCGGAAGCCATCAAGGCTGCCGCCGAACTGGGCAAGGCAGGTATTAGCTCTGAAGAGATCTTGGAACTGCTGCGCGCCGCGCATGAGTTGGGTCTGGATCCGGAAGCGATCAAGGCTGCAGCAGAACTGGGCAAAGCGGGTATTTCCAGCGAGGAAATTCTGGAGTTGCTGCGTGCGGCGCATGAATTGGGTGGCTCCGATGGTCAGGATAAAGGTTCTGATGGCCAAGATAAGGGCGGCTCCGAGTGGTACTACGGCAACGTTACGCGCCACCAAGCAGAGTGCGCTCTGAATGAACGCGGTGTTGAGGGCGACTTCCTGATCCGTGATAGCGAATCTTCCCCGAGCGACTTCAGCGTTTCCCTGAAGGCGTCTGGCAAGAACAAGCACTTTAAAGTTCAGCTGGTCGATAATGTCTACTGCATCGGTCAACGTCGTTTCCACACGATGGACGAGTTGGTGGAGCATTATAAAAAGGCTCCGATCTTCACGAGCGAGCATGGTGAGAAATTGTACCTGGTGCGCGCGCTGCAGGGCGGCAGCGACGGCCAGGATAAAGGCTCCGACGGCCAAGACAAGGGTGGTTTGGACCCGGAGGCGATCAAGGCAGCAGCCGAACTGGGTAAAGCCGGTATCTCTAGCGAAGAAATTCTGGAACTGCTGCGTGCGGCTCATGAGCTGGGCTTGGATCCGGAGGCTATTAAGGCCGCTGCGGAACTGGGTAAAGCTGGCATCTCCTCCGAAGAAATTTTGGAGCTGTTGCGTGCCGCACATGAGTTGGGTCTGGATCCGGAAGCGATTAAAGCCGCCGCCGAATTGGGCAAAGCGGGCATTAGCAGCGAAGAGATTTTGGAGCTGTTGCGTGCAGCGCATGAATTGGGCCTGGACCCGGAAGCAATCAAAGCGGCTGCAGAGTTGGGTAAGGCGGGCATTTCTAGCGAGGAGATTTTGGAACTGCTGCGCGCAGCGCATGAGCTGGGCCTGGACCCGGAGGCCATTAAGGCGGCTGCGGAATTGGGCAAGGCCGGTATTTCCAGCGAAGAAATTCTGGAGCTGCTGCGTGCAGCTCACGAGTTGGGCTTGGATCCGGAAGCCATTAAGGCTGCCGCGGAACTGGGTAAGGCCGGCATTAGCAGCGAGGAGATCTTGGAGCTGCTGCGTGCCGCGCACGAGTTGGGCGGTTCTGATGGCCAGGATAAGGGTTCCGATGGCCAGGACAAAGGCGGCTCCGAATGGTATTATGGTAACGTGACCCGCCACCAGGCTGAGTGCGCCCTGAACGAGCGTGGCGTCGAAGGTGACTTTCTGATCCGCGATAGCGAGAGCAGCCCGAGCGATTTTAGCGTGAGCCTGAAGGCATCTGGCAAAAACAAACACTTTAAAGTGCAATTGGTGGATAACGTTTACTGCATCGGCCAACGTCGTTTTCATACGATGGACGAACTGGTGGAACATTATAAGAAGGCGCCGATTTTTACGTCCGAACACGGTGAAAAACTGTACCTGGTCCGTGCATTGCAGGGTGGTTCCGACGGCCAGGACAAAGGTTCCGACGGCCAAGATAAAGGCGGTCTGGACCCGGAGGCAATCAAGGCTGCGGCTGAGTTGGGCAAGGCTGGTATCAGCAGCGAGGAAATCCTGGAGCTGTTGCGCGCGGCCCATGAACTGGGTTTGGATCCGGAAGCTATCAAGGCTGCGGCAGAGCTGGGCAAGGCGGGTATCAGCTCTGAGGAAATCTTGGAGTTGCTGCGTGCCGCACACGAACTGGGCCTGGATCCGGAATGTATCAAAGCGGCGGCGGAGCTGGGTAAAGCGGGCATTAGCAGCGAAGAAATCCTGGAACTGCTGCGTGCGGCGCATGAACTGGGTGGTTGGTAATAA (SEQ ID NO: 122)

FIG. 14 cont'd

**MASSHHHHHHSSGLVPRGSSMGLDCEAIKAAAELGKAGISSEEILELLRAAHELGLDPEAIKA
AAELGKAGISSEEILELLRAAHELGLDPEAIKAAAELGKAGISSEEILELLRAAHELGGSDGQD
KGSDGQDKGGSEWYYGNVTRHQAECALNERGVEGDFLIRDSESSPSDFSVSLKASGKNKHF
KVQLVDNVYCIGQRRFHTMDELVEHYKKAPIFTSEHGEKLYLVRALQGGSDGQDKGSDGQD
KGGLDPEAIKAAAELGKAGISSEEILELLRAAHELGLDPEAIKAAAELGKAGISSEEILELLRAA
HELGLDPEAIKAAAELGKAGISSEEILELLRAAHELGLDPEAIKAAAELGKAGISSEEILELLRA
AHELGLDPEAIKAAAELGKAGISSEEILELLRAAHELGLDPEAIKAAAELGKAGISSEEILELLR
AAHELGGSDGQDKGSDGQDKGGSEWYYGNVTRHQAECALNERGVEGDFLIRDSESSPSDF
SVSLKASGKNKHFKVQLVDNVYCIGQRRFHTMDELVEHYKKAPIFTSEHGEKLYLVRALQGG
SDGQDKGSDGQDKGGLDPEAIKAAAELGKAGISSEEILELLRAAHELGLDPEAIKAAAELGK
AGISSEEILELLRAAHELGLDPECIKAAAELGKAGISSEEILELLRAAHELGW** (SEQ ID NO:
123)

t-cTRP 24x8-SH2 protein sequence (with SH2 inserts underlined)
MGNSELAARILIILFQQLVELARLAIESGDEELLRRVSEWLEEVIKDMRRVVEQALREGNSELAA
RILIILFQQLVELARLAIESGDEELLRRVSEWLEEVIKDMRRVVEQALREGGGSDGQDKGSDGQ
DKGGSEWYYGNVTRHQAECALNERGVEGDFLIRDSESSPSDFSVSLKASGKNKHFKVQLVDN
VYCIGQRRFHTMDELVEHYKKAPIFTSEHGEKLYLVRALQGGSDGQDKGSDGQDKGNSELAA
RILIILFQQLVELARLAIESGDEELLRRVSEWLEEVIKDMRRVVEQALREGNSELAARILIILFQQLV
ELARLAIESGDEELLRRVSEWLEEVIKDMRRVVEQALREGNSELAARILIILFQQLVELARLAIES
GDEELLRRVSEWLEEVIKDMRRVVEQALREGNSELAARILIILFQQLVELARLAIESGDEELLRRV
SEWLEEVIKDMRRVVEQALREGGGSDGQDKGSDGQDKGGSEWYYGNVTRHQAECALNERG
VEGDFLIRDSESSPSDFSVSLKASGKNKHFKVQLVDNVYCIGQRRFHTMDELVEHYKKAPIFTS
EHGEKLYLVRALQGGSDGQDKGSDGQDKGNSELAARILIILFQQLVELARLAIESGDEELLRRV
SEWLEEVIKDMRRVVEQALREGNSELAARILIILFQQLVELARLAIESGDEELLRRVSEWLEEVIK
DMRRVVEQALREG (SEQ ID NO: 252)

FIG. 14 cont'd

>cTRP24_Sub6SS_scMHC (Construct containing 6 repeats and inserted fusions of single chain MHC)

ATGGAGACAGACACACTGCTGCTGTGGGTGCTGCTGCTGTGGGTGCCAGGCTCCACCGG
CAACCTGGTGCCTATGGTGGCAACAGTGGGATGCGGAGCCTCTGGAGGAGGAGGCAGCG
GCGGAGGAGGCTCCATCCAGAGGACCCCAAAGATCCAGGTGTACAGCCGCCACCCAGCA
GAGAACGGCAAGTCCAACTTCCTGAATTGTTACGTGAGCGGCTTTCACCCAAGCGACATC
GAGGTGGATCTGCTGAAGAATGGCGAGCGGATCGAGAAGGTGGAGCACTCTGACCTGAG
CTTCTCCAAGGATTGGAGCTTTTACCTGCTGTACTATACCGAGTTCACCCCAACAGAGAAG
GACGAGTATGCCTGCCGGGTGAATCACGTGACACTGTCTCAGCCCAAGATCGTGAAGTGG
GACAGAGATATGGGAGGAGGAGGCTCCGGAGGAGGAGGCTCTGGCGGCGGCGGCAGCG
GAGGCGGCGGCTCTGGCAGCCACTCCATGCGGTACTTCTTTACCTCTGTGAGCAGGCCTG
GAAGGGGAGAGCCACGGTTTATCGCAGTGGGCTATGTGGACGATACACAGTTCGTGAGAT
TTGACTCCGATGCAGCATCTCAGAGGATGGAGCCACGCGCCCCATGGATCGAGCAGGAG
GGACCAGAGTACTGGGACGGAGAGACACGGAAGGTGAAGGCCCACAGCCAGACCCACCG
GGTGGATCTGGGCACACTGAGAGGCTGCTACAACCAGAGCGAGGCAGGCTCCCACACCG
TGCAGAGAATGTATGGCTGTGACGTGGGCAGCGATTGGCGGTTCCTGAGAGGCTACCACC
AGTACGCCTATGACGGCAAGGATTATATCGCCCTGAAGGAGGACCTGAGGTCCTGGACCG
CAGCAGATATGGCAGCACAGACCACAAAGCACAAGTGGGAGGCAGCACACGTGGCAGAG
CAGCTGAGGGCCTACCTGGAGGGCACATGCGTGGAGTGGCTGCGGAGATATCTGGAGAA
TGGCAAGGAGACACTGCAGCGGACAGACGCCCCTAAGACCCACATGACACACCACGCCG
TGTCCGATCACGAGGCCACCCTGAGATGTTGGGCCCTGTCTTTCTACCCAGCCGAGATCA
CCCTGACATGGCAGAGGGACGGCGAGGATCAGACCCAGGACACAGAGCTGGTGGAGACA
CGGCCCGCAGGCGATGGCACATTTCAGAAGTGGGCAGCAGTGGTGGTGCCTTCCGGACA
GGAGCAGAGGTATACCTGTCACGTGCAGCACGAGGGCCTGCCCAAGCCTCTGACACTGC
GCTGGGAGCCTGGCGGCGGCGGATCCGGAGGAGGAGGCTCCTGCGAGGCCATCAAGGC
TGCCGCCGAGCTGGGCAAGGCAGGCATCTCTAGCGAGGAGATCCTGGAGCTGCTGAGGG
CAGCACACGAGCTGGGCCTGGACCCAGAAGCCATCAAGGCTGCCGCCGAACTGGGCAAG
GCCGGCATCTCCTCTGAAGAAATCCTGGAGCTGCTGAGAGCCGCCCATGAACTGGGCCTG
GACCCCGAAGCCATCAAGGCTGCCGCCGAGTTAGGCAAGGCAGGCATCAGCTCCGAAGA
AATCCTGGAGTTACTGAGAGCCGCCCATGAGCTGGGCCTGGACCCTGAGGCCATCAAGG
CTGCCGCCGAGCTAGGCAAGGCCGGCATCTCTAGCGAAGAAATCCTGGAGCTTCTGAGAG
CCGCCCACGAATTAGGCCTGGACCCCGAGGCCATCAAGGCTGCCGCCGAGCTTGGCAAG
GCAGGCATCTCCTCTGAAGAGATCCTGGAGTTATTAAGAGCCGCCCACGAACTTGGCCTG
GACCCCGAGTGTATCAAGGCTGCCGCCGAATTAGGCAAGGCCGGCATCAGCTCCGAAGA
GATCCTGGAGCTTTTACGGGCCGCCCACGAGCTGGGCCTGTAA (SEQ ID NO: 124)

**METDTLLLWVLLLWVPGSTGNLVPMVATVGCGASGGGGSGGGGSIQRTPKIQVYSRHPAEN
GKSNFLNCYVSGFHPSDIEVDLLKNGERIEKVEHSDLSFSKDWSFYLLYYTEFTPTEKDEYAC
RVNHVTLSQPKIVKWDRDMGGGGSGGGGSGGGGSGGGGSGSHSMRYFFTSVSRPGRGEP
RFIAVGYVDDTQFVRFDSDAASQRMEPRAPWIEQEGPEYWDGETRKVKAHSQTHRVDLGTL
RGCYNQSEAGSHTVQRMYGCDVGSDWRFLRGYHQYAYDGKDYIALKEDLRSWTAADMAA
QTTKHKWEAAHVAEQLRAYLEGTCVEWLRRYLENGKETLQRTDAPKTHMTHHAVSDHEAT
LRCWALSFYPAEITLTWQRDGEDQTQDTELVETRPAGDGTFQKWAAVVVPSGQEQRYTCHV
QHEGLPKPLTLRWEPGGGGSGGGGSCEAIKAAAELGKAGISSEEILELLRAAHELGLDPEAI
KAAAELGKAGISSEEILELLRAAHELGLDPEAIKAAAELGKAGISSEEILELLRAAHELGLDPE
AIKAAAELGKAGISSEEILELLRAAHELGLDPEAIKAAAELGKAGISSEEILELLRAAHELGLDP
ECIKAAAELGKAGISSEEILELLRAAHELGL** (SEQ ID NO: 125)

FIG. 14 cont'd

>cTRP24_Sub6_SS_mFAP (Construct containing 6 repeats and inserted fusions of mFAP fluorescent protein domains)
ATGGCTAGCAGCCATCATCATCATCATCATAGCAGCGGCCTGGTGCCGCGCGGCAGCTCC
ATGGGCCTGGATTGCGAGGCGATTAAGGCTGCGGCGGAACTGGGTAAAGCGGGCATCAG
CAGCGAGGAAATTCTGGAGCTGCTGCGTGCGGCGCATGAGCTGGGTCTGGACCCGGAAG
CGATCAAGGCTGCGGCGGAGCTGGGCAAGGCGGGCATCAGCAGCGAAGAAATTCTGGAA
CTGCTGCGCGCGGCGCATGAACTGGGTCTGGACCCGGAGGCGATCAAAGCTGCGGCGGA
GCTGGGTAAGGCTGGCATCAGCAGCGAAGAGATTCTGGAATTATTACGCGCTGCTCATGA
GTTAGGTCTGGACCCGGAAGCTATTAAAGCTGCGGCGGAACTGGGCAAAGCGGGTGGCG
GTAGCGGCGGTGGCAGCAGCCGTGCGGCGCAGCTGCTGCCGGGCACCTGGCAAGCGAC
CTTCACCAACGAAGATGGTCAGACCAGCCAGGGCCAATGGCACTTTCAACCGCGTAGCCC
GTACACGATGGACATCGTGGCGCAGGGCACCATCAGCGATGGCCGTCCGATCGTGGGTT
ACGGCAAGGCGACCGTTAAAACCCCGGACACCCTGGACATCGATATTACCTATCCGAGCC
TGGGTAACATTAAGGCGCAGGGCCAAATCACGATGGACAGCCCGACCCAATTCAAGTGGG
ATGCGACCACCAAAGGCGAGAACGACTTTCACGGTCGTCTGACCGGCACCCTGCAGCGTC
AAGAAGGTGGCGGTAGCGGCGGTGGCAGCGGTATCAGCAGCGAGGAGATTCTGGAGTTA
TTACGCGCTGCCCATGAGTTGGGTCTGGACCCGGAAGCAATTAAGGCTGCGGCGGAGTTA
GGCAAAGCTGGCATCAGCAGCGAGGAGATTCTGGAATTACTTCGCGCTGCTCATGAGCTT
GGTCTGGACCCGGAATGCATCAAGGCTGCGGCGGAATTAGGCAAGGCTGGCATCAGCAG
CGAGGAAATTCTGGAGTTACTGCGTGCGGCGCATGAACTGGGCTAA (SEQ ID NO: 126)

**MASSHHHHHHSSGLVPRGSSMGLDCEAIKAAAELGKAGISSEEILELLRAAHELGLDPEAIKA
AAELGKAGISSEEILELLRAAHELGLDPEAIKAAAELGKAGISSEEILELLRAAHELGLDPEAIK
AAAELGKAGGGSGGGSSRAAQLLPGTWQATFTNEDGQTSQGQWHFQPRSPYTMDIVAQG
TISDGRPIVGYGKATVKTPDTLDIDITYPSLGNIKAQGQITMDSPTQFKWDATTKGENDFHGRL
TGTLQRQEGGGSGGGSGISSEEILELLRAAHELGLDPEAIKAAAELGKAGISSEEILELLRAAH
ELGLDPECIKAAAELGKAGISSEEILELLRAAHELG** (SEQ ID NO: 127)

FIG. 14 cont'd

>cTRP24_Sub6SS_scMHC_mFAP (Construct containing 6 repeats and inserted fusions of scMHC and mFAP fluorescent protein domains)
ATGGAGACCGATACACTGCTGCTGTGGGTGCTGCTGCTGTGGGTGCCCGGCAGCACAGG
CTACATGCTGGACCTGCAGCCTGAGACTGGAGGAGGAGGATCCGGAGGAGGAGGCTCTG
GCGGCGGCGGCAGCATCCAGCGGACCCCAAAGATCCAGGTGTACAGCCGGCACCCAGCA
GAGAACGGCAAGAGCAACTTCCTGAATTGCTACGTGAGCGGCTTTCACCCCTCTGACATC
GAGGTGGATCTGCTGAAGAATGGCGAGAGAATCGAGAAGGTGGAGCACTCCGACCTGTCT
TTCAGCAAGGATTGGTCTTTTTACCTGCTGTACTATACAGAGTTCACCCCTACAGAGAAGG
ACGAGTATGCCTGTCGGGTGAACCACGTGACCCTGTCCCAGCCAAAGATCGTGAAGTGGG
ACAGAGATATGGGAGGAGGAGGCAGCGGCGGCGGAGGCTCCGGAGGCGGCGGCTCTGG
AGGAGGCGGCTCCGGCTCTCACAGCATGAGGTACTTCTTTACATCCGTGTCTAGGCCAGG
AAGGGGAGAGCCTCGGTTTATCGCCGTGGGCTATGTGGACGATACCCAGTTCGTGAGATT
TGACAGCGATGCAGCCTCCCAGAGGATGGAGCCACGCGCCCCCTGGATCGAGCAGGAGG
GCCCTGAGTACTGGGATGGCGAGACCAGGAAGGTGAAGGCCCACAGCCAGACACACAGG
GTGGACCTGGGCACCCTGAGAGGAGCCTACAACCAGTCTGAGGCAGGCAGCCACACCGT
GCAGAGGATGTATGGCTGCGACGTGGGCTCCGATTGGCGGTTCCTGAGAGGCTACCACC
AGTACGCCTATGACGGCAAGGATTATATCGCCCTGAAGGAGGACCTGCGGAGCTGGACAG
CAGCAGATATGGCAGCCCAGACCACAAAGCACAAGTGGGAGGCAGCACACGTGGCAGAG
CAGCTGAGAGCCTACCTGGAGGGCACCTGCGTGGAGTGGCTGCGGAGATACCTGGAGAA
TGGCAAGGAGACACTGCAGAGGACCGATGCCCCCAAGACCCACATGACACACCACGCCG
TGTCTGACCACGAGGCCACCCTGAGGTGTTGGGCACTGAGCTTCTACCCTGCCGAGATCA
CCCTGACATGGCAGAGGGACGGCGAGGATCAGACCCAGGATACAGAGCTGGTGGAGACA
AGGCCAGCAGGCGACGGCACCTTTCAGAAGTGGGCAGCAGTGGTGGTGCCCTCCGGACA
GGAGCAGAGGTATACATGCCACGTGCAGCACGAGGGACTGCCAAAGCCTCTGACCCTGA
GATGGGAGCCAGGAGGAGGAGGCAGCGGAGGAGGAGGCTCCTGTGAGGCCATCAAGGC
TGCCGCCGAGCTGGGCAAGGCAGGCATCAGCTCCGAGGAGATCCTGGAGCTGCTGAGGG
CAGCACACGAGCTGGGCCTGGACCCCGAAGCCATCAAGGCTGCCGCCGAACTGGGCAAG
GCCGGCATCTCTAGCGAAGAAATCCTGGAGCTGCTGAGAGCCGCCCATGAACTGGGCCT
GGACCCCGAGGCCATCAAGGCTGCCGCCGAGTTAGGCAAGGCAGGCATCTCCTCTGAAG
AGATCCTGGAGTTATTAAGAGCCGCCCATGAGTTAGGCCTGGACCCCGAGGCCATCAAGG
CTGCCGCCGAGCTAGGCAAGGCCGGCATCAGCTCCGAAGAAATCCTGGAGTTACTGAGA
GCCGCCCATGAGCTGGGCCTGGACCCAGAGGCCATCAAGGCTGCCGCCGAGCTTGGCAA
GGCAGGCATCTCTAGCGAAGAGATCCTGGAGCTTTTAAGAGCCGCCCACGAATTAGGCCT
GGACCCCGAGTGTATCAAGGCTGCCGCCGAGCTCGGCAAGGCCGGCATCTCCTCTGAGG
AAATCCTGGAGTTGTTAAGGGCCGCCCACGAGCTGGGAGGAGGCAGCTCCCGCGCCGCC
CAGCTGCTGCCCGGCACATGGCAGGCCACCTTCACAAATGAGGACGGACAGACCAGCCA
GGGACAGTGGCACTTTCAGCCTCGGTCCCCATACACAATGGACATCGTGGCACAGGGCAC
CATCAGCGACGGCAGACCTATCGTGGGCTACGGCAAGGCCACCGTGAAGACACCTGACA
CCCTGGACATCGACATCACCTATCCATCCCTGGGCAACATCAAGGCCCAGGGCCAGATCA
CAATGGACTCTCCAACCCAGTTCAAGTGGGATGCCACCACAAAGGGCGAGAATGACTTTC
ACGGCAGGCTGACCGGCACACTGCAGAGGCAGGAGTAA (SEQ ID NO: 128)

FIG. 14 cont'd

METDTLLLWVLLLWVPGSTGYMLDLQPETGGGGSGGGGSGGGGSIQRTPKIQVYSRHPAEN GKSNFLNCYVSGFHPSDIEVDLLKNGERIEKVEHSDLSFSKDWSFYLLYYTEFTPTEKDEYAC RVNHVTLSQPKIVKWDRDMGGGGSGGGGSGGGGSGGGGSGSHSMRYFFTSVSRPGRGEP RFIAVGYVDDTQFVRFDSDAASQRMEPRAPWIEQEGPEYWDGETRKVKAHSQTHRVDLGTL RGAYNQSEAGSHTVQRMYGCDVGSDWRFLRGYHQYAYDGKDYIALKEDLRSWTAADMAA QTTKHKWEAAHVAEQLRAYLEGTCVEWLRRYLENGKETLQRTDAPKTHMTHHAVSDHEAT LRCWALSFYPAEITLTWQRDGEDQTQDTELVETRPAGDGTFQKWAAVVVPSGQEQRYTCHV QHEGLPKPLTLRWEPGGGGSGGGGSCEAIKAAAELGKAGISSEEILELLRAAHELGLDPEAI KAAAELGKAGISSEEILELLRAAHELGLDPEAIKAAAELGKAGISSEEILELLRAAHELGLDPE AIKAAAELGKAGISSEEILELLRAAHELGLDPEAIKAAAELGKAGISSEEILELLRAAHELGLDP ECIKAAAELGKAGISSEEILELLRAAHELGGGSSRAAQLLPGTWQATFTNEDGQTSQGQWHF QPRSPYTMDIVAQGTISDGRPIVGYGKATVKTPDTLDIDITYPSLGNIKAQGQITMDSPTQFKW DATTKGENDFHGRLTGTLQRQE (SEQ ID NO: 129)

>Aqualysin fused to cTRP24_Sub6SS: (">Aqualysin-ToroidX6_SS_tetramer-His)
METDTLLLWVLLLWVPGSTGDYKDEATQSPAPWGLDRIDQRDLPLSNSYTYTATGRGVNVYVI DTGIRTTHREFGGRARVGYDALGGNGQDCNGHGTHVAGTIGGVTYGVAKAVNLYAVRVLDCD GSGSTSGVIAGVDWVTRNHRRPAVASMSLGGGVSTALDNAVKNSIAAGVVYAVAAGNDNANA CDYSPARVAEALTVGATTSSDARASFSNYGSCVDLFAPGASIPSAWYTSDTATQTLDGTSMAT PHVAGVAALYLEQNPSATPASVASAILNGATTGRLSGIGSGSPNRLLYSLLSSGSGGGGSGGG GSCEAIKAAAELGKAGISSEEILELLRAAHELGLDPEAIKAAAELGKAGISSEEILELLRAAHELGL DPEAIKAAAELGKAGISSEEILELLRAAHELGLDPEAIKAAAELGKAGISSEEILELLRAAHELGLD PEAIKAAAELGKAGISSEEILELLRAAHELGLDPECIKAAAELGKAGISSEEILELLRAAHELGLGG SHHHHHH (SEQ ID NO: 130)

>Clover-SpyTag (Clover fluorescent protein with N-terminal spytag)
ATGGGCAGCAGCCATCATCATCATCATCACAGCAGCGGCCTGGTGCCGCGCGGCAGCGC TCACATCGTTATGGTAGATGCGTACAAGCCCACCAAAGGGTCTAGCGGAAGTAGTGGTAG TCATATGATGGTGAGCAAGGGCGAGGAGCTGTTCACCGGGGTGGTGCCCATCCTGGTCG AGCTGGACGGCGACGTAAACGGCCACAAGTTCAGCGTCCGCGGCGAGGGCGAGGGCGA TGCCACCAACGGCAAGCTGACCCTGAAGTTCATCTGCACCACCGGCAAGCTGCCCGTGCC CTGGCCCACCCTCGTGACCACCTTCGGCTACGGCGTGGCCTGCTTCAGCCGCTACCCCG ACCACATGAAGCAGCACGACTTCTTCAAGTCCGCCATGCCCGAAGGCTACGTCCAGGAGC GCACCATCTCTTTCAAGGACGACGGTACCTACAAGACCCGCGCCGAGGTGAAGTTCGAGG GCGACACCCTGGTGAACCGCATCGAGCTGAAGGGCATCGACTTCAAGGAGGACGGCAAC ATCCTGGGGCACAAGCTGGAGTACAACTTCAACAGCCACAACGTCTATATCACGGCCGAC AAGCAGAAGAACGGCATCAAGGCTAACTTCAAGATCCGCCACAACGTTGAGGACGGCAGC GTGCAGCTCGCCGACCACTACCAGCAGAACACCCCCATCGGCGACGGCCCCGTGCTGCT GCCCGACAACCACTACCTGAGCCATCAGTCCGCCCTGAGCAAAGACCCCAACGAGAAGCG CGATCACATGGTCCTGCTGGAGTTCGTGACCGCCGCCTAG (SEQ ID NO: 131)

MGSSHHHHHHSSGLVPRGSAHIVMVDAYKPTKGSSGSSGSHMMVSKGEELFTGVVPILVEL DGDVNGHKFSVRGEGEGDATNGKLTLKFICTTGKLPVPWPTLVTTFGYGVACFSRYPDHMK QHDFFKSAMPEGYVQERTISFKDDGTYKTRAEVKFEGDTLVNRIELKGIDFKEDGNILGHKLE YNFNSHNVYITADKQKNGIKANFKIRHNVEDGSVQLADHYQQNTPIGDGPVLLPDNHYLSHQS ALSKDPNEKRDHMVLLEFVTAA (SEQ ID NO: 132)

FIG. 14 cont'd

Clover Fluorescent Protein
MVSKGEELFTGVVPILVELDGDVNGHKFSVRGEGEGDATNGKLTLKFICTTGKLPVPWPTLVTT
FGYGVACFSRYPDHMKQHDFFKSAMPEGYVQERTISFKDDGTYKTRAEVKFEGDTLVNRIELK
GIDFKEDGNILGHKLEYNFNSHNVYITADKQKNGIKANFKIRHNVEDGSVQLADHYQQNTPIGD
GPVLLPDNHYLSHQSALSKDPNEKRDHMVLLEFVTAA (SEQ ID NO: 133)

mKate Fluorescent Protein
MVSKGEELIKENMHMKLYMEGTVNNHHFKCTSEGEGKPYEGTQTMRIKAVEGGPLPFAFDILA
TSFMYGSKTFINHTQGIPDFFKQSFPEGFTWERVTTYEDGGVLTATQDTSLQDGCLIYNVKIRG
VNFPSNGPVMQKKTLGWEASTETLYPADGGLEGRADMALKLVGGGHLICNLKTTYRSKKPAK
NLKMPGVYYVDRRLERIKEADKETYVEQHEVAVARYCDLPSKLGHR (SEQ ID NO: 134)

>SH2-SpyTag (SH2 domain with N-terminal spytag)
ATGGGCAGCAGCCATCATCATCATCATCACAGCAGCGGCCTGGTGCCGCGCGGCAGCGC
TCACATCGTTATGGTAGATGCGTACAAGCCCACCAAAGGGTCTAGCGGAAGTAGTGGTAG
TCATATGTCCGAGTGGTACTACGGGAACGTGACGCGGCACCAGGCCGAGTGCGCCCTCA
ACGAGCGGGGCGTGGAGGGCGACTTCCTCATTAGGGACAGCGAGTCCTCGCCCAGCGAC
TTCTCCGTGTCCCTTAAAGCGTCAGGGAAGAACAAACACTTCAAGGTGCAGCTCGTGGACA
ATGTCTACTGCATTGGGCAGCGGCGCTTCCACACCATGGACGAGCTGGTGGAACACTACA
AAAAGGCGCCCATCTTCACCAGCGAGCACGGGGAGAAGCTCTACCTCGTCAGGGCCCTG
CAGTGA (SEQ ID NO: 135)

**MGSSHHHHHHSSGLVPRGSAHIVMVDAYKPTKGSSGSSGSHMSEWYYGNVTRHQAECALN
ERGVEGDFLIRDSESSPSDFSVSLKASGKNKHFKVQLVDNVYCIGQRRFHTMDELVEHYKKA
PIFTSEHGEKLYLVRALQ** (SEQ ID NO: 136)

>SH2 (Free SH2 domain)
ATGGCTAGCAGCCATCATCATCATCATCATAGCAGCGGCCTGGTGCCGCGCGGCAGCCAT
ATGTCCGAGTGGTACTACGGGAACGTGACGCGGCACCAGGCCGAGTGCGCCCTCAACGA
GCGGGGCGTGGAGGGCGACTTCCTCATTAGGGACAGCGAGTCCTCGCCCAGCGACTTCT
CCGTGTCCCTTAAAGCGTCAGGGAAGAACAAACACTTCAAGGTGCAGCTCGTGGACAATG
TCTACTGCATTGGGCAGCGGCGCTTCCACACCATGGACGAGCTGGTGGAACACTACAAAA
AGGCGCCCATCTTCACCAGCGAGCACGGGGAGAAGCTCTACCTCGTCAGGGCCCTGCAG
TGA (SEQ ID NO: 137)

**MASSHHHHHHSSGLVPRGSHMSEWYYGNVTRHQAECALNERGVEGDFLIRDSESSPSDFSV
SLKASGKNKHFKVQLVDNVYCIGQRRFHTMDELVEHYKKAPIFTSEHGEKLYLVRALQ** (SEQ
ID NO: 138)

>Spytagged single chain Fv (scFv) targeting IHF-1:
METDTLLLWVLLLWVPGSTGSGSSAHIVMVDAYKPTKDIVLTQAPGTLSLSPGDRATLSCRASQ
RLGGTSLAWYQHRSGQAPRLILYGTSNRATDTPDRFSGSGSGTDFVLTISSLEPEDFAVYYCQ
QYGSPPYTFGQGTTLDIKGGGGSGGGGSGGGGSQVQLVESGPGLVKPSETLSLTCRVSGDS
NRPSYWSWIRQAPGKAMEWIGYVYDSGVTIYNPSLKGRVTISLDTSKTRFSLKLTSVIAADTAV
YYCARERFDRTSYKSWWGQGTQVTVSSGGGGSHHHHHH (SEQ ID NO: 139)

FIG. 14 cont'd scFv_IHF1_TRL1068-Toroidx6_SS_tetramer-His:
METDTLLLWVLLLWVPGSTGQVQLVESGPGLVKPSETLSLTCRVSGDSNRPSYWSWIRQAPG
KAMEWIGYVYDSGVTIYNPSLKGRVTISLDTSKTRFSLKLTSVIAADTAVYYCARERFDRTSYKS
WWGQGTQVTVSSGGGSGGGSGGGSGGGSDIVLTQAPGTLSLSPGDRATLSCRASQRLGGT
SLAWYQHRSGQAPRLILYGTSNRATDTPDRFSGSGSGTDFVLTISSLEPEDFAVYYCQQYGSP
PYTFGQGTTLDIKGGGGSGGGGSCEAIKAAAELGKAGISSEEILELLRAAHELGLDPEAIKAAAE
LGKAGISSEEILELLRAAHELGLDPEAIKAAAELGKAGISSEEILELLRAAHELGLDPEAIKAAAEL
GKAGISSEEILELLRAAHELGLDPEAIKAAAELGKAGISSEEILELLRAAHELGLDPECIKAAAELG
KAGISSEEILELLRAAHELGLGGSHHHHHH (SEQ ID NO: 140)

MHC alpha chain
GSHSMRYFFTSVSRPGRGEPRFIAVGYVDDTQFVRFDSDAASQRMEPRAPWIEQEGPEYWD
GETRKVKAHSQTHRVDLGTLRGYYNQSEAGSHTVQRMYGCDVGSDWRFLRGYHQYAYDGK
DYIALKEDLRSWTAADMAAQTTKHKWEAAHVAEQLRAYLEGTCVEWLRRYLENGKETLQRTD
APKTHMTHHAVSDHEATLRCWALSFYPAEITLTWQRDGEDQTQDTELVETRPAGDGTFQKWA
AVVVPSGQEQRYTCHVQHEGLPKPLTLRWEP (SEQ ID NO: 141)

MHC beta chain
IQKTPQIQVYSRHPPENGKPNILNCYVTQFHPPHIEIQMLKNGKKIPKVEMSDMSFSKDWSFYIL
AHTEFTPTETDTYACRVKHASMAEPKTVYWDRDM (SEQ ID NO: 142)

IL-3
MSRLPVLLLLQLLVRPGLQAPMTQTTPLKTSWVNCSNMIDEIITHLKQPPLPLLDFNNLNGEDQ
DILMENNLRRPNLEAFNRAVKSLQNASAIESILKNLLPCLPLATAAPTRHPIHIKDGDWNEFRRKL
TFYLKTLENAQAQQTTLSLAIF (SEQ ID NO: 143)

Delta
MGSRCALALAVLSALLCQVWSSGVFELKLQEFVNKKGLLGNRNCCRGGAGPPPCACRTFFRV
CLKHYQASVSPEPPCTYGSAVTPVLGVDSFSLPDGGGADSAFSNPIRFPFGFTWPGTFSLIIEA
LHTDSPDDLATENPERLISRLATQRHLTVGEEWSQDLHSSGRTDLKYSYRFVCDEHYYGEGCS
VFCRPRDDAFGHFTCGERGEKVCNPGWKGPYCTEPICLPGCDEQHGFCDKPGECKCRVGW
QGRYCDECIRYPGCLHGTCQQPWQCNCQEGWGGLFCNQDLNYCTHHKPCKNGATCTNTGQ
GSYTCSCRPGYTGATCELGIDECDPSPCKNGGSCTDLENSYSCTCPPGFYGKICELSAMTCAD
GPCFNGGRCSDSPDGGYSCRCPVGYSGFNCEKKIDYCSSSPCSNGAKCVDLGDAYLCRCQA
GFSGRHCDDNVDDCASSPCANGGTCRDGVNDFSCTCPPGYTGRNCSAPVSRCEHAPCHNG
ATCHERGHRYVCECARGYGGPNCQFLLPELPPGPAVVDLTEKLEGQGGPFPWVAVCAGVILV
LMLLLGCAAVVVCVRLRLQKHRPPADPCRGETETMNNLANCQREKDISVSIIGATQIKNTNKKA
DFHGDHSADKNGFKARYPAVDYNLVQDLKGDDTAVRDAHSKRDTKCQPQGSSGEEKGTPTT
LRGGEASERKRPDSGCSTSKDTKYQSVYVISEEKDECVIATEV (SEQ ID NO: 144)

FIG. 14 cont'd

Jagged
MRSPRTRGRSGRPLSLLLALLCALRAKVCGASGQFELEILSMQNVNGELQNGNCCGGARNPG
DRKCTRDECDTYFKVCLKEYQSRVTAGGPCSFGSGSTPVIGGNTFNLKASRGNDRNRIVLPFS
FAWPRSYTLLVEAWDSSNDTVQPDSIIEKASHSGMINPSRQWQTLKQNTGVAHFEYQIRVTCD
DYYYGFGCNKFCRPRDDFFGHYACDQNGNKTCMEGWMGPECNRAICRQGCSPKHGSCKLP
GDCRCQYGWQGLYCDKCIPHPGCVHGICNEPWQCLCETNWGGQLCDKDLNYCGTHQPCLN
GGTCSNTGPDKYQCSCPEGYSGPNCEIAEHACLSDPCHNRGSCKETSLGFECECSPGWTGP
TCSTNIDDCSPNNCSHGGTCQDLVNGFKCVCPPQWTGKTCQLDANECEAKPCVNAKSCKNLI
ASYYCDCLPGWMGQNCDININDCLGQCQNDASCRDLVNGYRCICPPGYAGDHCERDIDECAS
NPCLNGGHCQNEINRFQCLCPTGFSGNLCQLDIDYCEPNPCQNGAQCYNRASDYFCKCPEDY
EGKNCSHLKDHCRTTPCEVIDSCTVAMASNDTPEGVRYISSNVCGPHGKCKSQSGGKFTCDC
NKGFTGTYCHENINDCESNPCRNGGTCIDGVNSYKCICSDGWEGAYCETNINDCSQNPCHNG
GTCRDLVNDFYCDCKNGWKGKTCHSRDSQCDEATCNNGGTCYDEGDAFKCMCPGGWEGT
TCNIARNSSCLPNPCHNGGTCVVNGESFTCVCKEGWEGPICAQNTNDCSPHPCYNSGTCVD
GDNWYRCECAPGFAGPDCRININECQSSPCAFGATCVDEINGYRCVCPPGHSGAKCQEVSG
RPCITMGSVIPDGAKWDDDCNTCQCLNGRIACSKVWCGPRPCLLHKGHSECPSGQSCIPILDD
QCFVHPCTGVGECRSSSLQPVKTKCTSDSYYQDNCANITFTFNKEMMSPGLTTEHICSELRNL
NILKNVSAEYSIYIACEPSPSANNEIHVAISAEDIRDDGNPIKEITDKIIDLVSKRDGNSSLIAAVAEV
RVQRRPLKNRTDFLVPLLSSVLTVAWICCLVTAFYWCLRKRRKPGSHTHSASEDNTTNNVREQ
LNQIKNPIEKHGANTVPIKDYENKNSKMSKIRTHNSEVEEDDMDKHQQKARFAKQPAYTLVDRE
EKPPNGTPTKHPNWTNKQDNRDLESAQSLNRMEYIV (SEQ ID NO: 145)

huOKT3 variable heavy chain
QVQLVQSGGGVVQPGRSLRLSCKASGYTFTRYTMHWVRQAPGKGLEWIGYINPSRGYTNYN
QKFKDRFTISRDNSKNTAFLQMDSLRPEDTGVYFCARYYDDHYSLDYWGQGTPVTVSS (SEQ ID NO: 146)

huOKT3 variable light chain
DIQMTQSPSSLSASVGDRVTITCSASSSVSYMNWYQQTPGKAPKRWIYDTSKLASGVPSRFSG
SGSGTDYTFTISSLQPEDIATYYCQQWSSNPFTFGQGTKLQITR (SEQ ID NO: 147)

huOKT3 CDR Regions according to Kabat numbering
CDRH1: GYTFTRYTMH (SEQ ID NO: 148);
CDRH2: INPSRGYTNYNQKFKD (SEQ ID NO: 149);
CDRH3: YYDDHYSLDY (SEQ ID NO: 150);
CDRL1: SASSSVSYMN (SEQ ID NO: 151);
CDRL2: DTSKLAS (SEQ ID NO: 152); and
CDRL3: QQWSSNPFT (SEQ ID NO: 153)

>scFv_CD3_hsOKT3-Toroidx6_SS_tetramer-His:
METDTLLLWVLLLWVPGSTGQVQLVQSGGGVVQPGRSLRLSCKASGYTFTRYTMHWVRQAP
GKGLEWIGYINPSRGYTNYNQKFKDRFTISRDNSKNTAFLQMDSLRPEDTGVYFCARYYDDHY
SLDYWGQGTPVTVSSGGGSGGGSGGGSGGGSDIQMTQSPSSLSASVGDRVTITCSASSSVS
YMNWYQQTPGKAPKRWIYDTSKLASGVPSRFSGSGSGTDYTFTISSLQPEDIATYYCQQWSS
NPFTFGQGTKLQITRGGGGSGGGGSCEAIKAAAELGKAGISSEEILELLRAAHELGLDPEAIKAA
AELGKAGISSEEILELLRAAHELGLDPEAIKAAAELGKAGISSEEILELLRAAHELGLDPEAIKAAA
ELGKAGISSEEILELLRAAHELGLDPEAIKAAAELGKAGISSEEILELLRAAHELGLDPECIKAAAE
LGKAGISSEEILELLRAAHELGLGGSHHHHHH (SEQ ID NO: 154)

FIG. 14 cont'd

>scFv_CD28_TGN1412-Toroidx6_SS_tetramer-His:
METDTLLLWVLLLWVPGSTGQVQLVQSGAEVKKPGASVKVSCKASGYTFTSYYIHWVRQAPG QGLEWIGCIYPGNVNTNYNEKFKDRATLTVDTSISTAYMELSRLRSDDTAVYFCTRSHYGLDW NFDVWGQGTTVTVSSGGGGSGGGGSGGGGSDIQMTQSPSSLSASVGDRVTITCHASQNIYV WLNWYQQKPGKAPKLLIYKASNLHTGVPSRFSGSGSGTDFTLTISSLQPEDFATYYCQQGQTY PYTFGGGTKVEIKGGGGSGGGGSCEAIKAAAELGKAGISSEEILELLRAAHELGLDPEAIKAAAE LGKAGISSEEILELLRAAHELGLDPEAIKAAAELGKAGISSEEILELLRAAHELGLDPEAIKAAAEL GKAGISSEEILELLRAAHELGLDPEAIKAAAELGKAGISSEEILELLRAAHELGLDPECIKAAAELG KAGISSEEILELLRAAHELGLGGSHHHHHH (SEQ ID NO: 155)

>cTRP246SS-scTrimer$^{4\text{-}1BBL}$ ('Sub6' cTRP construct containing 6 repeats, disulfide staples and inserted fusions of a single chain trimer targeting 4-1BB)
METDTLLLWVLLLWVPGSTGREGPELSPDDPAGLLDLRQGMFAQLVAQNVLLIDGPLSWYSDP GLAGVSLTGGLSYKEDTKELVVAKAGVYYVFFQLELRRVVAGEGSGSVSLALHLQPLRSAAGA AALALTVDLPPASSEARNSAFGFQGRLLHLSAGQRLGVHLHTEARARHAWQLTQGATVLGLFR VTPEIPAGLPSPRSEGGGGSREGPELSPDDPAGLLDLRQGMFAQLVAQNVLLIDGPLSWYSDP GLAGVSLTGGLSYKEDTKELVVAKAGVYYVFFQLELRRVVAGEGSGSVSLALHLQPLRSAAGA AALALTVDLPPASSEARNSAFGFQGRLLHLSAGQRLGVHLHTEARARHAWQLTQGATVLGLFR VTPEIPAGLPSPRSEGGGGSREGPELSPDDPAGLLDLRQGMFAQLVAQNVLLIDGPLSWYSDP GLAGVSLTGGLSYKEDTKELVVAKAGVYYVFFQLELRRVVAGEGSGSVSLALHLQPLRSAAGA AALALTVDLPPASSEARNSAFGFQGRLLHLSAGQRLGVHLHTEARARHAWQLTQGATVLGLFR VTPEIPAGLPSPRSEGGGGSGGGGSCEAIKAAAELGKAGISSEEILELLRAAHELGLDPEAIKAA AELGKAGISSEEILELLRAAHELGLDPEAIKAAAELGKAGISSEEILELLRAAHELGLDPEAIKAAA ELGKAGISSEEILELLRAAHELGLDPEAIKAAAELGKAGISSEEILELLRAAHELGLDPECIKAAAE LGKAGISSEEILELLRAAHELGLGGSHHHHHH (SEQ ID NO: 195)

>cTRP246SS-scTrimer$^{OX40L}$ ('Sub6' cTRP construct containing 6 repeats, disulfidestaples and inserted fusions of a single chain trimer targeting OX40)
METDTLLLWVLLLWVPGSTGQVSHRYPRIQSIKVQFTEYKKEKGFILTSQKEDEIMKVQNNSVII NCDGFYLISLKGYFSQEVNISLHYQKDEEPLFQLKKVRSVNSLMVASLTYKDKVYLNVTTDNTS LDDFHVNGGELILIHQNPGEFCVLGGGGSQVSHRYPRIQSIKVQFTEYKKEKGFILTSQKEDEIM KVQNNSVIINCDGFYLISLKGYFSQEVNISLHYQKDEEPLFQLKKVRSVNSLMVASLTYKDKVYL NVTTDNTSLDDFHVNGGELILIHQNPGEFCVLGGGGSQVSHRYPRIQSIKVQFTEYKKEKGFILT SQKEDEIMKVQNNSVIINCDGFYLISLKGYFSQEVNISLHYQKDEEPLFQLKKVRSVNSLMVASL TYKDKVYLNVTTDNTSLDDFHVNGGELILIHQNPGEFCVLGGGGSGGGGSCEAIKAAAELGKA GISSEEILELLRAAHELGLDPEAIKAAAELGKAGISSEEILELLRAAHELGLDPEAIKAAAELGKAGI SSEEILELLRAAHELGLDPEAIKAAAELGKAGISSEEILELLRAAHELGLDPEAIKAAAELGKAGIS SEEILELLRAAHELGLDPECIKAAAELGKAGISSEEILELLRAAHELGLGGSHHHHHH (SEQ ID NO: 196)

SEQUENCE LISTING

```
<160> NUMBER OF SEQ ID NOS: 254

<210> SEQ ID NO 1
<211> LENGTH: 33
<212> TYPE: PRT
<213> ORGANISM: Artificial Sequence
<220> FEATURE:
<223> OTHER INFORMATION: Synthesized

<400> SEQUENCE: 1

Gly Leu Asp Pro Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Glu
            20                  25                  30

Leu


<210> SEQ ID NO 2
<211> LENGTH: 14
<212> TYPE: PRT
<213> ORGANISM: Artificial Sequence
<220> FEATURE:
<223> OTHER INFORMATION: Synthesized

<400> SEQUENCE: 2

Ser Glu Glu Ile Leu Glu Leu Leu Arg Ala Ala His Glu Leu
1               5                   10


<210> SEQ ID NO 3
<211> LENGTH: 14
<212> TYPE: PRT
<213> ORGANISM: Artificial Sequence
<220> FEATURE:
<223> OTHER INFORMATION: Synthesized

<400> SEQUENCE: 3

Ser Glu Glu Ile Leu Glu Leu Leu Arg Ala Ala His Val Leu
1               5                   10


<210> SEQ ID NO 4
<211> LENGTH: 14
<212> TYPE: PRT
<213> ORGANISM: Artificial Sequence
<220> FEATURE:
<223> OTHER INFORMATION: Synthesized

<400> SEQUENCE: 4

Ser Glu Glu Ile Leu Glu Leu Leu Val Ala Ala His Leu Leu
1               5                   10


<210> SEQ ID NO 5
<211> LENGTH: 14
<212> TYPE: PRT
<213> ORGANISM: Artificial Sequence
<220> FEATURE:
<223> OTHER INFORMATION: Synthesized

<400> SEQUENCE: 5

Ser Ile Glu Ile Leu Glu Leu Leu Arg Ala Ala His Glu Leu
1               5                   10
```

```
<210> SEQ ID NO 6
<211> LENGTH: 14
<212> TYPE: PRT
<213> ORGANISM: Artificial Sequence
<220> FEATURE:
<223> OTHER INFORMATION: Synthesized

<400> SEQUENCE: 6

Ser Glu Glu Ile Lys Glu Leu Leu Arg Ala Ala His Glu Leu
1               5                   10


<210> SEQ ID NO 7
<211> LENGTH: 14
<212> TYPE: PRT
<213> ORGANISM: Artificial Sequence
<220> FEATURE:
<223> OTHER INFORMATION: Synthesized

<400> SEQUENCE: 7

Ser Glu Glu Ile Leu Glu Leu Leu Arg Ala Ala His Glu Lys
1               5                   10


<210> SEQ ID NO 8
<211> LENGTH: 13
<212> TYPE: PRT
<213> ORGANISM: Artificial Sequence
<220> FEATURE:
<223> OTHER INFORMATION: Synthesized

<400> SEQUENCE: 8

Pro Glu Ala Glu Lys Ala Ala Ala Glu Leu Gly Lys Ala
1               5                   10


<210> SEQ ID NO 9
<211> LENGTH: 13
<212> TYPE: PRT
<213> ORGANISM: Artificial Sequence
<220> FEATURE:
<223> OTHER INFORMATION: Synthesized

<400> SEQUENCE: 9

Pro Glu Ala Ile Lys Lys Ala Ala Glu Leu Gly Lys Ala
1               5                   10


<210> SEQ ID NO 10
<211> LENGTH: 13
<212> TYPE: PRT
<213> ORGANISM: Artificial Sequence
<220> FEATURE:
<223> OTHER INFORMATION: Synthesized

<400> SEQUENCE: 10

Pro Glu Ala Ile Lys Ala Ala Ala Glu Leu Gly Lys Ala
1               5                   10


<210> SEQ ID NO 11
<211> LENGTH: 13
<212> TYPE: PRT
<213> ORGANISM: Artificial Sequence
<220> FEATURE:
<223> OTHER INFORMATION: Synthesized

<400> SEQUENCE: 11

Pro Glu Cys Ile Lys Ala Ala Ala Glu Leu Gly Lys Ala
1               5                   10
```

<210> SEQ ID NO 12
<211> LENGTH: 13
<212> TYPE: PRT
<213> ORGANISM: Artificial Sequence
<220> FEATURE:
<223> OTHER INFORMATION: Synthesized

<400> SEQUENCE: 12

Pro Thr Glu Val Leu Leu Glu Leu Ile Ala Glu Ala Ser
1 5 10

<210> SEQ ID NO 13
<211> LENGTH: 13
<212> TYPE: PRT
<213> ORGANISM: Artificial Sequence
<220> FEATURE:
<223> OTHER INFORMATION: Synthesized

<400> SEQUENCE: 13

Pro Glu Leu Glu Tyr Ala Leu Ala Tyr Ala Lys Lys Val
1 5 10

<210> SEQ ID NO 14
<211> LENGTH: 14
<212> TYPE: PRT
<213> ORGANISM: Artificial Sequence
<220> FEATURE:
<223> OTHER INFORMATION: Synthesized

<400> SEQUENCE: 14

Ser Glu Glu Ile Leu Glu Leu Leu Arg Ala Ala His Ala Leu
1 5 10

<210> SEQ ID NO 15
<211> LENGTH: 14
<212> TYPE: PRT
<213> ORGANISM: Artificial Sequence
<220> FEATURE:
<223> OTHER INFORMATION: Synthesized

<400> SEQUENCE: 15

Ser Ala Glu Ile Leu Glu Leu Leu Met Ala Ala His Glu Leu
1 5 10

<210> SEQ ID NO 16
<211> LENGTH: 14
<212> TYPE: PRT
<213> ORGANISM: Artificial Sequence
<220> FEATURE:
<223> OTHER INFORMATION: Synthesized

<400> SEQUENCE: 16

Ser Glu Glu Ile Leu Glu Leu Leu Arg Ala Ala His Gly Leu
1 5 10

<210> SEQ ID NO 17
<211> LENGTH: 14
<212> TYPE: PRT
<213> ORGANISM: Artificial Sequence
<220> FEATURE:
<223> OTHER INFORMATION: Synthesized

<400> SEQUENCE: 17

Ser Glu Glu Ile Leu Glu Leu Leu Arg Ala Ala His Gly Gly
1 5 10

<210> SEQ ID NO 18
<211> LENGTH: 14
<212> TYPE: PRT
<213> ORGANISM: Artificial Sequence
<220> FEATURE:
<223> OTHER INFORMATION: Synthesized

<400> SEQUENCE: 18

Arg Glu Glu Val Lys Glu Lys Phe Leu Lys Glu Leu Arg Lys
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthesized

<400> SEQUENCE: 19

Lys Glu Glu Val Lys Glu Lys Phe Leu Lys Glu Leu Ser Phe
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthesized

<400> SEQUENCE: 20

Lys Glu Glu Val Lys Lys Lys Phe Trp Lys Glu Leu Ser Leu
1               5                   10

<210> SEQ ID NO 21
<211> LENGTH: 25
<212> TYPE: PRT
<213> ORGANISM: Artificial Sequence
<220> FEATURE:
<223> OTHER INFORMATION: Synthesized

<400> SEQUENCE: 21

Ser Glu Leu Ala Ala Arg Ile Leu Ile Ile Leu Phe Gln Gln Leu Val
1               5                   10                  15

Glu Leu Ala Arg Leu Ala Ile Glu Ser
            20                  25

<210> SEQ ID NO 22
<211> LENGTH: 28
<212> TYPE: PRT
<213> ORGANISM: Artificial Sequence
<220> FEATURE:
<223> OTHER INFORMATION: Synthesized

<400> SEQUENCE: 22

Glu Glu Leu Leu Arg Arg Val Ser Glu Trp Leu Glu Glu Val Ile Lys
1               5                   10                  15

Asp Met Arg Arg Val Val Glu Gln Ala Leu Arg Glu
            20                  25

<210> SEQ ID NO 23
<211> LENGTH: 27
<212> TYPE: PRT
<213> ORGANISM: Artificial Sequence
<220> FEATURE:
<223> OTHER INFORMATION: Synthesized

<400> SEQUENCE: 23

```
Glu Leu Leu Arg Arg Val Ser Glu Trp Leu Glu Glu Val Ile Lys Asp
1               5                   10                  15

Met Arg Arg Val Val Glu Gln Ala Leu Arg Glu
            20                  25


<210> SEQ ID NO 24
<211> LENGTH: 24
<212> TYPE: PRT
<213> ORGANISM: Artificial Sequence
<220> FEATURE:
<223> OTHER INFORMATION: Synthesized

<400> SEQUENCE: 24

Glu Leu Ala Leu Lys Ala Leu Gln Ile Leu Val Asn Ala Ala Tyr Val
1               5                   10                  15

Leu Ala Glu Ile Ala Arg Asp Arg
            20


<210> SEQ ID NO 25
<211> LENGTH: 27
<212> TYPE: PRT
<213> ORGANISM: Artificial Sequence
<220> FEATURE:
<223> OTHER INFORMATION: Synthesized

<400> SEQUENCE: 25

Glu Leu Leu Glu Lys Ala Ala Arg Leu Ala Glu Glu Ala Ala Arg Gln
1               5                   10                  15

Ala Glu Glu Ile Ala Arg Gln Ala Arg Lys Glu
            20                  25


<210> SEQ ID NO 26
<211> LENGTH: 25
<212> TYPE: PRT
<213> ORGANISM: Artificial Sequence
<220> FEATURE:
<223> OTHER INFORMATION: Synthesized

<400> SEQUENCE: 26

Leu Glu Leu Ala Leu Lys Ala Leu Gln Ile Leu Val Asn Ala Ala Tyr
1               5                   10                  15

Val Leu Ala Glu Ile Ala Arg Asp Arg
            20                  25


<210> SEQ ID NO 27
<211> LENGTH: 13
<212> TYPE: PRT
<213> ORGANISM: Artificial Sequence
<220> FEATURE:
<223> OTHER INFORMATION: Synthesized

<400> SEQUENCE: 27

Cys Glu Ala Ile Lys Ala Ala Ala Glu Leu Gly Lys Ala
1               5                   10


<210> SEQ ID NO 28
<211> LENGTH: 25
<212> TYPE: PRT
<213> ORGANISM: Artificial Sequence
<220> FEATURE:
<223> OTHER INFORMATION: Synthesized

<400> SEQUENCE: 28

Ser Glu Leu Ala Ala Arg Cys Leu Ile Ile Leu Phe Gln Gln Leu Val
```

```
1               5                   10                  15

Glu Leu Ala Arg Leu Ala Ile Glu Ser
            20                  25


<210> SEQ ID NO 29
<211> LENGTH: 13
<212> TYPE: PRT
<213> ORGANISM: Artificial Sequence
<220> FEATURE:
<223> OTHER INFORMATION: Synthesized

<400> SEQUENCE: 29

Cys Glu Ala Glu Lys Ala Ala Ala Glu Leu Gly Lys Ala
1               5                   10


<210> SEQ ID NO 30
<211> LENGTH: 13
<212> TYPE: PRT
<213> ORGANISM: Artificial Sequence
<220> FEATURE:
<223> OTHER INFORMATION: Synthesized

<400> SEQUENCE: 30

Cys Glu Ala Ile Lys Lys Ala Ala Glu Leu Gly Lys Ala
1               5                   10


<210> SEQ ID NO 31
<211> LENGTH: 13
<212> TYPE: PRT
<213> ORGANISM: Artificial Sequence
<220> FEATURE:
<223> OTHER INFORMATION: Synthesized

<400> SEQUENCE: 31

Cys Glu Cys Ile Lys Ala Ala Ala Glu Leu Gly Lys Ala
1               5                   10


<210> SEQ ID NO 32
<211> LENGTH: 13
<212> TYPE: PRT
<213> ORGANISM: Artificial Sequence
<220> FEATURE:
<223> OTHER INFORMATION: Synthesized

<400> SEQUENCE: 32

Cys Thr Glu Val Leu Leu Glu Leu Ile Ala Glu Ala Ser
1               5                   10


<210> SEQ ID NO 33
<211> LENGTH: 13
<212> TYPE: PRT
<213> ORGANISM: Artificial Sequence
<220> FEATURE:
<223> OTHER INFORMATION: Synthesized

<400> SEQUENCE: 33

Cys Glu Leu Glu Tyr Ala Leu Ala Tyr Ala Lys Lys Val
1               5                   10


<210> SEQ ID NO 34

<400> SEQUENCE: 34

000


<210> SEQ ID NO 35
```

<211> LENGTH: 25
<212> TYPE: PRT
<213> ORGANISM: Artificial Sequence
<220> FEATURE:
<223> OTHER INFORMATION: Synthesized

<400> SEQUENCE: 35

Ser Glu Leu Ala Cys Arg Ile Leu Ile Ile Leu Phe Gln Gln Leu Val
1 5 10 15

Glu Leu Ala Arg Leu Ala Ile Glu Ser
20 25

<210> SEQ ID NO 36
<211> LENGTH: 13
<212> TYPE: PRT
<213> ORGANISM: Artificial Sequence
<220> FEATURE:
<223> OTHER INFORMATION: Synthesized

<400> SEQUENCE: 36

Pro Glu Cys Glu Lys Ala Ala Ala Glu Leu Gly Lys Ala
1 5 10

<210> SEQ ID NO 37
<211> LENGTH: 13
<212> TYPE: PRT
<213> ORGANISM: Artificial Sequence
<220> FEATURE:
<223> OTHER INFORMATION: Synthesized

<400> SEQUENCE: 37

Pro Glu Cys Ile Lys Lys Ala Ala Glu Leu Gly Lys Ala
1 5 10

<210> SEQ ID NO 38

<400> SEQUENCE: 38

000

<210> SEQ ID NO 39
<211> LENGTH: 16
<212> TYPE: PRT
<213> ORGANISM: Artificial Sequence
<220> FEATURE:
<223> OTHER INFORMATION: Synthesized

<400> SEQUENCE: 39

Gly Leu Asp Pro Glu Ala Ile Lys Ala Ala Ala Glu Leu Gly Lys Ala
1 5 10 15

<210> SEQ ID NO 40
<211> LENGTH: 27
<212> TYPE: PRT
<213> ORGANISM: Artificial Sequence
<220> FEATURE:
<223> OTHER INFORMATION: Synthesized

<400> SEQUENCE: 40

Gly Asn Ser Glu Leu Ala Ala Arg Ile Leu Ile Ile Leu Phe Gln Gln
1 5 10 15

Leu Val Glu Leu Ala Arg Leu Ala Ile Glu Ser
20 25

<210> SEQ ID NO 41
<211> LENGTH: 16

<212> TYPE: PRT
<213> ORGANISM: Artificial Sequence
<220> FEATURE:
<223> OTHER INFORMATION: Synthesized

<400> SEQUENCE: 41

Gly Asp Glu Pro Glu Leu Glu Tyr Ala Leu Ala Tyr Ala Lys Lys Val
1 5 10 15

<210> SEQ ID NO 42
<211> LENGTH: 16
<212> TYPE: PRT
<213> ORGANISM: Artificial Sequence
<220> FEATURE:
<223> OTHER INFORMATION: Synthesized

<400> SEQUENCE: 42

Gly Leu Asn Pro Glu Ala Ile Lys Ala Ala Ala Glu Leu Gly Lys Ala
1 5 10 15

<210> SEQ ID NO 43
<211> LENGTH: 16
<212> TYPE: PRT
<213> ORGANISM: Artificial Sequence
<220> FEATURE:
<223> OTHER INFORMATION: Synthesized

<400> SEQUENCE: 43

Gly Leu Asp Cys Glu Ala Ile Lys Ala Ala Ala Glu Leu Gly Lys Ala
1 5 10 15

<210> SEQ ID NO 44
<211> LENGTH: 27
<212> TYPE: PRT
<213> ORGANISM: Artificial Sequence
<220> FEATURE:
<223> OTHER INFORMATION: Synthesized

<400> SEQUENCE: 44

Gly Asn Ser Glu Leu Ala Ala Arg Cys Leu Ile Ile Leu Phe Gln Gln
1 5 10 15

Leu Val Glu Leu Ala Arg Leu Ala Ile Glu Ser
20 25

<210> SEQ ID NO 45
<211> LENGTH: 16
<212> TYPE: PRT
<213> ORGANISM: Artificial Sequence
<220> FEATURE:
<223> OTHER INFORMATION: Synthesized

<400> SEQUENCE: 45

Gly Asp Glu Cys Glu Leu Glu Tyr Ala Leu Ala Tyr Ala Lys Lys Val
1 5 10 15

<210> SEQ ID NO 46
<211> LENGTH: 16
<212> TYPE: PRT
<213> ORGANISM: Artificial Sequence
<220> FEATURE:
<223> OTHER INFORMATION: Synthesized

<400> SEQUENCE: 46

Gly Leu Asn Cys Glu Ala Ile Lys Ala Ala Ala Glu Leu Gly Lys Ala
1 5 10 15

<210> SEQ ID NO 47
<211> LENGTH: 16
<212> TYPE: PRT
<213> ORGANISM: Artificial Sequence
<220> FEATURE:
<223> OTHER INFORMATION: Synthesized

<400> SEQUENCE: 47

```
Gly Leu Asp Pro Glu Cys Ile Lys Ala Ala Ala Glu Leu Gly Lys Ala
1               5                   10                  15
```

<210> SEQ ID NO 48
<211> LENGTH: 27
<212> TYPE: PRT
<213> ORGANISM: Artificial Sequence
<220> FEATURE:
<223> OTHER INFORMATION: Synthesized

<400> SEQUENCE: 48

```
Gly Asn Ser Glu Leu Ala Cys Arg Ile Leu Ile Ile Leu Phe Gln Gln
1               5                   10                  15

Leu Val Glu Leu Ala Arg Leu Ala Ile Glu Ser
            20                  25
```

<210> SEQ ID NO 49
<211> LENGTH: 16
<212> TYPE: PRT
<213> ORGANISM: Artificial Sequence
<220> FEATURE:
<223> OTHER INFORMATION: Synthesized

<400> SEQUENCE: 49

```
Gly Leu Asn Pro Glu Cys Ile Lys Ala Ala Ala Glu Leu Gly Lys Ala
1               5                   10                  15
```

<210> SEQ ID NO 50
<211> LENGTH: 27
<212> TYPE: PRT
<213> ORGANISM: Artificial Sequence
<220> FEATURE:
<223> OTHER INFORMATION: Synthesized

<400> SEQUENCE: 50

```
Gly Leu Asn Glu Leu Cys Ala Arg Ile Leu Ile Ile Leu Phe Gln Gln
1               5                   10                  15

Leu Val Glu Leu Ala Arg Leu Ala Ile Glu Ser
            20                  25
```

<210> SEQ ID NO 51
<211> LENGTH: 27
<212> TYPE: PRT
<213> ORGANISM: Artificial Sequence
<220> FEATURE:
<223> OTHER INFORMATION: Synthesized

<400> SEQUENCE: 51

```
Gly Leu Asn Glu Leu Cys Leu Lys Ala Leu Gln Ile Leu Val Asn Ala
1               5                   10                  15

Ala Tyr Val Leu Ala Glu Ile Ala Arg Asp Arg
            20                  25
```

<210> SEQ ID NO 52
<211> LENGTH: 19
<212> TYPE: PRT
<213> ORGANISM: Artificial Sequence
<220> FEATURE:

<223> OTHER INFORMATION: Synthesized

<400> SEQUENCE: 52

Gly Leu Asp Pro Glu Ala Ile Lys Ala Ala Ala Glu Leu Gly Lys Ala
1 5 10 15

Gly Ile Ser

<210> SEQ ID NO 53
<211> LENGTH: 29
<212> TYPE: PRT
<213> ORGANISM: Artificial Sequence
<220> FEATURE:
<223> OTHER INFORMATION: Synthesized

<400> SEQUENCE: 53

Gly Asn Ser Glu Leu Ala Ala Arg Ile Leu Ile Ile Leu Phe Gln Gln
1 5 10 15

Leu Val Glu Leu Ala Arg Leu Ala Ile Glu Ser Gly Asp
20 25

<210> SEQ ID NO 54
<211> LENGTH: 19
<212> TYPE: PRT
<213> ORGANISM: Artificial Sequence
<220> FEATURE:
<223> OTHER INFORMATION: Synthesized

<400> SEQUENCE: 54

Gly Lys Ser Pro Thr Glu Val Leu Leu Glu Leu Ile Ala Glu Ala Ser
1 5 10 15

Gly Thr Thr

<210> SEQ ID NO 55
<211> LENGTH: 19
<212> TYPE: PRT
<213> ORGANISM: Artificial Sequence
<220> FEATURE:
<223> OTHER INFORMATION: Synthesized

<400> SEQUENCE: 55

Gly Leu Asn Pro Glu Ala Ile Lys Ala Ala Ala Glu Leu Gly Lys Ala
1 5 10 15

Gly Ile Ser

<210> SEQ ID NO 56
<211> LENGTH: 19
<212> TYPE: PRT
<213> ORGANISM: Artificial Sequence
<220> FEATURE:
<223> OTHER INFORMATION: Synthesized

<400> SEQUENCE: 56

Gly Leu Asp Cys Glu Ala Ile Lys Ala Ala Ala Glu Leu Gly Lys Ala
1 5 10 15

Gly Ile Ser

<210> SEQ ID NO 57
<211> LENGTH: 29
<212> TYPE: PRT
<213> ORGANISM: Artificial Sequence
<220> FEATURE:
<223> OTHER INFORMATION: Synthesized

<400> SEQUENCE: 57

Gly Asn Ser Glu Leu Ala Ala Arg Cys Leu Ile Ile Leu Phe Gln Gln
1 5 10 15

Leu Val Glu Leu Ala Arg Leu Ala Ile Glu Ser Gly Asp
20 25

<210> SEQ ID NO 58
<211> LENGTH: 19
<212> TYPE: PRT
<213> ORGANISM: Artificial Sequence
<220> FEATURE:
<223> OTHER INFORMATION: Synthesized

<400> SEQUENCE: 58

Gly Lys Ser Cys Thr Glu Val Leu Leu Glu Leu Ile Ala Glu Ala Ser
1 5 10 15

Gly Thr Thr

<210> SEQ ID NO 59
<211> LENGTH: 19
<212> TYPE: PRT
<213> ORGANISM: Artificial Sequence
<220> FEATURE:
<223> OTHER INFORMATION: Synthesized

<400> SEQUENCE: 59

Gly Leu Asn Cys Glu Ala Ile Lys Ala Ala Ala Glu Leu Gly Lys Ala
1 5 10 15

Gly Ile Ser

<210> SEQ ID NO 60
<211> LENGTH: 19
<212> TYPE: PRT
<213> ORGANISM: Artificial Sequence
<220> FEATURE:
<223> OTHER INFORMATION: Synthesized

<400> SEQUENCE: 60

Gly Leu Asp Pro Glu Cys Ile Lys Ala Ala Ala Glu Leu Gly Lys Ala
1 5 10 15

Gly Ile Ser

<210> SEQ ID NO 61
<211> LENGTH: 29
<212> TYPE: PRT
<213> ORGANISM: Artificial Sequence
<220> FEATURE:
<223> OTHER INFORMATION: Synthesized

<400> SEQUENCE: 61

Gly Asn Ser Glu Leu Ala Cys Arg Ile Leu Ile Ile Leu Phe Gln Gln
1 5 10 15

Leu Val Glu Leu Ala Arg Leu Ala Ile Glu Ser Gly Asp
20 25

<210> SEQ ID NO 62
<211> LENGTH: 19
<212> TYPE: PRT
<213> ORGANISM: Artificial Sequence
<220> FEATURE:
<223> OTHER INFORMATION: Synthesized

<400> SEQUENCE: 62

Gly Leu Asn Pro Glu Cys Ile Lys Ala Ala Ala Glu Leu Gly Lys Ala 1 5 10 15

Gly Ile Ser

<210> SEQ ID NO 63
<211> LENGTH: 33
<212> TYPE: PRT
<213> ORGANISM: Artificial Sequence
<220> FEATURE:
<223> OTHER INFORMATION: Synthesized

<400> SEQUENCE: 63

Gly Leu Asp Pro Glu Ala Ile Lys Ala Ala Ala Glu Leu Gly Lys Ala
1 5 10 15

Gly Ile Ser Ser Glu Glu Ile Leu Glu Leu Leu Arg Ala Ala His Val
20 25 30

Leu

<210> SEQ ID NO 64
<211> LENGTH: 33
<212> TYPE: PRT
<213> ORGANISM: Artificial Sequence
<220> FEATURE:
<223> OTHER INFORMATION: Synthesized

<400> SEQUENCE: 64

Gly Leu Asp Pro Glu Ala Ile Lys Ala Ala Ala Glu Leu Gly Lys Ala
1 5 10 15

Gly Ile Ser Ser Glu Glu Ile Leu Glu Leu Leu Val Ala Ala His Leu
20 25 30

Leu

<210> SEQ ID NO 65
<211> LENGTH: 33
<212> TYPE: PRT
<213> ORGANISM: Artificial Sequence
<220> FEATURE:
<223> OTHER INFORMATION: Synthesized

<400> SEQUENCE: 65

Gly Leu Asp Pro Glu Ala Ile Lys Ala Ala Ala Glu Leu Gly Lys Ala
1 5 10 15

Gly Ile Ser Ser Ile Glu Ile Leu Glu Leu Leu Arg Ala Ala His Glu
20 25 30

Leu

<210> SEQ ID NO 66
<211> LENGTH: 57
<212> TYPE: PRT
<213> ORGANISM: Artificial Sequence
<220> FEATURE:
<223> OTHER INFORMATION: Synthesized

<400> SEQUENCE: 66

Gly Asn Ser Glu Leu Ala Ala Arg Ile Leu Ile Ile Leu Phe Gln Gln
1 5 10 15

Leu Val Glu Leu Ala Arg Leu Ala Ile Glu Ser Gly Asp Glu Glu Leu
20 25 30

Leu Arg Arg Val Ser Glu Trp Leu Glu Glu Val Ile Lys Asp Met Arg
35 40 45

Arg Val Val Glu Gln Ala Leu Arg Glu
50 55

<210> SEQ ID NO 67
<211> LENGTH: 33
<212> TYPE: PRT
<213> ORGANISM: Artificial Sequence
<220> FEATURE:
<223> OTHER INFORMATION: Synthesized

<400> SEQUENCE: 67

```
Gly Lys Ser Pro Thr Glu Val Leu Leu Glu Leu Ile Ala Glu Ala Ser
1               5                   10                  15

Gly Thr Thr Arg Glu Glu Val Lys Glu Lys Phe Leu Lys Glu Leu Arg
            20                  25                  30

Lys
```

<210> SEQ ID NO 68
<211> LENGTH: 33
<212> TYPE: PRT
<213> ORGANISM: Artificial Sequence
<220> FEATURE:
<223> OTHER INFORMATION: Synthesized

<400> SEQUENCE: 68

```
Gly Lys Ser Pro Thr Glu Val Leu Leu Glu Leu Ile Ala Glu Ala Ser
1               5                   10                  15

Gly Thr Thr Lys Glu Glu Val Lys Glu Lys Phe Leu Lys Glu Leu Ser
            20                  25                  30

Phe
```

<210> SEQ ID NO 69
<211> LENGTH: 33
<212> TYPE: PRT
<213> ORGANISM: Artificial Sequence
<220> FEATURE:
<223> OTHER INFORMATION: Synthesized

<400> SEQUENCE: 69

```
Gly Lys Ser Pro Thr Glu Val Leu Leu Glu Leu Ile Ala Glu Ala Ser
1               5                   10                  15

Gly Thr Thr Lys Glu Glu Val Lys Lys Lys Phe Trp Lys Glu Leu Ser
            20                  25                  30

Leu
```

<210> SEQ ID NO 70
<211> LENGTH: 33
<212> TYPE: PRT
<213> ORGANISM: Artificial Sequence
<220> FEATURE:
<223> OTHER INFORMATION: Synthesized

<400> SEQUENCE: 70

```
Gly Leu Asn Pro Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Glu
            20                  25                  30

Leu
```

<210> SEQ ID NO 71
<211> LENGTH: 33
<212> TYPE: PRT
<213> ORGANISM: Artificial Sequence
<220> FEATURE:

<223> OTHER INFORMATION: Synthesized

<400> SEQUENCE: 71

Gly Leu Asn Pro Glu Ala Ile Lys Ala Ala Ala Glu Leu Gly Lys Ala
1 5 10 15

Gly Ile Ser Ser Glu Glu Ile Leu Glu Leu Leu Arg Ala Ala His Ala
20 25 30

Leu

<210> SEQ ID NO 72
<211> LENGTH: 33
<212> TYPE: PRT
<213> ORGANISM: Artificial Sequence
<220> FEATURE:
<223> OTHER INFORMATION: Synthesized

<400> SEQUENCE: 72

Gly Leu Asn Pro Glu Ala Ile Lys Ala Ala Ala Glu Leu Gly Lys Ala
1 5 10 15

Gly Ile Ser Ser Ala Glu Ile Leu Glu Leu Leu Met Ala Ala His Glu
20 25 30

Leu

<210> SEQ ID NO 73
<211> LENGTH: 33
<212> TYPE: PRT
<213> ORGANISM: Artificial Sequence
<220> FEATURE:
<223> OTHER INFORMATION: Synthesized

<400> SEQUENCE: 73

Gly Leu Asn Pro Glu Ala Ile Lys Ala Ala Ala Glu Leu Gly Lys Ala
1 5 10 15

Gly Ile Ser Ser Glu Glu Ile Leu Glu Leu Leu Arg Ala Ala His Gly
20 25 30

Leu

<210> SEQ ID NO 74
<211> LENGTH: 33
<212> TYPE: PRT
<213> ORGANISM: Artificial Sequence
<220> FEATURE:
<223> OTHER INFORMATION: Synthesized

<400> SEQUENCE: 74

Gly Leu Asn Pro Glu Ala Ile Lys Ala Ala Ala Glu Leu Gly Lys Ala
1 5 10 15

Gly Ile Ser Ser Glu Glu Ile Leu Glu Leu Leu Arg Ala Ala His Gly
20 25 30

Gly

<210> SEQ ID NO 75
<211> LENGTH: 33
<212> TYPE: PRT
<213> ORGANISM: Artificial Sequence
<220> FEATURE:
<223> OTHER INFORMATION: Synthesized

<400> SEQUENCE: 75

Gly Leu Asp Cys Glu Ala Ile Lys Ala Ala Ala Glu Leu Gly Lys Ala
1 5 10 15

Gly Ile Ser Ser Glu Glu Ile Leu Glu Leu Leu Arg Ala Ala His Glu
20 25 30

Leu

<210> SEQ ID NO 76
<211> LENGTH: 57
<212> TYPE: PRT
<213> ORGANISM: Artificial Sequence
<220> FEATURE:
<223> OTHER INFORMATION: Synthesized

<400> SEQUENCE: 76

Gly Asn Ser Glu Leu Ala Ala Arg Cys Leu Ile Ile Leu Phe Gln Gln
1 5 10 15

Leu Val Glu Leu Ala Arg Leu Ala Ile Glu Ser Gly Asp Glu Glu Leu
20 25 30

Leu Arg Arg Val Ser Glu Trp Leu Glu Glu Val Ile Lys Asp Met Arg
35 40 45

Arg Val Val Glu Gln Ala Leu Arg Glu
50 55

<210> SEQ ID NO 77
<211> LENGTH: 33
<212> TYPE: PRT
<213> ORGANISM: Artificial Sequence
<220> FEATURE:
<223> OTHER INFORMATION: Synthesized

<400> SEQUENCE: 77

Gly Lys Ser Cys Thr Glu Val Leu Leu Glu Leu Ile Ala Glu Ala Ser
1 5 10 15

Gly Thr Thr Arg Glu Glu Val Lys Glu Lys Phe Leu Lys Glu Leu Arg
20 25 30

Lys

<210> SEQ ID NO 78
<211> LENGTH: 33
<212> TYPE: PRT
<213> ORGANISM: Artificial Sequence
<220> FEATURE:
<223> OTHER INFORMATION: Synthesized

<400> SEQUENCE: 78

Gly Lys Ser Cys Thr Glu Val Leu Leu Glu Leu Ile Ala Glu Ala Ser
1 5 10 15

Gly Thr Thr Lys Glu Glu Val Lys Glu Lys Phe Leu Lys Glu Leu Ser
20 25 30

Phe

<210> SEQ ID NO 79
<211> LENGTH: 33
<212> TYPE: PRT
<213> ORGANISM: Artificial Sequence
<220> FEATURE:
<223> OTHER INFORMATION: Synthesized

<400> SEQUENCE: 79

Gly Lys Ser Cys Thr Glu Val Leu Leu Glu Leu Ile Ala Glu Ala Ser
1 5 10 15

Gly Thr Thr Lys Glu Glu Val Lys Lys Lys Phe Trp Lys Glu Leu Ser
20 25 30

Leu

<210> SEQ ID NO 80
<211> LENGTH: 33
<212> TYPE: PRT
<213> ORGANISM: Artificial Sequence
<220> FEATURE:
<223> OTHER INFORMATION: Synthesized

<400> SEQUENCE: 80

Gly Leu Asp Cys Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Val
            20                  25                  30

Leu

<210> SEQ ID NO 81
<211> LENGTH: 33
<212> TYPE: PRT
<213> ORGANISM: Artificial Sequence
<220> FEATURE:
<223> OTHER INFORMATION: Synthesized

<400> SEQUENCE: 81

Gly Leu Asp Cys Glu Ala Ile Lys Ala Ala Ala Glu Leu Gly Lys Ala
1               5                   10                  15

Gly Ile Ser Ser Glu Glu Ile Leu Glu Leu Leu Val Ala Ala His Leu
            20                  25                  30

Leu

<210> SEQ ID NO 82
<211> LENGTH: 33
<212> TYPE: PRT
<213> ORGANISM: Artificial Sequence
<220> FEATURE:
<223> OTHER INFORMATION: Synthesized

<400> SEQUENCE: 82

Gly Leu Asp Cys Glu Ala Ile Lys Ala Ala Ala Glu Leu Gly Lys Ala
1               5                   10                  15

Gly Ile Ser Ser Ile Glu Ile Leu Glu Leu Leu Arg Ala Ala His Glu
            20                  25                  30

Leu

<210> SEQ ID NO 83
<211> LENGTH: 33
<212> TYPE: PRT
<213> ORGANISM: Artificial Sequence
<220> FEATURE:
<223> OTHER INFORMATION: Synthesized

<400> SEQUENCE: 83

Gly Leu Asn Cys Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Glu
            20                  25                  30

Leu

<210> SEQ ID NO 84
<211> LENGTH: 33
<212> TYPE: PRT
<213> ORGANISM: Artificial Sequence
<220> FEATURE:
<223> OTHER INFORMATION: Synthesized

<400> SEQUENCE: 84

Gly Leu Asn Cys Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Ala
            20                  25                  30

Leu

<210> SEQ ID NO 85
<211> LENGTH: 33
<212> TYPE: PRT
<213> ORGANISM: Artificial Sequence
<220> FEATURE:
<223> OTHER INFORMATION: Synthesized

<400> SEQUENCE: 85

Gly Leu Asn Cys Glu Ala Ile Lys Ala Ala Ala Glu Leu Gly Lys Ala
1               5                   10                  15

Gly Ile Ser Ser Ala Glu Ile Leu Glu Leu Leu Met Ala Ala His Glu
            20                  25                  30

Leu

<210> SEQ ID NO 86
<211> LENGTH: 33
<212> TYPE: PRT
<213> ORGANISM: Artificial Sequence
<220> FEATURE:
<223> OTHER INFORMATION: Synthesized

<400> SEQUENCE: 86

Gly Leu Asn Cys Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Gly
            20                  25                  30

Leu

<210> SEQ ID NO 87
<211> LENGTH: 33
<212> TYPE: PRT
<213> ORGANISM: Artificial Sequence
<220> FEATURE:
<223> OTHER INFORMATION: Synthesized

<400> SEQUENCE: 87

Gly Leu Asn Cys Glu Ala Ile Lys Ala Ala Ala Glu Leu Gly Lys Ala
1               5                   10                  15

Gly Ile Ser Ser Glu Glu Ile Leu Glu Leu Leu Arg Ala Ala His Gly
            20                  25                  30

Gly

<210> SEQ ID NO 88
<211> LENGTH: 33
<212> TYPE: PRT
<213> ORGANISM: Artificial Sequence
<220> FEATURE:
<223> OTHER INFORMATION: Synthesized

<400> SEQUENCE: 88

Gly Leu Asp Pro Glu Cys Ile Lys Ala Ala Ala Glu Leu Gly Lys Ala
1               5                   10                  15

```
Gly Ile Ser Ser Glu Glu Ile Leu Glu Leu Leu Arg Ala Ala His Glu
            20                  25                  30

Leu


<210> SEQ ID NO 89
<211> LENGTH: 57
<212> TYPE: PRT
<213> ORGANISM: Artificial Sequence
<220> FEATURE:
<223> OTHER INFORMATION: Synthesized

<400> SEQUENCE: 89

Gly Asn Ser Glu Leu Ala Cys Arg Ile Leu Ile Ile Leu Phe Gln Gln
1               5                   10                  15

Leu Val Glu Leu Ala Arg Leu Ala Ile Glu Ser Gly Asp Glu Glu Leu
            20                  25                  30

Leu Arg Arg Val Ser Glu Trp Leu Glu Glu Val Ile Lys Asp Met Arg
        35                  40                  45

Arg Val Val Glu Gln Ala Leu Arg Glu
    50                  55


<210> SEQ ID NO 90
<211> LENGTH: 33
<212> TYPE: PRT
<213> ORGANISM: Artificial Sequence
<220> FEATURE:
<223> OTHER INFORMATION: Synthesized

<400> SEQUENCE: 90

Gly Leu Asp Pro Glu Cys Ile Lys Ala Ala Ala Glu Leu Gly Lys Ala
1               5                   10                  15

Gly Ile Ser Ser Glu Glu Ile Leu Glu Leu Leu Arg Ala Ala His Val
            20                  25                  30

Leu


<210> SEQ ID NO 91
<211> LENGTH: 33
<212> TYPE: PRT
<213> ORGANISM: Artificial Sequence
<220> FEATURE:
<223> OTHER INFORMATION: Synthesized

<400> SEQUENCE: 91

Gly Leu Asp Pro Glu Cys Ile Lys Ala Ala Ala Glu Leu Gly Lys Ala
1               5                   10                  15

Gly Ile Ser Ser Glu Glu Ile Leu Glu Leu Leu Val Ala Ala His Leu
            20                  25                  30

Leu


<210> SEQ ID NO 92
<211> LENGTH: 33
<212> TYPE: PRT
<213> ORGANISM: Artificial Sequence
<220> FEATURE:
<223> OTHER INFORMATION: Synthesized

<400> SEQUENCE: 92

Gly Leu Asp Pro Glu Cys Ile Lys Ala Ala Ala Glu Leu Gly Lys Ala
1               5                   10                  15

Gly Ile Ser Ser Ile Glu Ile Leu Glu Leu Leu Arg Ala Ala His Glu
            20                  25                  30
```

Leu

<210> SEQ ID NO 93
<211> LENGTH: 33
<212> TYPE: PRT
<213> ORGANISM: Artificial Sequence
<220> FEATURE:
<223> OTHER INFORMATION: Synthesized

<400> SEQUENCE: 93

```
Gly Leu Asn Pro Glu Cys Ile Lys Ala Ala Ala Glu Leu Gly Lys Ala
1               5                   10                  15

Gly Ile Ser Ser Glu Glu Ile Leu Glu Leu Leu Arg Ala Ala His Glu
            20                  25                  30

Leu
```

<210> SEQ ID NO 94
<211> LENGTH: 33
<212> TYPE: PRT
<213> ORGANISM: Artificial Sequence
<220> FEATURE:
<223> OTHER INFORMATION: Synthesized

<400> SEQUENCE: 94

```
Gly Leu Asn Pro Glu Cys Ile Lys Ala Ala Ala Glu Leu Gly Lys Ala
1               5                   10                  15

Gly Ile Ser Ser Glu Glu Ile Leu Glu Leu Leu Arg Ala Ala His Ala
            20                  25                  30

Leu
```

<210> SEQ ID NO 95
<211> LENGTH: 33
<212> TYPE: PRT
<213> ORGANISM: Artificial Sequence
<220> FEATURE:
<223> OTHER INFORMATION: Synthesized

<400> SEQUENCE: 95

```
Gly Leu Asn Pro Glu Cys Ile Lys Ala Ala Ala Glu Leu Gly Lys Ala
1               5                   10                  15

Gly Ile Ser Ser Ala Glu Ile Leu Glu Leu Leu Met Ala Ala His Glu
            20                  25                  30

Leu
```

<210> SEQ ID NO 96
<211> LENGTH: 33
<212> TYPE: PRT
<213> ORGANISM: Artificial Sequence
<220> FEATURE:
<223> OTHER INFORMATION: Synthesized

<400> SEQUENCE: 96

```
Gly Leu Asn Pro Glu Cys Ile Lys Ala Ala Ala Glu Leu Gly Lys Ala
1               5                   10                  15

Gly Ile Ser Ser Glu Glu Ile Leu Glu Leu Leu Arg Ala Ala His Gly
            20                  25                  30

Leu
```

<210> SEQ ID NO 97
<211> LENGTH: 33
<212> TYPE: PRT

```
<213> ORGANISM: Artificial Sequence
<220> FEATURE:
<223> OTHER INFORMATION: Synthesized

<400> SEQUENCE: 97

Gly Leu Asn Pro Glu Cys Ile Lys Ala Ala Ala Glu Leu Gly Lys Ala
1               5                   10                  15

Gly Ile Ser Ser Glu Glu Ile Leu Glu Leu Leu Arg Ala Ala His Gly
            20                  25                  30

Gly


<210> SEQ ID NO 98
<211> LENGTH: 2454
<212> TYPE: DNA
<213> ORGANISM: Artificial Sequence
<220> FEATURE:
<223> OTHER INFORMATION: Synthesized cTRP24 (Single chain cTRP with 24
      repeats)

<400> SEQUENCE: 98

atggctagca gccatcatca tcatcatcat agcagcggcc tggtgccgcg cggcagctcc     60

atgggcctgg acccggaagc gatcaaagcg gctgcggaac tgggcaaagc tggtatctcg    120

tcagaagaaa tcctggaact gctgcgtgcg gcgcatgaac tgggcctgga tccggaagcc    180

attaaagccg cggcggaact gggcaaagcg ggtatcagca gcgaagaaat cctggaactg    240

ctgcgcgcgg cccatgaact gggtctggat ccggaagcca tcaaagccgc ggcggaactg    300

ggcaaagcgg gcatcagcag cgaagaaatc ctggaactgc tgcgcgccgc gcatgaactg    360

ggtctggatc cggaagcgat taaagccgcc gccgaactgg gtaaagcggg tattagcagc    420

gaagaaatcc tggaactgct gcgtgcggcg catgaactgg gcctggatcc ggaagccatc    480

aaagccgccg ccgaactggg taaagccggt atcagcagcg aagaaattct ggaactgctg    540

cgtgccgccc atgaactggg cctggatccg gaagcgatta aagccgccgc ggaactgggt    600

aaagccggta ttagcagcga agaaatcctg gaactgctgc gtgccgcgca tgaactgggt    660

ctggatccgg aagccatcaa agcggcggcc gaactgggta aagccggcat cagcagcgaa    720

gaaatcctgg aactgctgcg tgccgcccat gaactgggcc tggatccgga agcgatcaaa    780

gccgccgcgg aactgggtaa agccggcatt agcagcgaag aaatcctgga actgctgcgt    840

gccgcgcatg aactgggtct ggatccggaa gcgattaaag cggcggccga actgggcaaa    900

gccggtatta gcagcgaaga aatcctggaa ctgctgcgtg cggcccatga actgggcctg    960

gatccggaag cgatcaaagc ggcggccgaa ctgggtaaag cgggtatcag cagcgaagaa   1020

atcctggaac tgctgcgtgc cgcccatgaa ctgggtctgg atccggaagc cattaaagcg   1080

gcggcggaac tgggtaaagc gggcatcagc agcgaagaaa ttctggaact gctgcgcgcg   1140

gcgcatgaac tgggtctgga tccggaagcc attaaagccg ccgcggaact gggcaaagcg   1200

ggtattagca gcgaagaaat tctggaactg ctgcgcgcgg cgcatgaact gggcctggat   1260

ccggaagcga ttaaagccgc cgccgaactg ggcaaagccg gcatcagcag cgaagaaatt   1320

ctggaactgc tgcgcgccgc ccatgaactg ggcctggatc cggaagcgat caaagccgcc   1380

gcggaactgg gcaaagcggg catcagcagc gaagaaatcc tggaactgct gcgtgcggcg   1440

catgaactgg gtctggatcc ggaagccatt aaagccgcgg cggaactggg caaagccggc   1500

attagcagcg aagaaattct ggaactgctg cgtgcggcgc atgaactggg tctggatccg   1560

gaagccatca aagccgcggc ggaactgggt aaagcgggta ttagcagcga agaaattctg   1620
```

```
gaactgctgc gcgcggccca tgaactgggc ctggatccgg aagcgattaa agcggcggcc   1680

gaactgggca aagcgggcat tagcagcgaa gaaatcctgg aactgctgcg cgcggcgcat   1740

gaactgggtc tggatccgga agccattaaa gccgccgccg aactgggcaa agccggtatc   1800

agcagcgaag aaattctgga actgctgcgc gcggcccatg aactgggtct ggatccggaa   1860

gccatcaaag ccgccgcgga actgggtaaa gccggtatca gcagcgaaga aatcctggaa   1920

ctgctgcgcg ccgcccatga actgggcctg gatccggaag cgatcaaagc cgcggcggaa   1980

ctgggtaaag cgggcattag cagcgaagaa attctggaac tgctgcgtgc ggcccatgaa   2040

ctgggtctgg atccggaagc gatcaaagcc gcggccgaac tgggtaaagc gggcatcagc   2100

agcgaagaaa ttctggaact gctgcgtgcc gcgcatgaac tgggcctgga tccggaagcg   2160

attaaagccg cggccgaact gggcaaagcg ggcattagca gcgaagaaat tctggaactg   2220

ctgcgcgcgg cgcatgaact gggcctggat ccggaagcga ttaaagcggc ggccgaactg   2280

ggcaaagcgg gtatcagcag cgaagaaatc ctggaactgc tgcgcgccgc gcatgaactg   2340

ggcctggatc cggaagcgat taaagccgcg gccgaactgg gcaaagcggg tatctcgtct   2400

gaagaaatcc tggaactgct gcgtgctgcc catgaactgg gtggttggta ataa          2454
```

<210> SEQ ID NO 99
<211> LENGTH: 816
<212> TYPE: PRT
<213> ORGANISM: Artificial Sequence
<220> FEATURE:
<223> OTHER INFORMATION: Synthesized cTRP24 (Single chain cTRP with 24
      repeats)

<400> SEQUENCE: 99

```
Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140

Glu Leu Leu Arg Ala Ala His Glu Leu Gly Leu Asp Pro Glu Ala Ile
145                 150                 155                 160

Lys Ala Ala Ala Glu Leu Gly Lys Ala Gly Ile Ser Ser Glu Glu Ile
                165                 170                 175

Leu Glu Leu Leu Arg Ala Ala His Glu Leu Gly Leu Asp Pro Glu Ala
            180                 185                 190

Ile Lys Ala Ala Ala Glu Leu Gly Lys Ala Gly Ile Ser Ser Glu Glu
        195                 200                 205

Ile Leu Glu Leu Leu Arg Ala Ala His Glu Leu Gly Leu Asp Pro Glu
```

```
    210                 215                 220

Ala Ile Lys Ala Ala Ala Glu Leu Gly Lys Ala Gly Ile Ser Ser Glu
225                 230                 235                 240

Glu Ile Leu Glu Leu Leu Arg Ala Ala His Glu Leu Gly Leu Asp Pro
                245                 250                 255

Glu Ala Ile Lys Ala Ala Ala Glu Leu Gly Lys Ala Gly Ile Ser Ser
            260                 265                 270

Glu Glu Ile Leu Glu Leu Leu Arg Ala Ala His Glu Leu Gly Leu Asp
        275                 280                 285

Pro Glu Ala Ile Lys Ala Ala Ala Glu Leu Gly Lys Ala Gly Ile Ser
    290                 295                 300

Ser Glu Glu Ile Leu Glu Leu Leu Arg Ala Ala His Glu Leu Gly Leu
305                 310                 315                 320

Asp Pro Glu Ala Ile Lys Ala Ala Ala Glu Leu Gly Lys Ala Gly Ile
                325                 330                 335

Ser Ser Glu Glu Ile Leu Glu Leu Leu Arg Ala Ala His Glu Leu Gly
            340                 345                 350

Leu Asp Pro Glu Ala Ile Lys Ala Ala Ala Glu Leu Gly Lys Ala Gly
        355                 360                 365

Ile Ser Ser Glu Glu Ile Leu Glu Leu Leu Arg Ala Ala His Glu Leu
    370                 375                 380

Gly Leu Asp Pro Glu Ala Ile Lys Ala Ala Ala Glu Leu Gly Lys Ala
385                 390                 395                 400

Gly Ile Ser Ser Glu Glu Ile Leu Glu Leu Leu Arg Ala Ala His Glu
                405                 410                 415

Leu Gly Leu Asp Pro Glu Ala Ile Lys Ala Ala Ala Glu Leu Gly Lys
            420                 425                 430

Ala Gly Ile Ser Ser Glu Glu Ile Leu Glu Leu Leu Arg Ala Ala His
        435                 440                 445

Glu Leu Gly Leu Asp Pro Glu Ala Ile Lys Ala Ala Ala Glu Leu Gly
    450                 455                 460

Lys Ala Gly Ile Ser Ser Glu Glu Ile Leu Glu Leu Leu Arg Ala Ala
465                 470                 475                 480

His Glu Leu Gly Leu Asp Pro Glu Ala Ile Lys Ala Ala Ala Glu Leu
                485                 490                 495

Gly Lys Ala Gly Ile Ser Ser Glu Glu Ile Leu Glu Leu Leu Arg Ala
            500                 505                 510

Ala His Glu Leu Gly Leu Asp Pro Glu Ala Ile Lys Ala Ala Ala Glu
        515                 520                 525

Leu Gly Lys Ala Gly Ile Ser Ser Glu Glu Ile Leu Glu Leu Leu Arg
    530                 535                 540

Ala Ala His Glu Leu Gly Leu Asp Pro Glu Ala Ile Lys Ala Ala Ala
545                 550                 555                 560

Glu Leu Gly Lys Ala Gly Ile Ser Ser Glu Glu Ile Leu Glu Leu Leu
                565                 570                 575

Arg Ala Ala His Glu Leu Gly Leu Asp Pro Glu Ala Ile Lys Ala Ala
            580                 585                 590

Ala Glu Leu Gly Lys Ala Gly Ile Ser Ser Glu Glu Ile Leu Glu Leu
        595                 600                 605

Leu Arg Ala Ala His Glu Leu Gly Leu Asp Pro Glu Ala Ile Lys Ala
    610                 615                 620

Ala Ala Glu Leu Gly Lys Ala Gly Ile Ser Ser Glu Glu Ile Leu Glu
625                 630                 635                 640
```

```
Leu Leu Arg Ala Ala His Glu Leu Gly Leu Asp Pro Glu Ala Ile Lys
                645                 650                 655

Ala Ala Ala Glu Leu Gly Lys Ala Gly Ile Ser Ser Glu Glu Ile Leu
            660                 665                 670

Glu Leu Leu Arg Ala Ala His Glu Leu Gly Leu Asp Pro Glu Ala Ile
        675                 680                 685

Lys Ala Ala Ala Glu Leu Gly Lys Ala Gly Ile Ser Ser Glu Glu Ile
    690                 695                 700

Leu Glu Leu Leu Arg Ala Ala His Glu Leu Gly Leu Asp Pro Glu Ala
705                 710                 715                 720

Ile Lys Ala Ala Ala Glu Leu Gly Lys Ala Gly Ile Ser Ser Glu Glu
                725                 730                 735

Ile Leu Glu Leu Leu Arg Ala Ala His Glu Leu Gly Leu Asp Pro Glu
            740                 745                 750

Ala Ile Lys Ala Ala Ala Glu Leu Gly Lys Ala Gly Ile Ser Ser Glu
        755                 760                 765

Glu Ile Leu Glu Leu Leu Arg Ala Ala His Glu Leu Gly Leu Asp Pro
    770                 775                 780

Glu Ala Ile Lys Ala Ala Ala Glu Leu Gly Lys Ala Gly Ile Ser Ser
785                 790                 795                 800

Glu Glu Ile Leu Glu Leu Leu Arg Ala Ala His Glu Leu Gly Gly Trp
                805                 810                 815


<210> SEQ ID NO 100
<211> LENGTH: 372
<212> TYPE: DNA
<213> ORGANISM: Artificial Sequence
<220> FEATURE:
<223> OTHER INFORMATION: Synthesized cTRP24_Sub3 (Sub3 cTRP construct
      containing 3 repeats)

<400> SEQUENCE: 100

atggctagca gccatcatca tcatcatcat agcagcggcc tggtgccgcg cggcagctcc     60

atgggcctgg atccggaagc tattaaagcg gcggcagaac tgggcaaagc cggtattagc    120

tctgaagaaa tcctggaact gctgcgtgct gcgcatgaac tgggtctgga cccggaagca    180

atcaaagccg cagctgaact gggcaaagcg ggtattagtt ccgaagaaat tctggaactg    240

ctgcgtgccg cacatgaact gggtctggat ccggaagcca ttaaagcagc tgcggaactg    300

ggtaaagccg gtattagcag cgaggagatt ctggaactgc tgcgcgccgc acatgaactg    360

ggcggttggt aa                                                        372


<210> SEQ ID NO 101
<211> LENGTH: 123
<212> TYPE: PRT
<213> ORGANISM: Artificial Sequence
<220> FEATURE:
<223> OTHER INFORMATION: Synthesized cTRP24_Sub3 (Sub3 cTRP construct
      containing 3 repeats)

<400> SEQUENCE: 101

Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Ser Glu Glu Ile Leu Glu Leu Leu
        35                  40                  45
```

```
Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Gly Trp
        115                 120
```

```
<210> SEQ ID NO 102
<211> LENGTH: 471
<212> TYPE: DNA
<213> ORGANISM: Artificial Sequence
<220> FEATURE:
<223> OTHER INFORMATION: Synthesized cTRP24_Sub4 (Sub4 cTRP construct
      containing 4 repeats)

<400> SEQUENCE: 102

atggctagca gccatcatca tcatcatcat agcagcggcc tggtgccgcg cggcagctcc      60

atgggcctgg atccggaagc gattaaagcg gcggcagaac tgggcaaagc cggtattagc     120

tctgaagaaa tcctggaact gctgcgtgct gcgcatgaac tgggtctgga cccggaagca     180

atcaaagccg cagctgaact gggcaaagct ggtattagtt ccgaagaaat tctggaactg     240

ctgcgtgccg cacatgaact gggtctggat ccggaagcca tcaaagcagc tgcggaactg     300

ggtaaagcgg gtatttcatc ggaggagatc ctggaactgc tgcgcgcggc ccacgaactg     360

ggcctggatc cggaagctat caaagctgcg gccgaactgg gtaaagctgg tattagcagc     420

gaggagattc tggaactgct gcgcgcagct cacgaactgg gcggttggta a              471
```

```
<210> SEQ ID NO 103
<211> LENGTH: 156
<212> TYPE: PRT
<213> ORGANISM: Artificial Sequence
<220> FEATURE:
<223> OTHER INFORMATION: Synthesized cTRP24_Sub4 (Sub4 cTRP construct
      containing 4 repeats)

<400> SEQUENCE: 103

Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140
```

```
Glu Leu Leu Arg Ala Ala His Glu Leu Gly Gly Trp
145                 150                 155


<210> SEQ ID NO 104
<211> LENGTH: 669
<212> TYPE: DNA
<213> ORGANISM: Artificial Sequence
<220> FEATURE:
<223> OTHER INFORMATION: Synthesized cTRP24_Sub6 (Sub6 cTRP construct
      containing 6 repeats)

<400> SEQUENCE: 104

atggctagca gccatcatca tcatcatcat agcagcggcc tggtgccgcg cggcagctcc      60

atgggcctgg atccggaagc aattaaagcg gcggcagaac tgggcaaagc tggtattagc     120

tctgaagaaa tcctggaact gctgcgtgct gcgcatgaac tgggtctgga cccggaagca     180

atcaaagccg cagctgaact gggcaaagcg ggtattagtt ccgaagaaat tctggaactg     240

ctgcgtgccg cacatgaact gggtctggat ccggaagcca ttaaagcagc tgcggaactg     300

ggcaaagcag gtatttcatc ggaggagatc ctggaactgc tgcgcgcggc ccacgaactg     360

ggcctggacc cggaagcgat caaagctgcg gccgaactgg gcaaagccgg catctctagc     420

gaggagattc tggaactgct gcgcgcagct cacgaactgg gcctggatcc ggaagcgatc     480

aaggcggcgg cagagctggg caaagccggt attagttcag aggagatact ggaactgctg     540

cgcgccgccc acgagttagg tctggatccg gaagcgatta aggccgcagc tgagctgggt     600

aaagccggta ttagctccga ggagatatta gaactgctgc gtgccgcgca tgaactgggc     660

ggttggtaa                                                             669


<210> SEQ ID NO 105
<211> LENGTH: 222
<212> TYPE: PRT
<213> ORGANISM: Artificial Sequence
<220> FEATURE:
<223> OTHER INFORMATION: Synthesized cTRP24_Sub6 (Sub6 cTRP construct
      containing 6 repeats)

<400> SEQUENCE: 105

Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140

Glu Leu Leu Arg Ala Ala His Glu Leu Gly Leu Asp Pro Glu Ala Ile
145                 150                 155                 160
```

```
Lys Ala Ala Ala Glu Leu Gly Lys Ala Gly Ile Ser Ser Glu Glu Ile
                165                 170                 175

Leu Glu Leu Leu Arg Ala Ala His Glu Leu Gly Leu Asp Pro Glu Ala
            180                 185                 190

Ile Lys Ala Ala Ala Glu Leu Gly Lys Ala Gly Ile Ser Ser Glu Glu
        195                 200                 205

Ile Leu Glu Leu Leu Arg Ala Ala His Glu Leu Gly Gly Trp
    210                 215                 220


<210> SEQ ID NO 106
<211> LENGTH: 867
<212> TYPE: DNA
<213> ORGANISM: Artificial Sequence
<220> FEATURE:
<223> OTHER INFORMATION: Synthesized cTRP24_Sub8 (Sub8 cTRP construct
      containing 8 repeats)

<400> SEQUENCE: 106

atggctagca gccatcatca tcatcatcat agcagcggcc tggtgccgcg cggcagctcc      60

atgggcctgg atccggaagc gattaaagcg gcggcagaac tgggcaaagc cggtattagc     120

tctgaagaaa tcctggaact gctgcgtgct gcgcatgaac tgggtctgga cccggaagca     180

atcaaagccg cagctgaact gggcaaagct ggtattagtt ccgaagaaat tctggaactg     240

ctgcgtgccg cacatgaact gggtctggat ccggaagcaa ttaaagcagc tgcggaactg     300

ggcaaagcgg gtatttcatc ggaggagatc ctggaactgc tgcgcgccgc acatgtgctg     360

ggcctggatc cggaagccat caaagctgcg gccgaactgg gcaaagcagg catctctagc     420

gaggagattc tggaactgct ggttgcagct cacctgctgg gtttagaccc tgaagccatc     480

aaggcggcgg cagagctggg taaagcgggc atcagttccg aggagatact ggaactgctg     540

cgcgcggccc acgaactggg cctggacccg gaagcgatta aggccgcagc tgagctgggt     600

aaagcgggta tcagctcgga ggagatatta gaactgctgc gcgccgccca tgagttaggc     660

ctggacccgg aagccatcaa ggcagctgcg gagctgggta aagctggcat ctctagcgag     720

gaaattttag agctgctgcg tgcggcccac gagttaggtc tggacccgga agccattaag     780

gctgcggccg agctgggcaa agcgggtatc tcatccattg agatattgga gctgctgcgt     840

gcagctcacg aactgggcgg ttggtaa                                         867


<210> SEQ ID NO 107
<211> LENGTH: 288
<212> TYPE: PRT
<213> ORGANISM: Artificial Sequence
<220> FEATURE:
<223> OTHER INFORMATION: Synthesized cTRP24_Sub8 (Sub8 cTRP construct
      containing 8 repeats)

<400> SEQUENCE: 107

Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80
```

```
Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Val Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140

Glu Leu Leu Val Ala Ala His Leu Leu Gly Leu Asp Pro Glu Ala Ile
145                 150                 155                 160

Lys Ala Ala Ala Glu Leu Gly Lys Ala Gly Ile Ser Ser Glu Glu Ile
                165                 170                 175

Leu Glu Leu Leu Arg Ala Ala His Glu Leu Gly Leu Asp Pro Glu Ala
            180                 185                 190

Ile Lys Ala Ala Ala Glu Leu Gly Lys Ala Gly Ile Ser Ser Glu Glu
        195                 200                 205

Ile Leu Glu Leu Leu Arg Ala Ala His Glu Leu Gly Leu Asp Pro Glu
    210                 215                 220

Ala Ile Lys Ala Ala Ala Glu Leu Gly Lys Ala Gly Ile Ser Ser Glu
225                 230                 235                 240

Glu Ile Leu Glu Leu Leu Arg Ala Ala His Glu Leu Gly Leu Asp Pro
                245                 250                 255

Glu Ala Ile Lys Ala Ala Ala Glu Leu Gly Lys Ala Gly Ile Ser Ser
            260                 265                 270

Ile Glu Ile Leu Glu Leu Leu Arg Ala Ala His Glu Leu Gly Gly Trp
        275                 280                 285
```

<210> SEQ ID NO 108
<211> LENGTH: 1266
<212> TYPE: DNA
<213> ORGANISM: Artificial Sequence
<220> FEATURE:
<223> OTHER INFORMATION: Synthesized cTRP24_Sub12 (cTRP construct containing 12 repeats)

<400> SEQUENCE: 108

```
atggctagca gccatcatca tcatcatcat agcagcggcc tggtgccgcg cggcagctcc     60

atgggcctgg acccggaggc gatcaaggct gcggcggaac tgggtaaagc gggcatcagc    120

agcgaggaaa ttctggagct gctgcgtgcg gcgcatgagc tgggtctgga cccggaagcg    180

attaaggctg cggcggagct gggcaaggcg ggtatcagca gcgaagaaat tctggaactg    240

ctgcgcgcgg cgcatgagct gggcctggac ccggaagcga tcaaagctgc ggcggagctg    300

ggtaaggctg gtatcagcag cgaggagatt ctggaattat tacgcgcggc gcatgaactg    360

ggtctggacc cggaggcgat taaagctgcg gcggaactgg gcaaggcggg catcagcagc    420

gaagagattc tggaattact tcgtgctgcg catgaactgg gcctggaccc ggaggctatt    480

aaggctgcgg cggaattagg caaagctggc atcagcagcg aagaaattct ggaattactg    540

cgtgccgctc atgaattagg tctggacccg gaagctatca aagctgcggc ggaattaggt    600

aaggccggta tcagcagcga ggaaattctg gaattgttac gagctgctca tgaattaggc    660

ctggacccgg aggccattaa ggctgcggcg gagttaggca aagcgggtat cagcagcgag    720

gaaattctgg aacttttacg agctgctcat gagttaggtc tggacccgga ggctatcaag    780

gctgcggcgg agttgggcaa agccggcatc agcagcgagg agattctgga acttttacgg    840
```

gctgctcatg aacttggcct ggacccggag gcaattaagg ctgcggcgga gctaggcaag 900
gctggtatca gcagcgagga aattctggaa ctactgcgtg ccgcccatga attgggtctg 960
gacccggaag caatcaaggc tgcggcggag cttggcaagg ccggtatcag cagcgaggaa 1020
attctggaac tgttacgagc tgcccatgaa cttggtctgg acccggaagc cataaaagct 1080
gcggcggagt taggtaaggc aggtatcagc agcgaggaaa ttctggaact cctgcgtgcc 1140
gcacatgaac tcggtctgga cccggaggcc attaaagctg cggcggagtt gggtaaggcg 1200
ggtatcagca gcgaggaaat tctggagtta ctgcgtgccg cgcatgagct gggtggctgg 1260
taataa 1266

<210> SEQ ID NO 109
<211> LENGTH: 420
<212> TYPE: PRT
<213> ORGANISM: Artificial Sequence
<220> FEATURE:
<223> OTHER INFORMATION: Synthesized cTRP24_Sub12 (cTRP construct containing 12 repeats)

<400> SEQUENCE: 109

Met Ala Ser Ser His His His His His His Ser Ser Gly Leu Val Pro
1               5                   10                  15

Arg Gly Ser Ser Met Gly Leu Asp Pro Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140

Glu Leu Leu Arg Ala Ala His Glu Leu Gly Leu Asp Pro Glu Ala Ile
145                 150                 155                 160

Lys Ala Ala Ala Glu Leu Gly Lys Ala Gly Ile Ser Ser Glu Glu Ile
                165                 170                 175

Leu Glu Leu Leu Arg Ala Ala His Glu Leu Gly Leu Asp Pro Glu Ala
            180                 185                 190

Ile Lys Ala Ala Ala Glu Leu Gly Lys Ala Gly Ile Ser Ser Glu Glu
        195                 200                 205

Ile Leu Glu Leu Leu Arg Ala Ala His Glu Leu Gly Leu Asp Pro Glu
    210                 215                 220

Ala Ile Lys Ala Ala Ala Glu Leu Gly Lys Ala Gly Ile Ser Ser Glu
225                 230                 235                 240

Glu Ile Leu Glu Leu Leu Arg Ala Ala His Glu Leu Gly Leu Asp Pro
                245                 250                 255

Glu Ala Ile Lys Ala Ala Ala Glu Leu Gly Lys Ala Gly Ile Ser Ser
            260                 265                 270

Glu Glu Ile Leu Glu Leu Leu Arg Ala Ala His Glu Leu Gly Leu Asp

```
        275                 280                 285

Pro Glu Ala Ile Lys Ala Ala Ala Glu Leu Gly Lys Ala Gly Ile Ser
    290                 295                 300

Ser Glu Glu Ile Leu Glu Leu Leu Arg Ala Ala His Glu Leu Gly Leu
305                 310                 315                 320

Asp Pro Glu Ala Ile Lys Ala Ala Ala Glu Leu Gly Lys Ala Gly Ile
                325                 330                 335

Ser Ser Glu Glu Ile Leu Glu Leu Leu Arg Ala Ala His Glu Leu Gly
            340                 345                 350

Leu Asp Pro Glu Ala Ile Lys Ala Ala Ala Glu Leu Gly Lys Ala Gly
        355                 360                 365

Ile Ser Ser Glu Glu Ile Leu Glu Leu Leu Arg Ala Ala His Glu Leu
    370                 375                 380

Gly Leu Asp Pro Glu Ala Ile Lys Ala Ala Ala Glu Leu Gly Lys Ala
385                 390                 395                 400

Gly Ile Ser Ser Glu Glu Ile Leu Glu Leu Leu Arg Ala Ala His Glu
                405                 410                 415

Leu Gly Gly Trp
            420


<210> SEQ ID NO 110
<211> LENGTH: 1266
<212> TYPE: DNA
<213> ORGANISM: Artificial Sequence
<220> FEATURE:
<223> OTHER INFORMATION: Synthesized cTRP24_Sub12SS (cTRP construct
      containing 12 repeats and disulfide staples)

<400> SEQUENCE: 110

atggctagca gccatcatca tcatcatcat agcagcggcc tggtgccgcg cggcagctcc      60

atgggcctgg actgcgaggc gatcaaggct gcggcggaac tgggtaaagc gggcatcagc     120

agcgaggaaa ttctggagct gctgcgtgcg gcgcatgagc tgggtctgga cccggaagcg     180

attaaggctg cggcggagct gggcaaggcg ggtatcagca gcgaagaaat tctggaactg     240

ctgcgcgcgg cgcatgagct gggcctggac ccggaagcga tcaaagctgc ggcggagctg     300

ggtaaggctg gtatcagcag cgaggagatt ctggaattat tacgcgcggc gcatgaactg     360

ggtctggacc cggaggcgat taaagctgcg gcggaactgg gcaaggcggg catcagcagc     420

gaagagattc tggaattact tcgtgctgcg catgaactgg gcctggaccc ggaggctatt     480

aaggctgcgg cggaattagg caaagctggc atcagcagcg aagaaattct ggaattactg     540

cgtgccgctc atgaattagg tctggacccg gaagctatca aagctgcggc ggaattaggt     600

aaggccggta tcagcagcga ggaaattctg gaattgttac gagctgctca tgaattaggc     660

ctggacccgg aggccattaa ggctgcggcg gagttaggca aagcgggtat cagcagcgag     720

gaaattctgg aacttttacg agctgctcat gagttaggtc tggacccgga ggctatcaag     780

gctgcggcgg agttgggcaa agccggcatc agcagcgagg agattctgga acttttacgg     840

gctgctcatg aacttggcct ggacccggag gcaattaagg ctgcggcgga gctaggcaag     900

gctggtatca gcagcgagga aattctggaa ctactgcgtg ccgcccatga attgggtctg     960

gacccggaag caatcaaggc tgcggcggag cttggcaagg ccggtatcag cagcgaggaa    1020

attctggaac tgttacgagc tgcccatgaa cttggtctgg acccggaagc cataaaagct    1080

gcggcggagt taggtaaggc aggtatcagc agcgaggaaa ttctggaact cctgcgtgcc    1140

gcacatgaac tcggtctgga cccggaatgc ataaaggctg cggcggaatt gggcaaagct    1200
```

ggtatcagca gcgaggaaat tctggagtta ctgcgtgccg cgcatgagct gggtggctgg 1260
taataa 1266

<210> SEQ ID NO 111
<211> LENGTH: 420
<212> TYPE: PRT
<213> ORGANISM: Artificial Sequence
<220> FEATURE:
<223> OTHER INFORMATION: Synthesized cTRP24_Sub12SS (cTRP construct containing 12 repeats and disulfide staples)

<400> SEQUENCE: 111

Met Ala Ser Ser His His His His His His Ser Ser Gly Leu Val Pro
1 5 10 15

Arg Gly Ser Ser Met Gly Leu Asp Cys Glu Ala Ile Lys Ala Ala Ala
20 25 30

Glu Leu Gly Lys Ala Gly Ile Ser Ser Glu Glu Ile Leu Glu Leu Leu
35 40 45

Arg Ala Ala His Glu Leu Gly Leu Asp Pro Glu Ala Ile Lys Ala Ala
50 55 60

Ala Glu Leu Gly Lys Ala Gly Ile Ser Ser Glu Glu Ile Leu Glu Leu
65 70 75 80

Leu Arg Ala Ala His Glu Leu Gly Leu Asp Pro Glu Ala Ile Lys Ala
85 90 95

Ala Ala Glu Leu Gly Lys Ala Gly Ile Ser Ser Glu Glu Ile Leu Glu
100 105 110

Leu Leu Arg Ala Ala His Glu Leu Gly Leu Asp Pro Glu Ala Ile Lys
115 120 125

Ala Ala Ala Glu Leu Gly Lys Ala Gly Ile Ser Ser Glu Glu Ile Leu
130 135 140

Glu Leu Leu Arg Ala Ala His Glu Leu Gly Leu Asp Pro Glu Ala Ile
145 150 155 160

Lys Ala Ala Ala Glu Leu Gly Lys Ala Gly Ile Ser Ser Glu Glu Ile
165 170 175

Leu Glu Leu Leu Arg Ala Ala His Glu Leu Gly Leu Asp Pro Glu Ala
180 185 190

Ile Lys Ala Ala Ala Glu Leu Gly Lys Ala Gly Ile Ser Ser Glu Glu
195 200 205

Ile Leu Glu Leu Leu Arg Ala Ala His Glu Leu Gly Leu Asp Pro Glu
210 215 220

Ala Ile Lys Ala Ala Ala Glu Leu Gly Lys Ala Gly Ile Ser Ser Glu
225 230 235 240

Glu Ile Leu Glu Leu Leu Arg Ala Ala His Glu Leu Gly Leu Asp Pro
245 250 255

Glu Ala Ile Lys Ala Ala Ala Glu Leu Gly Lys Ala Gly Ile Ser Ser
260 265 270

Glu Glu Ile Leu Glu Leu Leu Arg Ala Ala His Glu Leu Gly Leu Asp
275 280 285

Pro Glu Ala Ile Lys Ala Ala Ala Glu Leu Gly Lys Ala Gly Ile Ser
290 295 300

Ser Glu Glu Ile Leu Glu Leu Leu Arg Ala Ala His Glu Leu Gly Leu
305 310 315 320

Asp Pro Glu Ala Ile Lys Ala Ala Ala Glu Leu Gly Lys Ala Gly Ile
325 330 335

```
Ser Ser Glu Glu Ile Leu Glu Leu Leu Arg Ala Ala His Glu Leu Gly
            340                 345                 350

Leu Asp Pro Glu Ala Ile Lys Ala Ala Ala Glu Leu Gly Lys Ala Gly
        355                 360                 365

Ile Ser Ser Glu Glu Ile Leu Glu Leu Leu Arg Ala Ala His Glu Leu
    370                 375                 380

Gly Leu Asp Pro Glu Cys Ile Lys Ala Ala Ala Glu Leu Gly Lys Ala
385                 390                 395                 400

Gly Ile Ser Ser Glu Glu Ile Leu Glu Leu Leu Arg Ala Ala His Glu
                405                 410                 415

Leu Gly Gly Trp
            420


<210> SEQ ID NO 112
<211> LENGTH: 1266
<212> TYPE: DNA
<213> ORGANISM: Artificial Sequence
<220> FEATURE:
<223> OTHER INFORMATION: Synthesized cTRP24_Sub12_capped (cTRP construct
      containing 12 repeats and mutations blocking dimerization)

<400> SEQUENCE: 112

atggctagca gccatcatca tcatcatcat agcagcggcc tggtgccgcg cggcagctcc      60

atgggcctgg acccggaggc ggaaaaggct gcggcggagc tgggtaaagc gggcatcagc     120

agcgaggaaa ttaaagaact gctgcgtgcg gcgcatgagc tgggtctgga cccggaagcg     180

atcaaagctg cggcggaact gggcaaggcg ggtatcagca gcgaagaaat tctggaactg     240

ctgcgcgcgg cgcatgagct gggcctggac ccggaagcga ttaaagctgc ggcggagctg     300

ggcaaggcgg gcatcagcag cgaagagatt ctggaattat tacgcgcggc gcatgaactg     360

ggtctggacc cggaggcgat caaggctgcg gcggaactgg gtaaggctgg tatcagcagc     420

gaggagattc tggaattact tcgtgctgcg catgaactgg gcctggaccc ggaggcgatt     480

aaggctgcgg cggagttagg caaagctggc atcagcagcg aagaaattct ggaattactg     540

cgtgccgctc atgaattagg tctggacccg gaagctatca aggctgcggc ggagttgggc     600

aaagccggca tcagcagcga ggagattctg gaacttttac gagctgctca tgaattaggc     660

ctggacccgg aagctattaa agctgcggcg gaattaggta aggccggtat cagcagcgag     720

gaaattctgg aattgttacg agctgctcat gagttaggtc tggacccgga ggctatcaaa     780

gctgcggcgg agttaggtaa ggcaggtatc agcagcgagg aaattctgga acttttacgg     840

gctgctcatg aacttggcct ggacccggaa gccatcaaag ctgcggcgga attagggaaa     900

gctggaatca gcagcgaaga gattctggaa cttcttcgtg ccgctcatga acttggtctg     960

gacccggagg ccattaaagc tgcggcggaa cttggtaagg cgggtatcag cagcgaggaa    1020

attctggaac tactgcgtgc cgcccatgaa ttgggtctgg acccggaagc aatcaaggct    1080

gcggcggagc ttggcaaagc aggtatcagc agcgaggaaa ttctggagtt attgcgtgcc    1140

gctcatgaac tcggtctgga cccggaagcc atcaagaaag cggcggaact gggcaaagca    1200

ggcatcagca gcgaagagat tctggagctg ctgcgtgcgg cgcacgaaaa aggtggctgg    1260

taataa                                                               1266


<210> SEQ ID NO 113
<211> LENGTH: 420
<212> TYPE: PRT
<213> ORGANISM: Artificial Sequence
<220> FEATURE:
```

<223> OTHER INFORMATION: Synthesized cTRP24_Sub12_capped (cTRP construct containing 12 repeats and mutations blocking dimerization)

<400> SEQUENCE: 113

```
Met Ala Ser Ser His His His His His His Ser Ser Gly Leu Val Pro
1               5                   10                  15

Arg Gly Ser Ser Met Gly Leu Asp Pro Glu Ala Glu Lys Ala Ala Ala
            20                  25                  30

Glu Leu Gly Lys Ala Gly Ile Ser Ser Glu Glu Ile Lys Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140

Glu Leu Leu Arg Ala Ala His Glu Leu Gly Leu Asp Pro Glu Ala Ile
145                 150                 155                 160

Lys Ala Ala Ala Glu Leu Gly Lys Ala Gly Ile Ser Ser Glu Glu Ile
                165                 170                 175

Leu Glu Leu Leu Arg Ala Ala His Glu Leu Gly Leu Asp Pro Glu Ala
            180                 185                 190

Ile Lys Ala Ala Ala Glu Leu Gly Lys Ala Gly Ile Ser Ser Glu Glu
        195                 200                 205

Ile Leu Glu Leu Leu Arg Ala Ala His Glu Leu Gly Leu Asp Pro Glu
    210                 215                 220

Ala Ile Lys Ala Ala Ala Glu Leu Gly Lys Ala Gly Ile Ser Ser Glu
225                 230                 235                 240

Glu Ile Leu Glu Leu Leu Arg Ala Ala His Glu Leu Gly Leu Asp Pro
                245                 250                 255

Glu Ala Ile Lys Ala Ala Ala Glu Leu Gly Lys Ala Gly Ile Ser Ser
            260                 265                 270

Glu Glu Ile Leu Glu Leu Leu Arg Ala Ala His Glu Leu Gly Leu Asp
        275                 280                 285

Pro Glu Ala Ile Lys Ala Ala Ala Glu Leu Gly Lys Ala Gly Ile Ser
    290                 295                 300

Ser Glu Glu Ile Leu Glu Leu Leu Arg Ala Ala His Glu Leu Gly Leu
305                 310                 315                 320

Asp Pro Glu Ala Ile Lys Ala Ala Ala Glu Leu Gly Lys Ala Gly Ile
                325                 330                 335

Ser Ser Glu Glu Ile Leu Glu Leu Leu Arg Ala Ala His Glu Leu Gly
            340                 345                 350

Leu Asp Pro Glu Ala Ile Lys Ala Ala Ala Glu Leu Gly Lys Ala Gly
        355                 360                 365

Ile Ser Ser Glu Glu Ile Leu Glu Leu Leu Arg Ala Ala His Glu Leu
    370                 375                 380

Gly Leu Asp Pro Glu Ala Ile Lys Lys Ala Ala Glu Leu Gly Lys Ala
385                 390                 395                 400
```

```
Gly Ile Ser Ser Glu Glu Ile Leu Glu Leu Leu Arg Ala Ala His Glu
                405                 410                 415

Lys Gly Gly Trp
            420


<210> SEQ ID NO 114
<211> LENGTH: 669
<212> TYPE: DNA
<213> ORGANISM: Artificial Sequence
<220> FEATURE:
<223> OTHER INFORMATION: Synthesized cTRP24_Sub6SS (Sub6SS cTRP
      construct containing 6 repeats and disulfide staples)

<400> SEQUENCE: 114

atggctagca gccatcatca tcatcatcat agcagcggcc tggtgccgcg cggcagctcc      60

atgggcctgg actgcgaggc cattaaggct gcggcggagt taggcaaagc gggtatcagc     120

agcgaggaaa ttctggaact tttacgagct gctcatgagt taggtctgga cccggaggct     180

atcaaggctg cggcggagtt gggcaaagcc ggcatcagca gcgaggagat tctggaactt     240

ttacgggctg ctcatgaact tggcctggac ccggaggcaa ttaaggctgc ggcggagcta     300

ggcaaggctg gtatcagcag cgaggaaatt ctggaactac tgcgtgccgc ccatgaattg     360

ggtctggacc cggaagcaat caaggctgcg gcggagcttg gcaaggccgg tatcagcagc     420

gaggaaattc tggaactgtt acgagctgcc catgaacttg gtctggaccc ggaagccata     480

aaagctgcgg cggagttagg taaggcaggt atcagcagcg aggaaattct ggaactcctg     540

cgtgccgcac atgaactcgg tctggacccg gagtgcatta aagctgcggc ggagttgggt     600

aaggcgggta tcagcagcga ggaaattctg gagttactgc gtgccgcgca tgagctgggt     660

ggctggtaa                                                             669


<210> SEQ ID NO 115
<211> LENGTH: 222
<212> TYPE: PRT
<213> ORGANISM: Artificial Sequence
<220> FEATURE:
<223> OTHER INFORMATION: Synthesized cTRP24_Sub6SS (Sub6SS cTRP
      construct containing 6 repeats and disulfide staples)

<400> SEQUENCE: 115

Met Ala Ser Ser His His His His His His Ser Ser Gly Leu Val Pro
1               5                   10                  15

Arg Gly Ser Ser Met Gly Leu Asp Cys Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Leu Asp Pro Glu Ala Ile Lys
        115                 120                 125

Ala Ala Ala Glu Leu Gly Lys Ala Gly Ile Ser Ser Glu Glu Ile Leu
    130                 135                 140
```

Glu Leu Leu Arg Ala Ala His Glu Leu Gly Leu Asp Pro Glu Ala Ile
145 150 155 160

Lys Ala Ala Ala Glu Leu Gly Lys Ala Gly Ile Ser Ser Glu Glu Ile
165 170 175

Leu Glu Leu Leu Arg Ala Ala His Glu Leu Gly Leu Asp Pro Glu Cys
180 185 190

Ile Lys Ala Ala Ala Glu Leu Gly Lys Ala Gly Ile Ser Ser Glu Glu
195 200 205

Ile Leu Glu Leu Leu Arg Ala Ala His Glu Leu Gly Gly Trp
210 215 220

<210> SEQ ID NO 116
<211> LENGTH: 172
<212> TYPE: PRT
<213> ORGANISM: Artificial Sequence
<220> FEATURE:
<223> OTHER INFORMATION: Synthesized thick cTRP sub3

<400> SEQUENCE: 116

Gly Asn Leu Glu Leu Ala Leu Lys Ala Leu Gln Ile Leu Val Asn Ala
1 5 10 15

Ala Tyr Val Leu Ala Glu Ile Ala Arg Asp Arg Gly Asn Glu Glu Leu
20 25 30

Leu Glu Lys Ala Ala Arg Leu Ala Glu Glu Ala Ala Arg Gln Ala Glu
35 40 45

Glu Ile Ala Arg Gln Ala Arg Lys Glu Gly Asn Leu Glu Leu Ala Leu
50 55 60

Lys Ala Leu Gln Ile Leu Val Asn Ala Ala Tyr Val Leu Ala Glu Ile
65 70 75 80

Ala Arg Asp Arg Gly Asn Glu Glu Leu Leu Glu Lys Ala Ala Arg Leu
85 90 95

Ala Glu Glu Ala Ala Arg Gln Ala Glu Glu Ile Ala Arg Gln Ala Arg
100 105 110

Lys Glu Gly Asn Leu Glu Leu Ala Leu Lys Ala Leu Gln Ile Leu Val
115 120 125

Asn Ala Ala Tyr Val Leu Ala Glu Ile Ala Arg Asp Arg Gly Asn Glu
130 135 140

Glu Leu Leu Glu Lys Ala Ala Arg Leu Ala Glu Glu Ala Ala Arg Gln
145 150 155 160

Ala Glu Glu Ile Ala Arg Gln Ala Arg Lys Glu Gly
165 170

<210> SEQ ID NO 117
<211> LENGTH: 342
<212> TYPE: PRT
<213> ORGANISM: Artificial Sequence
<220> FEATURE:
<223> OTHER INFORMATION: Synthesized thick cTRP sub6

<400> SEQUENCE: 117

Gly Asn Ser Glu Leu Ala Ala Arg Ile Leu Ile Ile Leu Phe Gln Gln
1 5 10 15

Leu Val Glu Leu Ala Arg Leu Ala Ile Glu Ser Gly Asp Glu Glu Leu
20 25 30

Leu Arg Arg Val Ser Glu Trp Leu Glu Glu Val Ile Lys Asp Met Arg
35 40 45

Arg Val Val Glu Gln Ala Leu Arg Glu Gly Asn Ser Glu Leu Ala Ala

```
    50                  55                  60

Arg Ile Leu Ile Ile Leu Phe Gln Gln Leu Val Glu Leu Ala Arg Leu
65                  70                  75                  80

Ala Ile Glu Ser Gly Asp Glu Glu Leu Leu Arg Arg Val Ser Glu Trp
                85                  90                  95

Leu Glu Glu Val Ile Lys Asp Met Arg Arg Val Val Glu Gln Ala Leu
            100                 105                 110

Arg Glu Gly Asn Ser Glu Leu Ala Ala Arg Ile Leu Ile Ile Leu Phe
        115                 120                 125

Gln Gln Leu Val Glu Leu Ala Arg Leu Ala Ile Glu Ser Gly Asp Glu
    130                 135                 140

Glu Leu Leu Arg Arg Val Ser Glu Trp Leu Glu Glu Val Ile Lys Asp
145                 150                 155                 160

Met Arg Arg Val Val Glu Gln Ala Leu Arg Glu Gly Asn Ser Glu Leu
                165                 170                 175

Ala Ala Arg Ile Leu Ile Ile Leu Phe Gln Gln Leu Val Glu Leu Ala
            180                 185                 190

Arg Leu Ala Ile Glu Ser Gly Asp Glu Glu Leu Leu Arg Arg Val Ser
        195                 200                 205

Glu Trp Leu Glu Glu Val Ile Lys Asp Met Arg Arg Val Val Glu Gln
    210                 215                 220

Ala Leu Arg Glu Gly Asn Ser Glu Leu Ala Ala Arg Ile Leu Ile Ile
225                 230                 235                 240

Leu Phe Gln Gln Leu Val Glu Leu Ala Arg Leu Ala Ile Glu Ser Gly
                245                 250                 255

Asp Glu Glu Leu Leu Arg Arg Val Ser Glu Trp Leu Glu Glu Val Ile
            260                 265                 270

Lys Asp Met Arg Arg Val Val Glu Gln Ala Leu Arg Glu Gly Asn Ser
        275                 280                 285

Glu Leu Ala Ala Arg Ile Leu Ile Ile Leu Phe Gln Gln Leu Val Glu
    290                 295                 300

Leu Ala Arg Leu Ala Ile Glu Ser Gly Asp Glu Glu Leu Leu Arg Arg
305                 310                 315                 320

Val Ser Glu Trp Leu Glu Glu Val Ile Lys Asp Met Arg Arg Val Val
                325                 330                 335

Glu Gln Ala Leu Arg Glu
            340


<210> SEQ ID NO 118
<211> LENGTH: 457
<212> TYPE: PRT
<213> ORGANISM: Artificial Sequence
<220> FEATURE:
<223> OTHER INFORMATION: Synthesized thick cTRP sub8

<400> SEQUENCE: 118

Gly Asn Ser Glu Leu Ala Ala Arg Ile Leu Ile Ile Leu Phe Gln Gln
1               5                   10                  15

Leu Val Glu Leu Ala Arg Leu Ala Ile Glu Ser Gly Asp Glu Glu Leu
            20                  25                  30

Leu Arg Arg Val Ser Glu Trp Leu Glu Glu Val Ile Lys Asp Met Arg
        35                  40                  45

Arg Val Val Glu Gln Ala Leu Arg Glu Gly Asn Ser Glu Leu Ala Ala
    50                  55                  60

Arg Ile Leu Ile Ile Leu Phe Gln Gln Leu Val Glu Leu Ala Arg Leu
```

```
65                  70                  75                  80

Ala Ile Glu Ser Gly Asp Glu Glu Leu Leu Arg Arg Val Ser Glu Trp
                85                  90                  95

Leu Glu Glu Val Ile Lys Asp Met Arg Arg Val Val Glu Gln Ala Leu
            100                 105                 110

Arg Glu Gly Asn Ser Glu Leu Ala Ala Arg Ile Leu Ile Ile Leu Phe
        115                 120                 125

Gln Gln Leu Val Glu Leu Ala Arg Leu Ala Ile Glu Ser Gly Asp Glu
    130                 135                 140

Glu Leu Leu Arg Arg Val Ser Glu Trp Leu Glu Glu Val Ile Lys Asp
145                 150                 155                 160

Met Arg Arg Val Val Glu Gln Ala Leu Arg Glu Gly Asn Ser Glu Leu
                165                 170                 175

Ala Ala Arg Ile Leu Ile Ile Leu Phe Gln Gln Leu Val Glu Leu Ala
            180                 185                 190

Arg Leu Ala Ile Glu Ser Gly Asp Glu Glu Leu Leu Arg Arg Val Ser
        195                 200                 205

Glu Trp Leu Glu Glu Val Ile Lys Asp Met Arg Arg Val Val Glu Gln
    210                 215                 220

Ala Leu Arg Glu Gly Asn Ser Glu Leu Ala Ala Arg Ile Leu Ile Ile
225                 230                 235                 240

Leu Phe Gln Gln Leu Val Glu Leu Ala Arg Leu Ala Ile Glu Ser Gly
                245                 250                 255

Asp Glu Glu Leu Leu Arg Arg Val Ser Glu Trp Leu Glu Glu Val Ile
            260                 265                 270

Lys Asp Met Arg Arg Val Val Glu Gln Ala Leu Arg Glu Gly Asn Ser
        275                 280                 285

Glu Leu Ala Ala Arg Ile Leu Ile Ile Leu Phe Gln Gln Leu Val Glu
    290                 295                 300

Leu Ala Arg Leu Ala Ile Glu Ser Gly Asp Glu Glu Leu Leu Arg Arg
305                 310                 315                 320

Val Ser Glu Trp Leu Glu Glu Val Ile Lys Asp Met Arg Arg Val Val
                325                 330                 335

Glu Gln Ala Leu Arg Glu Gly Asn Ser Glu Leu Ala Ala Arg Ile Leu
            340                 345                 350

Ile Ile Leu Phe Gln Gln Leu Val Glu Leu Ala Arg Leu Ala Ile Glu
        355                 360                 365

Ser Gly Asp Glu Glu Leu Leu Arg Arg Val Ser Glu Trp Leu Glu Glu
    370                 375                 380

Val Ile Lys Asp Met Arg Arg Val Val Glu Gln Ala Leu Arg Glu Gly
385                 390                 395                 400

Asn Ser Glu Leu Ala Ala Arg Ile Leu Ile Ile Leu Phe Gln Gln Leu
                405                 410                 415

Val Glu Leu Ala Arg Leu Ala Ile Glu Ser Gly Asp Glu Glu Leu Leu
            420                 425                 430

Arg Arg Val Ser Glu Trp Leu Glu Glu Val Ile Lys Asp Met Arg Arg
        435                 440                 445

Val Val Glu Gln Ala Leu Arg Glu Gly
    450                 455
```

<210> SEQ ID NO 119
<211> LENGTH: 457
<212> TYPE: PRT
<213> ORGANISM: Artificial Sequence
<220> FEATURE:
<223> OTHER INFORMATION: Synthesized thick cTRP sub8

<400> SEQUENCE: 119

```
Gly Asn Ser Glu Leu Ala Ala Arg Cys Leu Ile Ile Leu Phe Gln Gln
1               5                   10                  15

Leu Val Glu Leu Ala Arg Leu Ala Ile Glu Ser Gly Asp Glu Glu Leu
            20                  25                  30

Leu Arg Arg Val Ser Glu Trp Leu Glu Glu Val Ile Lys Asp Met Arg
        35                  40                  45

Arg Val Val Glu Gln Ala Leu Arg Glu Gly Asn Ser Glu Leu Ala Ala
    50                  55                  60

Arg Ile Leu Ile Ile Leu Phe Gln Gln Leu Val Glu Leu Ala Arg Leu
65                  70                  75                  80

Ala Ile Glu Ser Gly Asp Glu Glu Leu Leu Arg Arg Val Ser Glu Trp
                85                  90                  95

Leu Glu Glu Val Ile Lys Asp Met Arg Arg Val Val Glu Gln Ala Leu
            100                 105                 110

Arg Glu Gly Asn Ser Glu Leu Ala Ala Arg Ile Leu Ile Ile Leu Phe
        115                 120                 125

Gln Gln Leu Val Glu Leu Ala Arg Leu Ala Ile Glu Ser Gly Asp Glu
    130                 135                 140

Glu Leu Leu Arg Arg Val Ser Glu Trp Leu Glu Glu Val Ile Lys Asp
145                 150                 155                 160

Met Arg Arg Val Val Glu Gln Ala Leu Arg Glu Gly Asn Ser Glu Leu
                165                 170                 175

Ala Ala Arg Ile Leu Ile Ile Leu Phe Gln Gln Leu Val Glu Leu Ala
            180                 185                 190

Arg Leu Ala Ile Glu Ser Gly Asp Glu Glu Leu Leu Arg Arg Val Ser
        195                 200                 205

Glu Trp Leu Glu Glu Val Ile Lys Asp Met Arg Arg Val Val Glu Gln
    210                 215                 220

Ala Leu Arg Glu Gly Asn Ser Glu Leu Ala Ala Arg Ile Leu Ile Ile
225                 230                 235                 240

Leu Phe Gln Gln Leu Val Glu Leu Ala Arg Leu Ala Ile Glu Ser Gly
                245                 250                 255

Asp Glu Glu Leu Leu Arg Arg Val Ser Glu Trp Leu Glu Glu Val Ile
            260                 265                 270

Lys Asp Met Arg Arg Val Val Glu Gln Ala Leu Arg Glu Gly Asn Ser
        275                 280                 285

Glu Leu Ala Ala Arg Ile Leu Ile Ile Leu Phe Gln Gln Leu Val Glu
    290                 295                 300

Leu Ala Arg Leu Ala Ile Glu Ser Gly Asp Glu Glu Leu Leu Arg Arg
305                 310                 315                 320

Val Ser Glu Trp Leu Glu Glu Val Ile Lys Asp Met Arg Arg Val Val
                325                 330                 335

Glu Gln Ala Leu Arg Glu Gly Asn Ser Glu Leu Ala Ala Arg Ile Leu
            340                 345                 350

Ile Ile Leu Phe Gln Gln Leu Val Glu Leu Ala Arg Leu Ala Ile Glu
        355                 360                 365

Ser Gly Asp Glu Glu Leu Leu Arg Arg Val Ser Glu Trp Leu Glu Glu
    370                 375                 380

Val Ile Lys Asp Met Arg Arg Val Val Glu Gln Ala Leu Arg Glu Gly
385                 390                 395                 400
```

```
Asn Ser Glu Leu Ala Cys Arg Ile Leu Ile Ile Leu Phe Gln Gln Leu
                405                 410                 415

Val Glu Leu Ala Arg Leu Ala Ile Glu Ser Gly Asp Glu Glu Leu Leu
            420                 425                 430

Arg Arg Val Ser Glu Trp Leu Glu Glu Val Ile Lys Asp Met Arg Arg
        435                 440                 445

Val Val Glu Gln Ala Leu Arg Glu Gly
    450                 455
```

<210> SEQ ID NO 120
<211> LENGTH: 1947
<212> TYPE: DNA
<213> ORGANISM: Artificial Sequence
<220> FEATURE:
<223> OTHER INFORMATION: Synthesized cTRP24_Sub12_Spy (cTRP Construct containing 12 repeats and inserted fusions of spycatcher domains)

<400> SEQUENCE: 120

```
atggctagca gccatcatca tcatcatcat agcagcggcc tggtgccgcg cggcagctcc     60

atgggcctgg acccggaagc gattaaggcg gcggcggaac tgggcaaggc gggcattagc    120

agcgaggaga ttctggaact gctgcgtgcg gcgcatgagt tgggtctgga cccggaagcc    180

attaaggcag cggccgagct gggcaaggcc ggtatttcca gcgaggagat cttggaactg    240

ttgcgtgctg cacacgagct gggcctggac ccggaagcta ttaaagcggc tgcggagctg    300

ggtaaagctg gtatctccag cgaagaaatt ttggagttgc tgcgtgcggc acacgaactg    360

ggtggttccg acggtcaaga caaaggttcc gatggccaag acaagggtgg tgactccgcg    420

acccatatta aattttctaa gcgcgacgag gatggcaagg aattggcagg cgcgacgatg    480

gaactgcgcg attccagcgg caagaccatc tccacctgga tctctgacgg tcaggtgaaa    540

gatttttatc tgtacccggg taagtacacg ttcgtggaga cggcagcccc ggatggttat    600

gaggtggcca ccgcgatcac cttcacggtt aatgagcagg gccaggtcac cgttaatggt    660

ggctccgatg gtcaggataa gggttccgac ggtcaagata agggtggttt ggatccggag    720

gccatcaagg cggcagcaga gctgggcaaa gcgggcattt ccagcgaaga aatcctggag    780

ctgctgcgcg ctgctcacga actgggcttg gacccggagg cgatcaaagc agcagcggaa    840

ttgggcaaag cgggtattag ctctgaggaa atcctggaat tgttgcgtgc agcgcacgag    900

ctgggtttgg acccggaagc gattaaagcg gcggcggagt tgggtaaagc aggcattagc    960

agcgaagaga ttctggaact gttgcgtgcg gcacatgaac tgggtttgga tccggaggca   1020

attaaggccg ctgcagaact gggcaaggca ggtattagct ccgaagagat tctggaattg   1080

ctgcgcgcgg cgcacgaact gggtctggat ccggaagcaa ttaaggcggc agcagagctg   1140

ggtaaggcgg gtatctcttc tgaggagatc ctggagttgc tgcgtgcggc acacgaattg   1200

ggtctggatc cggaggcaat taaggctgcg gcggagctgg gcaaggcggg tatttcctcc   1260

gaggaaatct tggaactgct gcgcgcagca cacgaactgg gcggctctga cggtcaggat   1320

aaaggctccg acggccagga taaaggcggc gattccgcga cccacattaa atttagcaaa   1380

cgtgacgaag atggtaaaga gctggcaggt gcgacgatgg agctgcgcga tagctccggt   1440

aaaaccatca gcacctggat cagcgacggt caagttaagg acttctatct gtatccgggc   1500

aagtatacgt tcgtggaaac cgcagccccg gacggttacg aagtggctac cgcgattacc   1560

ttcaccgtga acgaacaggg ccaggtgacc gtcaacggcg gctctgacgg ccaagataaa   1620

ggctctgatg gccaggacaa gggcggcttg gacccggagg cgatcaaagc agccgcggag   1680
```

ttgggtaaag cgggcatctc tagcgaagag attttggagc tgttgcgtgc tgcgcacgag 1740
ctgggcttgg acccggaggc cattaaggcg gcagctgaac tgggtaaagc tggcattagc 1800
tccgaagaga tcttggagct gctgcgtgcc gcgcacgaat tgggcctgga tccggaagca 1860
atcaaggcag ctgctgagtt gggtaaggca ggcatcagca gcgaagaaat cctggaactg 1920
ctgcgtgcgg cgcatgaact gggttaa 1947

<210> SEQ ID NO 121
<211> LENGTH: 648
<212> TYPE: PRT
<213> ORGANISM: Artificial Sequence
<220> FEATURE:
<223> OTHER INFORMATION: Synthesized cTRP24_Sub12_Spy (cTRP Construct containing 12 repeats and inserted fusions of spycatcher domains)

<400> SEQUENCE: 121

Met Ala Ser Ser His His His His His His Ser Ser Gly Leu Val Pro
1 5 10 15

Arg Gly Ser Ser Met Gly Leu Asp Cys Glu Ala Ile Lys Ala Ala Ala
20 25 30

Glu Leu Gly Lys Ala Gly Ile Ser Ser Glu Glu Ile Leu Glu Leu Leu
35 40 45

Arg Ala Ala His Glu Leu Gly Leu Asp Pro Glu Ala Ile Lys Ala Ala
50 55 60

Ala Glu Leu Gly Lys Ala Gly Ile Ser Ser Glu Glu Ile Leu Glu Leu
65 70 75 80

Leu Arg Ala Ala His Glu Leu Gly Leu Asp Pro Glu Ala Ile Lys Ala
85 90 95

Ala Ala Glu Leu Gly Lys Ala Gly Ile Ser Ser Glu Glu Ile Leu Glu
100 105 110

Leu Leu Arg Ala Ala His Glu Leu Gly Gly Ser Asp Gly Gln Asp Lys
115 120 125

Gly Ser Asp Gly Gln Asp Lys Gly Gly Asp Ser Ala Thr His Ile Lys
130 135 140

Phe Ser Lys Arg Asp Glu Asp Gly Lys Glu Leu Ala Gly Ala Thr Met
145 150 155 160

Glu Leu Arg Asp Ser Ser Gly Lys Thr Ile Ser Thr Trp Ile Ser Asp
165 170 175

Gly Gln Val Lys Asp Phe Tyr Leu Tyr Pro Gly Lys Tyr Thr Phe Val
180 185 190

Glu Thr Ala Ala Pro Asp Gly Tyr Glu Val Ala Thr Ala Ile Thr Phe
195 200 205

Thr Val Asn Glu Gln Gly Gln Val Thr Val Asn Gly Gly Ser Asp Gly
210 215 220

Gln Asp Lys Gly Ser Asp Gly Gln Asp Lys Gly Gly Leu Asp Pro Glu
225 230 235 240

Ala Ile Lys Ala Ala Ala Glu Leu Gly Lys Ala Gly Ile Ser Ser Glu
245 250 255

Glu Ile Leu Glu Leu Leu Arg Ala Ala His Glu Leu Gly Leu Asp Pro
260 265 270

Glu Ala Ile Lys Ala Ala Ala Glu Leu Gly Lys Ala Gly Ile Ser Ser
275 280 285

Glu Glu Ile Leu Glu Leu Leu Arg Ala Ala His Glu Leu Gly Leu Asp
290 295 300

Pro Glu Ala Ile Lys Ala Ala Ala Glu Leu Gly Lys Ala Gly Ile Ser
305 310 315 320

Ser Glu Glu Ile Leu Glu Leu Leu Arg Ala Ala His Glu Leu Gly Leu
325 330 335

Asp Pro Glu Ala Ile Lys Ala Ala Ala Glu Leu Gly Lys Ala Gly Ile
340 345 350

Ser Ser Glu Glu Ile Leu Glu Leu Leu Arg Ala Ala His Glu Leu Gly
355 360 365

Leu Asp Pro Glu Ala Ile Lys Ala Ala Ala Glu Leu Gly Lys Ala Gly
370 375 380

Ile Ser Ser Glu Glu Ile Leu Glu Leu Leu Arg Ala Ala His Glu Leu
385 390 395 400

Gly Leu Asp Pro Glu Ala Ile Lys Ala Ala Ala Glu Leu Gly Lys Ala
405 410 415

Gly Ile Ser Ser Glu Glu Ile Leu Glu Leu Leu Arg Ala Ala His Glu
420 425 430

Leu Gly Gly Ser Asp Gly Gln Asp Lys Gly Ser Asp Gly Gln Asp Lys
435 440 445

Gly Gly Asp Ser Ala Thr His Ile Lys Phe Ser Lys Arg Asp Glu Asp
450 455 460

Gly Lys Glu Leu Ala Gly Ala Thr Met Glu Leu Arg Asp Ser Ser Gly
465 470 475 480

Lys Thr Ile Ser Thr Trp Ile Ser Asp Gly Gln Val Lys Asp Phe Tyr
485 490 495

Leu Tyr Pro Gly Lys Tyr Thr Phe Val Glu Thr Ala Ala Pro Asp Gly
500 505 510

Tyr Glu Val Ala Thr Ala Ile Thr Phe Thr Val Asn Glu Gln Gly Gln
515 520 525

Val Thr Val Asn Gly Gly Ser Asp Gly Gln Asp Lys Gly Ser Asp Gly
530 535 540

Gln Asp Lys Gly Gly Leu Asp Pro Glu Ala Ile Lys Ala Ala Ala Glu
545 550 555 560

Leu Gly Lys Ala Gly Ile Ser Ser Glu Glu Ile Leu Glu Leu Leu Arg
565 570 575

Ala Ala His Glu Leu Gly Leu Asp Pro Glu Ala Ile Lys Ala Ala Ala
580 585 590

Glu Leu Gly Lys Ala Gly Ile Ser Ser Glu Glu Ile Leu Glu Leu Leu
595 600 605

Arg Ala Ala His Glu Leu Gly Leu Asp Pro Glu Cys Ile Lys Ala Ala
610 615 620

Ala Glu Leu Gly Lys Ala Gly Ile Ser Ser Glu Glu Ile Leu Glu Leu
625 630 635 640

Leu Arg Ala Ala His Glu Leu Gly
645

<210> SEQ ID NO 122
<211> LENGTH: 2052
<212> TYPE: DNA
<213> ORGANISM: Artificial Sequence
<220> FEATURE:
<223> OTHER INFORMATION: Synthesized cTRP24_Sub12SS_SH2 (cTRP Construct containing 12 repeats and inserted fusions of SH2 domains)

<400> SEQUENCE: 122
atggctagca gccatcatca tcatcatcat agcagcggcc tggtgccgcg cggcagctcc 60

```
atgggcctgg attgcgaggc gatcaaagcg gcggcggaac tgggtaaagc gggtattagc    120

agcgaggaga ttctggaact gctgcgtgcg gcgcacgagt tgggtttgga tccggaagcc    180

atcaaggctg ccgccgaact gggcaaggca ggtattagct ctgaagagat cttggaactg    240

ctgcgcgccg cgcatgagtt gggtctggat ccggaagcga tcaaggctgc agcagaactg    300

ggcaaagcgg gtatttccag cgaggaaatt ctggagttgc tgcgtgcggc gcatgaattg    360

ggtggctccg atggtcagga taaaggttct gatggccaag ataagggcgg ctccgagtgg    420

tactacggca acgttacgcg ccaccaagca gagtgcgctc tgaatgaacg cggtgttgag    480

ggcgacttcc tgatccgtga tagcgaatct tccccgagcg acttcagcgt ttccctgaag    540

gcgtctggca agaacaagca ctttaaagtt cagctggtcg ataatgtcta ctgcatcggt    600

caacgtcgtt tccacacgat ggacgagttg gtggagcatt ataaaaaggc tccgatcttc    660

acgagcgagc atggtgagaa attgtacctg gtgcgcgcgc tgcagggcgg cagcgacggc    720

caggataaag gctccgacgg ccaagacaag ggtggtttgg acccggaggc gatcaaggca    780

gcagccgaac tgggtaaagc cggtatctct agcgaagaaa ttctggaact gctgcgtgcg    840

gctcatgagc tgggcttgga tccggaggct attaaggccg ctgcggaact gggtaaagct    900

ggcatctcct ccgaagaaat tttggagctg ttgcgtgccg cacatgagtt gggtctggat    960

ccggaagcga ttaaagccgc cgccgaattg ggcaaagcgg gcattagcag cgaagagatt   1020

ttggagctgt tgcgtgcagc gcatgaattg ggcctggacc cggaagcaat caaagcggct   1080

gcagagttgg gtaaggcggg catttctagc gaggagattt tggaactgct gcgcgcagcg   1140

catgagctgg gcctggaccc ggaggccatt aaggcggctg cggaattggg caaggccggt   1200

atttccagcg aagaaattct ggagctgctg cgtgcagctc acgagttggg cttggatccg   1260

gaagccatta aggctgccgc ggaactgggt aaggccggca ttagcagcga ggagatcttg   1320

gagctgctgc gtgccgcgca cgagttgggc ggttctgatg gccaggataa gggttccgat   1380

ggccaggaca aaggcggctc cgaatggtat tatggtaacg tgacccgcca ccaggctgag   1440

tgcgccctga acgagcgtgg cgtcgaaggt gactttctga tccgcgatag cgagagcagc   1500

ccgagcgatt ttagcgtgag cctgaaggca tctggcaaaa acaaacactt taaagtgcaa   1560

ttggtggata acgtttactg catcggccaa cgtcgttttc atacgatgga cgaactggtg   1620

gaacattata agaaggcgcc gatttttacg tccgaacacg gtgaaaaact gtacctggtc   1680

cgtgcattgc agggtggttc cgacggccag gacaaaggtt ccgacggcca agataaaggc   1740

ggtctggacc cggaggcaat caaggctgcg gctgagttgg gcaaggctgg tatcagcagc   1800

gaggaaatcc tggagctgtt gcgcgcggcc catgaactgg gtttggatcc ggaagctatc   1860

aaggctgcgg cagagctggg caaggcgggt atcagctctg aggaaatctt ggagttgctg   1920

cgtgccgcac acgaactggg cctggatccg gaatgtatca aagcggcggc ggagctgggt   1980

aaagcgggca ttagcagcga agaaatcctg gaactgctgc gtgcggcgca tgaactgggt   2040

ggttggtaat aa                                                      2052
```

<210> SEQ ID NO 123
<211> LENGTH: 681
<212> TYPE: PRT
<213> ORGANISM: Artificial Sequence
<220> FEATURE:
<223> OTHER INFORMATION: Synthesized cTRP24_Sub12SS_SH2 (cTRP Construct containing 12 repeats and inserted fusions of SH2 domains)

<400> SEQUENCE: 123

-continued

```
Met Ala Ser Ser His His His His His His Ser Ser Gly Leu Val Pro
1               5                   10                  15

Arg Gly Ser Ser Met Gly Leu Asp Cys Glu Ala Ile Lys Ala Ala Ala
            20                  25                  30

Glu Leu Gly Lys Ala Gly Ile Ser Ser Glu Glu Ile Leu Glu Leu Leu
        35                  40                  45

Arg Ala Ala His Glu Leu Gly Leu Asp Pro Glu Ala Ile Lys Ala Ala
    50                  55                  60

Ala Glu Leu Gly Lys Ala Gly Ile Ser Ser Glu Glu Ile Leu Glu Leu
65                  70                  75                  80

Leu Arg Ala Ala His Glu Leu Gly Leu Asp Pro Glu Ala Ile Lys Ala
                85                  90                  95

Ala Ala Glu Leu Gly Lys Ala Gly Ile Ser Ser Glu Glu Ile Leu Glu
            100                 105                 110

Leu Leu Arg Ala Ala His Glu Leu Gly Gly Ser Asp Gly Gln Asp Lys
        115                 120                 125

Gly Ser Asp Gly Gln Asp Lys Gly Gly Ser Glu Trp Tyr Tyr Gly Asn
    130                 135                 140

Val Thr Arg His Gln Ala Glu Cys Ala Leu Asn Glu Arg Gly Val Glu
145                 150                 155                 160

Gly Asp Phe Leu Ile Arg Asp Ser Glu Ser Ser Pro Ser Asp Phe Ser
                165                 170                 175

Val Ser Leu Lys Ala Ser Gly Lys Asn Lys His Phe Lys Val Gln Leu
            180                 185                 190

Val Asp Asn Val Tyr Cys Ile Gly Gln Arg Arg Phe His Thr Met Asp
        195                 200                 205

Glu Leu Val Glu His Tyr Lys Lys Ala Pro Ile Phe Thr Ser Glu His
    210                 215                 220

Gly Glu Lys Leu Tyr Leu Val Arg Ala Leu Gln Gly Gly Ser Asp Gly
225                 230                 235                 240

Gln Asp Lys Gly Ser Asp Gly Gln Asp Lys Gly Gly Leu Asp Pro Glu
                245                 250                 255

Ala Ile Lys Ala Ala Ala Glu Leu Gly Lys Ala Gly Ile Ser Ser Glu
            260                 265                 270

Glu Ile Leu Glu Leu Leu Arg Ala Ala His Glu Leu Gly Leu Asp Pro
        275                 280                 285

Glu Ala Ile Lys Ala Ala Ala Glu Leu Gly Lys Ala Gly Ile Ser Ser
    290                 295                 300

Glu Glu Ile Leu Glu Leu Leu Arg Ala Ala His Glu Leu Gly Leu Asp
305                 310                 315                 320

Pro Glu Ala Ile Lys Ala Ala Ala Glu Leu Gly Lys Ala Gly Ile Ser
                325                 330                 335

Ser Glu Glu Ile Leu Glu Leu Leu Arg Ala Ala His Glu Leu Gly Leu
            340                 345                 350

Asp Pro Glu Ala Ile Lys Ala Ala Ala Glu Leu Gly Lys Ala Gly Ile
        355                 360                 365

Ser Ser Glu Glu Ile Leu Glu Leu Leu Arg Ala Ala His Glu Leu Gly
    370                 375                 380

Leu Asp Pro Glu Ala Ile Lys Ala Ala Ala Glu Leu Gly Lys Ala Gly
385                 390                 395                 400

Ile Ser Ser Glu Glu Ile Leu Glu Leu Leu Arg Ala Ala His Glu Leu
                405                 410                 415

Gly Leu Asp Pro Glu Ala Ile Lys Ala Ala Ala Glu Leu Gly Lys Ala
```

```
            420                 425                 430

Gly Ile Ser Ser Glu Glu Ile Leu Glu Leu Leu Arg Ala Ala His Glu
        435                 440                 445

Leu Gly Gly Ser Asp Gly Gln Asp Lys Gly Ser Asp Gly Gln Asp Lys
    450                 455                 460

Gly Gly Ser Glu Trp Tyr Tyr Gly Asn Val Thr Arg His Gln Ala Glu
465                 470                 475                 480

Cys Ala Leu Asn Glu Arg Gly Val Glu Gly Asp Phe Leu Ile Arg Asp
                485                 490                 495

Ser Glu Ser Ser Pro Ser Asp Phe Ser Val Ser Leu Lys Ala Ser Gly
            500                 505                 510

Lys Asn Lys His Phe Lys Val Gln Leu Val Asp Asn Val Tyr Cys Ile
        515                 520                 525

Gly Gln Arg Arg Phe His Thr Met Asp Glu Leu Val Glu His Tyr Lys
    530                 535                 540

Lys Ala Pro Ile Phe Thr Ser Glu His Gly Glu Lys Leu Tyr Leu Val
545                 550                 555                 560

Arg Ala Leu Gln Gly Gly Ser Asp Gly Gln Asp Lys Gly Ser Asp Gly
                565                 570                 575

Gln Asp Lys Gly Gly Leu Asp Pro Glu Ala Ile Lys Ala Ala Ala Glu
            580                 585                 590

Leu Gly Lys Ala Gly Ile Ser Ser Glu Glu Ile Leu Glu Leu Leu Arg
        595                 600                 605

Ala Ala His Glu Leu Gly Leu Asp Pro Glu Ala Ile Lys Ala Ala Ala
    610                 615                 620

Glu Leu Gly Lys Ala Gly Ile Ser Ser Glu Glu Ile Leu Glu Leu Leu
625                 630                 635                 640

Arg Ala Ala His Glu Leu Gly Leu Asp Pro Glu Cys Ile Lys Ala Ala
                645                 650                 655

Ala Glu Leu Gly Lys Ala Gly Ile Ser Ser Glu Glu Ile Leu Glu Leu
            660                 665                 670

Leu Arg Ala Ala His Glu Leu Gly Trp
        675                 680


<210> SEQ ID NO 124
<211> LENGTH: 1941
<212> TYPE: DNA
<213> ORGANISM: Artificial Sequence
<220> FEATURE:
<223> OTHER INFORMATION: Synthesized cTRP24_Sub6SS_scMHC (Construct
      containing 6 repeats and inserted fusions of single chain MHC)

<400> SEQUENCE: 124

atggagacag acacactgct gctgtgggtg ctgctgctgt gggtgccagg ctccaccggc      60

aacctggtgc ctatggtggc aacagtggga tgcggagcct ctggaggagg aggcagcggc     120

ggaggaggct ccatccagag gaccccaaag atccaggtgt acagccgcca cccagcagag     180

aacggcaagt ccaacttcct gaattgttac gtgagcggct ttcacccaag cgacatcgag     240

gtggatctgc tgaagaatgg cgagcggatc gagaaggtgg agcactctga cctgagcttc     300

tccaaggatt ggagctttta cctgctgtac tataccgagt tcaccccaac agagaaggac     360

gagtatgcct gccgggtgaa tcacgtgaca ctgtctcagc ccaagatcgt gaagtgggac     420

agagatatgg gaggaggagg ctccggagga ggaggctctg gcggcggcgg cagcggaggc     480

ggcggctctg gcagccactc catgcggtac ttctttacct ctgtgagcag gcctggaagg     540
```

```
ggagagccac ggtttatcgc agtgggctat gtggacgata cacagttcgt gagatttgac     600

tccgatgcag catctcagag gatggagcca cgcgccccat ggatcgagca ggagggacca     660

gagtactggg acggagagac acggaaggtg aaggcccaca gccagaccca ccgggtggat     720

ctgggcacac tgagaggctg ctacaaccag agcgaggcag gctcccacac cgtgcagaga     780

atgtatggct gtgacgtggg cagcgattgg cggttcctga gaggctacca ccagtacgcc     840

tatgacggca aggattatat cgccctgaag gaggacctga ggtcctggac cgcagcagat     900

atggcagcac agaccacaaa gcacaagtgg gaggcagcac acgtggcaga gcagctgagg     960

gcctacctgg agggcacatg cgtggagtgg ctgcggagat atctggagaa tggcaaggag    1020

acactgcagc ggacagacgc ccctaagacc cacatgacac accacgccgt gtccgatcac    1080

gaggccaccc tgagatgttg ggccctgtct ttctacccag ccgagatcac cctgacatgg    1140

cagagggacg gcgaggatca gacccaggac acagagctgg tggagacacg gcccgcaggc    1200

gatggcacat ttcagaagtg ggcagcagtg gtggtgcctt ccggacagga gcagaggtat    1260

acctgtcacg tgcagcacga gggcctgccc aagcctctga cactgcgctg ggagcctggc    1320

ggcggcggat ccggaggagg aggctcctgc gaggccatca aggctgccgc cgagctgggc    1380

aaggcaggca tctctagcga ggagatcctg gagctgctga gggcagcaca cgagctgggc    1440

ctggacccag aagccatcaa ggctgccgcc gaactgggca aggccggcat ctcctctgaa    1500

gaaatcctgg agctgctgag agccgcccat gaactgggcc tggaccccga agccatcaag    1560

gctgccgccg agttaggcaa ggcaggcatc agctccgaag aaatcctgga gttactgaga    1620

gccgcccatg agctgggcct ggaccctgag gccatcaagg ctgccgccga gctaggcaag    1680

gccggcatct ctagcgaaga aatcctggag cttctgagag ccgcccacga attaggcctg    1740

gaccccgagg ccatcaaggc tgccgccgag cttggcaagg caggcatctc ctctgaagag    1800

atcctggagt tattaagagc cgcccacgaa cttggcctgg accccgagtg tatcaaggct    1860

gccgccgaat taggcaaggc cggcatcagc tccgaagaga tcctggagct tttacgggcc    1920

gcccacgagc tgggcctgta a                                              1941
```

<210> SEQ ID NO 125
<211> LENGTH: 646
<212> TYPE: PRT
<213> ORGANISM: Artificial Sequence
<220> FEATURE:
<223> OTHER INFORMATION: Synthesized cTRP24_Sub6SS_scMHC (Construct containing 6 repeats and inserted fusions of single chain MHC)

<400> SEQUENCE: 125

```
Met Glu Thr Asp Thr Leu Leu Leu Trp Val Leu Leu Leu Trp Val Pro
1               5                   10                  15

Gly Ser Thr Gly Asn Leu Val Pro Met Val Ala Thr Val Gly Cys Gly
            20                  25                  30

Ala Ser Gly Gly Gly Gly Ser Gly Gly Gly Gly Ser Ile Gln Arg Thr
        35                  40                  45

Pro Lys Ile Gln Val Tyr Ser Arg His Pro Ala Glu Asn Gly Lys Ser
    50                  55                  60

Asn Phe Leu Asn Cys Tyr Val Ser Gly Phe His Pro Ser Asp Ile Glu
65                  70                  75                  80

Val Asp Leu Leu Lys Asn Gly Glu Arg Ile Glu Lys Val Glu His Ser
                85                  90                  95

Asp Leu Ser Phe Ser Lys Asp Trp Ser Phe Tyr Leu Leu Tyr Tyr Thr
            100                 105                 110
```

```
Glu Phe Thr Pro Thr Glu Lys Asp Glu Tyr Ala Cys Arg Val Asn His
        115                 120                 125

Val Thr Leu Ser Gln Pro Lys Ile Val Lys Trp Asp Arg Asp Met Gly
    130                 135                 140

Gly Gly Gly Ser Gly Gly Gly Gly Ser Gly Gly Gly Gly Ser Gly Gly
145                 150                 155                 160

Gly Gly Ser Gly Ser His Ser Met Arg Tyr Phe Phe Thr Ser Val Ser
                165                 170                 175

Arg Pro Gly Arg Gly Glu Pro Arg Phe Ile Ala Val Gly Tyr Val Asp
            180                 185                 190

Asp Thr Gln Phe Val Arg Phe Asp Ser Asp Ala Ala Ser Gln Arg Met
        195                 200                 205

Glu Pro Arg Ala Pro Trp Ile Glu Gln Glu Gly Pro Glu Tyr Trp Asp
    210                 215                 220

Gly Glu Thr Arg Lys Val Lys Ala His Ser Gln Thr His Arg Val Asp
225                 230                 235                 240

Leu Gly Thr Leu Arg Gly Cys Tyr Asn Gln Ser Glu Ala Gly Ser His
                245                 250                 255

Thr Val Gln Arg Met Tyr Gly Cys Asp Val Gly Ser Asp Trp Arg Phe
            260                 265                 270

Leu Arg Gly Tyr His Gln Tyr Ala Tyr Asp Gly Lys Asp Tyr Ile Ala
        275                 280                 285

Leu Lys Glu Asp Leu Arg Ser Trp Thr Ala Ala Asp Met Ala Ala Gln
    290                 295                 300

Thr Thr Lys His Lys Trp Glu Ala Ala His Val Ala Glu Gln Leu Arg
305                 310                 315                 320

Ala Tyr Leu Glu Gly Thr Cys Val Glu Trp Leu Arg Arg Tyr Leu Glu
                325                 330                 335

Asn Gly Lys Glu Thr Leu Gln Arg Thr Asp Ala Pro Lys Thr His Met
            340                 345                 350

Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
    370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
                405                 410                 415

Glu Gln Arg Tyr Thr Cys His Val Gln His Glu Gly Leu Pro Lys Pro
            420                 425                 430

Leu Thr Leu Arg Trp Glu Pro Gly Gly Gly Gly Ser Gly Gly Gly Gly
        435                 440                 445

Ser Cys Glu Ala Ile Lys Ala Ala Ala Glu Leu Gly Lys Ala Gly Ile
    450                 455                 460

Ser Ser Glu Glu Ile Leu Glu Leu Leu Arg Ala Ala His Glu Leu Gly
465                 470                 475                 480

Leu Asp Pro Glu Ala Ile Lys Ala Ala Ala Glu Leu Gly Lys Ala Gly
                485                 490                 495

Ile Ser Ser Glu Glu Ile Leu Glu Leu Leu Arg Ala Ala His Glu Leu
            500                 505                 510

Gly Leu Asp Pro Glu Ala Ile Lys Ala Ala Ala Glu Leu Gly Lys Ala
        515                 520                 525
```

```
Gly Ile Ser Ser Glu Glu Ile Leu Glu Leu Leu Arg Ala Ala His Glu
    530                 535                 540

Leu Gly Leu Asp Pro Glu Ala Ile Lys Ala Ala Ala Glu Leu Gly Lys
545                 550                 555                 560

Ala Gly Ile Ser Ser Glu Glu Ile Leu Glu Leu Leu Arg Ala Ala His
                565                 570                 575

Glu Leu Gly Leu Asp Pro Glu Ala Ile Lys Ala Ala Ala Glu Leu Gly
            580                 585                 590

Lys Ala Gly Ile Ser Ser Glu Glu Ile Leu Glu Leu Leu Arg Ala Ala
        595                 600                 605

His Glu Leu Gly Leu Asp Pro Glu Cys Ile Lys Ala Ala Ala Glu Leu
    610                 615                 620

Gly Lys Ala Gly Ile Ser Ser Glu Glu Ile Leu Glu Leu Leu Arg Ala
625                 630                 635                 640

Ala His Glu Leu Gly Leu
                645
```

<210> SEQ ID NO 126
<211> LENGTH: 1056
<212> TYPE: DNA
<213> ORGANISM: Artificial Sequence
<220> FEATURE:
<223> OTHER INFORMATION: Synthesized cTRP24_Sub6_SS_mFAP (Construct containing 6 repeats and inserted fusions of mFAP fluorescent protein domains)

<400> SEQUENCE: 126

```
atggctagca gccatcatca tcatcatcat agcagcggcc tggtgccgcg cggcagctcc     60

atgggcctgg attgcgaggc gattaaggct gcggcggaac tgggtaaagc gggcatcagc    120

agcgaggaaa ttctggagct gctgcgtgcg gcgcatgagc tgggtctgga cccggaagcg    180

atcaaggctg cggcggagct gggcaaggcg ggcatcagca gcgaagaaat tctggaactg    240

ctgcgcgcgg cgcatgaact gggtctggac ccggaggcga tcaaagctgc ggcggagctg    300

ggtaaggctg gcatcagcag cgaagagatt ctggaattat tacgcgctgc tcatgagtta    360

ggtctggacc cggaagctat taaagctgcg gcggaactgg gcaaagcggg tggcggtagc    420

ggcggtggca gcagccgtgc ggcgcagctg ctgccgggca cctggcaagc gaccttcacc    480

aacgaagatg gtcagaccag ccagggccaa tggcactttc aaccgcgtag cccgtacacg    540

atggacatcg tggcgcaggg caccatcagc gatggccgtc cgatcgtggg ttacggcaag    600

gcgaccgtta aaaccccgga caccctggac atcgatatta cctatccgag cctgggtaac    660

attaaggcgc agggccaaat cacgatggac agcccgaccc aattcaagtg ggatgcgacc    720

accaaaggcg agaacgactt tcacggtcgt ctgaccggca ccctgcagcg tcaagaaggt    780

ggcggtagcg gcggtggcag cggtatcagc agcgaggaga ttctggagtt attacgcgct    840

gcccatgagt tgggtctgga cccggaagca attaaggctg cggcggagtt aggcaaagct    900

ggcatcagca gcgaggagat tctggaatta cttcgcgctg ctcatgagct tggtctggac    960

ccggaatgca tcaaggctgc ggcggaatta ggcaaggctg gcatcagcag cgaggaaatt   1020

ctggagttac tgcgtgcggc gcatgaactg ggctaa                             1056
```

<210> SEQ ID NO 127
<211> LENGTH: 351
<212> TYPE: PRT
<213> ORGANISM: Artificial Sequence
<220> FEATURE:
<223> OTHER INFORMATION: Synthesized cTRP24_Sub6_SS_mFAP (Construct containing 6 repeats and inserted fusions of mFAP fluorescent protein domains)

<400> SEQUENCE: 127

Met Ala Ser Ser His His His His His His Ser Ser Gly Leu Val Pro
1 5 10 15

Arg Gly Ser Ser Met Gly Leu Asp Cys Glu Ala Ile Lys Ala Ala Ala
20 25 30

Glu Leu Gly Lys Ala Gly Ile Ser Ser Glu Glu Ile Leu Glu Leu Leu
35 40 45

Arg Ala Ala His Glu Leu Gly Leu Asp Pro Glu Ala Ile Lys Ala Ala
50 55 60

Ala Glu Leu Gly Lys Ala Gly Ile Ser Ser Glu Glu Ile Leu Glu Leu
65 70 75 80

Leu Arg Ala Ala His Glu Leu Gly Leu Asp Pro Glu Ala Ile Lys Ala
85 90 95

Ala Ala Glu Leu Gly Lys Ala Gly Ile Ser Ser Glu Glu Ile Leu Glu
100 105 110

Leu Leu Arg Ala Ala His Glu Leu Gly Leu Asp Pro Glu Ala Ile Lys
115 120 125

Ala Ala Ala Glu Leu Gly Lys Ala Gly Gly Gly Ser Gly Gly Gly Ser
130 135 140

Ser Arg Ala Ala Gln Leu Leu Pro Gly Thr Trp Gln Ala Thr Phe Thr
145 150 155 160

Asn Glu Asp Gly Gln Thr Ser Gln Gly Gln Trp His Phe Gln Pro Arg
165 170 175

Ser Pro Tyr Thr Met Asp Ile Val Ala Gln Gly Thr Ile Ser Asp Gly
180 185 190

Arg Pro Ile Val Gly Tyr Gly Lys Ala Thr Val Lys Thr Pro Asp Thr
195 200 205

Leu Asp Ile Asp Ile Thr Tyr Pro Ser Leu Gly Asn Ile Lys Ala Gln
210 215 220

Gly Gln Ile Thr Met Asp Ser Pro Thr Gln Phe Lys Trp Asp Ala Thr
225 230 235 240

Thr Lys Gly Glu Asn Asp Phe His Gly Arg Leu Thr Gly Thr Leu Gln
245 250 255

Arg Gln Glu Gly Gly Gly Ser Gly Gly Gly Ser Gly Ile Ser Ser Glu
260 265 270

Glu Ile Leu Glu Leu Leu Arg Ala Ala His Glu Leu Gly Leu Asp Pro
275 280 285

Glu Ala Ile Lys Ala Ala Ala Glu Leu Gly Lys Ala Gly Ile Ser Ser
290 295 300

Glu Glu Ile Leu Glu Leu Leu Arg Ala Ala His Glu Leu Gly Leu Asp
305 310 315 320

Pro Glu Cys Ile Lys Ala Ala Ala Glu Leu Gly Lys Ala Gly Ile Ser
325 330 335

Ser Glu Glu Ile Leu Glu Leu Leu Arg Ala Ala His Glu Leu Gly
340 345 350

<210> SEQ ID NO 128
<211> LENGTH: 2292
<212> TYPE: DNA
<213> ORGANISM: Artificial Sequence
<220> FEATURE:
<223> OTHER INFORMATION: Synthesized cTRP24_Sub6SS_scMHC_mFAP (Construct containing 6 repeats and inserted fusions of scMHC and mFAP fluorescent protein domains)

<400> SEQUENCE: 128

```
atggagaccg atacactgct gctgtgggtg ctgctgctgt gggtgcccgg cagcacaggc     60
tacatgctgg acctgcagcc tgagactgga ggaggaggat ccggaggagg aggctctggc    120
ggcggcggca gcatccagcg gaccccaaag atccaggtgt acagccggca cccagcagag    180
aacggcaaga gcaacttcct gaattgctac gtgagcggct ttcacccctc tgacatcgag    240
gtggatctgc tgaagaatgg cgagagaatc gagaaggtgg agcactccga cctgtctttc    300
agcaaggatt ggtcttttta cctgctgtac tatacagagt tcacccctac agagaaggac    360
gagtatgcct gtcgggtgaa ccacgtgacc ctgtcccagc caaagatcgt gaagtgggac    420
agagatatgg gaggaggagg cagcggcggc ggaggctccg gaggcggcgg ctctggagga    480
ggcggctccg gctctcacag catgaggtac ttctttacat ccgtgtctag gccaggaagg    540
ggagagcctc ggtttatcgc cgtgggctat gtggacgata cccagttcgt gagatttgac    600
agcgatgcag cctcccagag gatggagcca cgcgccccct ggatcgagca ggagggccct    660
gagtactggg atggcgagac caggaaggtg aaggcccaca gccagacaca cagggtggac    720
ctgggcaccc tgagaggagc ctacaaccag tctgaggcag gcagccacac cgtgcagagg    780
atgtatggct gcgacgtggg ctccgattgg cggttcctga gaggctacca ccagtacgcc    840
tatgacggca aggattatat cgccctgaag gaggacctgc ggagctggac agcagcagat    900
atggcagccc agaccacaaa gcacaagtgg gaggcagcac acgtggcaga gcagctgaga    960
gcctacctgg agggcacctg cgtggagtgg ctgcggagat acctggagaa tggcaaggag   1020
acactgcaga ggaccgatgc ccccaagacc cacatgacac accacgccgt gtctgaccac   1080
gaggccaccc tgaggtgttg ggcactgagc ttctaccctg ccgagatcac cctgacatgg   1140
cagagggacg gcgaggatca gacccaggat acagagctgg tggagacaag gccagcaggc   1200
gacggcacct ttcagaagtg ggcagcagtg gtggtgccct ccggacagga gcagaggtat   1260
acatgccacg tgcagcacga gggactgcca aagcctctga ccctgagatg ggagccagga   1320
ggaggaggca gcggaggagg aggctcctgt gaggccatca aggctgccgc cgagctgggc   1380
aaggcaggca tcagctccga ggagatcctg gagctgctga gggcagcaca cgagctgggc   1440
ctggaccccg aagccatcaa ggctgccgcc gaactgggca aggccggcat ctctagcgaa   1500
gaaatcctgg agctgctgag agccgcccat gaactgggcc tggaccccga ggccatcaag   1560
gctgccgccg agttaggcaa ggcaggcatc tcctctgaag agatcctgga gttattaaga   1620
gccgcccatg agttaggcct ggaccccgag gccatcaagg ctgccgccga gctaggcaag   1680
gccggcatca gctccgaaga aatcctggag ttactgagag ccgcccatga gctgggcctg   1740
gacccagagg ccatcaaggc tgccgccgag cttggcaagg caggcatctc tagcgaagag   1800
atcctggagc ttttaagagc cgcccacgaa ttaggcctgg accccgagtg tatcaaggct   1860
gccgccgagc tcggcaaggc cggcatctcc tctgaggaaa tcctggagtt gttaagggcc   1920
gcccacgagc tgggaggagg cagctcccgc gccgcccagc tgctgcccgg cacatggcag   1980
gccaccttca caaatgagga cggacagacc agccagggac agtggcactt tcagcctcgg   2040
tccccataca caatggacat cgtggcacag ggcaccatca gcgacggcag acctatcgtg   2100
ggctacggca aggccaccgt gaagacacct gacaccctgg acatcgacat cacctatcca   2160
tccctgggca acatcaaggc ccagggccag atcacaatgg actctccaac ccagttcaag   2220
tgggatgcca ccacaaaggg cgagaatgac tttcacggca ggctgaccgg cacactgcag   2280
```

aggcaggagt aa 2292

<210> SEQ ID NO 129
<211> LENGTH: 763
<212> TYPE: PRT
<213> ORGANISM: Artificial Sequence
<220> FEATURE:
<223> OTHER INFORMATION: Synthesized cTRP24_Sub6SS_scMHC_mFAP

<400> SEQUENCE: 129

Met Glu Thr Asp Thr Leu Leu Leu Trp Val Leu Leu Leu Trp Val Pro
1 5 10 15

Gly Ser Thr Gly Tyr Met Leu Asp Leu Gln Pro Glu Thr Gly Gly Gly
20 25 30

Gly Ser Gly Gly Gly Gly Ser Gly Gly Gly Gly Ser Ile Gln Arg Thr
35 40 45

Pro Lys Ile Gln Val Tyr Ser Arg His Pro Ala Glu Asn Gly Lys Ser
50 55 60

Asn Phe Leu Asn Cys Tyr Val Ser Gly Phe His Pro Ser Asp Ile Glu
65 70 75 80

Val Asp Leu Leu Lys Asn Gly Glu Arg Ile Glu Lys Val Glu His Ser
85 90 95

Asp Leu Ser Phe Ser Lys Asp Trp Ser Phe Tyr Leu Leu Tyr Tyr Thr
100 105 110

Glu Phe Thr Pro Thr Glu Lys Asp Glu Tyr Ala Cys Arg Val Asn His
115 120 125

Val Thr Leu Ser Gln Pro Lys Ile Val Lys Trp Asp Arg Asp Met Gly
130 135 140

Gly Gly Gly Ser Gly Gly Gly Gly Ser Gly Gly Gly Gly Ser Gly Gly
145 150 155 160

Gly Gly Ser Gly Ser His Ser Met Arg Tyr Phe Phe Thr Ser Val Ser
165 170 175

Arg Pro Gly Arg Gly Glu Pro Arg Phe Ile Ala Val Gly Tyr Val Asp
180 185 190

Asp Thr Gln Phe Val Arg Phe Asp Ser Asp Ala Ala Ser Gln Arg Met
195 200 205

Glu Pro Arg Ala Pro Trp Ile Glu Gln Glu Gly Pro Glu Tyr Trp Asp
210 215 220

Gly Glu Thr Arg Lys Val Lys Ala His Ser Gln Thr His Arg Val Asp
225 230 235 240

Leu Gly Thr Leu Arg Gly Ala Tyr Asn Gln Ser Glu Ala Gly Ser His
245 250 255

Thr Val Gln Arg Met Tyr Gly Cys Asp Val Gly Ser Asp Trp Arg Phe
260 265 270

Leu Arg Gly Tyr His Gln Tyr Ala Tyr Asp Gly Lys Asp Tyr Ile Ala
275 280 285

Leu Lys Glu Asp Leu Arg Ser Trp Thr Ala Ala Asp Met Ala Ala Gln
290 295 300

Thr Thr Lys His Lys Trp Glu Ala Ala His Val Ala Glu Gln Leu Arg
305 310 315 320

Ala Tyr Leu Glu Gly Thr Cys Val Glu Trp Leu Arg Arg Tyr Leu Glu
325 330 335

Asn Gly Lys Glu Thr Leu Gln Arg Thr Asp Ala Pro Lys Thr His Met
340 345 350

-continued

```
Thr His His Ala Val Ser Asp His Glu Ala Thr Leu Arg Cys Trp Ala
        355                 360                 365

Leu Ser Phe Tyr Pro Ala Glu Ile Thr Leu Thr Trp Gln Arg Asp Gly
    370                 375                 380

Glu Asp Gln Thr Gln Asp Thr Glu Leu Val Glu Thr Arg Pro Ala Gly
385                 390                 395                 400

Asp Gly Thr Phe Gln Lys Trp Ala Ala Val Val Val Pro Ser Gly Gln
                405                 410                 415

Glu Gln Arg Tyr Thr Cys His Val Gln His Glu Gly Leu Pro Lys Pro
            420                 425                 430

Leu Thr Leu Arg Trp Glu Pro Gly Gly Gly Gly Ser Gly Gly Gly Gly
        435                 440                 445

Ser Cys Glu Ala Ile Lys Ala Ala Ala Glu Leu Gly Lys Ala Gly Ile
    450                 455                 460

Ser Ser Glu Glu Ile Leu Glu Leu Leu Arg Ala Ala His Glu Leu Gly
465                 470                 475                 480

Leu Asp Pro Glu Ala Ile Lys Ala Ala Ala Glu Leu Gly Lys Ala Gly
                485                 490                 495

Ile Ser Ser Glu Glu Ile Leu Glu Leu Leu Arg Ala Ala His Glu Leu
            500                 505                 510

Gly Leu Asp Pro Glu Ala Ile Lys Ala Ala Ala Glu Leu Gly Lys Ala
        515                 520                 525

Gly Ile Ser Ser Glu Glu Ile Leu Glu Leu Leu Arg Ala Ala His Glu
    530                 535                 540

Leu Gly Leu Asp Pro Glu Ala Ile Lys Ala Ala Ala Glu Leu Gly Lys
545                 550                 555                 560

Ala Gly Ile Ser Ser Glu Glu Ile Leu Glu Leu Leu Arg Ala Ala His
                565                 570                 575

Glu Leu Gly Leu Asp Pro Glu Ala Ile Lys Ala Ala Ala Glu Leu Gly
            580                 585                 590

Lys Ala Gly Ile Ser Ser Glu Glu Ile Leu Glu Leu Leu Arg Ala Ala
        595                 600                 605

His Glu Leu Gly Leu Asp Pro Glu Cys Ile Lys Ala Ala Ala Glu Leu
    610                 615                 620

Gly Lys Ala Gly Ile Ser Ser Glu Glu Ile Leu Glu Leu Leu Arg Ala
625                 630                 635                 640

Ala His Glu Leu Gly Gly Gly Ser Ser Arg Ala Ala Gln Leu Leu Pro
                645                 650                 655

Gly Thr Trp Gln Ala Thr Phe Thr Asn Glu Asp Gly Gln Thr Ser Gln
            660                 665                 670

Gly Gln Trp His Phe Gln Pro Arg Ser Pro Tyr Thr Met Asp Ile Val
        675                 680                 685

Ala Gln Gly Thr Ile Ser Asp Gly Arg Pro Ile Val Gly Tyr Gly Lys
    690                 695                 700

Ala Thr Val Lys Thr Pro Asp Thr Leu Asp Ile Asp Ile Thr Tyr Pro
705                 710                 715                 720

Ser Leu Gly Asn Ile Lys Ala Gln Gly Gln Ile Thr Met Asp Ser Pro
                725                 730                 735

Thr Gln Phe Lys Trp Asp Ala Thr Thr Lys Gly Glu Asn Asp Phe His
            740                 745                 750

Gly Arg Leu Thr Gly Thr Leu Gln Arg Gln Glu
        755                 760
```

```
<210> SEQ ID NO 130
<211> LENGTH: 521
<212> TYPE: PRT
<213> ORGANISM: Artificial Sequence
<220> FEATURE:
<223> OTHER INFORMATION: Synthesized Aqualysin fused to cTRP24_Sub6SS

<400> SEQUENCE: 130

Met Glu Thr Asp Thr Leu Leu Leu Trp Val Leu Leu Leu Trp Val Pro
1               5                   10                  15

Gly Ser Thr Gly Asp Tyr Lys Asp Glu Ala Thr Gln Ser Pro Ala Pro
            20                  25                  30

Trp Gly Leu Asp Arg Ile Asp Gln Arg Asp Leu Pro Leu Ser Asn Ser
        35                  40                  45

Tyr Thr Tyr Thr Ala Thr Gly Arg Gly Val Asn Val Tyr Val Ile Asp
    50                  55                  60

Thr Gly Ile Arg Thr Thr His Arg Glu Phe Gly Gly Arg Ala Arg Val
65                  70                  75                  80

Gly Tyr Asp Ala Leu Gly Gly Asn Gly Gln Asp Cys Asn Gly His Gly
                85                  90                  95

Thr His Val Ala Gly Thr Ile Gly Gly Val Thr Tyr Gly Val Ala Lys
            100                 105                 110

Ala Val Asn Leu Tyr Ala Val Arg Val Leu Asp Cys Asp Gly Ser Gly
        115                 120                 125

Ser Thr Ser Gly Val Ile Ala Gly Val Asp Trp Val Thr Arg Asn His
    130                 135                 140

Arg Arg Pro Ala Val Ala Ser Met Ser Leu Gly Gly Gly Val Ser Thr
145                 150                 155                 160

Ala Leu Asp Asn Ala Val Lys Asn Ser Ile Ala Ala Gly Val Val Tyr
                165                 170                 175

Ala Val Ala Ala Gly Asn Asp Asn Ala Asn Ala Cys Asp Tyr Ser Pro
            180                 185                 190

Ala Arg Val Ala Glu Ala Leu Thr Val Gly Ala Thr Thr Ser Ser Asp
        195                 200                 205

Ala Arg Ala Ser Phe Ser Asn Tyr Gly Ser Cys Val Asp Leu Phe Ala
    210                 215                 220

Pro Gly Ala Ser Ile Pro Ser Ala Trp Tyr Thr Ser Asp Thr Ala Thr
225                 230                 235                 240

Gln Thr Leu Asp Gly Thr Ser Met Ala Thr Pro His Val Ala Gly Val
                245                 250                 255

Ala Ala Leu Tyr Leu Glu Gln Asn Pro Ser Ala Thr Pro Ala Ser Val
            260                 265                 270

Ala Ser Ala Ile Leu Asn Gly Ala Thr Thr Gly Arg Leu Ser Gly Ile
        275                 280                 285

Gly Ser Gly Ser Pro Asn Arg Leu Leu Tyr Ser Leu Leu Ser Ser Gly
    290                 295                 300

Ser Gly Gly Gly Gly Ser Gly Gly Gly Gly Ser Cys Glu Ala Ile Lys
305                 310                 315                 320

Ala Ala Ala Glu Leu Gly Lys Ala Gly Ile Ser Ser Glu Glu Ile Leu
                325                 330                 335

Glu Leu Leu Arg Ala Ala His Glu Leu Gly Leu Asp Pro Glu Ala Ile
            340                 345                 350

Lys Ala Ala Ala Glu Leu Gly Lys Ala Gly Ile Ser Ser Glu Glu Ile
        355                 360                 365

Leu Glu Leu Leu Arg Ala Ala His Glu Leu Gly Leu Asp Pro Glu Ala
```

```
    370                 375                 380

Ile Lys Ala Ala Ala Glu Leu Gly Lys Ala Gly Ile Ser Ser Glu Glu
385                 390                 395                 400

Ile Leu Glu Leu Leu Arg Ala Ala His Glu Leu Gly Leu Asp Pro Glu
                405                 410                 415

Ala Ile Lys Ala Ala Ala Glu Leu Gly Lys Ala Gly Ile Ser Ser Glu
            420                 425                 430

Glu Ile Leu Glu Leu Leu Arg Ala Ala His Glu Leu Gly Leu Asp Pro
        435                 440                 445

Glu Ala Ile Lys Ala Ala Ala Glu Leu Gly Lys Ala Gly Ile Ser Ser
    450                 455                 460

Glu Glu Ile Leu Glu Leu Leu Arg Ala Ala His Glu Leu Gly Leu Asp
465                 470                 475                 480

Pro Glu Cys Ile Lys Ala Ala Ala Glu Leu Gly Lys Ala Gly Ile Ser
                485                 490                 495

Ser Glu Glu Ile Leu Glu Leu Leu Arg Ala Ala His Glu Leu Gly Leu
            500                 505                 510

Gly Gly Ser His His His His His His
        515                 520
```

<210> SEQ ID NO 131
<211> LENGTH: 813
<212> TYPE: DNA
<213> ORGANISM: Artificial Sequence
<220> FEATURE:
<223> OTHER INFORMATION: Synthesized Clover fluorescent protein with N-terminal spytag

<400> SEQUENCE: 131

```
atgggcagca gccatcatca tcatcatcac agcagcggcc tggtgccgcg cggcagcgct     60

cacatcgtta tggtagatgc gtacaagccc accaaagggt ctagcggaag tagtggtagt    120

catatgatgg tgagcaaggg cgaggagctg ttcaccgggg tggtgcccat cctggtcgag    180

ctggacggcg acgtaaacgg ccacaagttc agcgtccgcg gcgagggcga gggcgatgcc    240

accaacggca agctgaccct gaagttcatc tgcaccaccg gcaagctgcc cgtgccctgg    300

cccaccctcg tgaccacctt cggctacggc gtggcctgct tcagccgcta ccccgaccac    360

atgaagcagc acgacttctt caagtccgcc atgcccgaag gctacgtcca ggagcgcacc    420

atctctttca aggacgacgg tacctacaag acccgcgccg aggtgaagtt cgagggcgac    480

accctggtga accgcatcga gctgaagggc atcgacttca aggaggacgg caacatcctg    540

gggcacaagc tggagtacaa cttcaacagc cacaacgtct atatcacggc cgacaagcag    600

aagaacggca tcaaggctaa cttcaagatc cgccacaacg ttgaggacgg cagcgtgcag    660

ctcgccgacc actaccagca gaacaccccc atcggcgacg gccccgtgct gctgcccgac    720

aaccactacc tgagccatca gtccgccctg agcaaagacc ccaacgagaa gcgcgatcac    780

atggtcctgc tggagttcgt gaccgccgcc tag                                 813
```

<210> SEQ ID NO 132
<211> LENGTH: 270
<212> TYPE: PRT
<213> ORGANISM: Artificial Sequence
<220> FEATURE:
<223> OTHER INFORMATION: Synthesized Clover fluorescent protein with N-terminal spytag

<400> SEQUENCE: 132

```
Met Gly Ser Ser His His His His His His Ser Ser Gly Leu Val Pro
1               5                   10                  15

Arg Gly Ser Ala His Ile Val Met Val Asp Ala Tyr Lys Pro Thr Lys
            20                  25                  30

Gly Ser Ser Gly Ser Ser Gly Ser His Met Met Val Ser Lys Gly Glu
        35                  40                  45

Glu Leu Phe Thr Gly Val Val Pro Ile Leu Val Glu Leu Asp Gly Asp
    50                  55                  60

Val Asn Gly His Lys Phe Ser Val Arg Gly Glu Gly Glu Gly Asp Ala
65                  70                  75                  80

Thr Asn Gly Lys Leu Thr Leu Lys Phe Ile Cys Thr Thr Gly Lys Leu
                85                  90                  95

Pro Val Pro Trp Pro Thr Leu Val Thr Thr Phe Gly Tyr Gly Val Ala
            100                 105                 110

Cys Phe Ser Arg Tyr Pro Asp His Met Lys Gln His Asp Phe Phe Lys
        115                 120                 125

Ser Ala Met Pro Glu Gly Tyr Val Gln Glu Arg Thr Ile Ser Phe Lys
    130                 135                 140

Asp Asp Gly Thr Tyr Lys Thr Arg Ala Glu Val Lys Phe Glu Gly Asp
145                 150                 155                 160

Thr Leu Val Asn Arg Ile Glu Leu Lys Gly Ile Asp Phe Lys Glu Asp
                165                 170                 175

Gly Asn Ile Leu Gly His Lys Leu Glu Tyr Asn Phe Asn Ser His Asn
            180                 185                 190

Val Tyr Ile Thr Ala Asp Lys Gln Lys Asn Gly Ile Lys Ala Asn Phe
        195                 200                 205

Lys Ile Arg His Asn Val Glu Asp Gly Ser Val Gln Leu Ala Asp His
    210                 215                 220

Tyr Gln Gln Asn Thr Pro Ile Gly Asp Gly Pro Val Leu Leu Pro Asp
225                 230                 235                 240

Asn His Tyr Leu Ser His Gln Ser Ala Leu Ser Lys Asp Pro Asn Glu
                245                 250                 255

Lys Arg Asp His Met Val Leu Leu Glu Phe Val Thr Ala Ala
            260                 265                 270


<210> SEQ ID NO 133
<211> LENGTH: 228
<212> TYPE: PRT
<213> ORGANISM: Artificial Sequence
<220> FEATURE:
<223> OTHER INFORMATION: Synthesized Clover Fluorescent Protein

<400> SEQUENCE: 133

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Val Ala Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95
```

```
Arg Thr Ile Ser Phe Lys Asp Asp Gly Thr Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Lys Ile Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser His Gln Ser Ala Leu
        195                 200                 205

Ser Lys Asp Pro Asn Glu Lys Arg Asp His Met Val Leu Leu Glu Phe
    210                 215                 220

Val Thr Ala Ala
225


<210> SEQ ID NO 134
<211> LENGTH: 235
<212> TYPE: PRT
<213> ORGANISM: Artificial Sequence
<220> FEATURE:
<223> OTHER INFORMATION: Synthesized mKate Fluorescent Protein

<400> SEQUENCE: 134

Met Val Ser Lys Gly Glu Glu Leu Ile Lys Glu Asn Met His Met Lys
1               5                   10                  15

Leu Tyr Met Glu Gly Thr Val Asn Asn His His Phe Lys Cys Thr Ser
            20                  25                  30

Glu Gly Glu Gly Lys Pro Tyr Glu Gly Thr Gln Thr Met Arg Ile Lys
        35                  40                  45

Ala Val Glu Gly Gly Pro Leu Pro Phe Ala Phe Asp Ile Leu Ala Thr
    50                  55                  60

Ser Phe Met Tyr Gly Ser Lys Thr Phe Ile Asn His Thr Gln Gly Ile
65                  70                  75                  80

Pro Asp Phe Phe Lys Gln Ser Phe Pro Glu Gly Phe Thr Trp Glu Arg
                85                  90                  95

Val Thr Thr Tyr Glu Asp Gly Gly Val Leu Thr Ala Thr Gln Asp Thr
            100                 105                 110

Ser Leu Gln Asp Gly Cys Leu Ile Tyr Asn Val Lys Ile Arg Gly Val
        115                 120                 125

Asn Phe Pro Ser Asn Gly Pro Val Met Gln Lys Lys Thr Leu Gly Trp
    130                 135                 140

Glu Ala Ser Thr Glu Thr Leu Tyr Pro Ala Asp Gly Gly Leu Glu Gly
145                 150                 155                 160

Arg Ala Asp Met Ala Leu Lys Leu Val Gly Gly Gly His Leu Ile Cys
                165                 170                 175

Asn Leu Lys Thr Thr Tyr Arg Ser Lys Lys Pro Ala Lys Asn Leu Lys
            180                 185                 190

Met Pro Gly Val Tyr Tyr Val Asp Arg Arg Leu Glu Arg Ile Lys Glu
        195                 200                 205

Ala Asp Lys Glu Thr Tyr Val Glu Gln His Glu Val Ala Val Ala Arg
    210                 215                 220
```

```
Tyr Cys Asp Leu Pro Ser Lys Leu Gly His Arg
225                 230                 235


<210> SEQ ID NO 135
<211> LENGTH: 423
<212> TYPE: DNA
<213> ORGANISM: Artificial Sequence
<220> FEATURE:
<223> OTHER INFORMATION: Synthesized SH2-SpyTag (SH2 domain with
      N-terminal spytag)

<400> SEQUENCE: 135

atgggcagca gccatcatca tcatcatcac agcagcggcc tggtgccgcg cggcagcgct     60

cacatcgtta tggtagatgc gtacaagccc accaaagggt ctagcggaag tagtggtagt    120

catatgtccg agtggtacta cgggaacgtg acgcggcacc aggccgagtg cgccctcaac    180

gagcggggcg tggagggcga cttcctcatt agggacagcg agtcctcgcc cagcgacttc    240

tccgtgtccc ttaaagcgtc agggaagaac aaacacttca aggtgcagct cgtggacaat    300

gtctactgca ttgggcagcg gcgcttccac accatggacg agctggtgga acactacaaa    360

aaggcgccca tcttcaccag cgagcacggg gagaagctct acctcgtcag ggccctgcag    420

tga                                                                  423


<210> SEQ ID NO 136
<211> LENGTH: 140
<212> TYPE: PRT
<213> ORGANISM: artificial Sequence
<220> FEATURE:
<223> OTHER INFORMATION: Synthesized SH2-SpyTag (SH2 domain with
      N-terminal spytag)

<400> SEQUENCE: 136

Met Gly Ser Ser His His His His His His Ser Ser Gly Leu Val Pro
1               5                   10                  15

Arg Gly Ser Ala His Ile Val Met Val Asp Ala Tyr Lys Pro Thr Lys
            20                  25                  30

Gly Ser Ser Gly Ser Ser Gly Ser His Met Ser Glu Trp Tyr Tyr Gly
        35                  40                  45

Asn Val Thr Arg His Gln Ala Glu Cys Ala Leu Asn Glu Arg Gly Val
    50                  55                  60

Glu Gly Asp Phe Leu Ile Arg Asp Ser Glu Ser Ser Pro Ser Asp Phe
65                  70                  75                  80

Ser Val Ser Leu Lys Ala Ser Gly Lys Asn Lys His Phe Lys Val Gln
                85                  90                  95

Leu Val Asp Asn Val Tyr Cys Ile Gly Gln Arg Arg Phe His Thr Met
            100                 105                 110

Asp Glu Leu Val Glu His Tyr Lys Lys Ala Pro Ile Phe Thr Ser Glu
        115                 120                 125

His Gly Glu Lys Leu Tyr Leu Val Arg Ala Leu Gln
    130                 135                 140


<210> SEQ ID NO 137
<211> LENGTH: 360
<212> TYPE: DNA
<213> ORGANISM: Artificial Sequence
<220> FEATURE:
<223> OTHER INFORMATION: Synthesized SH2 (Free SH2 domain)

<400> SEQUENCE: 137

atggctagca gccatcatca tcatcatcat agcagcggcc tggtgccgcg cggcagccat     60
```

```
atgtccgagt ggtactacgg gaacgtgacg cggcaccagg ccgagtgcgc cctcaacgag    120

cggggcgtgg agggcgactt cctcattagg gacagcgagt cctcgcccag cgacttctcc    180

gtgtccctta aagcgtcagg gaagaacaaa cacttcaagg tgcagctcgt ggacaatgtc    240

tactgcattg ggcagcggcg cttccacacc atggacgagc tggtggaaca ctacaaaaag    300

gcgcccatct tcaccagcga gcacggggag aagctctacc tcgtcagggc cctgcagtga    360


<210> SEQ ID NO 138
<211> LENGTH: 119
<212> TYPE: PRT
<213> ORGANISM: Artificial Sequence
<220> FEATURE:
<223> OTHER INFORMATION: Synthesized SH2 (Free SH2 domain)

<400> SEQUENCE: 138

Met Ala Ser Ser His His His His His His Ser Ser Gly Leu Val Pro
1               5                   10                  15

Arg Gly Ser His Met Ser Glu Trp Tyr Tyr Gly Asn Val Thr Arg His
            20                  25                  30

Gln Ala Glu Cys Ala Leu Asn Glu Arg Gly Val Glu Gly Asp Phe Leu
        35                  40                  45

Ile Arg Asp Ser Glu Ser Ser Pro Ser Asp Phe Ser Val Ser Leu Lys
    50                  55                  60

Ala Ser Gly Lys Asn Lys His Phe Lys Val Gln Leu Val Asp Asn Val
65                  70                  75                  80

Tyr Cys Ile Gly Gln Arg Arg Phe His Thr Met Asp Glu Leu Val Glu
                85                  90                  95

His Tyr Lys Lys Ala Pro Ile Phe Thr Ser Glu His Gly Glu Lys Leu
            100                 105                 110

Tyr Leu Val Arg Ala Leu Gln
        115


<210> SEQ ID NO 139
<211> LENGTH: 290
<212> TYPE: PRT
<213> ORGANISM: Artificial Sequence
<220> FEATURE:
<223> OTHER INFORMATION: Synthesized Spytagged single chain Fv (scFv)
      targeting IHF-1

<400> SEQUENCE: 139

Met Glu Thr Asp Thr Leu Leu Leu Trp Val Leu Leu Leu Trp Val Pro
1               5                   10                  15

Gly Ser Thr Gly Ser Gly Ser Ser Ala His Ile Val Met Val Asp Ala
            20                  25                  30

Tyr Lys Pro Thr Lys Asp Ile Val Leu Thr Gln Ala Pro Gly Thr Leu
        35                  40                  45

Ser Leu Ser Pro Gly Asp Arg Ala Thr Leu Ser Cys Arg Ala Ser Gln
    50                  55                  60

Arg Leu Gly Gly Thr Ser Leu Ala Trp Tyr Gln His Arg Ser Gly Gln
65                  70                  75                  80

Ala Pro Arg Leu Ile Leu Tyr Gly Thr Ser Asn Arg Ala Thr Asp Thr
                85                  90                  95

Pro Asp Arg Phe Ser Gly Ser Gly Ser Gly Thr Asp Phe Val Leu Thr
            100                 105                 110

Ile Ser Ser Leu Glu Pro Glu Asp Phe Ala Val Tyr Tyr Cys Gln Gln
        115                 120                 125
```

Tyr Gly Ser Pro Pro Tyr Thr Phe Gly Gln Gly Thr Thr Leu Asp Ile
130 135 140

Lys Gly Gly Gly Gly Ser Gly Gly Gly Gly Ser Gly Gly Gly Gly Ser
145 150 155 160

Gln Val Gln Leu Val Glu Ser Gly Pro Gly Leu Val Lys Pro Ser Glu
165 170 175

Thr Leu Ser Leu Thr Cys Arg Val Ser Gly Asp Ser Asn Arg Pro Ser
180 185 190

Tyr Trp Ser Trp Ile Arg Gln Ala Pro Gly Lys Ala Met Glu Trp Ile
195 200 205

Gly Tyr Val Tyr Asp Ser Gly Val Thr Ile Tyr Asn Pro Ser Leu Lys
210 215 220

Gly Arg Val Thr Ile Ser Leu Asp Thr Ser Lys Thr Arg Phe Ser Leu
225 230 235 240

Lys Leu Thr Ser Val Ile Ala Ala Asp Thr Ala Val Tyr Tyr Cys Ala
245 250 255

Arg Glu Arg Phe Asp Arg Thr Ser Tyr Lys Ser Trp Trp Gly Gln Gly
260 265 270

Thr Gln Val Thr Val Ser Ser Gly Gly Gly Gly Ser His His His His
275 280 285

His His
290

<210> SEQ ID NO 140
<211> LENGTH: 479
<212> TYPE: PRT
<213> ORGANISM: Artificial Sequence
<220> FEATURE:
<223> OTHER INFORMATION: Synthesized scFv_IHF1_TRL1068-
Toroidx6_SS_tetramer-His

<400> SEQUENCE: 140

Met Glu Thr Asp Thr Leu Leu Leu Trp Val Leu Leu Leu Trp Val Pro
1 5 10 15

Gly Ser Thr Gly Gln Val Gln Leu Val Glu Ser Gly Pro Gly Leu Val
20 25 30

Lys Pro Ser Glu Thr Leu Ser Leu Thr Cys Arg Val Ser Gly Asp Ser
35 40 45

Asn Arg Pro Ser Tyr Trp Ser Trp Ile Arg Gln Ala Pro Gly Lys Ala
50 55 60

Met Glu Trp Ile Gly Tyr Val Tyr Asp Ser Gly Val Thr Ile Tyr Asn
65 70 75 80

Pro Ser Leu Lys Gly Arg Val Thr Ile Ser Leu Asp Thr Ser Lys Thr
85 90 95

Arg Phe Ser Leu Lys Leu Thr Ser Val Ile Ala Ala Asp Thr Ala Val
100 105 110

Tyr Tyr Cys Ala Arg Glu Arg Phe Asp Arg Thr Ser Tyr Lys Ser Trp
115 120 125

Trp Gly Gln Gly Thr Gln Val Thr Val Ser Ser Gly Gly Gly Ser Gly
130 135 140

Gly Gly Ser Gly Gly Gly Ser Gly Gly Gly Ser Asp Ile Val Leu Thr
145 150 155 160

Gln Ala Pro Gly Thr Leu Ser Leu Ser Pro Gly Asp Arg Ala Thr Leu
165 170 175

Ser Cys Arg Ala Ser Gln Arg Leu Gly Gly Thr Ser Leu Ala Trp Tyr

```
            180                 185                 190

Gln His Arg Ser Gly Gln Ala Pro Arg Leu Ile Leu Tyr Gly Thr Ser
        195                 200                 205

Asn Arg Ala Thr Asp Thr Pro Asp Arg Phe Ser Gly Ser Gly Ser Gly
    210                 215                 220

Thr Asp Phe Val Leu Thr Ile Ser Ser Leu Glu Pro Glu Asp Phe Ala
225                 230                 235                 240

Val Tyr Tyr Cys Gln Gln Tyr Gly Ser Pro Pro Tyr Thr Phe Gly Gln
                245                 250                 255

Gly Thr Thr Leu Asp Ile Lys Gly Gly Gly Gly Ser Gly Gly Gly Gly
            260                 265                 270

Ser Cys Glu Ala Ile Lys Ala Ala Ala Glu Leu Gly Lys Ala Gly Ile
        275                 280                 285

Ser Ser Glu Glu Ile Leu Glu Leu Leu Arg Ala Ala His Glu Leu Gly
    290                 295                 300

Leu Asp Pro Glu Ala Ile Lys Ala Ala Ala Glu Leu Gly Lys Ala Gly
305                 310                 315                 320

Ile Ser Ser Glu Glu Ile Leu Glu Leu Leu Arg Ala Ala His Glu Leu
                325                 330                 335

Gly Leu Asp Pro Glu Ala Ile Lys Ala Ala Ala Glu Leu Gly Lys Ala
            340                 345                 350

Gly Ile Ser Ser Glu Glu Ile Leu Glu Leu Leu Arg Ala Ala His Glu
        355                 360                 365

Leu Gly Leu Asp Pro Glu Ala Ile Lys Ala Ala Ala Glu Leu Gly Lys
    370                 375                 380

Ala Gly Ile Ser Ser Glu Glu Ile Leu Glu Leu Leu Arg Ala Ala His
385                 390                 395                 400

Glu Leu Gly Leu Asp Pro Glu Ala Ile Lys Ala Ala Ala Glu Leu Gly
                405                 410                 415

Lys Ala Gly Ile Ser Ser Glu Glu Ile Leu Glu Leu Leu Arg Ala Ala
            420                 425                 430

His Glu Leu Gly Leu Asp Pro Glu Cys Ile Lys Ala Ala Ala Glu Leu
        435                 440                 445

Gly Lys Ala Gly Ile Ser Ser Glu Glu Ile Leu Glu Leu Leu Arg Ala
    450                 455                 460

Ala His Glu Leu Gly Leu Gly Gly Ser His His His His His His
465                 470                 475


<210> SEQ ID NO 141
<211> LENGTH: 276
<212> TYPE: PRT
<213> ORGANISM: Artificial Sequence
<220> FEATURE:
<223> OTHER INFORMATION: Synthesized MHC alpha chain

<400> SEQUENCE: 141

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
```

```
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro
        275


<210> SEQ ID NO 142
<211> LENGTH: 99
<212> TYPE: PRT
<213> ORGANISM: Mus musculus

<400> SEQUENCE: 142

Ile Gln Lys Thr Pro Gln Ile Gln Val Tyr Ser Arg His Pro Pro Glu
1               5                   10                  15

Asn Gly Lys Pro Asn Ile Leu Asn Cys Tyr Val Thr Gln Phe His Pro
            20                  25                  30

Pro His Ile Glu Ile Gln Met Leu Lys Asn Gly Lys Lys Ile Pro Lys
        35                  40                  45

Val Glu Met Ser Asp Met Ser Phe Ser Lys Asp Trp Ser Phe Tyr Ile
    50                  55                  60

Leu Ala His Thr Glu Phe Thr Pro Thr Glu Thr Asp Thr Tyr Ala Cys
65                  70                  75                  80

Arg Val Lys His Ala Ser Met Ala Glu Pro Lys Thr Val Tyr Trp Asp
                85                  90                  95

Arg Asp Met


<210> SEQ ID NO 143
<211> LENGTH: 152
<212> TYPE: PRT
<213> ORGANISM: Homo sapiens

<400> SEQUENCE: 143

Met Ser Arg Leu Pro Val Leu Leu Leu Leu Gln Leu Leu Val Arg Pro
1               5                   10                  15
```

```
Gly Leu Gln Ala Pro Met Thr Gln Thr Thr Pro Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
    50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150


<210> SEQ ID NO 144
<211> LENGTH: 723
<212> TYPE: PRT
<213> ORGANISM: Homo sapiens

<400> SEQUENCE: 144

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
```

```
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
    530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
            580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
    610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655
```

```
Ala His Ser Lys Arg Asp Thr Lys Cys Gln Pro Gln Gly Ser Ser Gly
            660                 665                 670

Glu Glu Lys Gly Thr Pro Thr Thr Leu Arg Gly Gly Glu Ala Ser Glu
        675                 680                 685

Arg Lys Arg Pro Asp Ser Gly Cys Ser Thr Ser Lys Asp Thr Lys Tyr
    690                 695                 700

Gln Ser Val Tyr Val Ile Ser Glu Glu Lys Asp Glu Cys Val Ile Ala
705                 710                 715                 720

Thr Glu Val


<210> SEQ ID NO 145
<211> LENGTH: 1218
<212> TYPE: PRT
<213> ORGANISM: Homo sapiens

<400> SEQUENCE: 145

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300
```

```
Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720
```

-continued

```
Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile  Ala Cys Glu Pro Ser  Pro Ser Ala
        995                 1000                1005

Asn Asn  Glu Ile His Val Ala  Ile Ser Ala Glu Asp  Ile Arg Asp
    1010                1015                1020

Asp Gly  Asn Pro Ile Lys Glu  Ile Thr Asp Lys Ile  Ile Asp Leu
    1025                1030                1035

Val Ser  Lys Arg Asp Gly Asn  Ser Ser Leu Ile Ala  Ala Val Ala
    1040                1045                1050

Glu Val  Arg Val Gln Arg Arg  Pro Leu Lys Asn Arg  Thr Asp Phe
    1055                1060                1065

Leu Val  Pro Leu Leu Ser Ser  Val Leu Thr Val Ala  Trp Ile Cys
    1070                1075                1080

Cys Leu  Val Thr Ala Phe Tyr  Trp Cys Leu Arg Lys  Arg Arg Lys
    1085                1090                1095

Pro Gly  Ser His Thr His Ser  Ala Ser Glu Asp Asn  Thr Thr Asn
    1100                1105                1110

Asn Val  Arg Glu Gln Leu Asn  Gln Ile Lys Asn Pro  Ile Glu Lys
    1115                1120                1125

His Gly  Ala Asn Thr Val Pro  Ile Lys Asp Tyr Glu  Asn Lys Asn
```

```
    1130                1135                1140

Ser Lys  Met Ser Lys Ile Arg  Thr His Asn Ser Glu  Val Glu Glu
    1145                1150                1155

Asp Asp  Met Asp Lys His Gln  Gln Lys Ala Arg Phe  Ala Lys Gln
    1160                1165                1170

Pro Ala  Tyr Thr Leu Val Asp  Arg Glu Glu Lys Pro  Pro Asn Gly
    1175                1180                1185

Thr Pro  Thr Lys His Pro Asn  Trp Thr Asn Lys Gln  Asp Asn Arg
    1190                1195                1200

Asp Leu  Glu Ser Ala Gln Ser  Leu Asn Arg Met Glu  Tyr Ile Val
    1205                1210                1215


<210> SEQ ID NO 146
<211> LENGTH: 119
<212> TYPE: PRT
<213> ORGANISM: Artificial Sequence
<220> FEATURE:
<223> OTHER INFORMATION: Synthesized huOKT3 variable heavy chain

<400> SEQUENCE: 146

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115


<210> SEQ ID NO 147
<211> LENGTH: 107
<212> TYPE: PRT
<213> ORGANISM: Artificial Sequence
<220> FEATURE:
<223> OTHER INFORMATION: Synthesized huOKT3 variable light chain

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95
```

Phe Gly Gln Gly Thr Lys Leu Gln Ile Thr Arg
100 105

<210> SEQ ID NO 148
<211> LENGTH: 10
<212> TYPE: PRT
<213> ORGANISM: Artificial Sequence
<220> FEATURE:
<223> OTHER INFORMATION: Synthesized CDRH1 of huOKT3

<400> SEQUENCE: 148

Gly Tyr Thr Phe Thr Arg Tyr Thr Met His
1 5 10

<210> SEQ ID NO 149
<211> LENGTH: 16
<212> TYPE: PRT
<213> ORGANISM: Artificial Sequence
<220> FEATURE:
<223> OTHER INFORMATION: Synthesized CDRH2 of huOKT3

<400> SEQUENCE: 149

Ile Asn Pro Ser Arg Gly Tyr Thr Asn Tyr Asn Gln Lys Phe Lys Asp
1 5 10 15

<210> SEQ ID NO 150
<211> LENGTH: 10
<212> TYPE: PRT
<213> ORGANISM: Artificial Sequence
<220> FEATURE:
<223> OTHER INFORMATION: Synthesized CDRH3 of huOKT3

<400> SEQUENCE: 150

Tyr Tyr Asp Asp His Tyr Ser Leu Asp Tyr
1 5 10

<210> SEQ ID NO 151
<211> LENGTH: 10
<212> TYPE: PRT
<213> ORGANISM: Artificial Sequence
<220> FEATURE:
<223> OTHER INFORMATION: Synthesized CDRL1 of huOKT3

<400> SEQUENCE: 151

Ser Ala Ser Ser Ser Val Ser Tyr Met Asn
1 5 10

<210> SEQ ID NO 152
<211> LENGTH: 7
<212> TYPE: PRT
<213> ORGANISM: Artificial Sequence
<220> FEATURE:
<223> OTHER INFORMATION: Synthesized CDRL2 of huOKT3

<400> SEQUENCE: 152

Asp Thr Ser Lys Leu Ala Ser
1 5

<210> SEQ ID NO 153
<211> LENGTH: 9
<212> TYPE: PRT
<213> ORGANISM: Artificial Sequence
<220> FEATURE:
<223> OTHER INFORMATION: Synthesized CDRL3 of huOKT3

<400> SEQUENCE: 153

Gln Gln Trp Ser Ser Asn Pro Phe Thr

```
1               5


<210> SEQ ID NO 154
<211> LENGTH: 478
<212> TYPE: PRT
<213> ORGANISM: Artificial Sequence
<220> FEATURE:
<223> OTHER INFORMATION: Synthesized scFv_CD3_hsOKT3-
      Toroidx6_SS_tetramer-His

<400> SEQUENCE: 154

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Gly Gly Val Val
            20                  25                  30

Gln Pro Gly Arg Ser Leu Arg Leu Ser Cys Lys Ala Ser Gly Tyr Thr
        35                  40                  45

Phe Thr Arg Tyr Thr Met His Trp Val Arg Gln Ala Pro Gly Lys Gly
    50                  55                  60

Leu Glu Trp Ile Gly Tyr Ile Asn Pro Ser Arg Gly Tyr Thr Asn Tyr
65                  70                  75                  80

Asn Gln Lys Phe Lys Asp Arg Phe Thr Ile Ser Arg Asp Asn Ser Lys
                85                  90                  95

Asn Thr Ala Phe Leu Gln Met Asp Ser Leu Arg Pro Glu Asp Thr Gly
            100                 105                 110

Val Tyr Phe Cys Ala Arg Tyr Tyr Asp Asp His Tyr Ser Leu Asp Tyr
        115                 120                 125

Trp Gly Gln Gly Thr Pro Val Thr Val Ser Ser Gly Gly Gly Ser Gly
    130                 135                 140

Gly Gly Ser Gly Gly Gly Ser Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Ser Ala Ser Ser Ser Val Ser Tyr Met Asn Trp Tyr Gln Gln
            180                 185                 190

Thr Pro Gly Lys Ala Pro Lys Arg Trp Ile Tyr Asp Thr Ser Lys Leu
        195                 200                 205

Ala Ser Gly Val Pro Ser Arg Phe Ser Gly Ser Gly Ser Gly Thr Asp
    210                 215                 220

Tyr Thr Phe Thr Ile Ser Ser Leu Gln Pro Glu Asp Ile Ala Thr Tyr
225                 230                 235                 240

Tyr Cys Gln Gln Trp Ser Ser Asn Pro Phe Thr Phe Gly Gln Gly Thr
                245                 250                 255

Lys Leu Gln Ile Thr Arg Gly Gly Gly Gly Ser Gly Gly Gly Gly Ser
            260                 265                 270

Cys Glu Ala Ile Lys Ala Ala Ala Glu Leu Gly Lys Ala Gly Ile Ser
        275                 280                 285

Ser Glu Glu Ile Leu Glu Leu Leu Arg Ala Ala His Glu Leu Gly Leu
    290                 295                 300

Asp Pro Glu Ala Ile Lys Ala Ala Ala Glu Leu Gly Lys Ala Gly Ile
305                 310                 315                 320

Ser Ser Glu Glu Ile Leu Glu Leu Leu Arg Ala Ala His Glu Leu Gly
                325                 330                 335

Leu Asp Pro Glu Ala Ile Lys Ala Ala Ala Glu Leu Gly Lys Ala Gly
            340                 345                 350
```

Ile Ser Ser Glu Glu Ile Leu Glu Leu Leu Arg Ala Ala His Glu Leu
355 360 365

Gly Leu Asp Pro Glu Ala Ile Lys Ala Ala Ala Glu Leu Gly Lys Ala
370 375 380

Gly Ile Ser Ser Glu Glu Ile Leu Glu Leu Leu Arg Ala Ala His Glu
385 390 395 400

Leu Gly Leu Asp Pro Glu Ala Ile Lys Ala Ala Ala Glu Leu Gly Lys
405 410 415

Ala Gly Ile Ser Ser Glu Glu Ile Leu Glu Leu Leu Arg Ala Ala His
420 425 430

Glu Leu Gly Leu Asp Pro Glu Cys Ile Lys Ala Ala Ala Glu Leu Gly
435 440 445

Lys Ala Gly Ile Ser Ser Glu Glu Ile Leu Glu Leu Leu Arg Ala Ala
450 455 460

His Glu Leu Gly Leu Gly Gly Ser His His His His His His
465 470 475

<210> SEQ ID NO 155
<211> LENGTH: 478
<212> TYPE: PRT
<213> ORGANISM: Artificial Sequence
<220> FEATURE:
<223> OTHER INFORMATION: Synthesized scFv_CD28_TGN1412-Toroidx6_SS_tetramer-His

<400> SEQUENCE: 155

Met Glu Thr Asp Thr Leu Leu Leu Trp Val Leu Leu Leu Trp Val Pro
1 5 10 15

Gly Ser Thr Gly Gln Val Gln Leu Val Gln Ser Gly Ala Glu Val Lys
20 25 30

Lys Pro Gly Ala Ser Val Lys Val Ser Cys Lys Ala Ser Gly Tyr Thr
35 40 45

Phe Thr Ser Tyr Tyr Ile His Trp Val Arg Gln Ala Pro Gly Gln Gly
50 55 60

Leu Glu Trp Ile Gly Cys Ile Tyr Pro Gly Asn Val Asn Thr Asn Tyr
65 70 75 80

Asn Glu Lys Phe Lys Asp Arg Ala Thr Leu Thr Val Asp Thr Ser Ile
85 90 95

Ser Thr Ala Tyr Met Glu Leu Ser Arg Leu Arg Ser Asp Asp Thr Ala
100 105 110

Val Tyr Phe Cys Thr Arg Ser His Tyr Gly Leu Asp Trp Asn Phe Asp
115 120 125

Val Trp Gly Gln Gly Thr Thr Val Thr Val Ser Ser Gly Gly Gly Gly
130 135 140

Ser Gly Gly Gly Gly Ser Gly Gly Gly Gly Ser Asp Ile Gln Met Thr
145 150 155 160

Gln Ser Pro Ser Ser Leu Ser Ala Ser Val Gly Asp Arg Val Thr Ile
165 170 175

Thr Cys His Ala Ser Gln Asn Ile Tyr Val Trp Leu Asn Trp Tyr Gln
180 185 190

Gln Lys Pro Gly Lys Ala Pro Lys Leu Leu Ile Tyr Lys Ala Ser Asn
195 200 205

Leu His Thr Gly Val Pro Ser Arg Phe Ser Gly Ser Gly Ser Gly Thr
210 215 220

Asp Phe Thr Leu Thr Ile Ser Ser Leu Gln Pro Glu Asp Phe Ala Thr
225 230 235 240

```
Tyr Tyr Cys Gln Gln Gly Gln Thr Tyr Pro Tyr Thr Phe Gly Gly Gly
                245                 250                 255

Thr Lys Val Glu Ile Lys Gly Gly Gly Gly Ser Gly Gly Gly Gly Ser
            260                 265                 270

Cys Glu Ala Ile Lys Ala Ala Ala Glu Leu Gly Lys Ala Gly Ile Ser
        275                 280                 285

Ser Glu Glu Ile Leu Glu Leu Leu Arg Ala Ala His Glu Leu Gly Leu
    290                 295                 300

Asp Pro Glu Ala Ile Lys Ala Ala Ala Glu Leu Gly Lys Ala Gly Ile
305                 310                 315                 320

Ser Ser Glu Glu Ile Leu Glu Leu Leu Arg Ala Ala His Glu Leu Gly
                325                 330                 335

Leu Asp Pro Glu Ala Ile Lys Ala Ala Ala Glu Leu Gly Lys Ala Gly
            340                 345                 350

Ile Ser Ser Glu Glu Ile Leu Glu Leu Leu Arg Ala Ala His Glu Leu
        355                 360                 365

Gly Leu Asp Pro Glu Ala Ile Lys Ala Ala Ala Glu Leu Gly Lys Ala
    370                 375                 380

Gly Ile Ser Ser Glu Glu Ile Leu Glu Leu Leu Arg Ala Ala His Glu
385                 390                 395                 400

Leu Gly Leu Asp Pro Glu Ala Ile Lys Ala Ala Ala Glu Leu Gly Lys
                405                 410                 415

Ala Gly Ile Ser Ser Glu Glu Ile Leu Glu Leu Leu Arg Ala Ala His
            420                 425                 430

Glu Leu Gly Leu Asp Pro Glu Cys Ile Lys Ala Ala Ala Glu Leu Gly
        435                 440                 445

Lys Ala Gly Ile Ser Ser Glu Glu Ile Leu Glu Leu Leu Arg Ala Ala
    450                 455                 460

His Glu Leu Gly Leu Gly Gly Ser His His His His His His
465                 470                 475
```

<210> SEQ ID NO 156
<211> LENGTH: 4
<212> TYPE: PRT
<213> ORGANISM: Artificial Sequence
<220> FEATURE:
<223> OTHER INFORMATION: Synthesized linker sequence

<400> SEQUENCE: 156

```
Leu Pro His Asp
1
```

<210> SEQ ID NO 157
<211> LENGTH: 4
<212> TYPE: PRT
<213> ORGANISM: Artificial Sequence
<220> FEATURE:
<223> OTHER INFORMATION: Synthesized linker sequence

<400> SEQUENCE: 157

```
Asn Pro Asn Asp
1
```

<210> SEQ ID NO 158
<211> LENGTH: 4
<212> TYPE: PRT
<213> ORGANISM: Artificial Sequence
<220> FEATURE:
<223> OTHER INFORMATION: Synthesized linker sequence

<400> SEQUENCE: 158

Asp Pro Lys Asp
1

<210> SEQ ID NO 159
<211> LENGTH: 5
<212> TYPE: PRT
<213> ORGANISM: Artificial Sequence
<220> FEATURE:
<223> OTHER INFORMATION: Synthesized linker sequence

<400> SEQUENCE: 159

Gly Leu Glu Pro Asp
1 5

<210> SEQ ID NO 160
<211> LENGTH: 5
<212> TYPE: PRT
<213> ORGANISM: Artificial Sequence
<220> FEATURE:
<223> OTHER INFORMATION: Synthesized linker sequence

<400> SEQUENCE: 160

Gly Val Ser Leu Asp
1 5

<210> SEQ ID NO 161
<211> LENGTH: 5
<212> TYPE: PRT
<213> ORGANISM: Artificial Sequence
<220> FEATURE:
<223> OTHER INFORMATION: Synthesized linker sequence

<400> SEQUENCE: 161

Gly Val Leu Pro Asp
1 5

<210> SEQ ID NO 162
<211> LENGTH: 10
<212> TYPE: PRT
<213> ORGANISM: Artificial Sequence
<220> FEATURE:
<223> OTHER INFORMATION: Synthesized phosphotyrosyl-containing peptide
<220> FEATURE:
<221> NAME/KEY: MISC_FEATURE
<222> LOCATION: (4)..(4)
<223> OTHER INFORMATION: phosphotyrosyl

<400> SEQUENCE: 162

Glu His Ile Tyr Asp Glu Val Ala Ala Asp
1 5 10

<210> SEQ ID NO 163
<211> LENGTH: 9
<212> TYPE: PRT
<213> ORGANISM: Artificial Sequence
<220> FEATURE:
<223> OTHER INFORMATION: Synthesized immunogenic cytomegalovirus peptide

<400> SEQUENCE: 163

Asn Leu Val Pro Met Val Ala Thr Val
1 5

<210> SEQ ID NO 164
<211> LENGTH: 13
<212> TYPE: PRT

<213> ORGANISM: Artificial Sequence
<220> FEATURE:
<223> OTHER INFORMATION: Synthesized immunogenic peptide derived from in-frame deletion of exons 2 to 7

<400> SEQUENCE: 164

Leu Glu Glu Lys Lys Gly Asn Tyr Trp Thr Asp His Cys
1 5 10

<210> SEQ ID NO 165
<211> LENGTH: 18
<212> TYPE: PRT
<213> ORGANISM: Homo sapiens

<400> SEQUENCE: 165

Asp Pro Asn Ala Pro Lys Arg Pro Pro Ser Ala Phe Phe Leu Phe Cys
1 5 10 15

Ser Glu

<210> SEQ ID NO 166
<211> LENGTH: 37
<212> TYPE: PRT
<213> ORGANISM: Artificial Sequence
<220> FEATURE:
<223> OTHER INFORMATION: Synthesized LL-37: antimicrobial peptide

<400> SEQUENCE: 166

Leu Leu Gly Asp Phe Phe Arg Lys Ser Lys Glu Lys Ile Gly Lys Glu
1 5 10 15

Phe Lys Arg Ile Val Gln Arg Ile Lys Asp Phe Leu Arg Asn Leu Val
20 25 30

Pro Arg Thr Glu Ser
35

<210> SEQ ID NO 167
<211> LENGTH: 9
<212> TYPE: PRT
<213> ORGANISM: Artificial Sequence
<220> FEATURE:
<223> OTHER INFORMATION: Synthesized 1037: antimicrobial peptide

<400> SEQUENCE: 167

Lys Arg Phe Arg Ile Arg Val Arg Val
1 5

<210> SEQ ID NO 168
<211> LENGTH: 12
<212> TYPE: PRT
<213> ORGANISM: Artificial Sequence
<220> FEATURE:
<223> OTHER INFORMATION: Synthesized 1018: antimicrobial peptide

<400> SEQUENCE: 168

Val Arg Leu Ile Val Ala Val Arg Ile Trp Arg Arg
1 5 10

<210> SEQ ID NO 169
<211> LENGTH: 21
<212> TYPE: PRT
<213> ORGANISM: Artificial Sequence
<220> FEATURE:
<223> OTHER INFORMATION: Synthesized Esculentin-1a (121): antimicrobial peptide

<400> SEQUENCE: 169

```
Gly Ile Phe Ser Lys Leu Ala Gly Lys Lys Ile Lys Asn Leu Leu Ile
1               5                   10                  15

Ser Gly Leu Lys Gly
            20


<210> SEQ ID NO 170
<211> LENGTH: 23
<212> TYPE: PRT
<213> ORGANISM: Artificial Sequence
<220> FEATURE:
<223> OTHER INFORMATION: Synthesized Nisin A: antimicrobial peptide

<400> SEQUENCE: 170

Met Ser Thr Lys Asp Phe Asn Leu Asp Leu Val Ser Val Ser Lys Lys
1               5                   10                  15

Asp Ser Gly Ala Ser Pro Arg
            20


<210> SEQ ID NO 171
<211> LENGTH: 53
<212> TYPE: PRT
<213> ORGANISM: Artificial Sequence
<220> FEATURE:
<223> OTHER INFORMATION: Synthesized lacticin Q: antimicrobial peptide

<400> SEQUENCE: 171

Met Ala Gly Phe Leu Lys Val Val Gln Leu Leu Ala Lys Tyr Gly Ser
1               5                   10                  15

Lys Ala Val Gln Met Ala Trp Ala Asn Lys Gly Lys Ile Leu Asp Trp
            20                  25                  30

Leu Asn Ala Gly Gln Ala Ile Asp Lys Val Val Ser Lys Ile Lys Gln
        35                  40                  45

Ile Leu Gly Ile Lys
    50


<210> SEQ ID NO 172
<211> LENGTH: 30
<212> TYPE: PRT
<213> ORGANISM: Artificial Sequence
<220> FEATURE:
<223> OTHER INFORMATION: Synthesized RN3 (5-17P22-36): antimicrobial
      peptide

<400> SEQUENCE: 172

Arg Pro Phe Thr Arg Ala Gln Trp Phe Ala Ile Gln His Ile Ser Pro
1               5                   10                  15

Arg Thr Ile Ala Met Arg Ala Ile Asn Asn Tyr Arg Trp Arg
            20                  25                  30


<210> SEQ ID NO 173
<211> LENGTH: 16
<212> TYPE: PRT
<213> ORGANISM: Artificial Sequence
<220> FEATURE:
<223> OTHER INFORMATION: Synthesized S4 (116): antimicrobial peptide

<400> SEQUENCE: 173

Ala Leu Trp Lys Thr Leu Leu Lys Lys Val Leu Lys Ala Ala Ala Lys
1               5                   10                  15


<210> SEQ ID NO 174
<211> LENGTH: 22
<212> TYPE: PRT
<213> ORGANISM: Artificial Sequence
```

<220> FEATURE:
<223> OTHER INFORMATION: Synthesized P1: antimicrobial peptide

<400> SEQUENCE: 174

Phe Val Asp Arg Asn Arg Ile Pro Arg Ser Asn Asn Gly Pro Lys Ile
1 5 10 15

Pro Ile Ile Ser Asn Pro
20

<210> SEQ ID NO 175
<211> LENGTH: 15
<212> TYPE: PRT
<213> ORGANISM: Artificial Sequence
<220> FEATURE:
<223> OTHER INFORMATION: Synthesized L-K6L9: antimicrobial peptide

<400> SEQUENCE: 175

Leu Lys Leu Leu Lys Lys Leu Leu Lys Lys Leu Leu Lys Leu Leu
1 5 10 15

<210> SEQ ID NO 176
<211> LENGTH: 22
<212> TYPE: PRT
<213> ORGANISM: Artificial Sequence
<220> FEATURE:
<223> OTHER INFORMATION: Synthesized Piscidin-3: antimicrobial peptide

<400> SEQUENCE: 176

Phe Ile His His Ile Phe Arg Gly Ile Val His Ala Gly Arg Ser Ile
1 5 10 15

Gly Arg Phe Leu Thr Gly
20

<210> SEQ ID NO 177
<211> LENGTH: 21
<212> TYPE: PRT
<213> ORGANISM: Artificial Sequence
<220> FEATURE:
<223> OTHER INFORMATION: Synthesized PI: antimicrobial peptide

<400> SEQUENCE: 177

Pro Ala Arg Lys Ala Arg Ala Ala Thr Ala Ala Thr Ala Ala Thr Ala
1 5 10 15

Ala Thr Ala Ala Thr
20

<210> SEQ ID NO 178
<211> LENGTH: 20
<212> TYPE: PRT
<213> ORGANISM: Artificial Sequence
<220> FEATURE:
<223> OTHER INFORMATION: Synthesized Hepcidin 20: antimicrobial peptide

<400> SEQUENCE: 178

Ile Cys Ile Phe Cys Cys Gly Cys Cys His Arg Ser His Cys Gly Met
1 5 10 15

Cys Cys Lys Thr
20

<210> SEQ ID NO 179
<211> LENGTH: 45
<212> TYPE: PRT
<213> ORGANISM: Artificial Sequence
<220> FEATURE:
<223> OTHER INFORMATION: Synthesized Human beta-defensin 3 (hBD-3):

antimicrobial peptide

<400> SEQUENCE: 179

Gly Ile Ile Asn Thr Leu Gln Lys Tyr Tyr Cys Arg Val Arg Gly Gly
1 5 10 15

Arg Cys Ala Val Leu Ser Cys Leu Pro Lys Glu Glu Gln Ile Gly Lys
20 25 30

Cys Ser Thr Arg Gly Arg Lys Cys Cys Arg Arg Lys Lys
35 40 45

<210> SEQ ID NO 180
<211> LENGTH: 12
<212> TYPE: PRT
<213> ORGANISM: Artificial Sequence
<220> FEATURE:
<223> OTHER INFORMATION: Synthesized DJK-5: antimicrobial peptide

<400> SEQUENCE: 180

Val Gln Trp Arg Ala Ile Arg Val Arg Val Ile Arg
1 5 10

<210> SEQ ID NO 181
<211> LENGTH: 11
<212> TYPE: PRT
<213> ORGANISM: Artificial Sequence
<220> FEATURE:
<223> OTHER INFORMATION: Synthesized flexible Gly-Ser linker

<400> SEQUENCE: 181

Gly Gly Ser Gly Gly Gly Ser Gly Gly Ser Gly
1 5 10

<210> SEQ ID NO 182
<211> LENGTH: 10
<212> TYPE: PRT
<213> ORGANISM: Artificial Sequence
<220> FEATURE:
<223> OTHER INFORMATION: Synthesized flexible Gly-Ser linker

<400> SEQUENCE: 182

Gly Gly Ser Gly Gly Gly Ser Gly Ser Gly
1 5 10

<210> SEQ ID NO 183
<211> LENGTH: 8
<212> TYPE: PRT
<213> ORGANISM: Artificial Sequence
<220> FEATURE:
<223> OTHER INFORMATION: Synthesized flexible Gly-Ser linker

<400> SEQUENCE: 183

Gly Gly Ser Gly Gly Gly Ser Gly
1 5

<210> SEQ ID NO 184
<211> LENGTH: 10
<212> TYPE: PRT
<213> ORGANISM: Artificial Sequence
<220> FEATURE:
<223> OTHER INFORMATION: Synthesized flexible Gly-Ser linker

<400> SEQUENCE: 184

Gly Gly Gly Gly Ser Gly Gly Gly Gly Ser
1 5 10

<210> SEQ ID NO 185
<211> LENGTH: 8
<212> TYPE: PRT
<213> ORGANISM: Artificial Sequence
<220> FEATURE:
<223> OTHER INFORMATION: Synthesized flexible Gly-Ser linker

<400> SEQUENCE: 185

Gly Gly Gly Ser Gly Gly Gly Ser
1               5

<210> SEQ ID NO 186
<211> LENGTH: 6
<212> TYPE: PRT
<213> ORGANISM: Artificial Sequence
<220> FEATURE:
<223> OTHER INFORMATION: Synthesized flexible Gly-Ser linker

<400> SEQUENCE: 186

Gly Gly Ser Gly Gly Ser
1               5

<210> SEQ ID NO 187
<211> LENGTH: 16
<212> TYPE: PRT
<213> ORGANISM: Artificial Sequence
<220> FEATURE:
<223> OTHER INFORMATION: Synthesized Group VI

<400> SEQUENCE: 187

Gly Leu Asn Cys Glu Ala Glu Lys Ala Ala Ala Glu Leu Gly Lys Ala
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Synthesized Group VI

<400> SEQUENCE: 188

Gly Leu Asp Cys Glu Ala Glu Lys Ala Ala Ala Glu Leu Gly Lys Ala
1               5                   10                  15

<210> SEQ ID NO 189
<211> LENGTH: 19
<212> TYPE: PRT
<213> ORGANISM: Artificial Sequence
<220> FEATURE:
<223> OTHER INFORMATION: Synthesized Group IX

<400> SEQUENCE: 189

Gly Leu Asn Cys Glu Ala Glu Lys Ala Ala Ala Glu Leu Gly Lys Ala
1               5                   10                  15

Gly Thr Thr

<210> SEQ ID NO 190
<211> LENGTH: 19
<212> TYPE: PRT
<213> ORGANISM: Artificial Sequence
<220> FEATURE:
<223> OTHER INFORMATION: Synthesized Group IX

<400> SEQUENCE: 190

Gly Leu Asp Cys Glu Ala Glu Lys Ala Ala Ala Glu Leu Gly Lys Ala
1               5                   10                  15

Gly Ile Ser

<210> SEQ ID NO 191
<211> LENGTH: 16
<212> TYPE: PRT
<213> ORGANISM: Artificial Sequence
<220> FEATURE:
<223> OTHER INFORMATION: Synthesized Group VI

<400> SEQUENCE: 191

Gly Leu Asp Cys Glu Ala Ile Lys Lys Ala Ala Glu Leu Gly Lys Ala
1 5 10 15

<210> SEQ ID NO 192
<211> LENGTH: 16
<212> TYPE: PRT
<213> ORGANISM: Artificial Sequence
<220> FEATURE:
<223> OTHER INFORMATION: Synthesized Group VI

<400> SEQUENCE: 192

Gly Leu Asn Cys Glu Ala Ile Lys Lys Ala Ala Glu Leu Gly Lys Ala
1 5 10 15

<210> SEQ ID NO 193
<211> LENGTH: 19
<212> TYPE: PRT
<213> ORGANISM: Artificial Sequence
<220> FEATURE:
<223> OTHER INFORMATION: Synthesized Group IX

<400> SEQUENCE: 193

Gly Leu Asp Cys Glu Ala Ile Lys Lys Ala Ala Glu Leu Gly Lys Ala
1 5 10 15

Gly Thr Thr

<210> SEQ ID NO 194
<211> LENGTH: 19
<212> TYPE: PRT
<213> ORGANISM: Artificial Sequence
<220> FEATURE:
<223> OTHER INFORMATION: Synthesized Group IX

<400> SEQUENCE: 194

Gly Leu Asp Cys Glu Ala Ile Lys Lys Ala Ala Glu Leu Gly Lys Ala
1 5 10 15

Gly Ile Ser

<210> SEQ ID NO 195
<211> LENGTH: 798
<212> TYPE: PRT
<213> ORGANISM: Artificial Sequence
<220> FEATURE:
<223> OTHER INFORMATION: Sub6 cTRP construct containing 6 repeats,
disulfide staples and inserted fusions of a single chain trimer
targeting 4-1BB

<400> SEQUENCE: 195

Met Glu Thr Asp Thr Leu Leu Leu Trp Val Leu Leu Leu Trp Val Pro
1 5 10 15

Gly Ser Thr Gly Arg Glu Gly Pro Glu Leu Ser Pro Asp Asp Pro Ala
20 25 30

Gly Leu Leu Asp Leu Arg Gln Gly Met Phe Ala Gln Leu Val Ala Gln
35 40 45

Asn Val Leu Leu Ile Asp Gly Pro Leu Ser Trp Tyr Ser Asp Pro Gly
50 55 60

Leu Ala Gly Val Ser Leu Thr Gly Gly Leu Ser Tyr Lys Glu Asp Thr
65 70 75 80

Lys Glu Leu Val Val Ala Lys Ala Gly Val Tyr Tyr Val Phe Phe Gln
85 90 95

Leu Glu Leu Arg Arg Val Val Ala Gly Glu Gly Ser Gly Ser Val Ser
100 105 110

Leu Ala Leu His Leu Gln Pro Leu Arg Ser Ala Ala Gly Ala Ala Ala
115 120 125

Leu Ala Leu Thr Val Asp Leu Pro Pro Ala Ser Ser Glu Ala Arg Asn
130 135 140

Ser Ala Phe Gly Phe Gln Gly Arg Leu Leu His Leu Ser Ala Gly Gln
145 150 155 160

Arg Leu Gly Val His Leu His Thr Glu Ala Arg Ala Arg His Ala Trp
165 170 175

Gln Leu Thr Gln Gly Ala Thr Val Leu Gly Leu Phe Arg Val Thr Pro
180 185 190

Glu Ile Pro Ala Gly Leu Pro Ser Pro Arg Ser Glu Gly Gly Gly Gly
195 200 205

Ser Arg Glu Gly Pro Glu Leu Ser Pro Asp Asp Pro Ala Gly Leu Leu
210 215 220

Asp Leu Arg Gln Gly Met Phe Ala Gln Leu Val Ala Gln Asn Val Leu
225 230 235 240

Leu Ile Asp Gly Pro Leu Ser Trp Tyr Ser Asp Pro Gly Leu Ala Gly
245 250 255

Val Ser Leu Thr Gly Gly Leu Ser Tyr Lys Glu Asp Thr Lys Glu Leu
260 265 270

Val Val Ala Lys Ala Gly Val Tyr Tyr Val Phe Phe Gln Leu Glu Leu
275 280 285

Arg Arg Val Val Ala Gly Glu Gly Ser Gly Ser Val Ser Leu Ala Leu
290 295 300

His Leu Gln Pro Leu Arg Ser Ala Ala Gly Ala Ala Ala Leu Ala Leu
305 310 315 320

Thr Val Asp Leu Pro Pro Ala Ser Ser Glu Ala Arg Asn Ser Ala Phe
325 330 335

Gly Phe Gln Gly Arg Leu Leu His Leu Ser Ala Gly Gln Arg Leu Gly
340 345 350

Val His Leu His Thr Glu Ala Arg Ala Arg His Ala Trp Gln Leu Thr
355 360 365

Gln Gly Ala Thr Val Leu Gly Leu Phe Arg Val Thr Pro Glu Ile Pro
370 375 380

Ala Gly Leu Pro Ser Pro Arg Ser Glu Gly Gly Gly Gly Ser Arg Glu
385 390 395 400

Gly Pro Glu Leu Ser Pro Asp Asp Pro Ala Gly Leu Leu Asp Leu Arg
405 410 415

Gln Gly Met Phe Ala Gln Leu Val Ala Gln Asn Val Leu Leu Ile Asp
420 425 430

Gly Pro Leu Ser Trp Tyr Ser Asp Pro Gly Leu Ala Gly Val Ser Leu
435 440 445

Thr Gly Gly Leu Ser Tyr Lys Glu Asp Thr Lys Glu Leu Val Val Ala
450 455 460

Lys Ala Gly Val Tyr Tyr Val Phe Phe Gln Leu Glu Leu Arg Arg Val 465 470 475 480

Val Ala Gly Glu Gly Ser Gly Ser Val Ser Leu Ala Leu His Leu Gln
485 490 495

Pro Leu Arg Ser Ala Ala Gly Ala Ala Ala Leu Ala Leu Thr Val Asp
500 505 510

Leu Pro Pro Ala Ser Ser Glu Ala Arg Asn Ser Ala Phe Gly Phe Gln
515 520 525

Gly Arg Leu Leu His Leu Ser Ala Gly Gln Arg Leu Gly Val His Leu
530 535 540

His Thr Glu Ala Arg Ala Arg His Ala Trp Gln Leu Thr Gln Gly Ala
545 550 555 560

Thr Val Leu Gly Leu Phe Arg Val Thr Pro Glu Ile Pro Ala Gly Leu
565 570 575

Pro Ser Pro Arg Ser Glu Gly Gly Gly Gly Ser Gly Gly Gly Gly Ser
580 585 590

Cys Glu Ala Ile Lys Ala Ala Ala Glu Leu Gly Lys Ala Gly Ile Ser
595 600 605

Ser Glu Glu Ile Leu Glu Leu Leu Arg Ala Ala His Glu Leu Gly Leu
610 615 620

Asp Pro Glu Ala Ile Lys Ala Ala Ala Glu Leu Gly Lys Ala Gly Ile
625 630 635 640

Ser Ser Glu Glu Ile Leu Glu Leu Leu Arg Ala Ala His Glu Leu Gly
645 650 655

Leu Asp Pro Glu Ala Ile Lys Ala Ala Ala Glu Leu Gly Lys Ala Gly
660 665 670

Ile Ser Ser Glu Glu Ile Leu Glu Leu Leu Arg Ala Ala His Glu Leu
675 680 685

Gly Leu Asp Pro Glu Ala Ile Lys Ala Ala Ala Glu Leu Gly Lys Ala
690 695 700

Gly Ile Ser Ser Glu Glu Ile Leu Glu Leu Leu Arg Ala Ala His Glu
705 710 715 720

Leu Gly Leu Asp Pro Glu Ala Ile Lys Ala Ala Ala Glu Leu Gly Lys
725 730 735

Ala Gly Ile Ser Ser Glu Glu Ile Leu Glu Leu Leu Arg Ala Ala His
740 745 750

Glu Leu Gly Leu Asp Pro Glu Cys Ile Lys Ala Ala Ala Glu Leu Gly
755 760 765

Lys Ala Gly Ile Ser Ser Glu Glu Ile Leu Glu Leu Leu Arg Ala Ala
770 775 780

His Glu Leu Gly Leu Gly Gly Ser His His His His His His
785 790 795

<210> SEQ ID NO 196
<211> LENGTH: 645
<212> TYPE: PRT
<213> ORGANISM: Artificial Sequence
<220> FEATURE:
<223> OTHER INFORMATION: Sub6 cTRP construct containing 6 repeats, disulfidestaples and inserted fusions of a single chain trimer targeting OX40

<400> SEQUENCE: 196

Met Glu Thr Asp Thr Leu Leu Leu Trp Val Leu Leu Leu Trp Val Pro
1 5 10 15

Gly Ser Thr Gly Gln Val Ser His Arg Tyr Pro Arg Ile Gln Ser Ile
20 25 30

```
Lys Val Gln Phe Thr Glu Tyr Lys Lys Glu Lys Gly Phe Ile Leu Thr
        35                  40                  45

Ser Gln Lys Glu Asp Glu Ile Met Lys Val Gln Asn Asn Ser Val Ile
    50                  55                  60

Ile Asn Cys Asp Gly Phe Tyr Leu Ile Ser Leu Lys Gly Tyr Phe Ser
65                  70                  75                  80

Gln Glu Val Asn Ile Ser Leu His Tyr Gln Lys Asp Glu Glu Pro Leu
                85                  90                  95

Phe Gln Leu Lys Lys Val Arg Ser Val Asn Ser Leu Met Val Ala Ser
            100                 105                 110

Leu Thr Tyr Lys Asp Lys Val Tyr Leu Asn Val Thr Thr Asp Asn Thr
        115                 120                 125

Ser Leu Asp Asp Phe His Val Asn Gly Gly Glu Leu Ile Leu Ile His
    130                 135                 140

Gln Asn Pro Gly Glu Phe Cys Val Leu Gly Gly Gly Gly Ser Gln Val
145                 150                 155                 160

Ser His Arg Tyr Pro Arg Ile Gln Ser Ile Lys Val Gln Phe Thr Glu
                165                 170                 175

Tyr Lys Lys Glu Lys Gly Phe Ile Leu Thr Ser Gln Lys Glu Asp Glu
            180                 185                 190

Ile Met Lys Val Gln Asn Asn Ser Val Ile Ile Asn Cys Asp Gly Phe
        195                 200                 205

Tyr Leu Ile Ser Leu Lys Gly Tyr Phe Ser Gln Glu Val Asn Ile Ser
    210                 215                 220

Leu His Tyr Gln Lys Asp Glu Glu Pro Leu Phe Gln Leu Lys Lys Val
225                 230                 235                 240

Arg Ser Val Asn Ser Leu Met Val Ala Ser Leu Thr Tyr Lys Asp Lys
                245                 250                 255

Val Tyr Leu Asn Val Thr Thr Asp Asn Thr Ser Leu Asp Asp Phe His
            260                 265                 270

Val Asn Gly Gly Glu Leu Ile Leu Ile His Gln Asn Pro Gly Glu Phe
        275                 280                 285

Cys Val Leu Gly Gly Gly Gly Ser Gln Val Ser His Arg Tyr Pro Arg
    290                 295                 300

Ile Gln Ser Ile Lys Val Gln Phe Thr Glu Tyr Lys Lys Glu Lys Gly
305                 310                 315                 320

Phe Ile Leu Thr Ser Gln Lys Glu Asp Glu Ile Met Lys Val Gln Asn
                325                 330                 335

Asn Ser Val Ile Ile Asn Cys Asp Gly Phe Tyr Leu Ile Ser Leu Lys
            340                 345                 350

Gly Tyr Phe Ser Gln Glu Val Asn Ile Ser Leu His Tyr Gln Lys Asp
        355                 360                 365

Glu Glu Pro Leu Phe Gln Leu Lys Lys Val Arg Ser Val Asn Ser Leu
    370                 375                 380

Met Val Ala Ser Leu Thr Tyr Lys Asp Lys Val Tyr Leu Asn Val Thr
385                 390                 395                 400

Thr Asp Asn Thr Ser Leu Asp Asp Phe His Val Asn Gly Gly Glu Leu
                405                 410                 415

Ile Leu Ile His Gln Asn Pro Gly Glu Phe Cys Val Leu Gly Gly Gly
            420                 425                 430

Gly Ser Gly Gly Gly Gly Ser Cys Glu Ala Ile Lys Ala Ala Ala Glu
        435                 440                 445
```

```
Leu Gly Lys Ala Gly Ile Ser Ser Glu Glu Ile Leu Glu Leu Leu Arg
    450                 455                 460

Ala Ala His Glu Leu Gly Leu Asp Pro Glu Ala Ile Lys Ala Ala Ala
465                 470                 475                 480

Glu Leu Gly Lys Ala Gly Ile Ser Ser Glu Glu Ile Leu Glu Leu Leu
                485                 490                 495

Arg Ala Ala His Glu Leu Gly Leu Asp Pro Glu Ala Ile Lys Ala Ala
            500                 505                 510

Ala Glu Leu Gly Lys Ala Gly Ile Ser Ser Glu Glu Ile Leu Glu Leu
        515                 520                 525

Leu Arg Ala Ala His Glu Leu Gly Leu Asp Pro Glu Ala Ile Lys Ala
    530                 535                 540

Ala Ala Glu Leu Gly Lys Ala Gly Ile Ser Ser Glu Glu Ile Leu Glu
545                 550                 555                 560

Leu Leu Arg Ala Ala His Glu Leu Gly Leu Asp Pro Glu Ala Ile Lys
                565                 570                 575

Ala Ala Ala Glu Leu Gly Lys Ala Gly Ile Ser Ser Glu Glu Ile Leu
            580                 585                 590

Glu Leu Leu Arg Ala Ala His Glu Leu Gly Leu Asp Pro Glu Cys Ile
        595                 600                 605

Lys Ala Ala Ala Glu Leu Gly Lys Ala Gly Ile Ser Ser Glu Glu Ile
    610                 615                 620

Leu Glu Leu Leu Arg Ala Ala His Glu Leu Gly Leu Gly Gly Ser His
625                 630                 635                 640

His His His His His
                645
```

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205
<211> LENGTH: 13
<212> TYPE: PRT
<213> ORGANISM: Artificial Sequence
<220> FEATURE:
<223> OTHER INFORMATION: CDRH1 of OKT3 antibody

<400> SEQUENCE: 205

Lys Ala Ser Gly Tyr Thr Phe Thr Arg Tyr Thr Met His
1               5                   10

<210> SEQ ID NO 206

<400> SEQUENCE: 206

000

<210> SEQ ID NO 207
<211> LENGTH: 10
<212> TYPE: PRT
<213> ORGANISM: Artificial Sequence
<220> FEATURE:
<223> OTHER INFORMATION: CDRH3 of OKT3 antibody

<400> SEQUENCE: 207

Tyr Tyr Asp Asp His Tyr Cys Leu Asp Tyr
1               5                   10

<210> SEQ ID NO 208

<400> SEQUENCE: 208

000

<210> SEQ ID NO 209
<211> LENGTH: 11
<212> TYPE: PRT
<213> ORGANISM: Artificial Sequence
<220> FEATURE:
<223> OTHER INFORMATION: CDRL2 of OKT3 antibody

<400> SEQUENCE: 209

Arg Trp Ile Tyr Asp Thr Ser Lys Leu Ala Ser
1               5                   10

<210> SEQ ID NO 210

<400> SEQUENCE: 210

000

<210> SEQ ID NO 211
<211> LENGTH: 242

<212> TYPE: PRT
<213> ORGANISM: Artificial Sequence
<220> FEATURE:
<223> OTHER INFORMATION: OKT3 scFv

<400> SEQUENCE: 211

Gln Val Gln Leu Gln Gln Ser Gly Ala Glu Leu Ala Arg Pro Gly Ala
1 5 10 15

Ser Val Lys Met Ser Cys Lys Ala Ser Gly Tyr Thr Phe Thr Arg Tyr
20 25 30

Thr Met His Trp Val Lys Gln Arg Pro Gly Gln Gly Leu Glu Trp Ile
35 40 45

Gly Tyr Ile Asn Pro Ser Arg Gly Tyr Thr Asn Tyr Asn Gln Lys Phe
50 55 60

Lys Asp Lys Ala Thr Leu Thr Thr Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Tyr Tyr Asp Asp His Tyr Cys Leu Asp Tyr Trp Gly Gln Gly
100 105 110

Thr Thr Leu Thr Val Ser Ser Ser Gly Gly Gly Gly Ser Gly Gly Gly
115 120 125

Gly Ser Gly Gly Gly Gly Ser Gln Ile Val Leu Thr Gln Ser Pro Ala
130 135 140

Ile Met Ser Ala Ser Pro Gly Glu Lys Val Thr Met Thr Cys Ser Ala
145 150 155 160

Ser Ser Ser Val Ser Tyr Met Asn Trp Tyr Gln Gln Lys Ser Gly Thr
165 170 175

Ser Pro Lys Arg Trp Ile Tyr Asp Thr Ser Lys Leu Ala Ser Gly Val
180 185 190

Pro Ala His Phe Arg Gly Ser Gly Ser Gly Thr Ser Tyr Ser Leu Thr
195 200 205

Ile Ser Gly Met Glu Ala Glu Asp Ala Ala Thr Tyr Tyr Cys Gln Gln
210 215 220

Trp Ser Ser Asn Pro Phe Thr Phe Gly Ser Gly Thr Lys Leu Glu Ile
225 230 235 240

Asn Arg

<210> SEQ ID NO 212
<211> LENGTH: 11
<212> TYPE: PRT
<213> ORGANISM: Artificial Sequence
<220> FEATURE:
<223> OTHER INFORMATION: CDRL1 of 20G6-F3 antibody

<400> SEQUENCE: 212

Gln Ser Leu Val His Asn Asn Gly Asn Thr Tyr
1 5 10

<210> SEQ ID NO 213
<211> LENGTH: 9
<212> TYPE: PRT
<213> ORGANISM: Artificial Sequence
<220> FEATURE:
<223> OTHER INFORMATION: CDRL3 of 20G6-F3 antibody w

<400> SEQUENCE: 213

Gly Gln Gly Thr Gln Tyr Pro Phe Thr
1 5

<210> SEQ ID NO 214
<211> LENGTH: 8
<212> TYPE: PRT
<213> ORGANISM: Artificial Sequence
<220> FEATURE:
<223> OTHER INFORMATION: CDRH1 of 20G6-F3 antibody

<400> SEQUENCE: 214

Gly Phe Thr Phe Thr Lys Ala Trp
1 5

<210> SEQ ID NO 215
<211> LENGTH: 10
<212> TYPE: PRT
<213> ORGANISM: Artificial Sequence
<220> FEATURE:
<223> OTHER INFORMATION: CDRH2 of 20G6-F3 antibody

<400> SEQUENCE: 215

Ile Lys Asp Lys Ser Asn Ser Tyr Ala Thr
1 5 10

<210> SEQ ID NO 216
<211> LENGTH: 12
<212> TYPE: PRT
<213> ORGANISM: Artificial Sequence
<220> FEATURE:
<223> OTHER INFORMATION: CDRH3 of 20G6-F3 antibody

<400> SEQUENCE: 216

Arg Gly Val Tyr Tyr Ala Leu Ser Pro Phe Asp Tyr
1 5 10

<210> SEQ ID NO 217
<211> LENGTH: 11
<212> TYPE: PRT
<213> ORGANISM: Artificial Sequence
<220> FEATURE:
<223> OTHER INFORMATION: CDRL1 of 4B4-D7 antibody

<400> SEQUENCE: 217

Gln Ser Leu Val His Asp Asn Gly Asn Thr Tyr
1 5 10

<210> SEQ ID NO 218

<400> SEQUENCE: 218

000

<210> SEQ ID NO 219
<211> LENGTH: 8
<212> TYPE: PRT
<213> ORGANISM: Artificial Sequence
<220> FEATURE:
<223> OTHER INFORMATION: CDRH1 of 4B4-D7 antibody

<400> SEQUENCE: 219

Gly Phe Thr Phe Ser Asn Ala Trp
1 5

<210> SEQ ID NO 220
<211> LENGTH: 10
<212> TYPE: PRT
<213> ORGANISM: Artificial Sequence
<220> FEATURE:

<223> OTHER INFORMATION: CDRH2 of 4B4-D7 antibody

<400> SEQUENCE: 220

Ile Lys Ala Arg Ser Asn Asn Tyr Ala Thr
1 5 10

<210> SEQ ID NO 221
<211> LENGTH: 12
<212> TYPE: PRT
<213> ORGANISM: Artificial Sequence
<220> FEATURE:
<223> OTHER INFORMATION: CDRH3 of 4B4-D7 antibody

<400> SEQUENCE: 221

Arg Gly Thr Tyr Tyr Ala Ser Lys Pro Phe Asp Tyr
1 5 10

<210> SEQ ID NO 222
<211> LENGTH: 11
<212> TYPE: PRT
<213> ORGANISM: Artificial Sequence
<220> FEATURE:
<223> OTHER INFORMATION: CDRL1 of 4E7-C9 antibody

<400> SEQUENCE: 222

Gln Ser Leu Glu His Asn Asn Gly Asn Thr Tyr
1 5 10

<210> SEQ ID NO 223

<400> SEQUENCE: 223

000

<210> SEQ ID NO 224

<400> SEQUENCE: 224

000

<210> SEQ ID NO 225
<211> LENGTH: 10
<212> TYPE: PRT
<213> ORGANISM: Artificial Sequence
<220> FEATURE:
<223> OTHER INFORMATION: CDRH2 of 4E7-C9 antibody

<400> SEQUENCE: 225

Ile Lys Asp Lys Ser Asn Asn Tyr Ala Thr
1 5 10

<210> SEQ ID NO 226
<211> LENGTH: 13
<212> TYPE: PRT
<213> ORGANISM: Artificial Sequence
<220> FEATURE:
<223> OTHER INFORMATION: CDRH3 of 4E7-C9 antibody

<400> SEQUENCE: 226

Arg Tyr Val His Tyr Gly Ile Gly Tyr Ala Met Asp Ala
1 5 10

<210> SEQ ID NO 227
<211> LENGTH: 11
<212> TYPE: PRT
<213> ORGANISM: Artificial Sequence
<220> FEATURE:

<223> OTHER INFORMATION: CDRL1 of 18F5-H10 antibody

<400> SEQUENCE: 227

Gln Ser Leu Val His Thr Asn Gly Asn Thr Tyr
1 5 10

<210> SEQ ID NO 228
<211> LENGTH: 9
<212> TYPE: PRT
<213> ORGANISM: Artificial Sequence
<220> FEATURE:
<223> OTHER INFORMATION: CDRL3 of 18F5-H10 antibody

<400> SEQUENCE: 228

Gly Gln Gly Thr His Tyr Pro Phe Thr
1 5

<210> SEQ ID NO 229
<211> LENGTH: 8
<212> TYPE: PRT
<213> ORGANISM: Artificial Sequence
<220> FEATURE:
<223> OTHER INFORMATION: CDRH1 of 18F5-H10 antibody

<400> SEQUENCE: 229

Gly Phe Thr Phe Thr Asn Ala Trp
1 5

<210> SEQ ID NO 230
<211> LENGTH: 9
<212> TYPE: PRT
<213> ORGANISM: Artificial Sequence
<220> FEATURE:
<223> OTHER INFORMATION: CDRH2 of 18F5-H10 antibody

<400> SEQUENCE: 230

Lys Asp Lys Ser Asn Asn Tyr Ala Thr
1 5

<210> SEQ ID NO 231
<211> LENGTH: 13
<212> TYPE: PRT
<213> ORGANISM: Artificial Sequence
<220> FEATURE:
<223> OTHER INFORMATION: CDRH3 of 18F5-H10 antibody

<400> SEQUENCE: 231

Arg Tyr Val His Tyr Arg Phe Ala Tyr Ala Leu Asp Ala
1 5 10

<210> SEQ ID NO 232
<211> LENGTH: 120
<212> TYPE: PRT
<213> ORGANISM: Artificial Sequence
<220> FEATURE:
<223> OTHER INFORMATION: variable heavy chain of TGN1412

<400> SEQUENCE: 232

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Ile His Trp Val Arg Gln Ala Pro Gly Gln Gly Leu Glu Trp Ile
35 40 45

Gly Cys Ile Tyr Pro Gly Asn Val Asn Thr Asn Tyr Asn Glu Lys Phe

```
    50                  55                  60

Lys Asp Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Phe Cys
                85                  90                  95

Thr Arg Ser His Tyr Gly Leu Asp Trp Asn Phe Asp Val Trp Gly Gln
            100                 105                 110

Gly Thr Thr Val Thr Val Ser Ser
        115                 120


<210> SEQ ID NO 233
<211> LENGTH: 107
<212> TYPE: PRT
<213> ORGANISM: Artificial Sequence
<220> FEATURE:
<223> OTHER INFORMATION: variable light chain of TGN1412

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys His Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Gln Thr Tyr Pro Tyr
                85                  90                  95

Thr Phe Gly Gly Gly Thr Lys Val Glu Ile Lys
            100                 105


<210> SEQ ID NO 234
<211> LENGTH: 11
<212> TYPE: PRT
<213> ORGANISM: Artificial Sequence
<220> FEATURE:
<223> OTHER INFORMATION: CDRL1 of TGN1412 antibody

<400> SEQUENCE: 234

His Ala Ser Gln Asn Ile Tyr Val Trp Leu Asn
1               5                   10


<210> SEQ ID NO 235
<211> LENGTH: 7
<212> TYPE: PRT
<213> ORGANISM: Artificial Sequence
<220> FEATURE:
<223> OTHER INFORMATION: CDRL2 of TGN1412 antibody

<400> SEQUENCE: 235

Lys Ala Ser Asn Leu His Thr
1               5


<210> SEQ ID NO 236
<211> LENGTH: 9
<212> TYPE: PRT
<213> ORGANISM: Artificial Sequence
<220> FEATURE:
<223> OTHER INFORMATION: CDRL3 of TGN1412 antibody
```

<400> SEQUENCE: 236

Gln Gln Gly Gln Thr Tyr Pro Tyr Thr
1 5

<210> SEQ ID NO 237
<211> LENGTH: 10
<212> TYPE: PRT
<213> ORGANISM: Artificial Sequence
<220> FEATURE:
<223> OTHER INFORMATION: CDRH1 of TGN1412 antibody

<400> SEQUENCE: 237

Gly Tyr Thr Phe Thr Ser Tyr Tyr Ile His
1 5 10

<210> SEQ ID NO 238
<211> LENGTH: 5
<212> TYPE: PRT
<213> ORGANISM: Artificial Sequence
<220> FEATURE:
<223> OTHER INFORMATION: CDRH1 of TGN1412 antibody

<400> SEQUENCE: 238

Ser Tyr Tyr Ile His
1 5

<210> SEQ ID NO 239
<211> LENGTH: 14
<212> TYPE: PRT
<213> ORGANISM: Artificial Sequence
<220> FEATURE:
<223> OTHER INFORMATION: CDRH2 of TGN1412 antibody

<400> SEQUENCE: 239

Cys Ile Tyr Pro Gly Asn Val Asn Thr Asn Tyr Asn Glu Lys
1 5 10

<210> SEQ ID NO 240
<211> LENGTH: 11
<212> TYPE: PRT
<213> ORGANISM: Artificial Sequence
<220> FEATURE:
<223> OTHER INFORMATION: CDRH3 of TGN1412 antibody

<400> SEQUENCE: 240

Ser His Tyr Gly Leu Asp Trp Asn Phe Asp Val
1 5 10

<210> SEQ ID NO 241
<211> LENGTH: 7
<212> TYPE: PRT
<213> ORGANISM: Artificial Sequence
<220> FEATURE:
<223> OTHER INFORMATION: 4-1BB CDRL1

<400> SEQUENCE: 241

Arg Ala Ser Gln Ser Val Ser
1 5

<210> SEQ ID NO 242
<211> LENGTH: 6
<212> TYPE: PRT
<213> ORGANISM: Artificial Sequence
<220> FEATURE:
<223> OTHER INFORMATION: 4-1BB CDRL2

<400> SEQUENCE: 242

Ala Ser Asn Arg Ala Thr
1 5

<210> SEQ ID NO 243
<211> LENGTH: 10
<212> TYPE: PRT
<213> ORGANISM: Artificial Sequence
<220> FEATURE:
<223> OTHER INFORMATION: 4-1BB CDRL3

<400> SEQUENCE: 243

Gln Arg Ser Asn Trp Pro Pro Ala Leu Thr
1 5 10

<210> SEQ ID NO 244
<211> LENGTH: 4
<212> TYPE: PRT
<213> ORGANISM: Artificial Sequence
<220> FEATURE:
<223> OTHER INFORMATION: 4-1BB CDRH1

<400> SEQUENCE: 244

Tyr Tyr Trp Ser
1

<210> SEQ ID NO 245
<211> LENGTH: 12
<212> TYPE: PRT
<213> ORGANISM: Artificial Sequence
<220> FEATURE:
<223> OTHER INFORMATION: 4-1BB CDRH3

<400> SEQUENCE: 245

Tyr Gly Pro Gly Asn Tyr Asp Trp Tyr Phe Asp Leu
1 5 10

<210> SEQ ID NO 246
<211> LENGTH: 11
<212> TYPE: PRT
<213> ORGANISM: Artificial Sequence
<220> FEATURE:
<223> OTHER INFORMATION: 4-1BB CDRL1

<400> SEQUENCE: 246

Ser Gly Asp Asn Ile Gly Asp Gln Tyr Ala His
1 5 10

<210> SEQ ID NO 247
<211> LENGTH: 7
<212> TYPE: PRT
<213> ORGANISM: Artificial Sequence
<220> FEATURE:
<223> OTHER INFORMATION: 4-1BB CDRL2

<400> SEQUENCE: 247

Gln Asp Lys Asn Arg Pro Ser
1 5

<210> SEQ ID NO 248
<211> LENGTH: 11
<212> TYPE: PRT
<213> ORGANISM: Artificial Sequence
<220> FEATURE:
<223> OTHER INFORMATION: 4-1BB CDRL3

<400> SEQUENCE: 248

Ala Thr Tyr Thr Gly Phe Gly Ser Leu Ala Val
1               5                   10

<210> SEQ ID NO 249
<211> LENGTH: 10
<212> TYPE: PRT
<213> ORGANISM: Artificial Sequence
<220> FEATURE:
<223> OTHER INFORMATION: 4-1BB CDRH1

<400> SEQUENCE: 249

Gly Tyr Ser Phe Ser Thr Tyr Trp Ile Ser
1               5                   10

<210> SEQ ID NO 250
<211> LENGTH: 14
<212> TYPE: PRT
<213> ORGANISM: Artificial Sequence
<220> FEATURE:
<223> OTHER INFORMATION: 4-1BB CDRH2

<400> SEQUENCE: 250

Lys Ile Tyr Pro Gly Asp Ser Tyr Thr Asn Tyr Ser Pro Ser
1               5                   10

<210> SEQ ID NO 251
<211> LENGTH: 7
<212> TYPE: PRT
<213> ORGANISM: Artificial Sequence
<220> FEATURE:
<223> OTHER INFORMATION: 4-1BB CDRH3

<400> SEQUENCE: 251

Gly Tyr Gly Ile Phe Asp Tyr
1               5

<210> SEQ ID NO 252
<211> LENGTH: 720
<212> TYPE: PRT
<213> ORGANISM: Artificial Sequence
<220> FEATURE:
<223> OTHER INFORMATION: t-cTRP 24x8-SH2 protein sequence

<400> SEQUENCE: 252

Met Gly Asn Ser Glu Leu Ala Ala Arg Ile Leu Ile Ile Leu Phe Gln
1               5                   10                  15

Gln Leu Val Glu Leu Ala Arg Leu Ala Ile Glu Ser Gly Asp Glu Glu
            20                  25                  30

Leu Leu Arg Arg Val Ser Glu Trp Leu Glu Glu Val Ile Lys Asp Met
        35                  40                  45

Arg Arg Val Val Glu Gln Ala Leu Arg Glu Gly Asn Ser Glu Leu Ala
    50                  55                  60

Ala Arg Ile Leu Ile Ile Leu Phe Gln Gln Leu Val Glu Leu Ala Arg
65                  70                  75                  80

Leu Ala Ile Glu Ser Gly Asp Glu Glu Leu Leu Arg Arg Val Ser Glu
                85                  90                  95

Trp Leu Glu Glu Val Ile Lys Asp Met Arg Arg Val Val Glu Gln Ala
            100                 105                 110

Leu Arg Glu Gly Gly Gly Ser Asp Gly Gln Asp Lys Gly Ser Asp Gly
        115                 120                 125

Gln Asp Lys Gly Gly Ser Glu Trp Tyr Tyr Gly Asn Val Thr Arg His
    130                 135                 140

```
Gln Ala Glu Cys Ala Leu Asn Glu Arg Gly Val Glu Gly Asp Phe Leu
145                 150                 155                 160

Ile Arg Asp Ser Glu Ser Ser Pro Ser Asp Phe Ser Val Ser Leu Lys
                165                 170                 175

Ala Ser Gly Lys Asn Lys His Phe Lys Val Gln Leu Val Asp Asn Val
            180                 185                 190

Tyr Cys Ile Gly Gln Arg Arg Phe His Thr Met Asp Glu Leu Val Glu
        195                 200                 205

His Tyr Lys Lys Ala Pro Ile Phe Thr Ser Glu His Gly Glu Lys Leu
    210                 215                 220

Tyr Leu Val Arg Ala Leu Gln Gly Gly Ser Asp Gly Gln Asp Lys Gly
225                 230                 235                 240

Ser Asp Gly Gln Asp Lys Gly Asn Ser Glu Leu Ala Ala Arg Ile Leu
                245                 250                 255

Ile Ile Leu Phe Gln Gln Leu Val Glu Leu Ala Arg Leu Ala Ile Glu
            260                 265                 270

Ser Gly Asp Glu Glu Leu Leu Arg Arg Val Ser Glu Trp Leu Glu Glu
        275                 280                 285

Val Ile Lys Asp Met Arg Arg Val Val Glu Gln Ala Leu Arg Glu Gly
    290                 295                 300

Asn Ser Glu Leu Ala Ala Arg Ile Leu Ile Ile Leu Phe Gln Gln Leu
305                 310                 315                 320

Val Glu Leu Ala Arg Leu Ala Ile Glu Ser Gly Asp Glu Glu Leu Leu
                325                 330                 335

Arg Arg Val Ser Glu Trp Leu Glu Glu Val Ile Lys Asp Met Arg Arg
            340                 345                 350

Val Val Glu Gln Ala Leu Arg Glu Gly Asn Ser Glu Leu Ala Ala Arg
        355                 360                 365

Ile Leu Ile Ile Leu Phe Gln Gln Leu Val Glu Leu Ala Arg Leu Ala
    370                 375                 380

Ile Glu Ser Gly Asp Glu Glu Leu Leu Arg Arg Val Ser Glu Trp Leu
385                 390                 395                 400

Glu Glu Val Ile Lys Asp Met Arg Arg Val Val Glu Gln Ala Leu Arg
                405                 410                 415

Glu Gly Asn Ser Glu Leu Ala Ala Arg Ile Leu Ile Ile Leu Phe Gln
            420                 425                 430

Gln Leu Val Glu Leu Ala Arg Leu Ala Ile Glu Ser Gly Asp Glu Glu
        435                 440                 445

Leu Leu Arg Arg Val Ser Glu Trp Leu Glu Glu Val Ile Lys Asp Met
    450                 455                 460

Arg Arg Val Val Glu Gln Ala Leu Arg Glu Gly Gly Gly Ser Asp Gly
465                 470                 475                 480

Gln Asp Lys Gly Ser Asp Gly Gln Asp Lys Gly Gly Ser Glu Trp Tyr
                485                 490                 495

Tyr Gly Asn Val Thr Arg His Gln Ala Glu Cys Ala Leu Asn Glu Arg
            500                 505                 510

Gly Val Glu Gly Asp Phe Leu Ile Arg Asp Ser Glu Ser Ser Pro Ser
        515                 520                 525

Asp Phe Ser Val Ser Leu Lys Ala Ser Gly Lys Asn Lys His Phe Lys
    530                 535                 540

Val Gln Leu Val Asp Asn Val Tyr Cys Ile Gly Gln Arg Arg Phe His
545                 550                 555                 560

Thr Met Asp Glu Leu Val Glu His Tyr Lys Lys Ala Pro Ile Phe Thr
```

```
                565                 570                 575

Ser Glu His Gly Glu Lys Leu Tyr Leu Val Arg Ala Leu Gln Gly Gly
            580                 585                 590

Ser Asp Gly Gln Asp Lys Gly Ser Asp Gly Gln Asp Lys Gly Asn Ser
        595                 600                 605

Glu Leu Ala Ala Arg Ile Leu Ile Ile Leu Phe Gln Gln Leu Val Glu
    610                 615                 620

Leu Ala Arg Leu Ala Ile Glu Ser Gly Asp Glu Glu Leu Leu Arg Arg
625                 630                 635                 640

Val Ser Glu Trp Leu Glu Glu Val Ile Lys Asp Met Arg Arg Val Val
                645                 650                 655

Glu Gln Ala Leu Arg Glu Gly Asn Ser Glu Leu Ala Ala Arg Ile Leu
            660                 665                 670

Ile Ile Leu Phe Gln Gln Leu Val Glu Leu Ala Arg Leu Ala Ile Glu
        675                 680                 685

Ser Gly Asp Glu Glu Leu Leu Arg Arg Val Ser Glu Trp Leu Glu Glu
    690                 695                 700

Val Ile Lys Asp Met Arg Arg Val Val Glu Gln Ala Leu Arg Glu Gly
705                 710                 715                 720


<210> SEQ ID NO 253
<211> LENGTH: 261
<212> TYPE: PRT
<213> ORGANISM: Artificial Sequence
<220> FEATURE:
<223> OTHER INFORMATION: cTRP24 subunit, FLAG tag, and TEV-His-Avi tag

<400> SEQUENCE: 253

Met Glu Thr Asp Thr Leu Leu Leu Trp Val Leu Leu Leu Trp Val Pro
1               5                   10                  15

Gly Ser Thr Gly Asp Tyr Lys Asp Glu Gly Gly Gly Ser Cys Glu Ala
            20                  25                  30

Ile Lys Ala Ala Ala Glu Leu Gly Lys Ala Gly Ile Ser Ser Glu Glu
        35                  40                  45

Ile Leu Glu Leu Leu Arg Ala Ala His Glu Leu Gly Leu Asp Pro Glu
    50                  55                  60

Ala Ile Lys Ala Ala Ala Glu Leu Gly Lys Ala Gly Ile Ser Ser Glu
65                  70                  75                  80

Glu Ile Leu Glu Leu Leu Arg Ala Ala His Glu Leu Gly Leu Asp Pro
                85                  90                  95

Glu Ala Ile Lys Ala Ala Ala Glu Leu Gly Lys Ala Gly Ile Ser Ser
            100                 105                 110

Glu Glu Ile Leu Glu Leu Leu Arg Ala Ala His Glu Leu Gly Leu Asp
        115                 120                 125

Pro Glu Ala Ile Lys Ala Ala Ala Glu Leu Gly Lys Ala Gly Ile Ser
    130                 135                 140

Ser Glu Glu Ile Leu Glu Leu Leu Arg Ala Ala His Glu Leu Gly Leu
145                 150                 155                 160

Asp Pro Glu Ala Ile Lys Ala Ala Ala Glu Leu Gly Lys Ala Gly Ile
                165                 170                 175

Ser Ser Glu Glu Ile Leu Glu Leu Leu Arg Ala Ala His Glu Leu Gly
            180                 185                 190

Leu Asp Pro Glu Cys Ile Lys Ala Ala Ala Glu Leu Gly Lys Ala Gly
        195                 200                 205

Ile Ser Ser Glu Glu Ile Leu Glu Leu Leu Arg Ala Ala His Glu Leu
```

```
    210                 215                 220

Gly Leu Gly Gly Gly Ser Glu Asn Leu Tyr Phe Gln Gly Ser His His
225                 230                 235                 240

His His His His Gly Ser Gly Leu Asn Asp Ile Phe Glu Ala Gln Lys
                245                 250                 255

Ile Glu Trp His Glu
            260


<210> SEQ ID NO 254
<211> LENGTH: 327
<212> TYPE: PRT
<213> ORGANISM: Artificial Sequence
<220> FEATURE:
<223> OTHER INFORMATION: cTRP24 subunit, FLAG tag, and TEV-His-Avi tag

<400> SEQUENCE: 254

Met Glu Thr Asp Thr Leu Leu Leu Trp Val Leu Leu Leu Trp Val Pro
1               5                   10                  15

Gly Ser Thr Gly Asp Tyr Lys Asp Glu Gly Gly Gly Ser Cys Glu Ala
            20                  25                  30

Ile Lys Ala Ala Ala Glu Leu Gly Lys Ala Gly Ile Ser Ser Glu Glu
        35                  40                  45

Ile Leu Glu Leu Leu Arg Ala Ala His Glu Leu Gly Leu Asp Pro Glu
    50                  55                  60

Ala Ile Lys Ala Ala Ala Glu Leu Gly Lys Ala Gly Ile Ser Ser Glu
65                  70                  75                  80

Glu Ile Leu Glu Leu Leu Arg Ala Ala His Glu Leu Gly Leu Asp Pro
                85                  90                  95

Glu Ala Ile Lys Ala Ala Ala Glu Leu Gly Lys Ala Gly Ile Ser Ser
            100                 105                 110

Glu Glu Ile Leu Glu Leu Leu Arg Ala Ala His Glu Leu Gly Leu Asp
        115                 120                 125

Pro Glu Ala Ile Lys Ala Ala Ala Glu Leu Gly Lys Ala Gly Ile Ser
    130                 135                 140

Ser Glu Glu Ile Leu Glu Leu Leu Arg Ala Ala His Glu Leu Gly Leu
145                 150                 155                 160

Asp Pro Glu Ala Ile Lys Ala Ala Ala Glu Leu Gly Lys Ala Gly Ile
                165                 170                 175

Ser Ser Glu Glu Ile Leu Glu Leu Leu Arg Ala Ala His Glu Leu Gly
            180                 185                 190

Leu Asp Pro Glu Ala Ile Lys Ala Ala Ala Glu Leu Gly Lys Ala Gly
        195                 200                 205

Ile Ser Ser Glu Glu Ile Leu Glu Leu Leu Arg Ala Ala His Glu Leu
    210                 215                 220

Gly Leu Asp Pro Glu Ala Ile Lys Ala Ala Ala Glu Leu Gly Lys Ala
225                 230                 235                 240

Gly Ile Ser Ser Glu Glu Ile Leu Glu Leu Leu Arg Ala Ala His Glu
                245                 250                 255

Leu Gly Leu Asp Pro Glu Cys Ile Lys Ala Ala Ala Glu Leu Gly Lys
            260                 265                 270

Ala Gly Ile Ser Ser Glu Glu Ile Leu Glu Leu Leu Arg Ala Ala His
        275                 280                 285
```

```
Glu Leu Gly Leu Gly Gly Gly Ser Glu Asn Leu Tyr Phe Gln Gly Ser
    290                 295                 300

His His His His His His Gly Ser Gly Leu Asn Asp Ile Phe Glu Ala
305                 310                 315                 320

Gln Lys Ile Glu Trp His Glu
                325
```

SELF-ASSEMBLING CIRCULAR TANDEM REPEAT PROTEINS WITH INCREASED STABILITY

CROSS-REFERENCE TO RELATED APPLICATIONS

This application is a U.S. National Phase Patent Application based on International Patent Application No. PCT/US2020/040733 filed Jul. 2, 2020, which claims priority to U.S. Provisional Patent Application No. 62/870,005 filed Jul. 2, 2019 and to U.S. Provisional Patent Application No. 62/984,706 filed Mar. 3, 2020, the contents of each of which are incorporated by reference herein in their entirety.

STATEMENT OF GOVERNMENT INTEREST

This invention was made with government support under grant numbers GM106117, GM049857, and GM115545 awarded by the National Institutes of Health. The government has certain rights in the invention.

STATEMENT REGARDING SEQUENCE LISTING

The Sequence Listing associated with this application is provided in text format in lieu of a paper copy and is hereby incorporated by reference into the specification. The name of the text file containing the Sequence Listing is 2M23051 ST25.txt The text file is 224 KB, was created on Dec. 17, 2021, and is being submitted electronically via EFS-Web.

FIELD OF THE DISCLOSURE

The present disclosure provides artificially designed self-assembling circular tandem repeat proteins (cTRPs) with increased stability. The proteins are circular, handed, and include alpha-helical repeat proteins. The cTRPs have a number of uses as scaffolds for geometrically precise, arrayed presentation of functional domains including fluorescent proteins, protein capture domains, single chain major histocompatibility proteins, thermostable proteases, and others.

BACKGROUND OF THE DISCLOSURE

Protein engineering has greatly matured over the past few years and is now a powerful approach for the design and generation of a wide variety of novel protein folds and assemblages.

Repeat proteins are formed by repetition of modular units of protein sub-structures. The overall structural architecture of repeat proteins is dictated by the internal geometry of the protein and the local packing of the repeat building blocks. These features are generated by underlying patterns of amino acid sequences, that themselves, are repetitive in nature.

Naturally existing repeat proteins play important biological roles as macromolecular binding and scaffolding domains, enzymes, and building blocks for the assembly of fibrous materials. The structure and identity of these repeat proteins are highly diverse, ranging from extended, super-helical folds that bind peptide, DNA, and RNA partners, to closed and compact conformations with internal cavities suitable for small molecule binding and catalysis.

WO2017/096236 describes repeat proteins designed purely by geometric criteria defining the inter-repeat geometry, without reference to the sequences and structures of naturally existing repeat protein families. Because the design methodology did not rely on a template sequence or structural information taken from natural repeat proteins, the resulting repeat proteins were unlike those seen in nature. More particularly, the designed repeat proteins had repetitive alpha (α)-helical structures joined by linkers. The particular structure of the proteins was based on the formula $(a\text{-}b\text{-}x\text{-}y)_n$ wherein a and x represent linker sequences; b represents an amino acid sequence that forms an α helix; y represents an amino acid sequence that forms a second α helix; n=3 or more; and wherein each (a-b-x-y) unit is structurally repetitive to an adjacent (a-b-x-y) unit; the protein is handed; and the N-termini ("first segment") and C-termini ("last segment") of the protein create a circular architecture. The circular architecture of these proteins occurred because the inter-repeat packing geometry was constrained so as to naturally juxtapose the N- and C-termini of the protein within 10 Å following expression and folding. These proteins are referred to as circular tandem repeat proteins, or "cTRPs".

The described cTRPs have numerous uses as biomaterials. For example, the cTRPs can be used as scaffolds for geometrically precise, arrayed presentation of cell-signaling and/or immune-related protein and peptide epitopes, as well as numerous other therapeutic, diagnostic, and nanotechnological uses. In particular embodiments, functional domains were inserted between α-helical sequences and/or linker sequences without significantly altering the cTRPs' engineered parameters (e.g., circular, handed, α-helical repeats).

SUMMARY OF THE DISCLOSURE

The current disclosure describes self-assembling cTRPs with increased stability. Self-assembling cTRPs with increased stability were generated by adopting one of two approaches. The first approach includes selecting amino acid sequences that form an alpha (α) helix and introducing precisely placed cysteine mutations within the N-terminal and C-terminal segments of the b position of the $(a\text{-}b\text{-}x\text{-}y)_n$ formula. These precisely placed cysteine mutations create di-sulfide bonds which serve as a "staple" to fully close the proteins circular architecture. That is, the closed self-assembled cTRPs have an N-terminus and a C-terminus that are physically linked rather than simply constrained by inter-repeat packing geometry.

In particular embodiments, a selected α-helix-forming protein has 13 amino acid residues with a cysteine at position 1 for use in the N-terminal b segment of $(a\text{-}b\text{-}x\text{-}y)_n$. In particular embodiments, a selected α-helix-forming protein has 13 amino acid residues with a cysteine at position 3 for use in the C-terminal b segment of $(a\text{-}b\text{-}x\text{-}y)_n$. In particular embodiments, a selected α-helix-forming protein has 13 amino acid residues with a proline at position 1. The position 1 proline can be modified to cysteine in the N-terminal b segment of $(a\text{-}b\text{-}x\text{-}y)_n$. In particular embodiments, a selected α-helix-forming protein has 13 amino acid residues with an alanine at position 3. The position 3 alanine can be modified to cysteine in the C-terminal b segment of $(a\text{-}b\text{-}x\text{-}y)_n$. These selections and mutations create self-assembled, closed ("stapled") cTRPs with increased stability over a non-closed circular architecture.

In particular embodiments, a selected α-helix-forming protein has 25 amino acid residues with a cysteine at position 7 for use in the N-terminal b segment of $(a\text{-}b\text{-}x\text{-}y)_n$. In particular embodiments, a selected α-helix-forming protein has 25 amino acid residues with a cysteine at position 5 for use in the C-terminal b segment of $(a\text{-}b\text{-}x\text{-}y)_n$. In particular embodiments, a selected α-helix-forming protein has 25 amino acid residues with an alanine at position 5. The position 5 alanine can be modified to cysteine in the C-terminal b segment of $(a\text{-}b\text{-}x\text{-}y)_n$. In particular embodiments, a selected α-helix-forming protein has 25 amino acid residues with an isoleucine at position 7. The position 7 isoleucine can be modified to cysteine in the N-terminal b segment of $(a\text{-}b\text{-}x\text{-}y)_n$. These selections and mutations create self-assembled, closed cTRPs with increased stability over a non-closed circular architecture.

The second approach to creating self-assembling cTRPs with increased stability includes selecting amino acid sequences that form an α helix wherein the selected amino acid sequences each have at least 23 amino acid residues (creating "thick" self-assembling cTRPs).

The first and second approaches can be practiced together to create self-assembling cTRPs that are both closed and thick.

Particular embodiments include self-assembled cTRPs harboring 24 (a-b-x-y) repeats. In particular embodiments, each repeat is identical. In particular embodiments, each repeat is identical but for inclusion of cysteine mutations in N- and C-terminal b domains. In particular embodiments, each repeat is not identical, but is structurally repetitive.

A variety of functional domains can be provided at defined positions around the periphery of self-assembled cTRPs. The functional domains can be selected for a wide range of purposes that depend only on the nature and function of the cargo that is displayed by the underlying self-assembled cTRPs. Self-assembled cTRPs are particularly useful to display multiple functional domains when high avidity molecular interactions, and/or interactions that require clustering of cell surface proteins, are sought. Particular embodiments display multiple copies of large proteins at symmetrically distributed positions around the peripheral of a self-assembling cTRP.

Exemplary functional domains include fluorescent proteins, protein capture domains, single chain major histocompatibility proteins, binding domains that activate immune cells, and thermostable proteases, although numerous additional functional domains can be used and are described herein.

DESCRIPTION OF THE FIGURES

(FIGS. 1A, 1B) Topology, dimensions (1A), sequence (SEQ ID NO: 1) and secondary structure content (FIG. 1B) of a computational model of the protein nanoparticle. The engineered construct ('cTRP24') contains 24 repeated structural units (a left-handed 2-helix bundle) corresponding to exact repeats of a 33 amino acid sequence. The interface between the N- and C-terminal repeats (#1 and #24) is identical to that between all other internal repeats. The outer diameter of the cTRP24 is 100 Å, its width is 20 Å and the inner diameter is 60 Å. (FIG. 1C) Computational model showing the fold and side chain distribution of a single structural repeat (left) and of the interface between two consecutive structural repeats (right). The inner and outer surfaces of the cTRP24 are primarily lined with pairs of lysine and glutamate residues.

(FIG. 2A) Circular dichroism (CD) spectra of cTRP24 at 22° and 95° C. shows preservation of secondary structure at high temperature. (FIG. 2B) Small angle x-ray scattering (SAXS) spectra measured for cTRP24 (left), calculated SAXS spectrum derived from the atomic model of the designed protein construct (middle) and a superposition of the experimental and calculated spectra (right). (FIG. 2C) Negative-stain electron microscopy images of cTRP24. The dimensions and thickness of the observed nanoparticles are in close agreement with those corresponding to a space-filled model of the designed construct.

(FIG. 3A) Constructs containing 3, 4, 6, 8, 12 or 24 repeats were individually expressed and purified from *E. coli* using identical protocols (see Example 1 Methods); each construct was run at concentrations of 10 mg/mL. The elution profiles indicate that the smaller constructs (containing 3 to 8 repeats per subunit) fail to assemble into a full, 24-repeat cTRP. The largest subunit (containing 12 repeats; '$cTRP24_{12}$') migrates with the full sized cTRP24, consistent with an intact dimer, but a long tail extending from the peak indicates that the construct is in dynamic equilibrium between dimeric and monomeric species (the latter probably sampling a range of conformations). (FIG. 3B) Assembly behavior of $cTRP24_{12}$ construct as a function of pH. Between pH 6.5 and 8.5 the elution behavior of the construct appears to be largely unchanged. (FIG. 3C) SEC analysis of a 12-repeat construct, with a pair of point mutations (P4C and A6C, shown in computational structural models on the right) introduced at the interface of the N- and C-terminal repeats create a disulfide 'stapled' protein homodimer ('$cTRP24_{12}SS$'). The resulting construct eluted as a single symmetric peak at the same elution volume as the monomeric cTRP24 construct. SDS-PAGE analyses under reducing and non-reducing conditions also support formation of a disulfide-stapled dimer (FIGS. 4A, 4B). An additional construct, harboring four mutations to physically prevent dimerization ('$cTRP24_{12}Capped$') was used as a negative control for dimeric assembly.

(FIG. 4A) The cTRP2412SS construct, assembled from dimerization of two identical protein subunits each harboring 12 repeats, with the N- and C-terminal repeat of each containing a cysteine residue (described in Example 1 and in FIGS. 3A-3B) that enable disulfide stapling. SEC analyses (shown in FIG. 3C) and electrophoretic analyses (right panel) both indicate formation of a dimer that contains a mixture of one or two disulfide staples, both of which behave in solution similarly to a monomeric, single chain 24-repeat cTRP. (FIG. 4B) A cTRP246SS construct, assembled from four identical protein subunits each harboring 6 repeats, with the N- and C-terminal repeat of each containing a cysteine residue (described in Example 1 and in FIGS. 3A-3B) that enable disulfide stapling. SEC analyses indicate that expression and purification yield a cTRP24 that behaves in solution in a similar manner to a monomeric, single chain 24-repeat cTRP. Electrophoretic analyses of the same construct generated either via cytosolic expression in *E. coli* (and then oxidized in the presence of air during purification) or via secretion from human HEK cells (oxidized as part of eukaryotic disulfide bond formation mechanism during secretion) indicate that disulfides are formed in both cases. However, expression from bacteria generates a mixture of species (harboring 2, 3 or 4 disulfides), whereas expression and secretion from human cells generated a more homogeneous population of species primarily consisting of a full complement of disulfide bonds.

5A) Two step purification of cTRPs that do not harbor internal cysteine residues or disulfide staples. (FIG. 5B) Three step purification of cTRPs with internal cysteine residues that form disulfide staples.

(FIG. 5C) Three consecutive chromatographic purification steps (metal-dependent affinity chromatography via an N-terminal polyhistidine tag, HiTrap Q ion exchange chromatography, and size exclusion chromatography) were employed. The larger band on the final column and gel corresponds to incompletely reduced, disulfide-stapled t-cTRPs. (FIG. 5D) CryoEM micrographs of t-cTRP_24x$_8$-SS construct (corresponding to a circular particle containing 24 total repeats, which self-assembled from three identical subunits containing eight repeats each, with disulfide staples incorporated at the interface of each subunit). Images were acquired at two different protein concentrations Cryo-electron microscopy ('CryoEM'). (Data were collected on a ThermoFisher Glacios microscope with a Gatan K2 direct electron detector; microscope operating at 200 KV, 1.16 Å/pixel, total dose 40 e–/Å$^2$). (FIG. 5E) Selected 2-dimensional class averages generated from 197,089 separate particles imaged via CryoEM microscopy. (FIG. 5F) CryoEM electron density map and molecular model of t-cTRP_24x$_8$-SS construct, viewed from the side of the t-cTRP toroid ring. The three symmetrically distributed features of density extending above the protein nanoparticle correspond to the N-terminal polyhistidine affinity tag located at the N-termini of each protein subunit. (FIG. 5G) CryoEM electron density map and molecular model of t-cTRP_24x$_8$-SS construct, viewed from the bottom of the t-cTRP toroid ring.

(FIG. 5H) secreted cTRP24$_6$SS protein (naked tetramer (SEQ ID NO: 253)); (FIG. 5I) secreted cTRP24$_8$SS protein (naked trimer; (SEQ ID NO: 254)).

(FIG. 6C) Four copies of an engineered fluorescence activating protein ('mFAP') are inserted into four evenly distributed surface loops around the bottom face of the cTRP ('cTRP246SS-mFAP').

(FIG. 7A) Ribbon diagram of a computational model showing the structure of cTRP24$_6$SS-scMHC expressed from human HEK 293 cells. The construct is composed of a disulfide-stapled tetramer, wherein each subunit includes an N-terminal single chain MHC trimer ('scMHC') fused to six cTRP repeats. (FIG. 7B) Negative-stain EM images of a field of cTRP24$_6$SS-scMHC particles. The four-fold symmetric arrangement of the scMHC domains around each particle, many of which are oriented with the cTRP in the plane of the grid, is clearly visible. Inset, top view of model is visible in the panel on the left. (FIG. 7C) Denaturing electrophoretic and size exclusion chromatographic analyses of disulfide-stapled, tetrameric cTRP24-scMHC (left gel insert and solid elution trace) and unstapled, monomeric cTRP-scMHC (right gel insert and dotted elution trace). Denaturing electrophoretic analyses of purified protein constructs were performed under non-reducing and reducing conditions. The change in mobility under reducing conditions is due to the dissolution of the tetrameric assemblage and/or loss of disulfides in the scMHC cargo for the two respective constructs. (FIG. 7D) T-cell staining with cTRP24-scMHC. A CMVpp65-reactive CD8$^+$ T-cell line was stained with monomeric or tetrameric cTRP24-scMHC (CMV) constructs (a protocol involving secondary staining with an anti-HisTag antibody labeled with iFluor647) or with a tetrameric streptavidin-scMHC(CMV) (which harbors a conjugated allophycocyanin (APC; a different, brighter fluorescent moiety). Also shown are histograms for unstained cells and anti-His iFluor647 stained cell as controls. While the monomeric cTRP produces a negligible fluorescent staining signal, both the tetrameric scMHC-harboring constructs label close to 100% of the cells. The difference in fluorescent intensity reflects the different fluorescent moieties incorporated into the two labeling constructs. Background staining of peripheral blood mononuclear cells (PBMC) from a cytomegalovirus (CMV) donor is also shown with the same staining conditions. Off-set histograms were gated from lymphocyte (FSC-SSC) and live cell (DAPI$^-$) populations as indicated. (FIGS. 7E-7H) Detection of CMV pp65-reactive CD8+ T cells diluted into donor PBMCs using cTRP246SS-scMHC and streptavidinallophycocyanin (APC) tetramers. In FIGS. 7E-7H, the same clone utilized to generate the data presented in (FIG. 7D) was diluted into fresh PBMCs to examine the limit of detection. (FIG. 7E) Forward versus side scatter plot showing an overlay of CMV pp65-reactive T-cells (red contour designated as "Live t-cells") and donor PBMCs (blue contour designated as "Live PBMCs") and the lymphocyte gating strategy used for further analysis. This strategy was used to quantitate CMV pp65-reactive T-cells diluted into donor PBMCs as shown in panels (FIG. 7F) and (FIG. 7G). (FIG. 7F) Scatter plot showing an overlay of the DAPI-negative lymphocyte gates stained with an anti-His-APC secondary antibody (Biolegend #362605). Results confirm that the secondary antibody used to detect cTRP246SS-scMHC does not result in unwanted background staining of live cells. (FIG. 7G) Representative flow cytometry scatter plot showing quantitation of CMV pp65-reactive T-cells diluted into donor PBMCs at a ratio of 1:4 respectively. (FIG. 7H) Quantitation of CMV pp65-reactive T-cells at various dilutions using both the cTRP246SS-scMHC (detected using the anti-His-APC secondary) and streptavidin-APC scMHC tetramer (SA-Tetramer). Note that the ratios in the first column (CMV:PBMC) represent raw cell counts prior to staining.

(FIG. 9A) Left: Size exclusion chromatographic (SEC) elution profiles of (1) a 24x cTRP ('cTRP'); (2) a 24x cTRP harboring four copies of an SH2 domain ('cTRP-SH2'); (3) a 24x cTRP harboring four copies of a spycatcher domain ('cTRP-Spy') and (4) a 24x cTRP harboring four copies of a spycatcher domain that has been conjugated with four corresponding copies of a spy-tagged SH2 domain ('cTRP-Spy-SH2'). All constructs include a homodimeric assembly of two subunits containing 12 cTRP repeats. The fully assembled constructs are stabilized by disulfide 'staples' at each subunit interface as illustrated in FIG. 9C. Right, Top: Electrophoretic visualization of each purified construct. Right, bottom: Demonstration of covalent capture and ligation of a 'Spytagged' cargo domain (spy-SH2) by the 24x_sub12-SS-Spycatcher construct. Ligation proceeds to completion within 15 minutes at room temperature. (FIG. 9B) Peptide binding in solution by free SH2 and by cTRP24-displayed SH2 domains. Fluorescent polarization (FP) with labeled phosphotyrosyl peptide (corresponding to the physiological binding target for the Lck SH2 domain) was performed using purified free SH2 domain, cTRP24-SH2 (a direct fusion of four SH2 domains around the periphery of the dimerized 24-repeat construct) and cTRP24_Spy-SH2 (in which four 'spytagged' SH2 domains are captured by four Spycatcher domains, arranged at the same positions around the dimerized 24-repeat construct). A control experiment was also conducted using a free cTRP nanoparticle harboring no functional protein domains. The protein concentration is normalized to account for the 4:1 ratio of SH2 domains per molecule (4 per cTRP; 1 per free SH2). All three constructs display saturable binding and a $K_D$ of 200 to 300 nM pTyr-peptide. The specific activity of the cTRP-displayed SH2 domain may be slightly enhanced (by no more than a factor of 2 to 3) but that difference is near the limit of precision when comparing different ligand binding constructs and preps. (FIG. 9C) Free SH2 and cTRP24-displayed SH2 domains binding to surface bound peptide. SPR was used to measure the binding of purified free SH2 domain, cTRP24-SH2 and cTRP24-Spy-SH2 to captured biotinylated phosphotyrosyl peptide. In this experiment, the chip harbors a 7-fold lower density of captured peptide on the chip as compared to the experiment illustrated in FIGS. 10A, 10B and gives similar results, although with a smaller difference in off-rate between free SH2 and constructs harboring four displayed copies of SH2. Inset: A control experiment using a cTRP24 construct without SH2 domains did not display measurable peptide binding.

(FIG. 10A) Surface Plasmon Resonance ('SPR' i.e. 'Biacore') measurements were used to measure the binding of immobilized phosphotyrosyl peptide by purified free SH2 domain and cTRP_Spy-SH2 (in which four 'spytagged' SH2 domains are captured by four Spycatcher domains, arranged at the same positions around the dimerized 24-repeat construct; black). This experiment used a chip harboring a 7-fold higher density of immobilized peptide on the chip, relative to the experiment shown in FIG. 9C, and gave similar results, although with a larger difference in off-rate between free SH2 and constructs harboring four displayed copies of SH2 (which could not be fully liberated from the chip over the course of an extended overnight wash). Similar to the experiments performed in solution, a control experiment using a cTRP that was not decorated with SH2 domains did not display measurable peptide binding. (FIG. 10B) A t-cTRP_24$x_8$-SH2 (SEQ ID NO: 252) corresponding to a circular particle containing 24 total repeats, which self-assembled from three identical subunits containing eight repeats each was functionalized via the incorporation of two peptide-binding SH2 domains per subunit. The SH2 domains were inserted via their N- and C-termini within surface loops located at the boundary between repeats 2/3 and 6/7 in each subunit. The final assembled construct therefore contains total copies of the SH2 domain, distributed evenly between every fourth repeat in the assembled construct. The construct was expressed and purified, and tested for peptide binding via SPR. SPR experiments were performed at 25° C. on a Biacore T100 instrument (GE Healthcare) with a Series S SA chip using a running buffer of 10 mM HEPES, pH 7.4, 150 mM NaCl, 3 mM EDTA, 0.05% surfactant P20 with 0.1 mg/mL bovine serum albumin. Biotinylated Tir-10_v2 at 10 ng/mL was injected at 10 μL/minute over a flow cell to capture 15 RUs of peptide. The reference surface was blank streptavidin alone. Analytes were repurified by size exclusion chromatography just prior to use. Buffer blanks and samples (10 nM 24x25/28_sub8_3, 60 nM free SH2, and 10 nM 24x25/28_3_2SH2) were injected at 50 μL/minute with 7 minutes of association and 10 minutes of dissociation. An overlay plot of double-referenced data was generated, then normalized for off-rate comparison by dividing each curve by its maximum response in Scrubber2.0b software (BioLogic Software). Maximum binding responses observed were 125 and 123 RUs for free SH2 and 24x25/28_3_2SH2, respectively. The 24x25/28_sub8_3 control did not bind. The figure was made in Prism 7 (GraphPad) for Mac OS X version 7.0d.

(FIG. 11A) A 24-repeat cTRP harboring four copies of spycatcher is fully conjugated with four copies of a spytagged GFP derivative ('Clover'). The cTRP corresponds to a '24x-cTRP_sub12-SS-Spy' construct, assembled from dimerization of two identical protein subunits each harboring 12 repeats, with the N- and C-terminal repeat of each containing a cysteine residue that enable disulfide stapling. As a result, in this reducing gel two bands are observed as a result of addition of Spycatcher, corresponding to capture of 1 or 2 copies of the tagged Clover domain by each 12-repeat protein subunit. (FIG. 11B) Fluorescence of free Clover and cTRP-Clover nanoparticles, as a function of normalized Clover concentrations. (FIG. 11C) Purification and fluorescence activity of a 24-repeat construct harboring four copies of an engineered fluorescence activating protein ('mFAP') that has previously been demonstrated to fluoresce in the presence of exogenous, bound DHFBI fluorophore. The two curves that demonstrate increasing fluorescence as a function of protein concentration correspond to the cTRP-mFAP nanoparticle and to free mFAP; as in FIG. 11B the protein concentrations are normalized relative to the one-versus-four copies of mFAP per molecule. The three curves that do not demonstrate an increase in fluorescence as a function of protein concentration correspond to the 'naked' cTRP, the naked cTRP plus DHFBI, and DHFBI alone. For the latter two constructs, the DHFBI concentration is equivalent at each protein concentration to that which is present in the active constructs.

(FIG. 12A, Left) structural diagram showing top-down view of the designed cTRP24$_6$SS-scFv$^{CD28}$ construct. The properly assembled, disulfide-stapled construct displays four copies of the scFv region of an anti-CD28 antibody (derived from TGN1412). The scFv is rendered as a black and white space-filling model; heavy chain variable ($V_H$) and light chain variable ($V_L$) regions are indicated. (FIG. 12A, Right) SEC and SDS-PAGE analyses of purified cTRP24$_6$SS-scFv$^{CD28}$ expressed in human 293 cells indicate proper assembly of the tetrameric construct. SEC was performed on a Superose 6 10/300 GL (GE) column and SDS-PAGE were performed under non-reducing (NR) and reducing (R) conditions. (FIG. 12B) Jurkat T-cell activation assay using anti-CD3 and anti-CD28 agonists. Jurkat T-cells expressing an NF-κB luciferase reporter for T-cell activation were incubated with soluble cTRP24$_6$SS-scFv$^{CD28}$ or the superagonistic monoclonal antibody (mAb) TGN1412 in the presence or absence of plate-bound anti-CD3 mAb OKT3. In the presence of OKT3, cTRP24$_6$SS-scFv$^{CD28}$ efficiently induced T-cell activation. Data shown as mean and s.d. for n=2 independent experiments. (FIG. 12C) A CFSE-based T-cell expansion assay. CFSE dilution as a function of human CD8$^+$ T-cell proliferation using plate-bound OKT3 (5 μg/mL) alone and in combination with soluble anti-CD28 superagonists TGN1412 mAb (1 μg/mL) or cTRP24$_6$SS-scFv$^{CD28}$ (1 μg/mL). Non-activated CD8+ T cells were considered as CFSE$^{hi}$ non-proliferating controls.

(FIG. 13A) (Left) structural diagram showing side view of the cTRP24$_6$SS-scTrimer$^{4\text{-}1BBL}$, with the single chain trimer rendered in space fill. (FIG. 13A, Right) structural model (looking down at the T-cell surface) showing theoretical 4-1BB receptor clustering in which the nanoparticle simultaneously engages up to twelve individual receptors. 4-1BB and 4-1BBL complex structures were built using PDB 6A3V. (FIG. 13B) Both of these tetramers secreted well from 293-F cells and ran as monodispersed, tetrameric proteins. (FIG. 13C) Staining of 4-1BB receptor on activated CD8+ T-cells using cTRP246SS-scTrimer$^{4\text{-}1BBL}$. Flow cytometry histogram showing staining of activated CD8+ T-cells (4 days post stimulation with anti-CD3/anti-CD28 beads) with cTRP246SS-scTrimer$^{4\text{-}1BBL}$ using a secondary anti-His iFluor647 antibody or unstained T cells (left) and a PE-labeled anti-4-1BB mAb (right). (FIG. 13D) Surface expression of OX40 receptor as determined by antibody and cTRP tetramer staining. Staining of activated CD8$^+$ T-cells (4 days post stimulation with anti-CD3/anti-CD28 beads) using an APC-labeled anti-OX40 mAb (top) and cTRP24$_6$SS-scTrimer$^{OX40L}$ using a secondary anti-His-iFluor647 antibody (bottom). Unstained controls are shown (black).

FIG. 14. Sequences supporting the disclosure: Group I: sequences that form alpha-helical segments with N-terminal or C-terminal mutation positions bolded and underlined (sequences with no potential mutation positions or no naturally occurring cysteines at position 1 or 3 are not included in the 1st alpha helix of N-terminal or C-terminal segments (SEQ ID NOs: 2-20); Group II: thick cTRP sequences that form alpha-helical segments with N-terminal or C-terminal mutation n positions at 5 and 7 bolded and underlined (SEQ ID NOs: 21-26); Group III: modified N-terminal segments (SEQ ID NOs: 27-33); Group IV: modified C-terminal segments (SEQ ID NOs: 11, 31, 35-37); Group V: sequences with N-terminal segment mutation positions and/or C-terminal segment mutation positions underlined and bolded with leading linker sequences (SEQ ID NOs: 39-42); Group VI: sequences with N-terminal segment mutations with leading linker sequences (SEQ ID NOs: 43-46, 187, 188, 190, and 192); Group VII: sequences with C-terminal segment mutations with leading linker sequences (SEQ ID NOs: 47-51); Group VIII: sequences with N-terminal segment mutation positions and/or C-terminal segment mutation positions underlined and bolded with leading and following linker sequences (SEQ ID NOs: 52-55); Group IX: sequences with N-terminal segment cysteine mutations with leading and following linker sequences (SEQ ID NOs: 56-59, 189, 190, 193, and 194); Group X: sequences with C-terminal segment cysteine mutations with leading and following linker sequences (SEQ ID NOs: 60-62); Group XI: sequences with N-terminal segment mutation positions and/or C-terminal segment mutation positions underlined and bolded with leading and following linker sequences as well as secondary alpha helix forming sequence (SEQ ID NOs: 1 and 63-74); Group XII: sequences with N-terminal segment cysteine mutations underlined and bolded with leading and following linker sequences as well as secondary alpha helix forming sequence (SEQ ID NOs: 75-87); Group XIII: sequences with C-terminal segment cysteine mutations underlined and bolded with leading and following linker sequences as well as secondary alpha helix forming sequence (SEQ ID NOs: 88-97); single chain cTRP with 24 repeats (see FIGS. 1A-1C (SEQ ID NOs: 98 & 99); where provided in FIG. 14, DNA sequences are reading frames for translated protein sequences); cTRP24_Sub3 ('Sub3' cTRP construct containing 3 repeats; see FIG. 3A; (SEQ ID NOs: 100 & 101)); cTRP24_Sub4 ('Sub4' cTRP construct containing 4 repeats; see FIG. 3A; (SEQ ID NOs: 102 & 103)); cTRP24_Sub6 ('Sub6' cTRP construct containing 6 repeats; see FIG. 3A; (SEQ ID NOs: 104 & 105)); secreted cTRP24$_6$SS protein sequence (naked tetramer (SEQ ID NO: 253)); cTRP24_Sub8 ('Sub8' cTRP construct containing 8 repeats; see FIG. 3A; (SEQ ID NOs: 106 & 107)); secreted cTRP24$_8$SS protein sequence (naked trimer (SEQ ID NO: 254)); cTRP24_Sub12 (cTRP construct containing 12 repeats; see FIGS. 3A, 3B; (SEQ ID NOs: 108 & 109)); cTRP24_Sub12SS (cTRP construct containing 12 repeats and disulfide staples; see FIGS. 3C, 4A, 4B; (SEQ ID NOs: 110 & 111)); cTRP24_Sub12_capped (cTRP construct containing 12 repeats and mutations blocking dimerization; see FIG. 3C; (SEQ ID NOs: 112 & 113)); cTRP24_Sub6SS ('Sub6SS' cTRP construct containing 6 repeats and disulfide staples; see FIG. 4B; (SEQ ID NOs: 114 & 115)); thick cTRP sub3, this construct has 3 total repeats and is designed to trimerize to form a 9-repeat ring (SEQ ID NO: 116); thick cTRP sub6; this construct has 6 total repeats and is designed to tetramerize to form a 24 repeat ring (SEQ ID NO: 117); thick cTRP sub8; this construct has 8 total repeats and is designed to trimerize to form a 24 repeat ring (SEQ ID NO: 118); thick cTRP sub8 with 2 cysteines underlined (SEQ ID NO: 119); cTRP24_Sub12_Spy (cTRP Construct containing 12 repeats and inserted fusions of spycatcher domains; see FIG. 6B; (SEQ ID NOs: 120 & 121)); cTRP24_Sub12SS_SH2 (cTRP Construct containing 12 repeats and inserted fusions of SH2 domains; see FIGS. 6A and 3A-3C; (SEQ ID NOs: 122 & 123)); t-cTRP 24x$_8$-SH2 protein sequence (SEQ ID NO: 252; in this sequence there are three subunits (each containing 8 repeats, plus two inserted SH2 domain sequences; the protein forms a circular trimer containing 24 repeats total interrupted every 4 repeats by one of 6 total SH2 domains); cTRP24_Sub6SS_scMHC (Construct containing 6 repeats and inserted fusions of single chain MHC; see FIGS. 7A, 7C and 7D; (SEQ ID NO: 124 & 125)); cTRP24_Sub6_SS_mFAP (Construct containing 6 repeats and inserted fusions of mFAP fluorescent protein domains; see FIGS. 6C and 11C; (SEQ ID NO: 126 & 127)); cTRP24_Sub6SS_scMHC_mFAP (Construct containing 6 repeats and inserted fusions of scMHC and mFAP fluorescent protein domains; see FIG. 8; (SEQ ID NO: 128 & 129)); Aqualysin fused to cTRP24_Sub6SS: (">Aqualysin-ToroidX6_SS_tetramer-His) (SEQ ID NOs: 130); Clover-SpyTag (Clover fluorescent protein with N-terminal spytag; see FIGS. 11A, 11B; (SEQ ID NOs: 131 & 132)); Clover fluorescent protein (SEQ ID NO: 133); MKate fluorescent protein (SEQ ID NO: 134); SH2-SpyTag (SH2 domain with N-terminal spytag; see FIGS. 9A-9C; (SEQ ID NOs: 135 & 136)); SH2 (Free SH2 domain; see FIGS. 9A-9C; (SEQ ID NOs: 137 & 138)); Spytagged single chain Fv (scFv) targeting IHF-1 (SEQ ID NO: 139); scFv_IHF1_TRL1068-Toroidx6_SS_tetramer-His: (SEQ ID NO: 140); MHC alpha chain (SEQ ID NO: 141); MHC beta chain (SEQ ID NO: 142); IL-3 (SEQ ID NO: 143); Delta (SEQ ID NO: 144); Jagged (SEQ ID NO: 145); huOKT3 variable heavy chain (SEQ ID NO: 146); huOKT3 variable light chain (SEQ ID NO: 147); huOKT3 CDR Regions according to Kabat numbering (SEQ ID NOs: 148-153); scFv_CD3_hsOKT3-Toroidx6_SS_tetramer-His: (SEQ ID NO: 154); scFv_CD28_TGN1412-Toroidx6_SS_tetramer-His: (SEQ ID NO: 155; see FIGS. 12A-12C); cTRP246SS-scTrimer$^{4\text{-}1BBL}$ ('Sub6' cTRP construct containing 6 repeats, disulfide staples and inserted fusions of a single chain trimer targeting 4-1BB; See FIGS. 13A-13C) (SEQ ID NO: 195); and cTRP246SS-scTrimer$^{OX4OL}$ ('Sub6' cTRP construct containing 6 repeats, disulfide staples and inserted fusions of a single chain trimer targeting OX40; See FIG. 13D) (SEQ ID NO: 196).

DETAILED DESCRIPTION

Figure 1A:
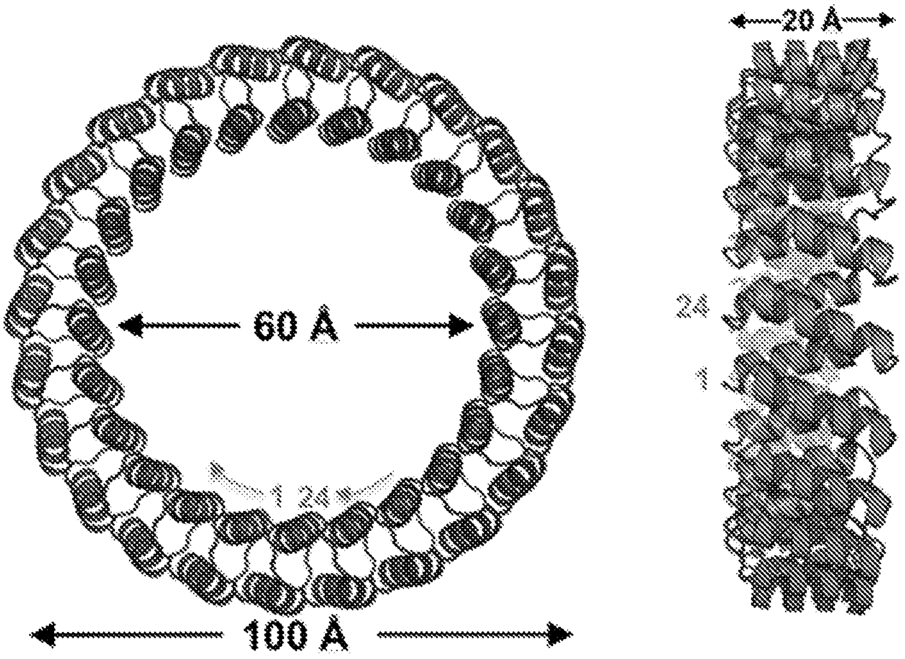
FIGS. 1A-1C. Properties of an engineered 24-repeat circular tandem repeat protein.

Repeat proteins are formed by repetition of modular units of protein sub-structures. The overall structural architecture of repeat proteins is dictated by the internal geometry of the protein and the local packing of the repeat building blocks. These features are generated by underlying patterns of amino acid sequences, that themselves, are repetitive in nature.

Naturally existing repeat proteins play important biological roles as macromolecular binding and scaffolding domains, enzymes, and building blocks for the assembly of fibrous materials. The structure and identity of these repeat proteins are highly diverse, ranging from extended, superhelical folds that bind peptide, DNA, and RNA partners, to closed and compact conformations with internal cavities suitable for small molecule binding and catalysis.

Tandem repeat proteins ('TRPs') correspond to a wide variety of unrelated proteins that harbor multiple repetitious peptide sequences, usually spanning between 20 to 40 residues each. Itzhaki & Lowe, Advances in experimental medicine and biology 747, 153-166 (2012); Matsushima et al., Protein and peptide letters 16, 1297-1322 (2009); Javadi & Itzhaki, Current opinion in structural biology 23, 622-631 (2013). Such repeated sequences, which are found in 15% to over 25% of proteins in various organisms, form highly similar folded topologies that self-associate to form symmetric toroidal or fibrillar protein scaffolds. The modularity of repeated sequences and structures found within tandem repeat proteins is directly coupled to a corresponding modularity of function, particularly with respect to molecular recognition and binding. Those same structural and functional properties are also amenable to recapitulation and manipulation in a laboratory setting, using computational approaches for protein engineering.

WO2017/096236 describes repeat proteins designed purely by geometric criteria defining the inter-repeat geometry, without reference to the sequences and structures of naturally existing repeat protein families. Because the design methodology did not rely on a template sequence or structural information taken from natural repeat proteins, the resulting repeat proteins were unlike those seen in nature. More particularly, the designed repeat proteins had repetitive alpha (α)-helical structures joined by linkers. The particular structure of the proteins was based on the formula $(a\text{-}b\text{-}x\text{-}y)_n$ wherein a and x represent linker sequences; b represents an amino acid sequence that forms an α helix; y represents an amino acid sequence that forms a second α helix; n=3 or more; and wherein each (a-b-x-y) unit is structurally repetitive to an adjacent (a-b-x-y) unit; the protein is handed; and the N- and C-termini of the protein create a circular architecture. The circular architecture of the proteins occurred because the inter-repeat packing geometry was constrained so as to naturally juxtapose the N- and C-termini of the protein within 10 Å following expression and folding. These proteins were referred to as circular tandem repeat proteins, or "cTRPs".

The described cTRPs can have numerous uses as biomaterials. For example, the cTRPs can be used as scaffolds for geometrically precise, arrayed presentation of cell-signaling and/or immune-related protein and peptide epitopes, as well as numerous other therapeutic, diagnostic, and nanotechnological uses. In particular embodiments, functional domains were inserted between α-helical sequences and/or linker sequences without significantly altering the cTRPs' engineered parameters (e.g., circular, handed, α-helical repeats).

The current disclosure describes self-assembling cTRPs with increased stability. Self-assembling cTRPs with increased stability were generated by adopting one of two approaches. The first approach includes selecting amino acid sequences that form an α helix and introducing precisely placed cysteine mutations within the N-terminal and C-terminal segments of the b position of the $(a\text{-}b\text{-}x\text{-}y)_n$ formula. These precisely placed cysteine mutations create di-sulfide bonds which serve as a "staple" to fully close the proteins circular architecture. That is, the closed self-assembled cTRPs have an N-terminus and a C-terminus that are physically linked rather than simply constrained by inter-repeat packing geometry.

Exemplary sequences that form an α helix are provided in FIG. 14 as SEQ ID NOs: 2-26. In particular embodiments, a selected α-helix-forming protein has 13 amino acid residues with a cysteine at position 1 for use in the N-terminal b segment of $(a\text{-}b\text{-}x\text{-}y)_n$. In particular embodiments, a selected α-helix-forming protein has 13 amino acid residues with a cysteine at position 3 for use in the C-terminal b segment of $(a\text{-}b\text{-}x\text{-}y)_n$ (e.g., SEQ ID NO: 11). In particular embodiments, a selected α-helix-forming protein has 13 amino acid residues with a proline at position 1 (e.g., SEQ ID NOs. 8-13). The position 1 proline can be modified to cysteine in the N-terminal b segment of $(a\text{-}b\text{-}x\text{-}y)_n$ (e.g., SEQ ID NOs. 27 and 29-33). In particular embodiments, a selected α-helix-forming protein has 13 amino acid residues with an alanine at position 3 (e.g., SEQ ID NOs. 8-10). The position 3 alanine can be modified to cysteine in the C-terminal b segment of $(a\text{-}b\text{-}x\text{-}y)_n$ (e.g., SEQ ID NOs. 11, 36, 37). These selections and mutations create self-assembled, closed ("stapled") cTRPs with increased stability over a non-closed circular architecture.

Particular embodiments include selecting α-helix forming sequences with a proline, alanine, or isoleucine at a defined position and selectively mutating the proline, alanine, and/or isoleucine to cysteine, so that the subsequences self-assemble into cTRPs based on the creation of di-sulfide bonds.

In particular embodiments, a selected α-helix-forming protein has 25 amino acid residues with a cysteine at position 7 for use in the N-terminal b segment of $(a\text{-}b\text{-}x\text{-}y)_n$. In particular embodiments, a selected α-helix-forming protein has 25 amino acid residues with a cysteine at position 5 for use in the C-terminal b segment of $(a\text{-}b\text{-}x\text{-}y)_n$. In particular embodiments, a selected α-helix-forming protein has 25 amino acid residues with an alanine at position 5

(e.g., SEQ ID NO. 21). The position 5 alanine can be modified to cysteine in the C-terminal b segment of $(a\text{-}b\text{-}x\text{-}y)_n$ (e.g., SEQ ID NO. 35). In particular embodiments, a selected α-helix-forming protein has 25 amino acid residues with an isoleucine at position 7 (e.g., SEQ ID NO. 21). The position 7 isoleucine can be modified to cysteine in the N-terminal b segment of $(a\text{-}b\text{-}x\text{-}y)_n$ (e.g., SEQ ID NO. 28). These selections and mutations create self-assembled, closed cTRPs with increased stability over a non-closed circular architecture.

The second approach to creating self-assembling cTRPs with increased stability includes selecting amino acid sequences that form an α helix wherein the selected amino acid sequences each have at last 23 amino acid residues (creating "thick" self-assembling cTRPs).

For example, thicker cTRPs include α-helix forming sequences of at least 23 amino acids, at least 24 amino acids, at least 25 amino acids, at least 26 amino acids, at least 27 amino acids, at least 28 amino acids, at least 29 amino acids, at least 30 amino acids, at least 31 amino acids, at least 32 amino acids, at least 33 amino acids, at least 34 amino acids, at least 35 amino acids, at least 36 amino acids, at least 37 amino acids, at least 38 amino acids, at least 39 amino acids, or at least 40 amino acids.

The first and second approaches can be practiced together to create closed and thick self-assembling cTRPs with increased stability.

A and x segments of the $(a\text{-}b\text{-}x\text{-}y)_n$ formula represent linker sequences. Generally, a and x linker sequences utilized within self-assembling cTRPs are from 1-5 amino acids in length.

In particular embodiments, cTRPs are left-handed. The left-handedness of particular cTRPs is due in part to the use of inter-helical turns whose geometry naturally imparts a handedness to the resulting helical bundle. The 3-residue 'GBB' (αL-β-β) turn type used in particular embodiments prefers a left-handed dihedral twist between the connected helices. This turn type is also compatible with canonical helix capping interactions, which may explain their selection by the design procedure (helix capping guarantees satisfaction of backbone polar groups and also strengthens sequence-encoding of local structure). In particular embodiments, cTRPs are right-handed. For example, thick cTRPs can be right-handed.

Based on the foregoing, and as stated, in particular embodiments linkers between α helix residues can utilize a GBB format. In particular embodiments, the G residue is glycine. In particular embodiments, the G residue is not isoleucine or valine. In particular embodiments, the second of the two B residues are selected from serine, threonine, asparagine, or glutamine. Exemplary GBB linkers include GLD, GLN, GLS, GLT, GID, GIN, GIT, GIS, GVD, GVN, GVT, GVS, GTD, GTN, GTT, GTS, GKS, GYS, and GNS. As will be understood by one of ordinary skill in the art, particular residues that fall within a G or B classification can depend on the particular protein at issue. Therefore, while representative (and common) selection options within these groups are provided, such examples are not exclusive to use of other potential residues. Without being bound by theory, and in particular embodiments, GBB linkers are utilized because they facilitate formation of left-handed proteins. It is worthwhile to note that while the described formula "starts" with a linker, due to the circular architecture of the disclosed repeat proteins, they can in fact "begin" or "end" with any residue at the N- or C-terminus. Thus, in particular embodiments, a and x segments could constitute α helix forming sequences while b and y segments could constitute the linking sequences. For consistency in explanation, however, the disclosure will continue to refer to b and y as α helix forming sequences and a and x as linkers.

Particular embodiments utilize 2 amino acid linkers, such as GD, GN, GS, and GT; 4 amino acid linkers such as LPHD (SEQ ID NO: 156), NPND (SEQ ID NO: 157) and DPKD (SEQ ID NO: 158); and 5 amino acid linkers such as GLEPD (SEQ ID NO: 159), GVSLD (SEQ ID NO: 160), and GVLPD (SEQ ID NO: 161).

FIG. 14 provides exemplary [a-b] sequences as SEQ ID NOs. 39-51, exemplary [a-b-x] sequences as SEQ ID NOs. 52-62, and exemplary [a-b-x-y] sequences as SEQ ID NOs. 1 and 63-97.

As used herein, "self-assembling" means the spontaneous generation of a full-sized cTRP molecules from smaller protein subunits that harbor a fraction of the total number of repeats found in the full-sized cTRP. For example, a fully sized 24x cTRP might be spontaneously generated from the assembly (tetramerization) of four subunits that each contain 6 repeats.

As used herein, "increased stability" means the protein does not significantly unfold at temperatures of up to 95° C., as measured via a thermal denaturation analysis using circular dichroism spectroscopy.

In addition to being self-assembled, circular, handed, and structurally repetitive, the cTRPs disclosed herein also demonstrate high thermostability and high solubility. High thermostability means that the self-assembled cTRPs retain their overall secondary structure (including α-helices), tertiary structures (defined by the fold of and association between repeats within each protein subunit) and quaternary structures (defined by the assembly of a full-sized cTRP from smaller subunits that each contain a fraction of the total repeats in the full-sized cTRP) at temperatures as high as 95° C. High solubility means that the self-assembled cTRPs can be concentrated to levels of 10 mg/mL or higher at physiological pH and salt concentrations without formation of soluble protein aggregates or protein precipitate.

As indicated, particular embodiments include self-assembled cTRPs harboring 24 (a-b-x-y) repeats. In particular embodiments, each repeat is identical. In particular embodiments, each repeat is identical but for inclusion of cysteine mutations in N- and C-terminal b domains. In particular embodiments, each (a-b-x-y) segment has at least 99%, at least 98%, at least 97%, at least 96%, at least 95%, at least 94%, at least 93%, at least 92%, at least 91%, or at least 90% sequence identity to an adjacent (a-b-x-y) segment.

In particular embodiments, each repeat is not identical, but is structurally repetitive. In structurally repetitive repeats, each repeat includes an outer α-helix and an inner α-helix. α-helical structures between repeat units are repetitive (i.e., structurally repetitive) when following (i) stacking with an adjacent α-helical structure; and (ii) comparison using root-mean-square-deviation (RMSD), the distance between corresponding atoms of the stacked outer α-helices and the stacked inner α-helices is within 2 angstrom (Å); within 1.5 Å; within 1 Å; within 0.5 Å; within 0.4 Å; or within 0.2 Å.

In particular embodiments, a self-assembled cTRP has a ring-like structure with an outer diameter of less than 200 Å, less than 190 Å, less than 180 Å, less than 170 Å, less than 160 Å, less than 150 Å, less than 140 Å, less than 130 Å, less than 120 Å, or less than 110 Å. In particular embodiments, a self-assembled cTRP has a ring-like structure with an outer diameter of 100 Å.

In particular embodiments, a self-assembled cTRP has a ring-like structure with an inner diameter of less than 140 Å, less than 130 Å, less than 120 Å, less than 110 Å, less than 100 Å, less than 90 Å, less than 80 Å, or less than 70 Å. In particular embodiments, a self-assembled cTRP has a ring-like structure with an inner diameter of 60 Å.

In particular embodiments, a self-assembled cTRP has a ring-like structure with a thickness of 5 Å, 10 Å, 15 Å, 20 Å, 25 Å, 30 Å, 35 Å, 40 Å, 45 Å, 50 Å, 55 Å, 60 Å, 65 Å, 70 Å, 75 Å, 80 Å, 85 Å, 90 Å, 95 Å, or 100 Å.

Figure 3A:
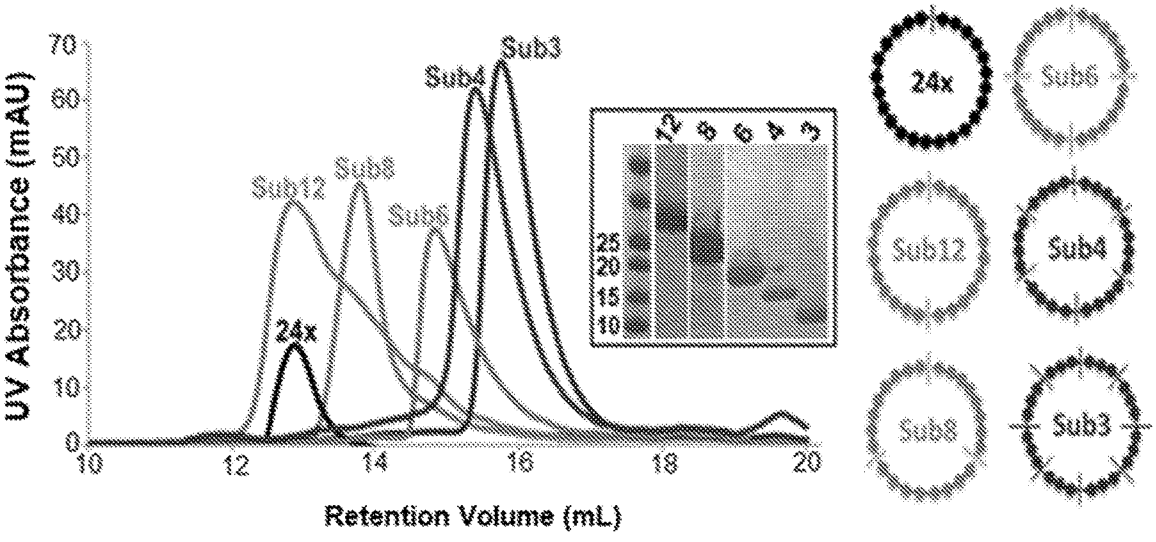
FIGS. 3A-3C. Assembly of $cTRP24_x$ nanoparticles from smaller protein subunits, verified by size exclusion chromatography (SEC) analyses.
Figure 4A:
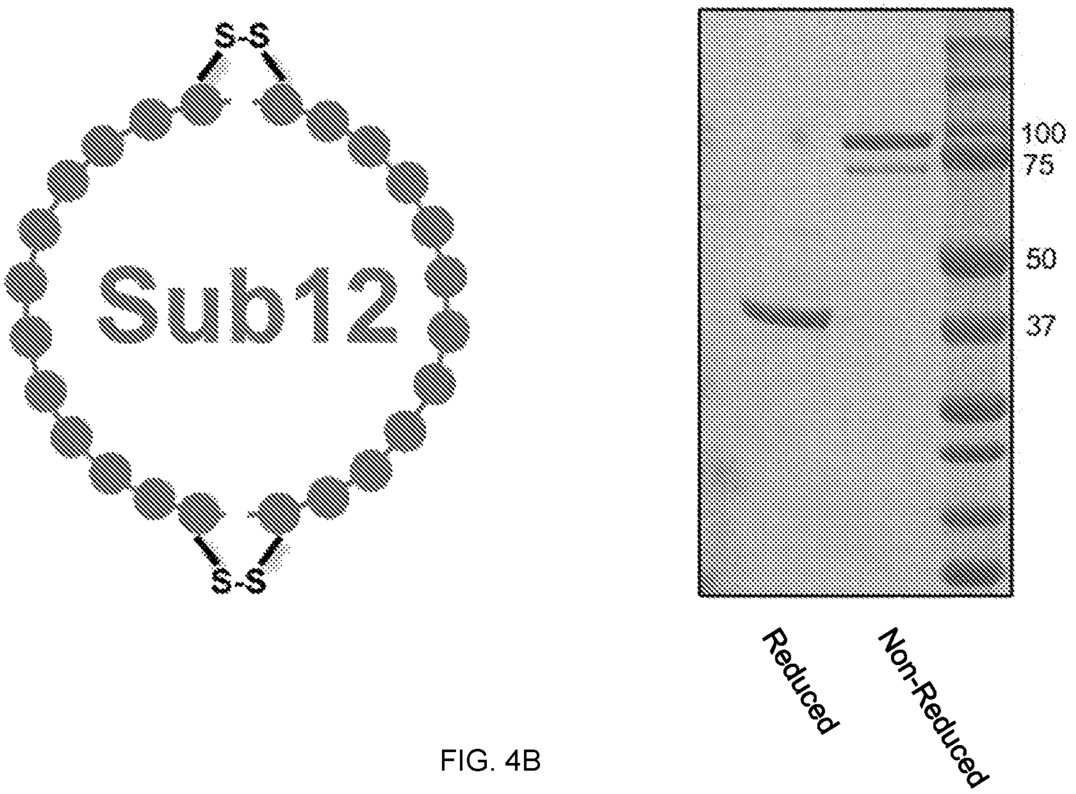
FIGS. 4A, 4B. Design and electrophoretic gel visualization of self-assembling, disulfide-stapled cTRP24 nanoparticles.

Referring to FIGS. 3A and 4A, in particular embodiments, self-assembling cTRPs have 24 repeats including 2 self-assembled segments of 12 repeating units or 4 self-assembled segments of 6 repeating units. In particular embodiments, self-assembling cTRPs have 24 repeats comprised of 6 self-assembled segments of 4 repeating units, 3 self-assembled segments of 8 repeating units, or 8 self-assembled segments of 3 repeating units. In particular embodiments, 2 self-assembled segments of 12 repeating units or 4 self-assembled segments of 6 repeating units are preferred.

Aspects of the current disclosure are now described with additional options and details as follows: (i) Functional Domains; (ii) Linkers; (iii) cTRP Compositions for Administration; (iv) T Cell Classes; (v) Cell Sample Collection and T Cell Enrichment; (vi) T Cell Activating Culture Conditions; (vii) Genetically Modifying T Cell Populations to Express Recombinant Molecules; (viii) Ex Vivo Manufactured Cell Formulations; (ix) Experimental Example; and (x) Closing Paragraphs.

(i) Functional Domains. A variety of functional domains can be provided at positions around the periphery of self-assembled cTRPs. The functional domains can be selected for a wide range of purposes that depend only on the nature and function of the domain that is displayed by the underlying self-assembled cTRP. See, e.g., Mak, et al., Science 335, 716-719, (2012); Deng, et al., Science 335, 720-723, (2012); Barkan, et al., PLoS Genet. 8, e1002910, doi: 10.1371/journal.pgen.1002910 (2012); Reichen et al., J. Struct. Biol. 185, 147-162, (2014); Werenga, FEBS Lett. 492, 193-198 (2001).

Self-assembled cTRPs are particularly useful to display multiple functional domains when high avidity molecular interactions are sought. The display complex arrangements of multiple peptide and/or protein moieties onto stable self-assembled cTRPs, with well-defined symmetry and distances separating those individual components, can facilitate high avidity molecular interactions.

Particular embodiments display multiple copies of large proteins at symmetrically distributed positions around the peripheral of a self-assembling cTRP. An average or median protein is 33 kD in size (i.e. about 300 amino acids in length). A 'large protein' is one that is larger than average, i.e. greater than 300 amino acids in size. As one example of a large protein, an scMHC protein described herein is 439 amino acids in length.

Particular embodiments provide use of self-assembled cTRPs in imaging techniques including magnetic resonance imaging (MRI), magnetic resonance tomography (MRT), positron emission tomography (PET), computer tomography (CT), single-photon emission computed tomography (SPECT) and optical imaging, such as x-ray.

Particular embodiments provide use of self-assembled cTRPs to display multiple copies of protein or peptide ligands for use as cell-stimulating growth factors and in vaccine development. Without being bound by theory, it is hypothesized that the creation of growth factor reagents and vaccines with exceptional biological activity will result due to (i) formation of high avidity interactions at the cell surface, and (ii) the ability to induce clustering of receptor complexes when the functional domains encounter their extracellular targets in vivo.

Particular embodiments provide use of self-assembled cTRPs in cell manufacturing. Cell manufacturing (e.g., the expansion of T cells or hematopoietic stem cells (and especially from limiting starting pools of such cells such as infant cord blood)) involves the addition of mixtures of cytokines and growth factors in various combinations to cell cultures. The overall biological activities of commercial cytokine and growth factor preparations in cell culture are suboptimal, being limited by the hostile environment of the cell incubator and media (which results in rapid protein degradation) and low activity in the wide-open spaces and volumes of the incubator (which negates the close intercellular distances that govern cytokine action in a living body). Therefore, the consumption, cost and effectiveness of these reagents is a clear target for improvement by a next generation of improved cell culture reagents, such as the self-assembling cTRPs described herein. When used for cell manufacturing, the extreme physical and thermal stability of the underlying self-assembling cTRP protein scaffolds (which have been shown to remain intact at temperatures up to 95° C.) greatly increases the stability and lifetime of the molecules used during manufacturing.

Particular embodiments provide use of self-assembled cTRPs to stain, identify, stimulate, activate, differentiate, remove and/or isolate various cell types (e.g., T cells, NK cells, macrophages or hematopoietic stem and progenitor cells), to enhance or inhibit cytokine or growth factor production, to induce proliferation or neural growth, to influence cell differentiation, to disrupt biofilms, to degrade proteins or nucleic acids, and to increase immunogenicity for antibody generation or vaccine development.

Exemplary classes of functional domains that can be used in the purposes described above (or other additional purposes) include detectable labels, protein capture domains, cytokines, Notch ligands, receptor ectodomains, nanobodies (e.g., single domains from camelid antibodies), single chain variable regions, single chain major histocompatibility (MHC) proteins, single chain MHC proteins displaying immunogenic peptides, immunogenic peptide vaccine candidates, peptide adjuvants, thermostable proteases, tumor specific antigens, binding domains that activate immune cells, and enzyme domains. As will be understood by one of ordinary skill in the art, certain functional domains and classes of functional domains may serve more than one purpose.

Detectable labels can include any suitable label or detectable group detectable by, for example, optical, spectroscopic, photochemical, biochemical, immunochemical, electrical, optical or chemical means. Such detectable labels include fluorescent proteins, radiolabels, radioacoustic labels, enzyme labels, chemiluminescence labels, fluorescence labels, gold beads, magnetic beads (e.g. Dynabeads™), and biotin (with labeled avidin or streptavidin).

Fluorescent proteins can be particularly useful in cell staining, identification, and isolation uses. Exemplary fluorescent proteins include blue fluorescent proteins (e.g. eBFP, eBFP2, Azurite, mKalamal, GFPuv, Sapphire, T-sapphire); cyan fluorescent proteins (e.g. eCFP, Cerulean, CyPet, AmCyanl, Midoriishi-Cyan, mTurquoise); green fluorescent proteins (e.g. GFP, GFP-2, tagGFP, turboGFP, EGFP, Emerald, Azami Green, Monomeric Azami Green (mAzami-green)), CopGFP, AceGFP, avGFP, ZsGreenl, Oregon Green™ (Thermo Fisher Scientific)); Luciferase; orange fluorescent proteins (mOrange, mKO, Kusabira-Orange, Monomeric Kusabira-Orange, mTangerine, tdTomato); red fluorescent proteins (mKate, mKate2, mPlum, DsRed monomer, mCherry, mRuby, mRFP1, DsRed-Express, DsRed2, DsRed-Monomer, HcRed-Tandem, HcRed1, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowl); and tandem conjugates.

Particular embodiments include clover fluorescent protein (Lam et al., Nat Methods. 2012. 9(10): p. 1005-1012; FIG. 14 (SEQ ID NO: 133)), Mfap (FIG. 14; within SEQ ID NOs: 127 and 129), or teal fluorescent protein mTFP1. mTFP1 is a protein generated from a tetrameric cyan fluorescent protein cFP484 isolated from coral belonging to the genus *Clavularia.*

GFP is composed of 238 amino acids (26.9 kDa), originally isolated from the jellyfish Aequorea victoria/Aequorea aequorea/Aequorea forskalea that fluoresces green when exposed to blue light. The GFP from A. victoria has a major excitation peak at a wavelength of 395 nm and a minor one at 475 nm. Its emission peak is at 509 nm which is in the lower green portion of the visible spectrum. The GFP from the sea pansy (Renilla reniformis) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted $\epsilon$), also known as its optical cross section of 9.13x10−21 $m^2$/molecule, also quoted as 55,000 L/(mol●cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from Aequorea victoria. Its excitation peak is 514 nm and its emission peak is 527 nm.

SEQ ID NOs. 126-129, 131 and 132 provide exemplary embodiments utilizing fluorescent proteins as a functional domain (e.g., Clover and mFAP).

Exemplary radiolabels include $^{35}S$ $^{125}I$, $^{32}P$, $^{3}H$, $^{14}O$, and $^{131}I$.

Exemplary enzyme labels include horseradish peroxidase, hydrolases, and alkaline phosphatase. Exemplary fluorescence labels include rhodamine, phycoerythrin, and fluorescein.

Exemplary protein capture domains include Spycatcher which makes a covalent bond with a target protein. Exemplary protein binding domains include SH2 domains, SH3 domains, protein L, LIM domains, SAM domains, PDZ domains, FERM domains, Pleckstrin homology domains, WW domains, and immunoglobulin domains (IgG).

SEQ ID NOs. 120, 121, 135 and 136 provide exemplary embodiments utilizing Spycatcher as a functional domain.

SH2 domains are protein domains that can bind particular peptides or proteins motifs that contain a phosphorylated tyrosine. SEQ ID NOs. 122, 123, 135, and 136 provide exemplary embodiments utilizing Sh2 as a functional domain. In particular embodiments the SH2 domain displayed on the surface of cTRPs is derived from the human Nck2 adapter protein, and binds a peptide with the sequence EHIpYDEVAAD (SEQ ID NO: 162).

SH3 domains are protein domains that can bind particular peptides or protein motifs that contain two or more prolines.

Protein L exhibits very well-studied binding affinity and specificity towards IgG, and also has been used extensively as a model system for protein folding and stability (Kobe & Kajava, Trends Biochem. Sci. 25, 509-515 (2000); Main, et al., Structure 11, 497-508 (2003)).

Particular embodiments include a protein antigen that serves to capture an Fc for antibody purification.

Particular embodiments include a single chain MHC for T cell staining, identification, activation, and/or isolation. Particular embodiments include a single chain MHC tetramer. Particular embodiments include single chain MHC tetramers harboring a detectable label, such as a fluorescent reporter. These constructs can reduce the cost and complexity of using MHC tetramers for T cell staining and isolation which can otherwise rely on multiple processing steps that require secondary antibody treatments to visualize stained cells. SEQ ID NOs. 124, 125, 128, and 129 provide exemplary embodiments utilizing single chain MHC as a functional domain.

Particular embodiments include a single chain MHC tetramer harboring an immunogenic peptide. In particular embodiments, scMHC harboring an immunogenic peptides are provided as tetramers. In particular embodiments, four copies of a scMHC harboring an immunogenic peptides are provided as functional domains in a self-assembled cTRP.

MHC molecules are heterodimers ($\alpha$ chain and beta chain) that are expressed on the surface of cells and present peptides/antigens to T cells. There are several classes of MHC molecules and the best studied are class I and class II. Class I MHC molecules are expressed by all nucleated cells, and present non-self peptides. Class II MHC molecules are expressed on antigen presenting cells and can present both self and non-self peptides. Single chain, scMHC molecules can be recombinant MHC proteins wherein functional fragments of an MHC $\alpha$ chain and an MHC $\beta$ chain are expressed from the same polypeptide. In particular embodiments the MHC $\alpha$ and $\beta$ chains can be derived from class I MHC molecules. In particular embodiments, the MHC $\alpha$ chain domain can be SEQ ID NO: 141. In particular embodiments, the MHC beta chain domain can be SEQ ID NO: 142. In particular embodiments, the immunogenic peptide can be derived from human cytomegalovirus. In particular embodiments, the immunogenic cytomegalovirus peptide can be NLVPMVATV (SEQ ID NO: 163). In particular embodiments, the immunogenic peptide is a T cell receptor reactive epitope, such as Wilms tumor gene (WT1), MLSN, and human papillomavirus (HPV)-peptides and HPV-related peptides.

In particular embodiments, functional domains can include cell markers and/or tumor specific antigens including A33, BAGE, Bcl-2, β-catenin, BCMA, B7H4, BTLA, CA125, CA19-9, CD2, CD3, CD4, CD5, CD6, CD8, CD18, CD19, CD20, CD21, CD22, CD25, CD28, CD30, CD33, CD37, CD38, CD40, CD52, CD44v6, CD45, CD45RA, CD45RO, CD56, CD79b, CD80, CD81, CD86, CD123, CD134, CD137, CD151, CD154, CD171, CD276, CEA, CEACAM6, c-Met, CS-1, CTLA-4, cyclin B1, DAGE, EBNA, EGFR, EGFRvIII, ephrinB2, ErbB2, ErbB3, ErbB4, EphA2, estrogen receptor, FAP, ferritin, α-fetoprotein (AFP), FLT1, FLT4, folate-binding protein, Frizzled, GAGE, G250, GD-2, GHRHR, GHR, GITR, GM2, GPRC5D, gp75, gp100 (Pmel 17), gp130, HLA, HER-2/neu, HPV E6, HPV E7, hTERT, HVEM, IGF1R, IL6R, KDR, Ki-67, Lewis A, Lewis Y, LIFRβ, LRP, LRP5, LTβR, MAGE, MART, mesothelin, MUC, MUC1, MUM-1-B, myc, NYESO-1, O-acetyl GD-2, O-acetyl GD3, OSMRβ, p53, PD1, PD-L1, PD-L2, PRAME, progesterone receptor, PSA, PSMA, PTCH1, RANK, ras, Robo1, ROR1, survivin, TCRα, TCRβ, tenascin, TGFBR1, TGFBR2, TLR7, TLR9, TNFR1, TNFR2, TNFRSF4, TWEAK-R, TSTA tyrosinase, VEGF, and WT1.

Particular embodiments can include antibodies, bi-specific antibodies, Fc, scFv, variable domains, heavy chains, light chains, superantigens, natural ligands, or ligand fusion proteins as functional domains.

Particular embodiments utilize cytokines as functional domains. Exemplary cytokines include IL-2, IL-17c, and IL-3.

In particular embodiments cTRPs that display IL-2 functional domains can be useful for stimulating T cells. Particular embodiments display multiple copies of IL-2 on the surface of cTRPs to enhance IL-2 and/or T cell activity.

In particular embodiments, a variable number of copies of the IL-17c cytokine can be displayed on cTRPs disclosed herein. IL-17c has recently been shown to act as a potent neural growth factor. Because signaling is believed to be driven by ligand binding-induced multimerization of cell-surface IL-17RA and IL-17RE receptors, it is hypothesized that the presence of multiple copies IL-17c on the surface of the cTRPs can enhance signaling activity of the ligand.

In particular embodiments, a variable number of copies of IL-3 can be displayed on the surface of cTRPs disclosed herein. IL-3 is a cytokine that stimulates cells of the myeloid lineage, such as monocytes and dendritic cells. An example of an IL-3 sequence is SEQ ID NO: 143.

In particular embodiments, a variable number of copies of Notch ligands (e.g. Delta or Jagged), or fragments and combinations thereof, can be displayed on the surface of cTRPs. Notch is a transmembrane protein with an extracellular EGF domain and intracellular domains that are involved in signaling. Notch proteins can be involved in embryogenesis and cell fate decisions, such as hematopoietic progenitor cell differentiation. An example of a human Delta (also known as Delta-like protein) is SEQ ID NO: 144. An example of a human Jagged protein is SEQ ID NO: 145. The extracellular domains of Delta and Jagged proteins can interact with the extracellular domain of Notch protein. In particular embodiments, the extracellular domains of Notch and/or Jagged can be displayed on the surface of cTRPs.

In particular embodiments, the OKT-3 binding domain can be utilized as a functional domain to activate T cells. The OKT3 antibody is described in detail in U.S. Pat. No. 5,929,212; see also U.S. Pat. No. 4,361,549; ATCC® CRL-8001™; and Arakawa et al., J. Biochem. 120, 657-662 (1996). In particular embodiments, the variable light chain of huOKT3 includes:

(SEQ ID NO: 147)

DIQMTQSPSSLSASVGDRVTITCSASSSVSYMNWYQQTPGKAP

KRWIYDTSKLASGVPSRFSGSGSGTDYTFTISSLQPEDIATYY

CQQWSSNPFTFGQGTKLQITR.

In particular embodiments, the variable heavy chain of huOKT3 includes:

(SEQ ID NO: 146)

QVQLVQSGGGVVQPGRSLRLSCKASGYTFTRYTMHVRQAPGKG

LEWIGYINPSRGYTNYNQKFKDRFTISRDNSKNTAFLQMDSLR

PEDTGVYFCARYYDDHYSLDYWGQGTPVTVSS.

In particular embodiments, the CDR regions of huOKT3 include: CDRH1: GYTFTRYTMH (SEQ ID NO: 148); CDRH2: INPSRGYTNYNQKFKD (SEQ ID NO: 149); CDRH3: YYDDHYSLDY (SEQ ID NO: 150); CDRL1: SASSSVSYMN (SEQ ID NO: 151); CDRL2: DTSKLAS (SEQ ID NO: 152); and CDRL3: QQWSSNPFT (SEQ ID NO: 153).

In particular embodiments, the CD3 binding domain is derived from the OKT3 antibody with the following CDRs: CDRH1 (KASGYTFTRYTMH (SEQ ID NO: 205)), CDRH2 (INPSRGYTNYNQKFKD (SEQ ID NO: 149)), and CDRH3 (YYDDHYCLDY (SEQ ID NO: 207)), CDRL1 (SASSSVSYMN (SEQ ID NO: 151)), CDRL2 (RWIYDTSKLAS (SEQ ID NO: 209)), and CDRL3 (QQWSSNPFT (SEQ ID NO: 153)).

The following sequence is an scFv derived from OKT3 which retains the capacity to bind CD3: QVQLQQSGAELARPGASVKMSCKASGYTFTRYTMHVVKQRPGQGLEWIGYINPSRGYTNYNQKFKDKATLTTDKSSSTAYMQLSSLTSEDSAVYYCARYYDDHYCLDYWGQGTTLTVSS SGGGGSGGGGSGGGGSQIVLTQSPAIMSASPGEKVTMTCSASSSVSYMNVVYQQKSGTSPKR WIYDTSKLASGVPAHFRGSGSGTSYSLTISGMEAEDAATYYCQQWSSNPFTFGSGTKLEINR (SEQ ID NO: 211).

In particular embodiments, a CD3 binding domain is derived from the 20G6-F3 antibody with the following CDRs: CDRL1 (QSLVHNNGNTY (SEQ ID NO: 212)), CDRL2 (KVS), CDRL3 (GQGTQYPFT (SEQ ID NO: 213)); CDRH1 (GFTFTKAW (SEQ ID NO: 214)), CDRH2 (IKDKSNSYAT (SEQ ID NO: 215)), and CDRH3 (RGVYYALSPFDY (SEQ ID NO: 216)).

In particular embodiments, a CD3 binding domain is an scFv derived from the 4B4-D7 antibody with the following CDRs: CDRL1 (QSLVHDNGNTY (SEQ ID NO: 217)), CDRL2 (KVS), CDRL3 (GQGTQYPFT (SEQ ID NO: 213)), CDRH1 (GFTFSNAW (SEQ ID NO: 219)), CDRH2 (IKARSNNYAT (SEQ ID NO: 220)), and CDRH3 (RGTYYASKPFDY (SEQ ID NO: 221)).

In particular embodiments, a CD3 binding domain is derived from the 4E7-C9 antibody with the following CDRs: CDRL1 (QSLEHNNGNTY (SEQ ID NO: 222)), CDRL2 (KVS), CDRL3 (GQGTQYPFT (SEQ ID NO: 213)), CDRH1 (GFTFSNAW (SEQ ID NO: 219)), CDRH2 (IKDKSNNYAT (SEQ ID NO: 225)), and CDRH3 (RYVHYGIGYAMDA (SEQ ID NO: 226)).

In particular embodiments, a CD3 binding domain is derived from the 18F5-H10 antibody with the following CDRs: CDRL1 (QSLVHTNGNTY (SEQ ID NO: 227)), CDRL2 (KVS), CDRL3 (GQGTHYPFT (SEQ ID NO: 228)), CDRH1 (GFTFTNAW (SEQ ID NO: 229)), CDRH2 (KDKSNNYAT (SEQ ID NO: 230)), and CDRH3 (RYVHYRFAYALDA (SEQ ID NO: 231)).

Additional examples of anti-CD3 antibodies, binding domains, and CDRs can be found in WO2016/116626. TR66 may also be used.

SEQ ID NO: 154 provides an scFv_CD3_hsOKT3_toroidX6_SS-tetramer_His sequence.

An exemplary binding domain to activate CD28 that can be used as a functional domain can include or be derived from TGN1412. In particular embodiments, the variable heavy chain of TGN1412 includes:

```
                                      (SEQ ID NO: 232)
QVQLVQSGAEVKKPGASVKVSCKASGYTFTSYYIHWRQAPGQ

GLEWIGCIYPGNVNTNYNEKFKDRATLTVDTSISTAYMELSR

LRSDDTAVYFCTRSHYGLDWNFDVWGQGTTVTVSS.
```

In particular embodiments, the variable light chain of TGN1412 includes:

```
                                      (SEQ ID NO: 233)
DIQMTQSPSSLSASVGDRVTITCHASQNIYVWLNWYQQKPGK

APKLLIYKASNLHTGVPSRFSGSGSGTDFTLTISSLQPEDFA

TYYCQQGQTYPYTFGGGTKVEIK.
```

In particular embodiments, the CDR regions of TGN1412 include: CDRL1 (HASQNIYVWLN (SEQ ID NO: 234)), CDRL2 (KASNLHT (SEQ ID NO: 235)), CDRL3 (QQGQTYPYT (SEQ ID NO: 236)), CDRH1 (GYTFTSYYIH (SEQ ID NO: 237) or SYYIH (SEQ ID NO: 238)), CDRH2 (CIYPGNVNTNYNEK (SEQ ID NO: 239)), and CDRH3 (SHYGLDWNFDV (SEQ ID NO: 240)).

In particular embodiments, a CD28 binding domain (e.g., scFv) is derived from CD80, CD86 or the 9D7 antibody. Additional antibodies that bind CD28 include 9.3, KOLT-2, 15E8, 248.23.2, EX5.3D10, and CD28.3 (deposited as a synthetic single chain Fv construct under GenBank Accession No. AF451974.1; see also Vanhove et al., BLOOD, 15 Jul. 2003, Vol. 102, No. 2, pages 564-570). Further, 1YJD provides a crystal structure of human CD28 in complex with the Fab fragment of a mitogenic antibody (5.11A1). In particular embodiments, antibodies that do not compete with 9D7 are selected.

SEQ ID NO: 155 particularly provides an scFv_CD28_TGN1412_toroidX6_SS_tetramer_His construct.

In particular embodiments, a 4-1BB binding domain that can be used as a functional domain includes the CDRs: CDRL1 (RASQSVS (SEQ ID NO: 241)), CDRL2 (ASNRAT (SEQ ID NO: 242)), CDRL3 (QRSNWPPALT (SEQ ID NO: 243)), CDRH1 (YYWS (SEQ ID NO: 244)), CDRH2 (INH), and CDRH3 (YGPGNYDWYFDL (SEQ ID NO: 245)).

In particular embodiments, a 4-1BB binding domain includes the CDRs: CDRL1 (SGDNIGDQYAH (SEQ ID NO: 246)), CDRL2 (QDKNRPS (SEQ ID NO: 247)), CDRL3 (ATYTGFGSLAV (SEQ ID NO: 248)), CDRH1 (GYSFSTYWIS (SEQ ID NO: 249)), CDRH2 (KIYPGDSYTNYSPS (SEQ ID NO: 250)), and CDRH3 (GYGIFDY (SEQ ID NO: 251)).

Additional 4-1BB binding domains can be derived from LOB12, IgG2a, LOB12.3, or IgG1 as described in Taraban et al. Eur J Immunol. 2002 December; 32(12):3617-27.

In particular embodiments a 4-1BB binding domain is derived from a monoclonal antibody described in U.S. Pat. No. 9,382,328. Additional 4-1BB binding domains are described in U.S. Pat. Nos. 6,569,997, 6,303,121, and Mittler et al. Immunol Res. 2004; 29(1-3):197-208. An exemplary 4-1BB ligand is also provided within cTRP construct, cTRP246SS-scTrimer$^{4\text{-}1BBL}$, provided in FIG. 14.

OX40 (CD134) and/or ICOS activation may also be used. OX40 binding domains are described in US20100196359, US 20150307617, WO 2015/153513, WO2013/038191 and Melero et al. Clin Cancer Res. 2013 Mar. 1; 19(5):1044-53. Exemplary binding domains that can bind and activate ICOS are described in e.g., US20080279851 and Deng et al. Hybrid Hybridomics. 2004 June; 23(3):176-82. An exemplary OX40 ligand is also provided within cTRP construct, cTRP246SS-scTrimer$^{OX40L}$, provided in FIG. 14.

In particular embodiments, a variable number of immunogenic peptide vaccine candidates (e.g., derived from a mutated growth factor receptor that acts as a commonly observed cancer-associated neoantigen) on one surface, along with multiple copies of a peptide adjuvant (e.g. derived from the HMGB1 high mobility group box protein) on the other can be displayed on cTRPs disclosed herein. For example, LEEKKGNYWTDHC (SEQ ID NO: 164) is an immunogenic peptide derived from in-frame deletion of exons 2 to 7 in the EGFR gene that results in an oncogenic growth factor receptor while also creating a high-frequency neoantigen across a wide variety of tumor types. This peptide is already very well studied as a peptide vaccine for treatment of Glioblastoma multiforme under the trade name 'Rindopepimut' (Boersma & Pluckthun, Curr. Opin. Biotechnol. 22, 849-857, (2011); Ramisch, et al., Proc. Natl. Acad. Sci. U.S.A. 111, 17875-17880, (2014).

The peptide adjuvant (termed 'HP91; sequence DPNAPKRPPSAFFLFCSE (SEQ ID NO: 165)), which is derived from the B box domain of HMGB1 and induces activation of human and murine dendritic cells) can also be displayed. As described in Grove, et al., (Curr. Opin. Struct. Biol. 18, 507-515, (2008)) one of the simplest tests of immunogenicity of a vaccine candidate/adjuvant combination is an ELISPOT assay to monitor the activation of dendritic cells in vitro, as a function of the addition of the vaccine candidate molecules.

Biofilms are communities of microbes encased in a self-produced matrix that often contains polysaccharides, extracellular bacterial DNA (eDNA), and proteins (Yasir M. et al. Materials (Basel). 2018 December; 11(12): 2468). Biofilm-related infections account for at least 65% of all human infections, but there are no available antimicrobials that specifically target biofilms and their elimination by available treatments is inefficient since biofilm cells are between 10- and 1,000-fold more resistant to conventional antibiotics than planktonic cells (Reffuveille F. et al, Antimicrob Agents Chemother. 2014 September; 58(9): 5363-537).

In particular embodiments, a functional domain linked to a self-assembling cTRP can include a binding domain that binds Integration Host Factor (IHF). IHF is a small heterodimeric protein that is often found in association with eDNA and is critical for the structural integrity of bacterial communities that utilize eDNA as a matrix component. To date, treatment of all biofilms tested with antibodies directed against IHF results in significant disruption of biofilms that contain eDNA (Brockson M. E. Mol Microbiol. 2014 September; 93(6): 1246-1258).

Particular embodiments can utilize an scFv binding domain that binds IHF-1 to disrupt biofilms (see FIG. 14; SEQ ID NO: 139 and 140). In particular embodiments, an anti-IHF Mab derived against the tip peptides of the α and β subunit of IHFNTHI (nontypeable Haemophilus influenzae's IHF) as described in Novotny et al. (Novotny et al, EBioMedicine, Volume 10, August 2016, Pages 33-44) can be used. In particular embodiments, the anti-IHF antibody is a polyclonal rabbit antiserum against *E. coli* IHF (or 'anti-IHFE. coli').

In particular embodiments, functional domains can include antimicrobial peptides (AMPs). In particular embodiments, the AMP linked to a cTRP can be a peptide that destroys the membrane potential of biofilm embedded cells, such as nisin A, lacticin Q, nukacin ISK-1 and esculentin (Esc (1-21).

Exemplary AMPs include:

TABLE 1

Exemplary AMPs.

| AMP | Protein Sequence |
|---|---|
| LL-37 | LLGDFFRKSKEKIGKEFKRIVQRIK DFLRNLVPRTES (SEQ ID NO: 166) |
| 1037 | KRFRIRVRV (SEQ ID NO: 167) |
| 1018 | VRLIVAVRIWRR (SEQ ID NO: 168) |
| Esculentin-1a (1-21) | GIFSKLAGKKIKNLLISGLKG (SEQ ID NO: 169) |
| Nisin A | MSTKDFNLDLVSVSKKDSGASPR (SEQ ID NO: 170) |
| lacticin Q | MAGFLKVVQLLAKYGSKAVQMAWANK GKILDWLNAGQAIDKVVSKIKQILGI K (SEQ ID NO: 171) |
| RN3 (5-17P22-36) | RPFTRAQWFAIQHISPRTIAMRAINN YRWR (SEQ ID NO: 172) |
| S4 (1-16) | ALWKTLLKKVLKAAAK (SEQ ID NO: 173) |
| P1 | FVDRNRIPRSNNGPKIPIISNP (SEQ ID NO: 174) |
| L-K6L9 | LKLLKKLLKKLLKLL (SEQ ID NO: 175) |
| Piscidin-3 | FIHHIFRGIVHAGRSIGRFLTG (SEQ ID NO: 176) |
| PI | PARKARAATAATAATAATAAT (SEQ ID NO: 177) |
| Hepcidin 20 | ICIFCCGCCHRSHCGMCCKT (SEQ ID NO: 178) |
| Human β-defensin 3 (hBD-3) | GIINTLQKYYCRVRGGRCAVLSC LPKEEQIGKCSTRGRKCCRRKK (SEQ ID NO: 179) |
| DJK-5 | VQWRAIRVRVIR (SEQ ID NO: 180) |

Particular embodiments include proteases (e.g., thermostable proteases) as functional domains. Proteases break down proteins. Exemplary proteases include aqualysin (FIG. 14; SEQ ID NO: 130), savinase, alcalase, keratinase, and thermitase.

In particular embodiments, a functional domain linked to a self-assembling cTRP can be an enzyme, or a combination thereof, capable of biodegrading Poly (ethylene terephthalate), or PET. PET is a highly versatile plastic whose resistance to natural degradation presents a serious and growing environmental concern, and is the primary material used in the production of bottles, clothing and carpets, among other products. Austin, Proc. Natl. Acad. Sci. U.S.A. 115, E4350-E4357 (2018). *Ideonella sakaiensis*, a bacterium recently isolated from outside a plastic bottle recycling facility, has the unusual ability to use PET as a carbon and energy source in a two-step process involving two enzymes that likely act synergistically. First, PETase (PET-digesting enzyme) converts PET to 2-mono(2-hydroxyethyl) terephthalic acid (MHET), and then a second enzyme, MHETase (MHET-digesting enzyme), further converts MHET into two monomers: TPA and ethylene glycol (EG). Yoshida, Science 351, 1196-1199 (2016). In particular embodiments, the functional domain linked to the cTRP includes two enzymes from *Ideonella sakaiensis*, PETase and MHETase, that work synergistically to degrade PET into TPA and ethylene glycol (EG). In particular embodiments, the PETase is a mutant version of the wild type PETase from *Ideonella sakaiensis* that includes substitutions such as S238F/W159H (Austin, Proc. Natl. Acad. Sci. U.S.A. 115, E4350-E4357 (2018), R132G/S160A (Han, Nat Commun. 2017; 8: 2106).

Figure 8:
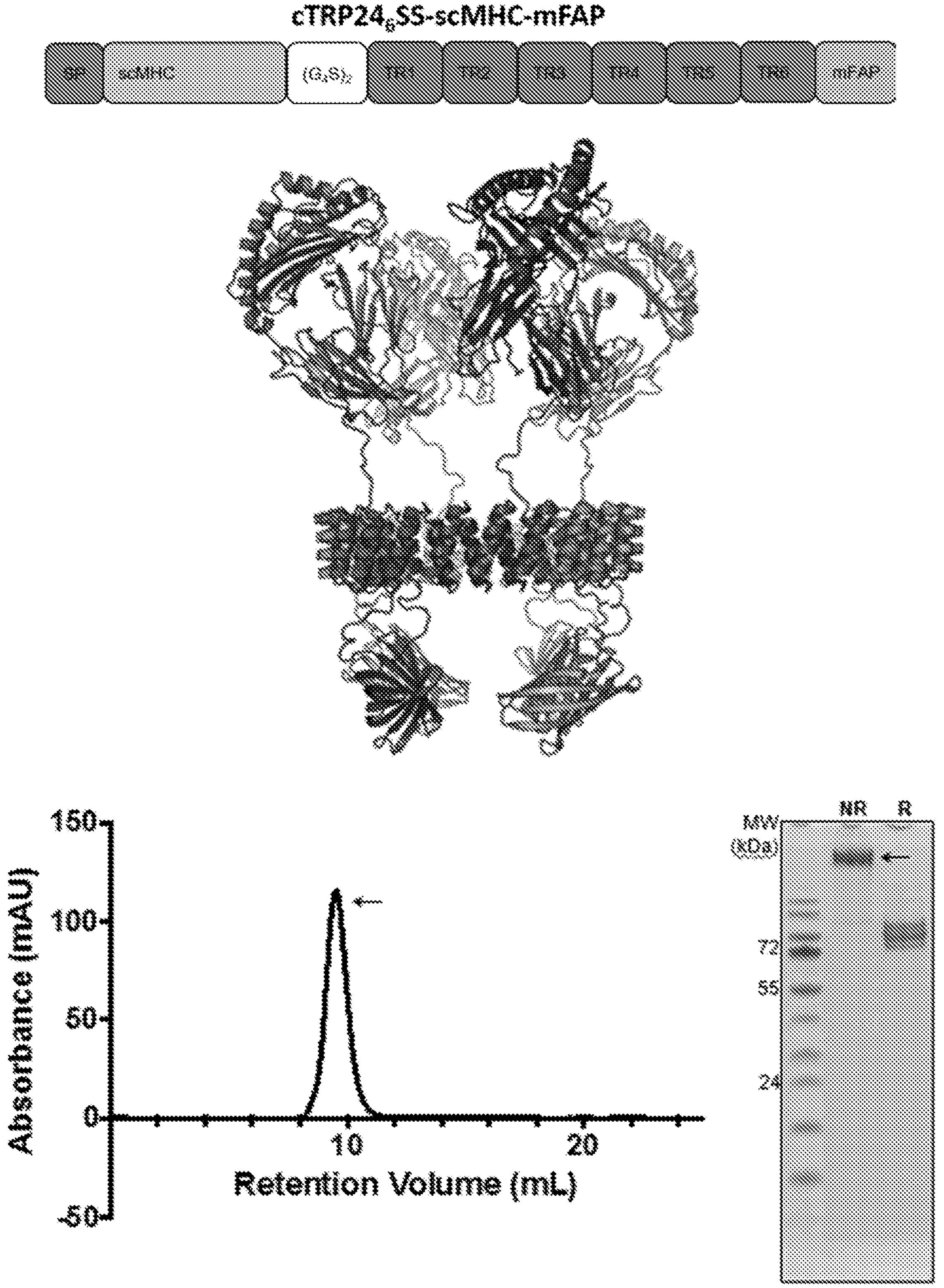
FIG. 8. Design and behavior of a tetrameric cTRP harboring multiple copies of two separate species of protein cargo. The protein (a tetramer of four subunits each containing 6 repeats, stabilized with disulfide staples) displays four copies of a single chain class I MHC ('scMHC') at each N-terminus around the top of the cTRP, and four copies of a designed fluorescent protein ('mFAP') at four loops around the bottom of the cTRP. The protein is secreted from human HEK cells and purified with yields of 200 mg per liter of culture.

As shown in FIG. 8, functional domains can be configured to extend from the "top" and/or the "bottom" of a ring-like cTRP structure. Particular embodiments include single chain MHC extending from the top of a cTRP and fluorescent protein extending from the bottom of the same Ctrp (FIG. 8). Any such complementary pair of functional domains can be selected for inclusion on opposite sides of a cTRP. In these "top" and/or the "bottom" embodiments, each "a" linker providing a functional domain on the "top" of a cTRP and each "x" linker position providing a functional domain on the "bottom" of a cTRP (or vice versa). Any portion of a linker loop can serve as the site for insertion of a functional domain so long as the insertion does not impact the integrity of the flanking helices and the folding and function of the inserted functional domain.

Functional domains can be inserted within an "a" or "x" linker sequence, or in particular embodiments, can replace an "a" or "x" linker sequence or can replace 1, 2, or 3 residues of an "a" or "x" linker sequence. In particular embodiments, the loops of interest at each position around the top or the bottom of a cTRP can be used as insertion sites for fused protein cargo in a variety of discrete ways, either by interrupting the loops internally (leaving the residues including the first positions and last positions of any loop flanking either side of the cargo) or by inserting adjacent to the loops.

In particular embodiments, the linker sequence is 2 amino acid residues and the functional domain is inserted between the 2 residues. In particular embodiments, the linker sequence is 2 amino acid residues and the functional domain replaces the 1st and/or the 2nd residue of the linker.

In particular embodiments, the linker sequence is 3 amino acid residues and the functional domain is inserted N-terminally after the 1st residue of the linker sequence. In particular embodiments, the linker sequence is 3 amino acid residues and the functional domain is inserted N-terminally after the 2nd residue of the linker sequence. In particular embodiments, the linker sequence is 3 amino acid residues and the functional domain replaces the middle residue of the linker sequence.

In particular embodiments, the linker sequence is 5 amino acid residues and the functional domain replaces the middle residue of linker. In particular embodiments, the linker sequence is 5 amino acid residues and the functional domain is inserted between the 2nd and 3rd residues of the linker or the 3rd and 4th residues of the linker.

In particular embodiments, functional protein domains (e.g., fluorescent proteins) can be directly inserted into cTRP sequences for expression and self-assembly. In particular embodiments, functional protein domains (e.g., fluorescent proteins) can be captured by protein capture domains (e.g., Spycatcher or Snoop domains) that are directly inserted into cTRP sequences for expression and self-assembly.

(ii) Linkers. In particular embodiments incorporating functional domains, linkers can be utilized between the self-assembling cTRP and the functional domain. Linkers can be used that fuse domains together and result in stably expressed, functional proteins. Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target. Commonly used flexible linkers include Gly-Ser linkers such as GGSGGGSGGSG (SEQ ID NO: 181), GGSGGGSGSG (SEQ ID NO: 182) and GGSGGGSG (SEQ ID NO: 183). Additional examples include: GGGGSGGGGS (SEQ ID NO: 184); GGGSGGGS (SEQ ID NO: 185); and GGSGGS (SEQ ID NO: 186).

In some situations, flexible linkers may be incapable of maintaining a distance or positioning of functional domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

The rigidity of protein linkers refers to the degree of flexibility of the protein backbone over the entire length of a short, single chain protein as measured by the average root-mean-square (RMS) ($RMS^{fluct}$) of all internal torsion angles ($\Phi$, $\psi$)) over the length of a given single chain protein linker.

$RMS^{fluct}$ of a torsion angle is the standard deviation of the torsion angle value about the time-averaged value in a CHARMm molecular dynamics simulation, wherein $RMS^{fluct}$ is calculated as follows:

$$RMS^{fluct} = \sqrt{\frac{1}{N_f}\sum_f \left(\theta^f - \theta^{ave}\right)^2}$$

where f refers to the frame number, N is the total number of frames in the trajectory file, and $\theta^f$ and $\theta^{ave}$ are the current value and the average value for the torsion angle, respectively.

"CHARMm" (Chemistry at HARvard Macromolecular Mechanics) refers to a computer simulation engine (see Brooks et al., (1983) J Comp Chem 4: 187-217; MacKerell, et al., (1998) J. Phys. Chem. B 102(18): 3586-3616; and "CHARMM: The Energy Function and Its Parameterization with an Overview of the Program", by MacKerell et al., in The Encyclopedia of Computational Chemistry, Volume 1, 271-277, by Paul von Raque Schleyer et al., editors (John Wiley & Sons: Chichester, United Kingdom (1998)); and Brooks, et al., (2009) J. Comp. Chem., 30:1545-1615 (2009).

In particular embodiments, the average $RMS^{fluct}$ can be calculated using the formula: (average $RMS^{fluct}$ phi ($\Phi$)+average $RMS^{fluct}$ psi ($\psi$))/2. The average RMS fluctuation of all internal backbone torsion angles over the length of the protein can be used to quantify the rigidity of the protein linker. The more rigid the protein is the smaller the average RMS fluctuation should be due to a more limited conformational space accessible to the protein.

In particular embodiments, a rigid protein linker refers to a linker having an average RMSfluct of 25 or less, 20 or less 15 or less when measured using CHARMm modeling over a production run of 200 picoseconds (ps). In particular embodiments, a semi-rigid protein linker refers to a linker having an average RMSfluct of 45-25 when measured using CHARMm modeling over a production run of 200 picoseconds (ps).

(iii) cTRP Compositions for Administration. In some instances, a self-assembling cTRP is administered to a subject, for example, when a cTRP is used as part of a vaccine. Thus, self-assembling cTRPs disclosed herein can be formulated into compositions for administration to a subject. Subjects can include humans, veterinary animals (dogs, cats, reptiles, birds, etc.) livestock (horses, cattle, goats, pigs, chickens, etc.) and research animals (monkeys, rats, mice, fish, etc.).

Compositions include at least one repeat protein and at least one pharmaceutically acceptable carrier. In particular embodiments, the compositions include repeat proteins of at least 0.1%-99% w/v of the composition or from 0.1% w/w-99% w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E. Exemplary buffering agents include citrate buffers, succinate buffers, tartrate buffers, fumarate buffers, and/or gluconate buffers. An exemplary chelating agent is EDTA. Exemplary isotonic agents include polyhydric sugar alcohols including trihydric or higher sugar alcohols, such as glycerin, erythritol, arabitol, xylitol, sorbitol, or mannitol. Exemplary preservatives include phenol, benzyl alcohol, meta-cresol, methyl paraben, propyl paraben, and/or octadecyldimethylbenzyl ammonium chloride.

Stabilizers refer to a broad category of excipients which can range in function from a bulking agent to an additive which solubilizes the repeat proteins or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g. lactose, sucrose, mannitol and sorbitol. If desired, disintegrating agents can be added, such as corn starch, potato starch, alginic acid, cross-linked polyvinylpyrrolidone, agar, or alginic acid. If desired, solid dosage forms can be sugar-coated or enteric-coated using standard techniques. Flavoring agents can also be used.

Compositions can be formulated as an aerosol. In one embodiment, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. Capsules and cartridges of gelatin for use in an inhaler or insufflator may also be formulated containing a powder mix of repeat proteins and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers including at least one cTRP. Various sustained-release materials have been established and are well known by those of ordinary skill in the art.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

(iv) T Cell Classes. As indicated elsewhere herein, cTRPs can be used in the manufacture of T cells. Several different subsets of T-cells have been discovered, each with a distinct function. For example, a majority of T-cells have a T-cell receptor (TCR) existing as a complex of several proteins. The actual T-cell receptor is composed of two separate peptide chains, which are produced from the independent T-cell receptor alpha and beta (TCRα and TCRβ) genes and are called α- and β-TCR chains.

γδ T-cells represent a small subset of T-cells that possess a distinct T-cell receptor (TCR) on their surface. In γδ T-cells, the TCR is made up of one γ-chain and one δ-chain. This group of T-cells is much less common (2% of total T-cells) than the αβ T-cells.

CD3 is expressed on all mature T cells. Activated T-cells express 4-1BB (CD137), CD69, and CD25.

T-cells can further be classified into helper cells (CD4+ T-cells) and cytotoxic T-cells (CTLs, CD8+ T-cells), which include cytolytic T-cells. T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells and are also implicated in transplant rejection. These cells are also known as CD8+ T-cells because they express the CD8 glycoprotein on their surface. These cells recognize their targets by binding to antigen associated with MHC class I, which is present on the surface of nearly every cell of the body.

"Central memory" T-cells (or "TCM") as used herein refers to an antigen experienced CTL that expresses CD62L or CCR7 and CD45RO on the surface thereof and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells. TCM can also be identified based on a CCR7+/CD45RO+ marker profile.

"Effector memory" T-cell (or "TEM") as used herein refers to an antigen experienced T-cell that does not express or has decreased expression of CD62L on the surface thereof as compared to central memory cells and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T-cells are positive for granzyme B and perforin as compared to memory or naive T-cells. TEM can also be identified based on a CCR7−/CD45RO+ marker profile.

"Naive" T-cells as used herein refers to a non-antigen experienced T cell that expresses CD62L and CD45RA and does not express CD45RO as compared to central or effector memory cells. In particular embodiments, naive CD8+ T lymphocytes are characterized by the expression of phenotypic markers of naive T-cells including CD62L, CCR7, CD28, CD127, and CD45RA. Naïve T cells can also be identified based on a CCR7+/CD45RO− marker profile.

In particular embodiments, memory T cells show up-regulated gene expression of TCF7, LEF1, and CD27. In particular embodiments, memory T cells show down-regulated gene expression of NOTCH1, PRDM1, GZMB, PRF1, and EOMES.

A statement that a cell or population of cells is "positive" for or expressing a particular marker refers to the detectable presence on or in the cell of the particular marker. When referring to a surface marker, the term can refer to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

A statement that a cell or population of cells is "negative" for a particular marker or lacks expression of a marker refers to the absence of substantial detectable presence on or in the cell of a particular marker. When referring to a surface marker, the term can refer to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

(v) Cell Sample Collection and T Cell Enrichment. Methods of sample collection and enrichment are known by those skilled in the art. In some embodiments, cells are derived from T cell lines. The cells in some embodiments are obtained from a xenogeneic source, for example, from mouse, rat, non-human primate, or pig. In particular embodiments, T cells are derived from humans.

In some embodiments, T cells are derived or isolated from samples such as whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. In some aspects, the T cells are derived or isolated from blood or a blood-derived sample, or is or is derived from an apheresis or leukapheresis product. In relation to a particular subject, T cells can be autologous or allogeneic.

In some embodiments, blood cells collected from a subject are washed, e.g., to remove the plasma fraction and to place the cells in an appropriate buffer or media for subsequent processing steps. In particular embodiments, the cells are washed with phosphate buffered saline (PBS). In some embodiments, the wash solution lacks calcium and/or magnesium and/or many or all divalent cations. Washing can be accomplished using a semi-automated "flow-through" centrifuge (for example, the Cobe 2991 cell processor, Baxter) according to the manufacturer's instructions. Tangential flow filtration (TFF) can also be performed. In particular embodiments, cells can re-suspended in a variety of biocompatible buffers after washing, such as, Ca++/Mg++ free PBS.

In particular embodiments, a sample can be enriched for T cells by using density-based cell separation methods and related methods. For example, white blood cells can be separated from other cell types in the peripheral blood by lysing red blood cells and centrifuging the sample through a Percoll or Ficoll gradient.

In particular embodiments, a bulk T cell population can be used that has not been enriched for a particular T cell type. In particular embodiments, a selected T cell type can be enriched for and/or isolated based on cell-marker based positive and/or negative selection. In positive selection, cells having bound cellular markers are retained for further use. In negative selection, cells not bound by a capture agent, such as an antibody to a cellular marker are retained for further use. In some examples, both fractions can be retained for a further use.

The separation need not result in 100% enrichment or removal of a particular cell population or cells expressing a particular marker. For example, positive selection of or enrichment for cells of a particular type refers to increasing the number or percentage of such cells but need not result in a complete absence of cells not expressing the marker. Likewise, negative selection, removal, or depletion of cells of a particular type refers to decreasing the number or percentage of such cells but need not result in a complete removal of all such cells.

In some examples, multiple rounds of separation steps are carried out, where the positively or negatively selected fraction from one step is subjected to another separation step, such as a subsequent positive or negative selection.

In some embodiments, an antibody or binding domain for a cellular marker is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ); see also U.S. Pat Nos. 4,452,773; 4,795,698; 5,200,084; and EP 452342.

In some embodiments, affinity-based selection is via magnetic-activated cell sorting (MACS) (Miltenyi Biotec, Auburn, CA). MACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376). In both cases, cells can be labeled with multiple markers, allowing for the isolation of well-defined T cell subsets at high purity.

Cell-markers for different T cell subpopulations are described above. In particular embodiments, specific subpopulations of T cells, such as cells positive or expressing high levels of one or more surface markers, e.g., CCR7, CD45RO, CD8, CD27, CD28, CD62L, CD127, CD4, and/or CD45RA T cells, are isolated by positive or negative selection techniques.

$CD3^{+}$, CD28+ T cells can be positively selected for and expanded using anti-CD3/anti-CD28 conjugated magnetic beads (e.g., DYNABEADS® M-450 CD3/CD28 T Cell Expander).

In particular embodiments, a CD8+ or CD4+ selection step is used to separate CD4+ helper and CD8+ cytotoxic T cells. Such CD8+ and CD4+ populations can be further sorted into sub-populations by positive or negative selection for markers expressed or expressed to a relatively higher degree on one or more naive, memory, and/or effector T cell subpopulations.

In some embodiments, enrichment for central memory T (TCM) cells is carried out. In particular embodiments, memory T cells are present in both CD62L subsets of CD8+ peripheral blood lymphocytes. PBMC can be enriched for or depleted of CD62L, CD8 and/or CD62L+CD8+ fractions, such as by using anti-CD8 and anti-CD62L antibodies.

In some embodiments, the enrichment for central memory T (TCM) cells is based on positive or high surface expression of CCR7, CD45RO, CD27, CD62L, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CCR7, CD45RO, and/or CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or RORI, and positive selection based on a marker characteristic of central memory T cells, such as CCR7, CD45RO, and/or CD62L, where the positive and negative selections are carried out in either order.

In particular embodiments, cell enrichment results in a bulk CD8+ FACs-sorted cell population.

(vi) T Cell Activating Culture Conditions. Cell populations can be incubated in a culture-initiating composition including a cTRP with a functional domain to expand T cell populations. The T cell stimulating cTRP can be in soluble form or bound to a solid substrate, The incubation can be carried out in a culture vessel, such as a bag, cell culture plate, flask, chamber, chromatography column, cross-linked gel, cross-linked polymer, column, culture dish, hollow fiber, microtiter plate, silica-coated glass plate, tube, tubing set, well, vial, or other container for culture or cultivating cells.

In particular embodiments, CD3 stimulating cTRPs and/or molecules can be included within culture media at a concentration of at least 0.25 or 0.5 ng/ml or at a concentration of 2.5-10 μg/ml. Particular embodiments utilize a CD3 stimulating molecule (e.g., OKT3) at 5 μg/ml.

Engineered cTRP with a CD3, CD28, 4-1BB, and/or OX40 binding domain can be included within the activating T cell culture conditions. Engineered cTRP with a CD3, CD28, 4-1BB, and/or OX40 ligand functional domain can be included within a culture media at, for example, 0.5-20 μg/ml (e.g., 2 μg/ml, 5 μg/ml, or 10 μg/ml). Particular embodiments utilize 0.1 μg/ml, 0.2 μg/ml, 0.5 μg/ml, 1 μg/ml, 2 μg/ml, 5 μg/ml or 10 μg/ml of a cTRP with a CD3, CD28, 4-1BB, and/or OX40 ligand functional domain. In particular embodiments, cells can be incubated at 37° C. with 2 μg/mL scFv_CD3_hsOKT3-Toroidx6_SS_tetramer; scFv_CD28_TGN1412-Toroidx6_SS_tetramer, cTRP$24_6$SS-scTrimer$^{4\text{-}1BBL}$ and/or cTRP$24_6$SS-scTrimer$^{OX40L}$.

Molecules that stimulate other T cell activating epitopes may also be included within T cell activating culture conditions. Examples of additional T cell stimulating epitopes in addition to CD3, CD28, 4-1BB, and/or OX40 include CD2, CD4, CD5, CD7, CD8, CD30, CD40, CD56, CD83, CD90, CD95, B7-H3, CTLA-4, Frizzled-1 (FZD1), FZD2, FZD3, FZD4, FZD5, FZD6, FZD7, FZD8, FZD9, FZD10, HVEM, ICOS, IL-1R, LAT, LFA-1, LIGHT, MHCI, MHCII, NKG2D, ROR2 and RTK.

T cell activating conditions can additionally include one or more cytokines, for example, interleukin (IL)-2, IL-7, IL-15 and/or IL-21. IL-2 can be included at a range of 10-1,000 IU/ml (e.g., 50 U/ml); IL-7 at a range of 5-100 ng/ml (e.g., 10 ng/ml); IL-15 at a range of 5-100 ng/ml (e.g., 10 ng/ml); and IL-21 at a range of 5-100 ng/ml. Particular embodiments utilize only IL-2. Particular embodiments utilize IL-7 in combination with IL-15. Particular embodiments utilize IL-2 in combination with IL-7 and IL-15. Particular embodiments utilize IL-2 in combination with IL-15 and IL-21.

As indicated, in particular embodiments, T cell stimulating agents are in soluble form and/or immobilized on a solid phase within the culture media. In particular embodiments, the solid phase is a cTRP, the surface of the culture vessel (e.g., bag, cell culture plate, chamber, chromatography column, cross-linked gel, cross-linked polymer, column, culture dish, hollow fiber, microtiter plate, silica-coated glass plate, tube, tubing set, well, vial, other structure or container for culture or cultivation of cells). Also as indicated, a cTRP can be a solid phase to which activating molecules are bound and can also themselves be bound to another solid substrate.

In particular embodiments, a solid phase can be added to a culture media. Such solid phases can include, for example, a cTRP, beads, hollow fibers, resins, membranes, and polymers.

cTRPs are described throughout this disclosure. Exemplary beads include magnetic beads, polymeric beads, and resin beads (e.g., Strep-Tactin® Sepharose, Strep-Tactin® Superflow, and Strep-Tactin® MacroPrep IBA GmbH, Gottingen)). Anti-CD3/anti-CD28 beads are commercially available reagents for T cell expansion (Invitrogen). These beads are uniform, 4.5 μm superparamagnetic, sterile, non-pyrogenic polystyrene beads coated with a mixture of affinity purified monoclonal antibodies against the CD3 and CD28 cell surface molecules on human T cells. Hollow fibers are available from TerumoBCT Inc. (Lakewood, Colo., USA). Resins include metal affinity chromatography (IMAC) resins (e.g., TALON® resins (Westburg, Leusden)). Membranes include paper as well as the membrane substrate of a chromatography matrix (e.g., a nitrocellulose membrane or a polyvinylidene difluoride (PVDF) membrane).

Exemplary polymers include polysaccharides, such as polysaccharide matrices. Such matrices include agarose gels (e.g., Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare.

Synthetic polymers that may be used include polyacrylamide, polymethacrylate, a co-polymer of polysaccharide and agarose (e.g. a polyacrylamide/agarose composite) or a polysaccharide and N,N'-methylenebisacrylamide. An example of a copolymer of a dextran and N,N'-methylenebisacrylamide is the Sephacryl® (Pharmacia Fine Chemicals, Inc., Piscataway, NJ) series of materials.

Particular embodiments may utilize silica particles coupled to a synthetic or to a natural polymer, such as polysaccharide grafted silica, polyvinylpyrrolidone grafted silica, polyethylene oxide grafted silica, poly(2-hydroxyethylaspartamide) silica and poly(N-isopropylacrylamide) grafted silica.

Culture conditions can also include one or more of particular media, temperature, oxygen content, carbon dioxide content, time, agents, e.g., nutrients, amino acids, antibiotics, and/or ions. In some aspects, incubation is carried out in accordance with techniques such as those described in U.S. Pat. No. 6,040,177, Klebanoff et al. (2012) J Immunother. 35(9): 651-660, Terakura et al. (2012) Blood. 1:72-82, and/or Wang et al. (2012) J Immunother. 35(9):689-701.

Exemplary culture media for culturing T cells include (i) RPMI supplemented with non-essential amino acids, sodium pyruvate, and penicillin/streptomycin; (ii) RPMI with HEPES, 5-15% human serum, 1-3% L-Glutamine, 0.5-1.5% penicillin/streptomycin, and 0.25×10-4-0.75×10-4M β-MercaptoEthanol; (iii) RPMI-1640 supplemented with 10% fetal bovine serum (FBS), 2 mM L-glutamine, 10 mM HEPES, 100 U/ml penicillin and 100 m/mL streptomycin; (iv) DMEM medium supplemented with 10% FBS, 2 mM L-glutamine, 10 mM HEPES, 100 U/ml penicillin and 100 m/mL streptomycin; and (v) X-Vivo 15 medium (Lonza, Walkersville, MD) supplemented with 5% human AB serum (Gemcell, West Sacramento, CA), 1% HEPES (Gibco, Grand Island, NY), 1% Pen-Strep (Gibco), 1% GlutaMax (Gibco), and 2% N-acetyl cysteine (Sigma-Aldrich, St. Louis, MO). T cell culture media are also commercially available from Hyclone (Logan, UT).

In some embodiments, the T cells are expanded by adding to the culture-initiating composition feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can include gamma-irradiated PBMC feeder cells. In some embodiments, the PBMC are irradiated with gamma rays in the range of 3000 to 3600 rads to prevent cell division. In some aspects, the feeder cells are added to culture medium prior to the addition of the populations of T cells.

Optionally, the incubation may further include adding non-dividing EBV-transformed lymphoblastoid cells (LCL) as feeder cells. LCL can be irradiated with gamma rays in the range of 6000 to 10,000 rads. The LCL feeder cells in some aspects is provided in any suitable amount, such as a ratio of LCL feeder cells to initial T lymphocytes of at least 10:1.

In some embodiments, the stimulating conditions include temperature suitable for the growth of human T lymphocytes, for example, at least 25° C., at least 30° C., or 37° C.

(vii) Genetically Modifying T Cell Populations to Express Recombinant Molecules. In particular embodiments, T cell populations are genetically modified to express chimeric antigen receptors (CAR) or other molecules, such as engineered TCR or TCR/CAR hybrids. CAR proteins include several distinct subcomponents that allow the genetically modified T cells to recognize and kill unwanted cells, such as cancer cells or virally-infected. The subcomponents include at least an extracellular component and an intracellular component. The extracellular component includes a binding domain that specifically binds a marker that is preferentially present on the surface of unwanted cells. When the binding domain binds such markers, the intracellular component activates the T cell to destroy the bound cell. CAR additionally include a transmembrane domain that links the extracellular component to the intracellular component, and other subcomponents that can increase the CAR's function. For example, the inclusion of one or more linker sequences, such as a spacer region, can allow the CAR to have additional conformational flexibility, often increasing the binding domain's ability to bind the targeted cell marker.

For additional information regarding CAR, see WO2000/014257; WO2012/129514; WO2013/126726; WO2013/166321; WO2013/071154; WO2013/123061; WO2014/055668; WO2014/031687; US2002131960; US2013287748; US20130149337; U.S. Pat. Nos. 6,410,319; 6,451,995; 7,070,995; 7,265,209; 7,354,762; 7,446,179; 7,446,190; 7,446,191; 8,252,592; 8,324,353; 8,339,645; 8,398,282; 8,479,118; EP2537416; Brentjens et al., Sci Transl Med. 2013 5(177); Davila et al. (2013) PLoS ONE 8(4): e61338; Kochenderfer et al., 2013, Nature Reviews Clinical Oncology, 10, 267-276 (2013); Sadelain et al., Cancer Discov. 2013 April; 3(4): 388-398; Turtle et al., Curr. Opin. Immunol., 2012 October; 24(5): 633-39; Wang et al. (2012) J. Immunother. 35(9): 689-701; and Wu et al., Cancer, 2012 Mar. 18(2): 160-75.

CAR/TCR hybrids refer to proteins having an element of a TCR and an element of a CAR. For example, a CAR/TCR hybrid could have a naturally occurring TCR binding domain with an effector domain that the TCR binding domain is not naturally associated with. A CAR/TCR hybrid could have a mutated TCR binding domain and an ITAM signaling domain. A CAR/TCR hybrid could have a naturally occurring TCR with an inserted non-naturally occurring spacer region or transmembrane domain.

Particular CAR/TCR hybrids include TRuC® (T Cell Receptor Fusion Construct) hybrids; TCR2 Therapeutics, Cambridge, MA By way of example, the production of TCR fusion proteins is described in International Patent Publications WO 2018/026953 and WO 2018/067993, and in US 2017/0166622.

In particular embodiments, CAR/TCR hybrids include a "T-cell receptor (TCR) fusion protein" or "TFP". A TFP includes a recombinant polypeptide derived from the various polypeptides including the TCR that is generally capable of i) binding to a surface antigen on target cells and ii) interacting with other polypeptide components of the intact TCR complex, typically when co-located in or on the surface of a T-cell.

Desired genes encoding CAR, TCR, CAR/TCR hybrids or other molecules can be introduced into cells by any method known in the art, including transfection, electroporation, microinjection, lipofection, calcium phosphate mediated transfection, infection with a viral or bacteriophage vector including the gene sequences, cell fusion, chromosome-mediated gene transfer, microcell-mediated gene transfer, sheroplast fusion, in vivo nanoparticle-mediated delivery, etc. Numerous techniques are known in the art for the introduction of foreign genes into cells (see e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92) and may be used, provided that the necessary developmental and physiological functions of the recipient cells are not unduly disrupted. The technique can provide for the stable transfer of the gene to the cell, so that the gene is expressible by the cell and, in certain instances, preferably heritable and expressible by its cell progeny.

The term "gene" refers to a nucleic acid sequence (used interchangeably with polynucleotide or nucleotide sequence) that encodes a molecule described herein. This definition includes various sequence polymorphisms, mutations, and/or sequence variants wherein such alterations do not substantially affect the function of the encoded CAR. The term "gene" may include not only coding sequences but also regulatory regions such as promoters, enhancers, and termination regions. The term further can include all introns and other DNA sequences spliced from an mRNA transcript, along with variants resulting from alternative splice sites. Gene sequences encoding the molecule can be DNA or RNA that directs the expression of a molecule. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Portions of complete gene sequences are referenced throughout the disclosure as is understood by one of ordinary skill in the art.

Gene sequences encoding molecules can be readily prepared by synthetic or recombinant methods from the relevant amino acid sequences and other description provided herein. In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In embodiments, the gene sequence encoding the sequences can be codon optimized for expression in mammalian cells.

"Encoding" refers to the property of specific sequences of nucleotides in a gene, such as a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "gene sequence encoding a protein" includes all nucleotide sequences that are degenerate versions of each other and that code for the same amino acid sequence or amino acid sequences of substantially similar form and function.

Polynucleotide gene sequences encoding more than one portion of an expressed molecule can be operably linked to each other and relevant regulatory sequences. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions, into the same reading frame.

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, Meth. Enzymol. 217:581-599) can be used. In such embodiments, the gene to be expressed is cloned into the retroviral vector for its delivery into cells. In particular embodiments, a retroviral vector includes all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, Biotherapy 6:291-302; Clowes, et al., 1994, J. Clin. Invest. 93:644-651; Kiem, et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114. Adenoviruses, adena-associated viruses (AAV) and alphaviruses can also be used. See Kozarsky and Wilson, 1993, Current Opinion in Genetics and Development 3:499-503, Rosenfeld, et al., 1991, Science 252:431-434; Rosenfeld, et al., 1992, Cell 68:143-155; Mastrangeli, et al., 1993, J. Clin. Invest. 91:225-234; Walsh, et al., 1993, Proc. Soc. Exp. Bioi. Med. 204:289-300; and Lundstrom, 1999, J. Recept. Signal Transduct. Res. 19: 673-686. Other methods of gene delivery include use of mammalian artificial chromosomes (Vos, 1998, Curr. Op. Genet. Dev. 8:351-359); liposomes (Tarahovsky and lvanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

There are a large number of available viral vectors suitable within the current disclosure, including those identified for human gene therapy applications (see Pfeifer and Verma, 2001, Ann. Rev. Genomics Hum. Genet. 2:177). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles including CAR transgenes are described in, e.g., U.S. Pat. No. 8,119,772; Walchli, et al., 2011, PLoS One 6:327930; Zhao, et al., 2005, J. Immunol. 174:4415; Engels, et al., 2003, Hum. Gene Ther. 14:1155; Frecha, et al., 2010, Mol. Ther. 18:1748; and Verhoeyen, et al., 2009, Methods Mol. Biol. 506:97. Retroviral and lentiviral vector constructs and expression systems are also commercially available.

Targeted genetic engineering approaches may also be utilized. The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. For information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; US 2003/0232410 and US 2009/0203140 as well as Gaj et al., Nat Methods, 2012, 9(8):805-7; Ramirez et al., Nucl Acids Res, 2012, 40(12):5560-8; Kim et al., Genome Res, 2012, 22(7): 1327-33; Urnov et al., Nature Reviews Genetics, 2010, 11:636-646; Miller, et al. Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. For information regarding TALENs, see U.S. Pat. Nos. 8,440,431; 8,440,432; 8,450,471; 8,586,363; and 8,697,853; as well as Joung and Sander, Nat Rev Mol Cell Biot, 2013, 14(I):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

(viii) Ex Vivo Manufactured Cell Formulations. In particular embodiments, expanded and/or genetically-modified cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions or formulations can be greater than 102 cells, greater than 103 cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In compositions and formulations disclosed herein, cells are generally in a volume of a liter or less, 500 mls or less, 250 mls or less or 100 mls or less. Hence the density of administered cells is typically greater than 104 cells/ml, 107 cells/ml or 108 cells/ml.

The cell-based compositions disclosed herein can be prepared for administration by, e.g., injection, infusion, perfusion, or lavage. The compositions can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

(ix) Experimental Examples (Example 1). Introduction. Structure-based protein engineering has enabled the creation of designed molecular scaffolds that display a wide variety of sizes, shapes, symmetry, and subunit composition, ranging from small designed folds to large multi-protein assemblages. Such constructs offer the possibility to create protein-based nanoparticles for the organization and display of multiple functional protein domains, leading to enhanced properties as the result of increased avidity and improved solution behavior and stability. Here the creation and characterization of a computationally designed circular tandem repeat protein ('cTRP') harboring 24 identical repeated motifs, and the display of a variety of functional protein domains at defined positions around its periphery are described. It is demonstrated that cTRP nanoparticles can self-assemble from smaller individual subunits, can host a wide range of functional protein domains, can be produced from prokaryotic and human expression platforms, and can be used for applications requiring high avidity molecular interactions.

Figure 1B:
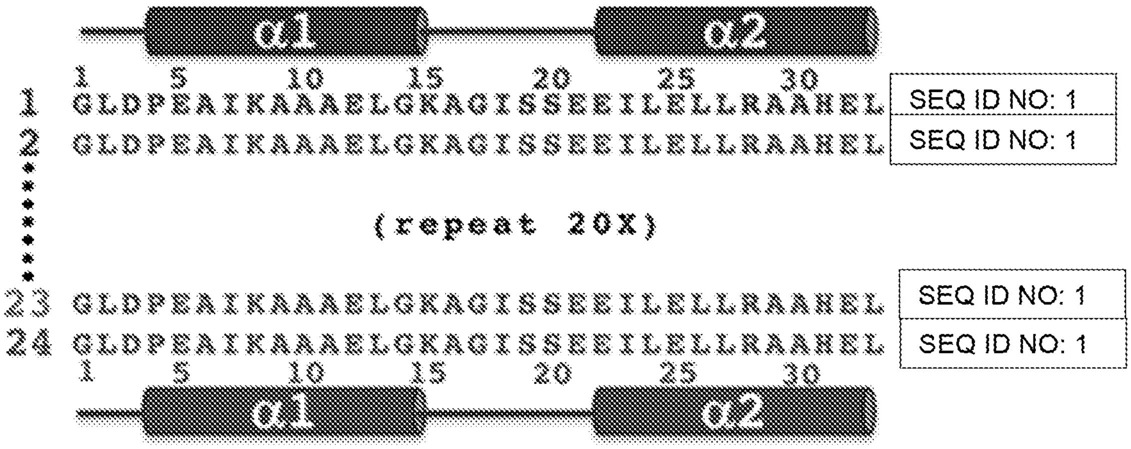
Figure 1C:
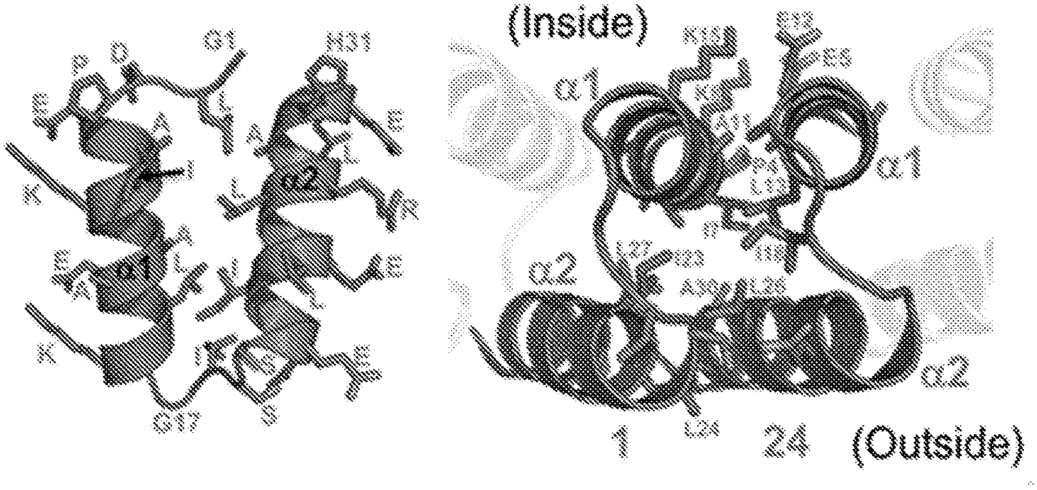
Figure 2A:
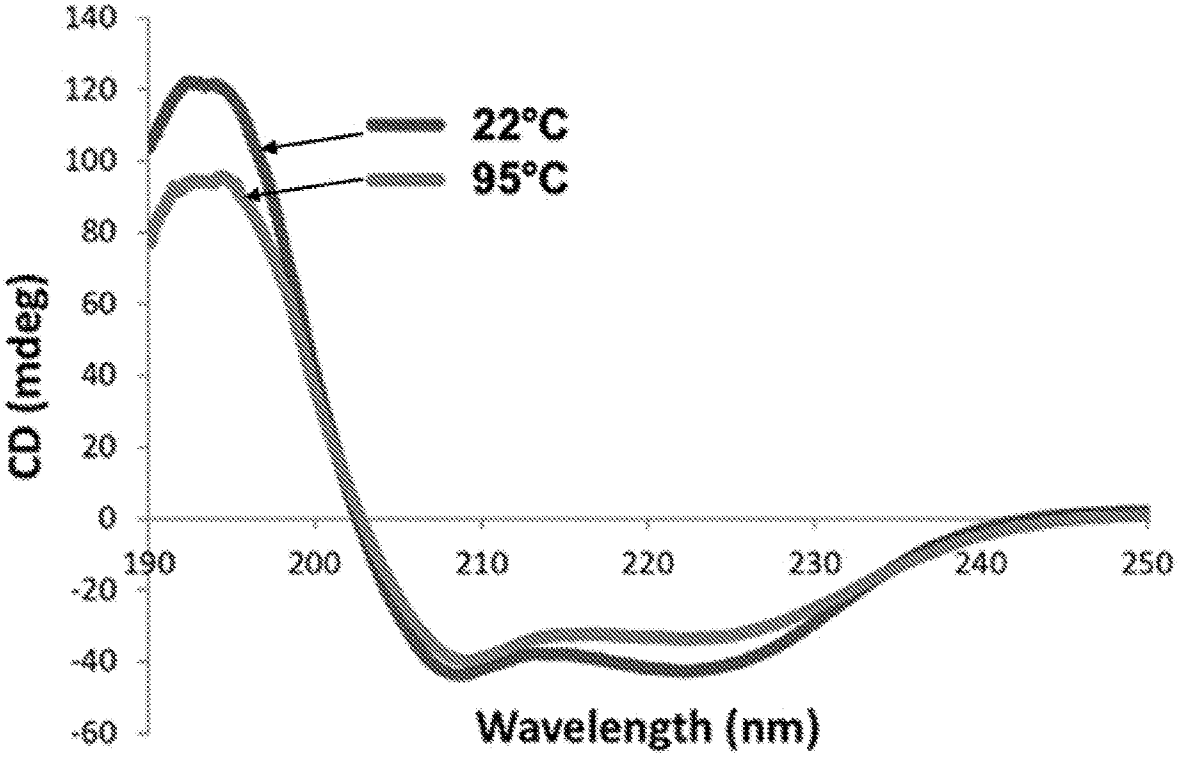
FIGS. 2A-2C. Characterization of an engineered 24-repeat cTRP.
Figure 2B:
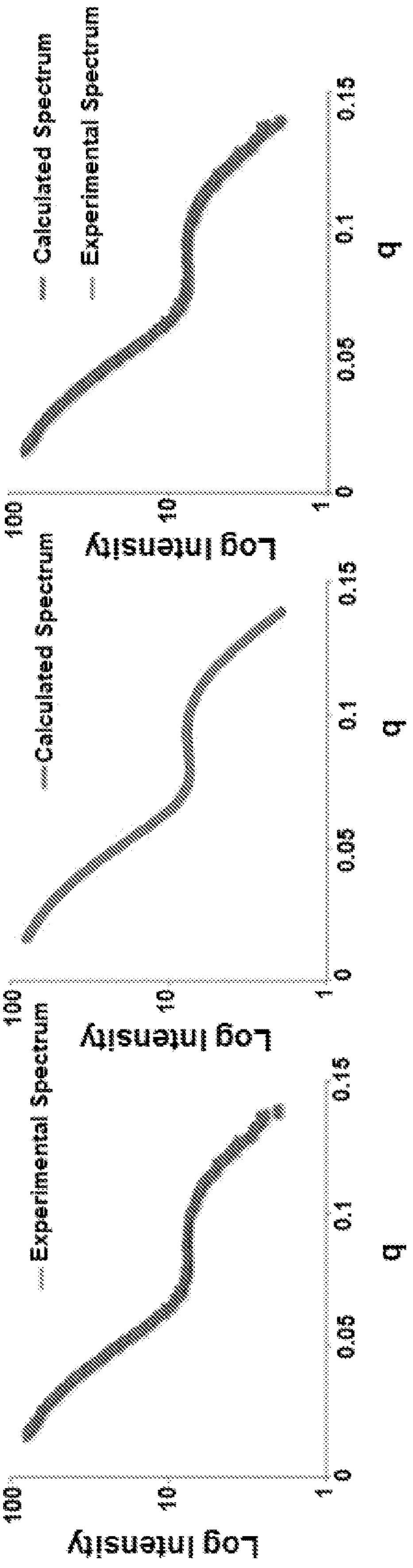
Figure 2C:
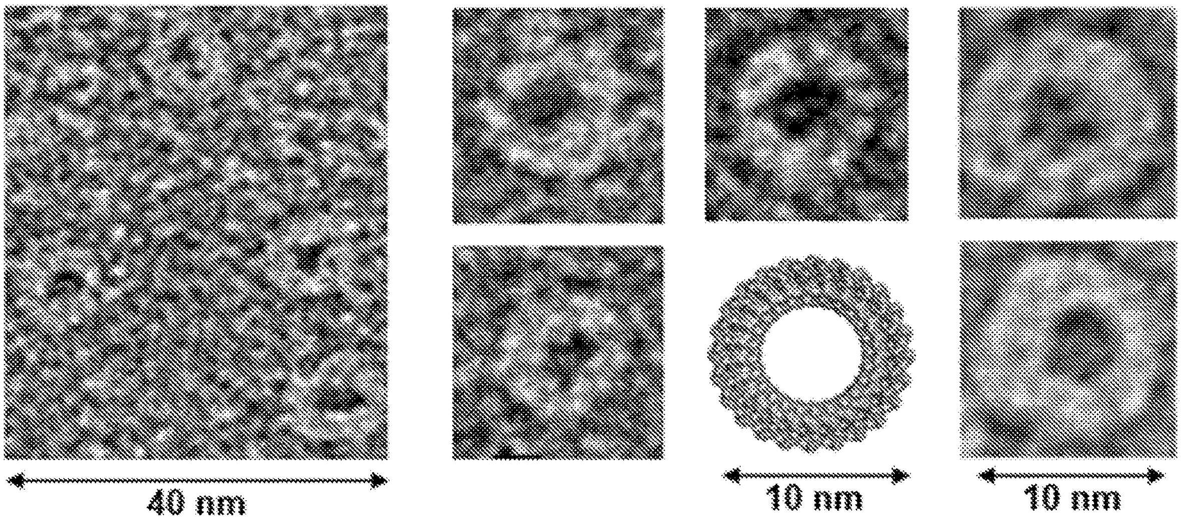
Figure 10A:
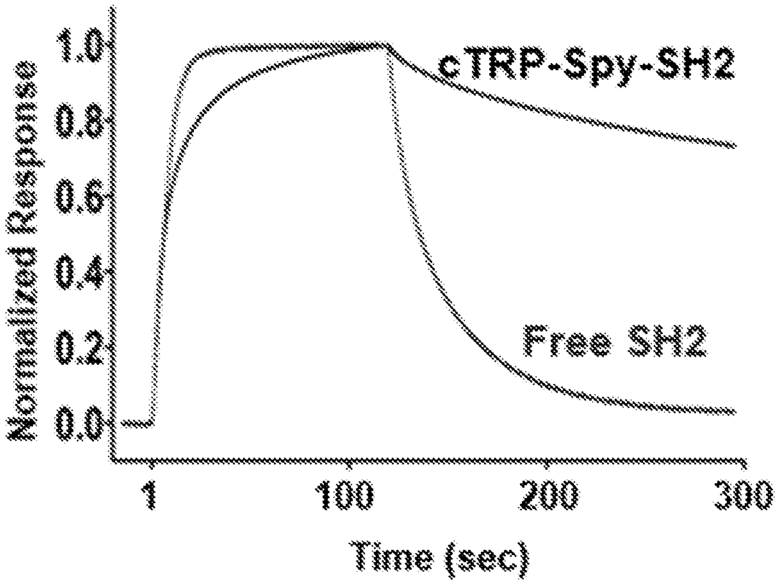
FIGS. 10A, 10B. Peptide binding on a surface by free SH2 and by cTRP-displayed SH2 domains.
Figure 10B:
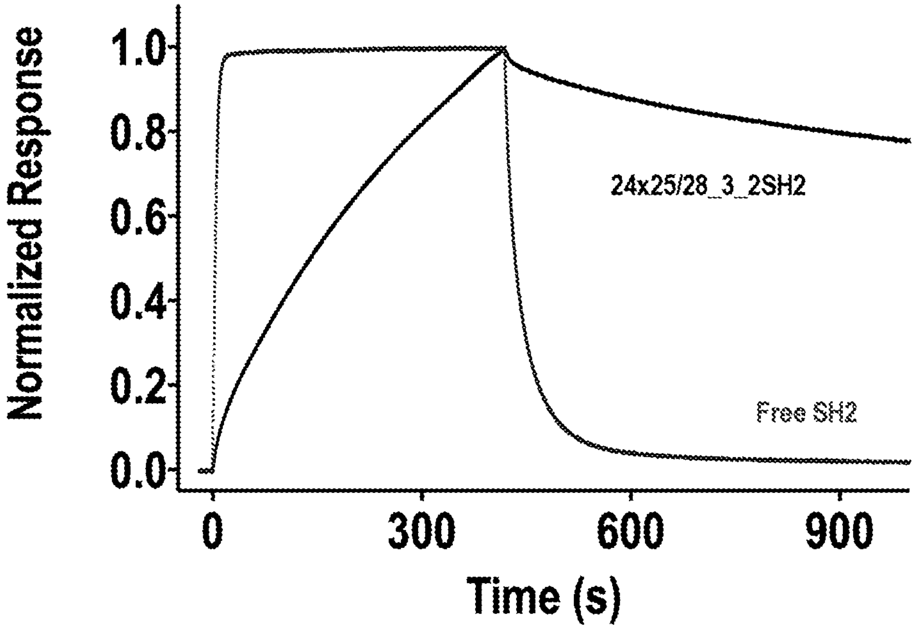

Results. De novo Design. The initial designed protein, referred to as 'cTRP24', is shown in FIG. 1A. It includes a circular tandem repeat architecture containing 24 identical structural units (SEQ ID NO: 1), folded into a ring with a 100 Å (10 nm) outer diameter, a 60 Å inner diameter and a 20 Å thickness perpendicular to the plane of the ring. Each repeat includes an identical 33 residue sequence (FIG. 1B) folded into a left-handed bundle containing two antiparallel α-helices (FIG. 10). The inner and outer helices are 13 and 14 residues in length, respectively, and are connected by a three-residue loop (spanning residues 17 to 19 in each repeat). Twenty-four identical copies of that loop are all located on the same side of the model. An additional series of identical three-residue loops (spanning residues 1 to 3 in each repeat) are located on the opposing surface of the cTRP, where they connect each consecutive repeat (with the exception of the same three residues at the protein's N-terminus). The individual repeats are amphipathic (FIG. 10), with the interfaces between α-helices comprised largely of alanine, leucine and isoleucine residues, while the solvent-exposed surfaces of the same helices are comprised largely of lysine and glutamate residues. The sequence of this construct is provided in FIG. 14 as SEQ ID NO: 98.

cTRP24 was expressed at high levels (>20 mg per liter of bacterial cell culture) and was easily concentrated to millimolar concentrations (50 to 100 mg/mL), with no evidence of significant aggregation, precipitation or loss of material during concentration. The purified protein was examined using circular dichroism spectroscopy (CD), small angle X-ray scattering (SAXS) and electron microscopy visualization (EM). CD spectra (FIG. 2A) confirmed the predominantly α-helical nature of the protein and retention of folded structure up to 95° C. SAXS analyses (FIG. 2B) produced well-behaved experimental spectra that were reproducible across a wide range of protein concentration and not prone to significant degradation over the course of the X-ray exposure. The experimentally measured SAXS spectrum was closely superimposable on a theoretical spectrum calculated from the model coordinates of the designed cTRP structure. Finally, the shape of the protein visualized via EM analyses (FIG. 2C) revealed uniform nanoparticles displaying circular shapes 100 Å (10 nm) across their outer diameter, with obvious internal pores. The overall thickness of the visualized nanoparticle ring is similar to the thickness of the protein design.

The protein was also crystallized, however all specimens diffracted to very low (less than 10 Å) resolution. It is believed that result is due to very high solvent content (promoted in part by the large internal pores of the cTRP construct) and also to rotational averaging of the symmetric molecule throughout the lattice.

Assembly from smaller subunits. The ultimate goal of this Example was to display multiple copies of large protein domains (i.e. functional 'cargo') at symmetrically distributed positions around the periphery of the cTRP nanoparticle. To reduce the size and complexity of such constructs (and to generate constructs containing multiple termini for the fusion of functional protein domains, in addition to surface-exposed loops) assembly of the cTRP from smaller fragments was investigated. The constructs tested each contained a number of repeats that might evenly assemble into a construct containing a total of 24 repeats (i.e. subunits encoding proteins with 3, 4, 6, 8, or 12 repeats, that might assemble into a full-sized cTRP via octamerization, hexamerization, tetramerization, trimerization, or dimerization, respectively).

These constructs are referred to for the remainder of this Example as 'cTRP24_subX', where 'X' denotes the number of repeats within each individual subunit. For example, 'cTRP24_sub6' refers to a protein subunit containing 6 repeats, where that construct is intended to tetramerize and thereby form an assembled circular particle harboring 24 repeats in total.

Figure 3B:
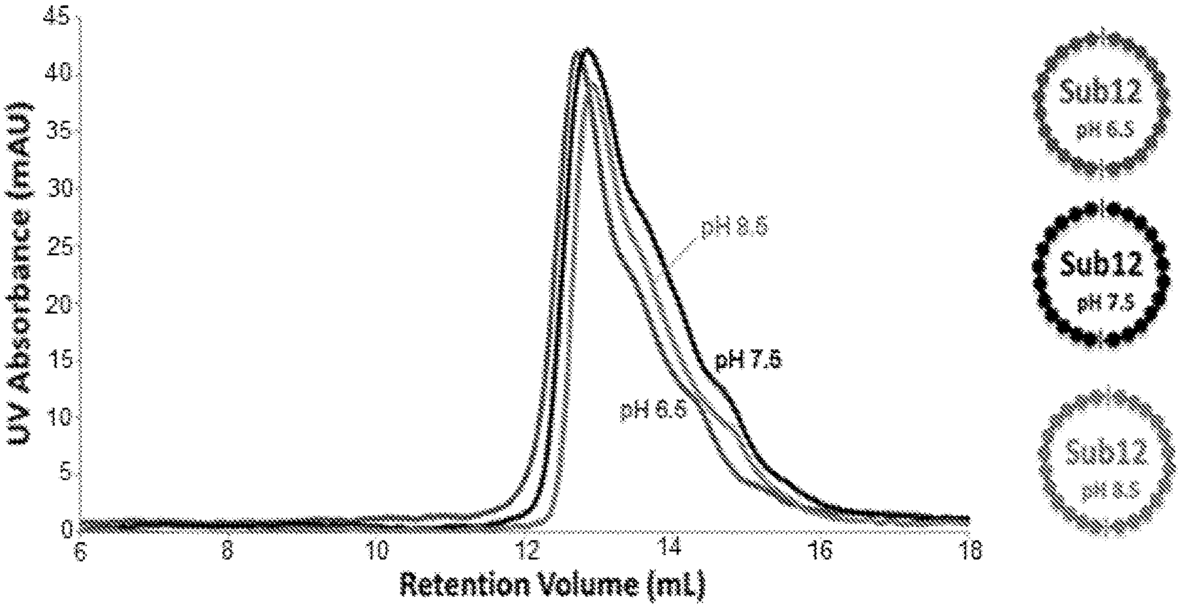

These constructs all expressed at very high levels, were readily purified to homogeneity (FIG. 3A; inset) and displayed excellent solution behaviors that were similar to the original full-length cTRP protein. However, size exclusion chromatography (SEC) analysis showed that the smallest four constructs eluted at volumes consistent with their monomeric size, indicating a failure to assemble into the desired 24 repeat construct. The largest of the constructs ('cTRP24_sub12', which contains 12 repeats and was expected to dimerize to form the full-sized protein) co-eluted at the same volume as the full-length cTRP24 protein; however, a significant tail extending from the main protein peak indicated that the protein appeared to sample an equilibrium between dimers and monomers. Subsequent repeats of this experiment at various pH values ranging from 6.5 to 8.5 produced similar elution patterns (FIG. 3B).

Figure 3C:
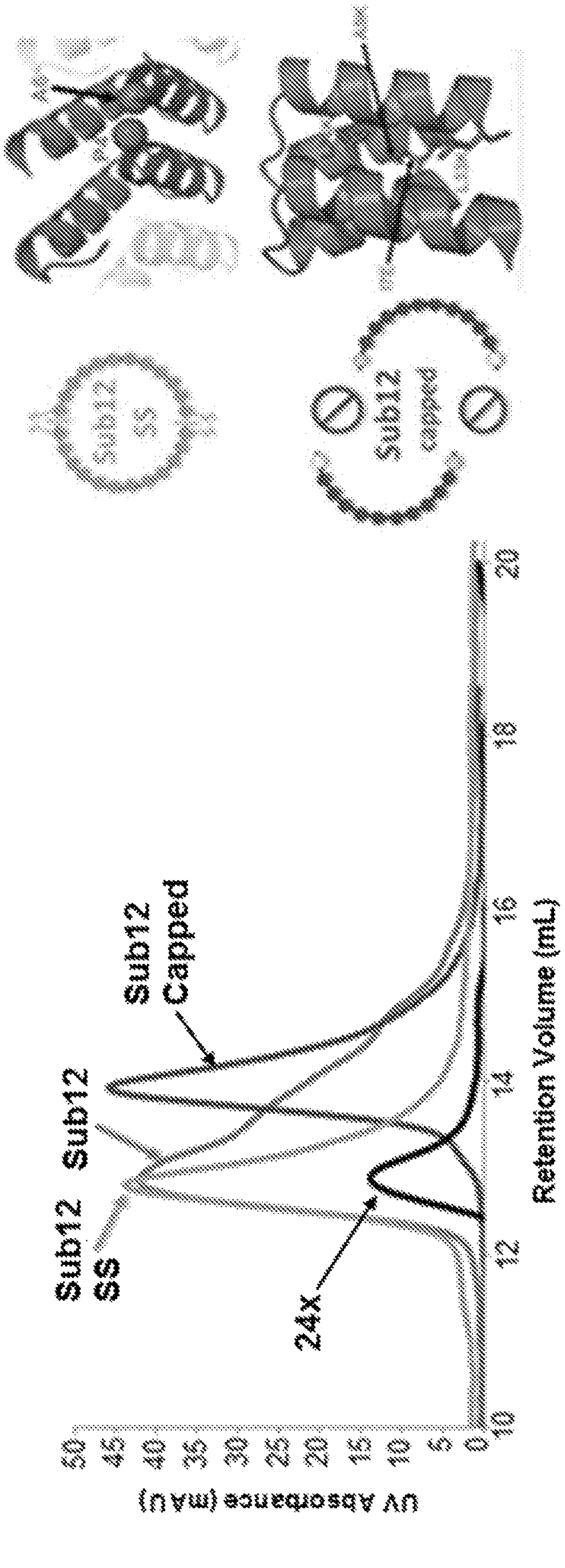

It was hypothesized that cTRP assembly might be encouraged by introducing disulfide staples into the interfaces between individual protein subunits. A pair of positions within neighboring helices of the N- and C-terminal repeats of each subunit (proline 4 on the N-terminal repeat, and alanine 6 on the C-terminal repeat) that might support disulfide formation in assembled cTRP nanoparticles if mutated to cysteines (FIG. 3C; right) was identified. Generation of a construct harboring 12 repeats that harbored those substitutions in its first and last repeats ('cTRP24_sub12SS') and subsequent electrophoretic analyses under reducing and non-reducing conditions, confirmed the formation of a disulfide-coupled construct (FIG. 4A). SEC analyses (FIG. 3C; left) revealed that the stapled construct co-elutes at the same volume as the full-length cTRP construct, but now as a much sharper peak corresponding to a uniform size distribution. An additional negative control, in which the original 12-repeat construct was mutated at multiple positions in the dimer interface to sterically block subunit association, resulted in elution at a significantly retarded volume corresponding to a smaller monomeric construct (FIG. 3C; 'cTRP24_sub12-capped').

Figure 4B:
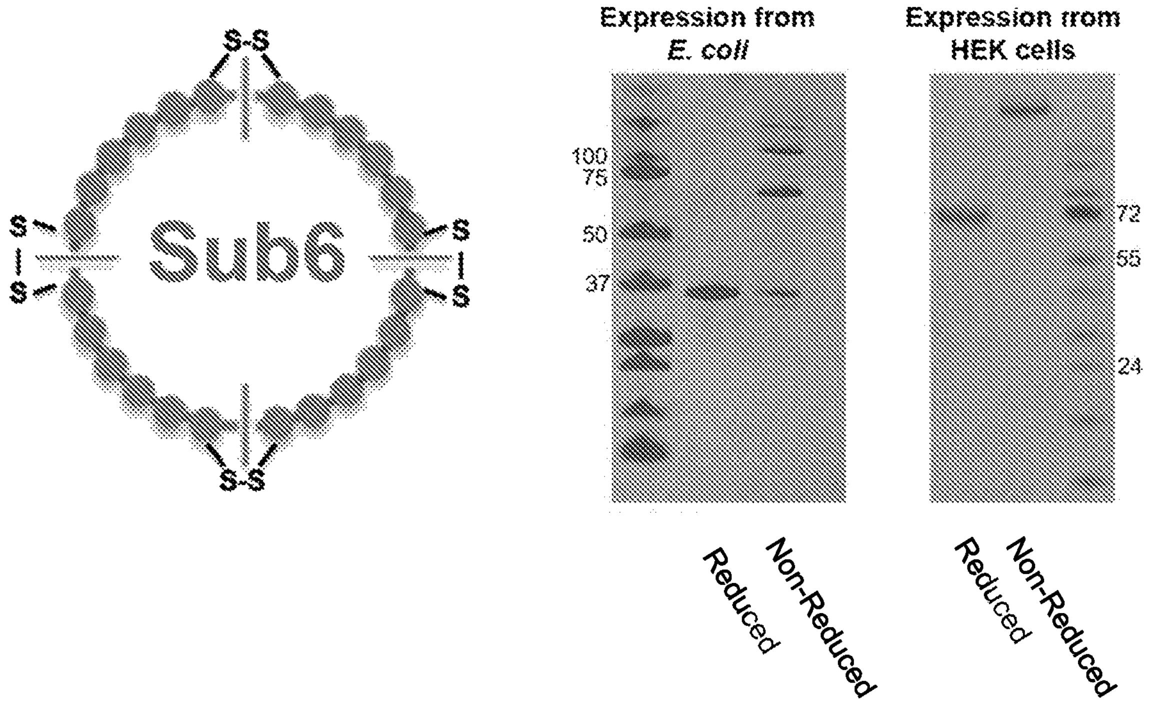

The same experiments were repeated also using subunits containing only 6 repeats per protein chain, that were expected to assemble into tetramers, again with the assistance of disulfide staples at each interface ('cTRP24_sub6SS'). When expressed in bacterial cells (FIG. 4B, middle panel), the resulting protein displayed an elution profile during SEC corresponding to a cTRP tetramer containing 24 total repeats, but it contains an incomplete, heterogeneous complement of internal disulfide bonds (indicated by a ladder of protein bands under non-reducing conditions). In contrast, when expressed and secreted from eukaryotic/human cells (FIG. 4B; right panel), the same nanoparticle displays a far more uniform and complete complement of internal disulfide bonds.

Figure 6A:
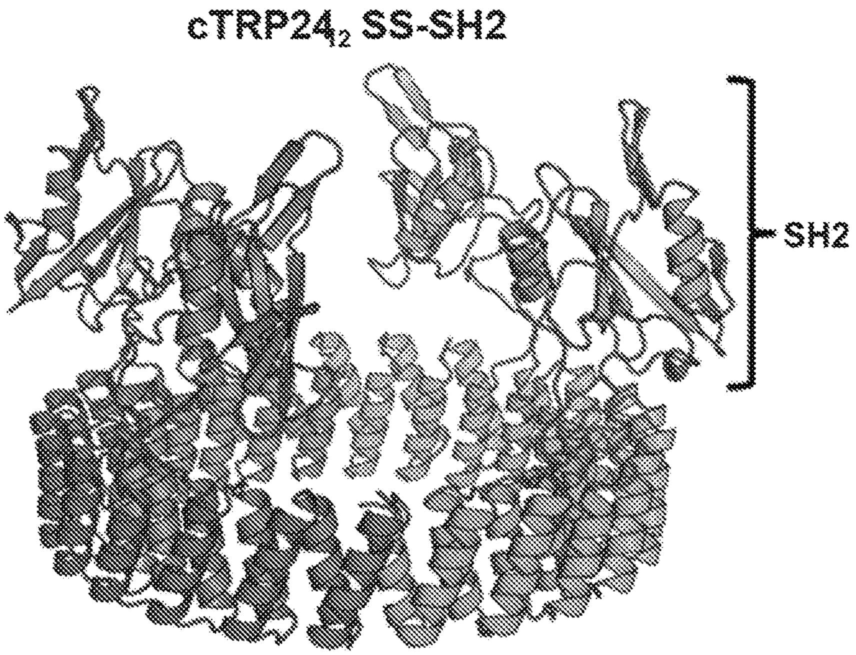
FIGS. 6A-6C. Computational models and characterization of functionalized 24-repeat cTRP constructs. The sequence-specific peptide binding SH2 domain and the SpyCatcher ligation domain are modeled into four evenly distributed loops around the top face of the cTRP ('cTRP24$_{12}$SS-SH2' (FIG. 6A); 'cTRP24$_{12}$SS-Spy' (FIG. 6B)). Ribbon diagrams represent models of designed constructs.
Figure 6B:
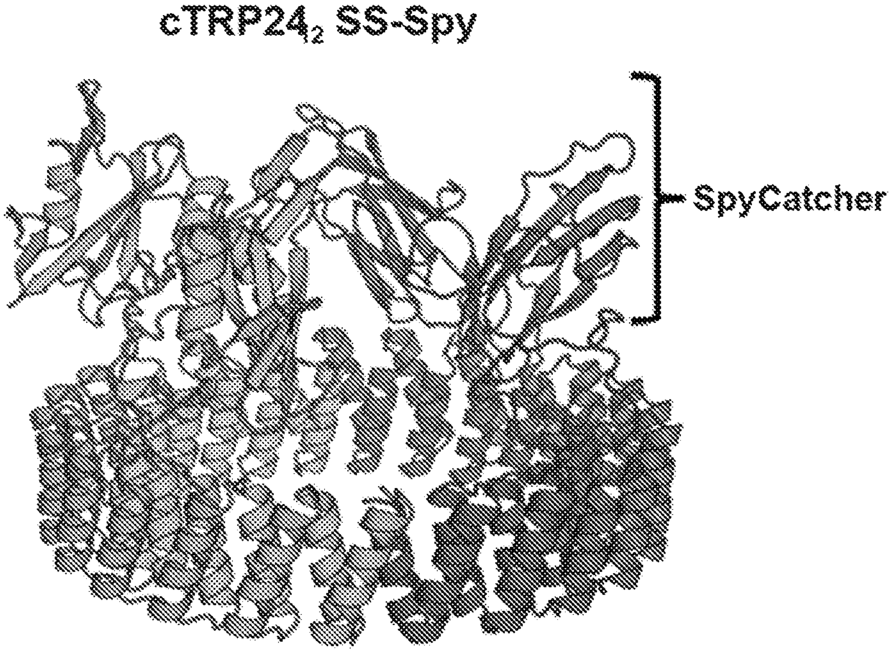

Display and characterization of functional protein domains. Armed with self-assembling cTRP constructs harboring 24 repeats that are well-behaved, the ability to display multiple copies of functional protein domains at positions distributed evenly around the periphery of the cTRP protein scaffold, and the effect of such fusions on their function was investigated. For that purpose, direct fusion of cargo at either the N- or C-termini of the cTRP subunits, as well as within surface loop positions evenly distributed around the periphery of either the top or bottom face of cTRP was investigated. These loop positions occur within "a" and/or "x" linkers, and functional domains within a linker may mask the identity of the linker sequence within a construct. Insertions can also replace linker residues. For these experiments, constructs that display multiple copies of:

(1 and 2): Constructs harboring either a sequence-specific SH2 peptide-binding domain (Frese et al., J Biol Chem 281, 18236-18245 (2006)) (FIG. 6A) or a 'Spycatcher' protein ligation domain (Zakeri et al., Proc Natl Acad Sci USA 109, E690-697 (2012)) (FIG. 6B) were generated. Each was inserted within 4 equivalent loops around the top of the cTRP. The construct harboring the Spycatcher domain was subsequently used to capture a 'Spytagged' version of the SH2 domain.

Figure 6C:
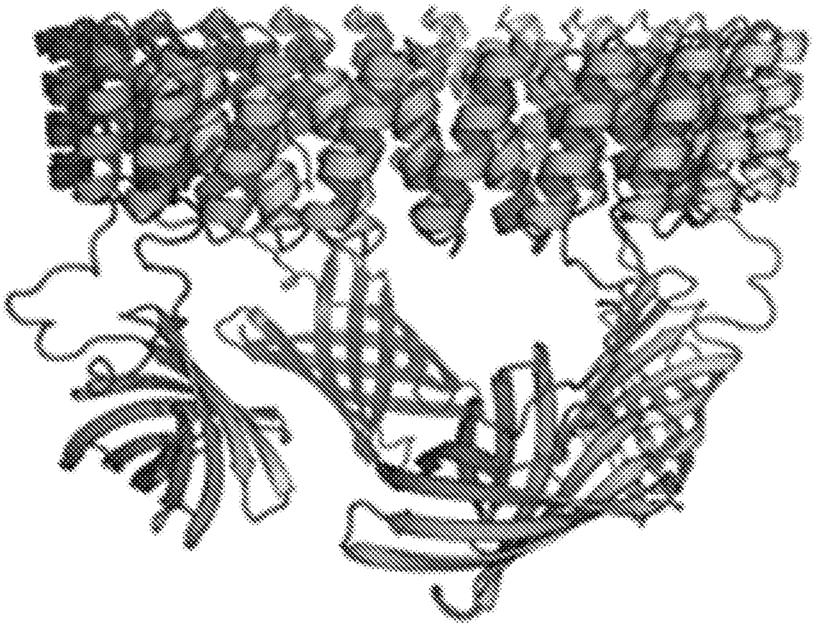

(3) An engineered fluorescent protein (Dou et al., Nature 561, 485-491 (2018)) inserted within 4 loops distributed around the bottom of the cTRP (FIG. 6C).

(4) A single chain class I MHC trimer ('scMHC') (Yu et al., J Immunol 168, 3145-3149 (2002)) displaying a viral antigenic peptide (CMV-pp65 from cytomegalovirus), fused to 4 equivalent N-termini distributed around an assembled cTRP tetramer (FIG. 6D). This final construct was created to examine a cTRP harboring a multidomain protein construct requiring expression from a eukaryotic expression platform, and also to demonstrate its resulting performance for a specific cell biology application (staining and identification of human T-cells harboring receptors specific for that cognate class I MHC-peptide complex).

(5) Four copies each of two entirely different folded protein domains, each distributed around a unique face of the protein scaffold (FIG. 8), by combining the protein domains found in (3) and (4) above.

Additional cTRP constructs such as scFv_CD3_hsOKT3-Toroidx6_SS_tetramer; scFv_CD28_TGN1412-Toroidx6_SS_tetramer, cTRP24$_6$SS-scTrimer$^{4\text{-}1BBL}$ and cTRP24$_6$SS-scTrimer$^{OX40L}$ were also created.

Figure 7A:
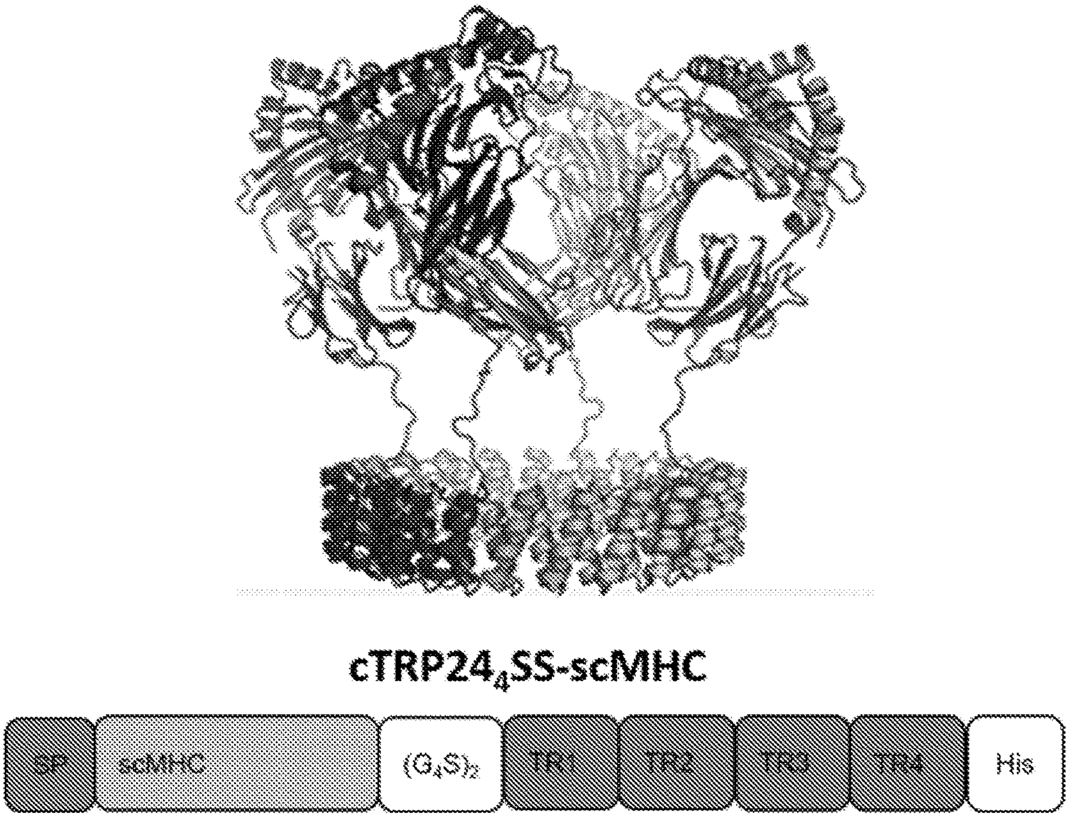
FIGS. 7A-7H. Characterization of an scMHC tetramer.
Figure 7B:
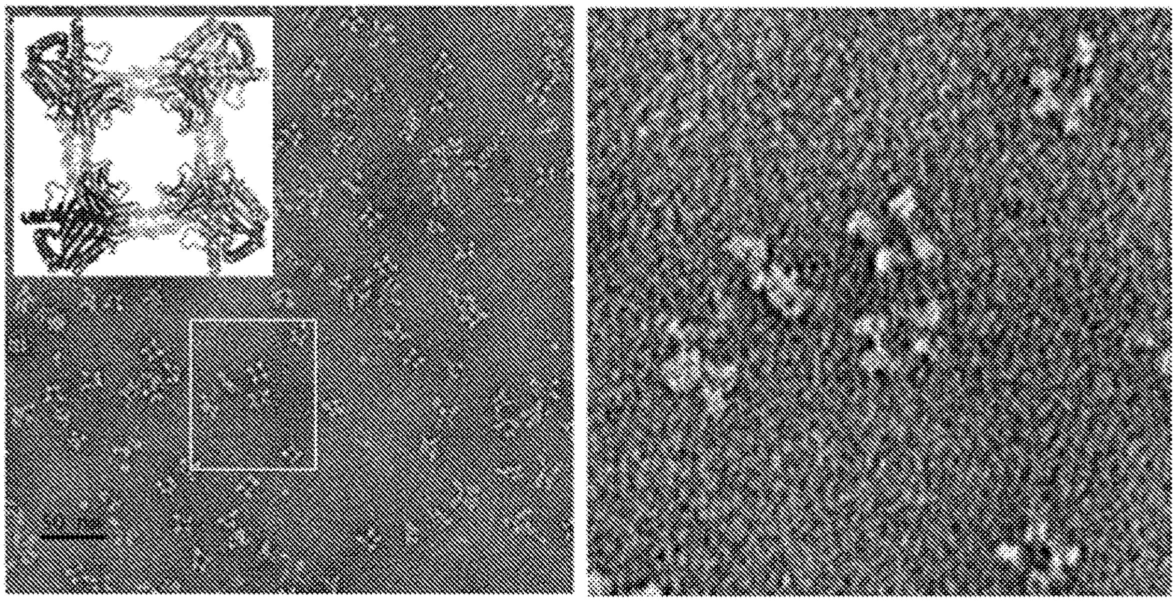

The expression and purification of all these constructs were confirmed by gel electrophoresis and SEC, and the tetrameric organization and geometry of the functionalized nanoparticle harboring scMHC was again visualized via EM microscopy (FIG. 7B).

The behavior of the two constructs containing functional protein domains (the SH2 domain and the Spycatcher protein ligation domain) inserted into loops around the top of the cTRP surface (FIG. 6A, 6B) was examined first. The SH2 domain from the human Nck2 adapter protein binds a phosphotyrosyl-containing peptide (EHIpYDEVAAD (SEQ ID NO: 162)) in a sequence-specific manner. Frese et al., J Biol Chem 281, 18236-18245 (2006). The protein ligation domain (termed a 'Spycatcher' protein) captures protein domains that harbor an N-terminal 'Spytag' sequence and then forms a covalent isopeptide bond between a lysine in its own fold and an aspartate within the tag. Zakeri et al., Proc Natl Acad Sci U.S.A. 109, E690-697 (2012). By creating a cTRP containing internal insertions of the Spycatcher protein domain, the goal was to create a generic cTRP capable of covalently capturing various types of tagged protein cargo. The first cargo tested in that manner was an N-terminal 'spytagged' version of the SH2 domain, so that the function of a direct internal fusion of the cTRP with that protein to a cTRP harboring a covalently captured version of the same cargo could be compared.

Figure 9A:
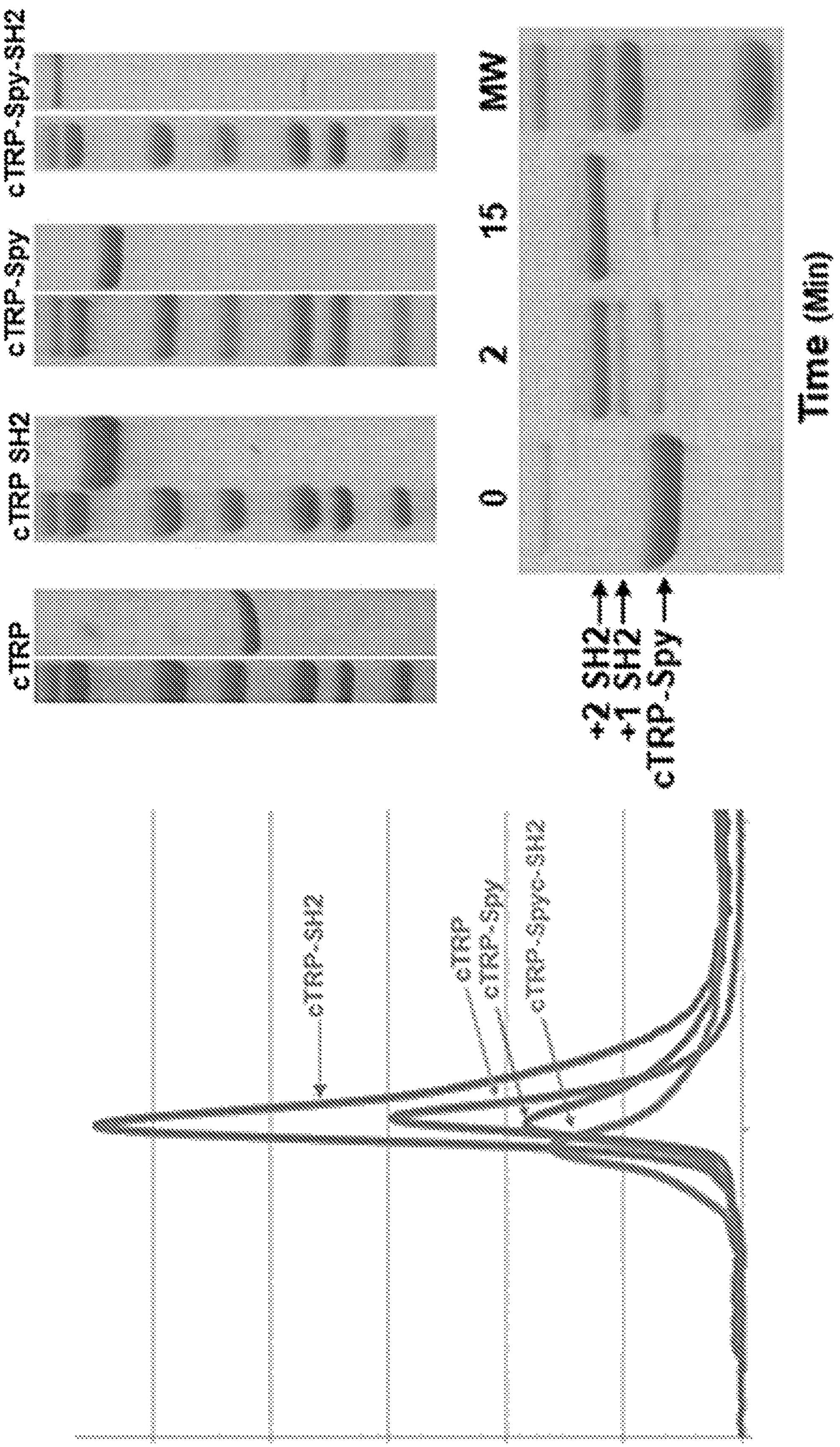
FIGS. 9A-9C. Functional characterization of cTRP24 constructs harboring functional protein domains inserted in loops around the top surface of the cTRP.
Figure 9B:
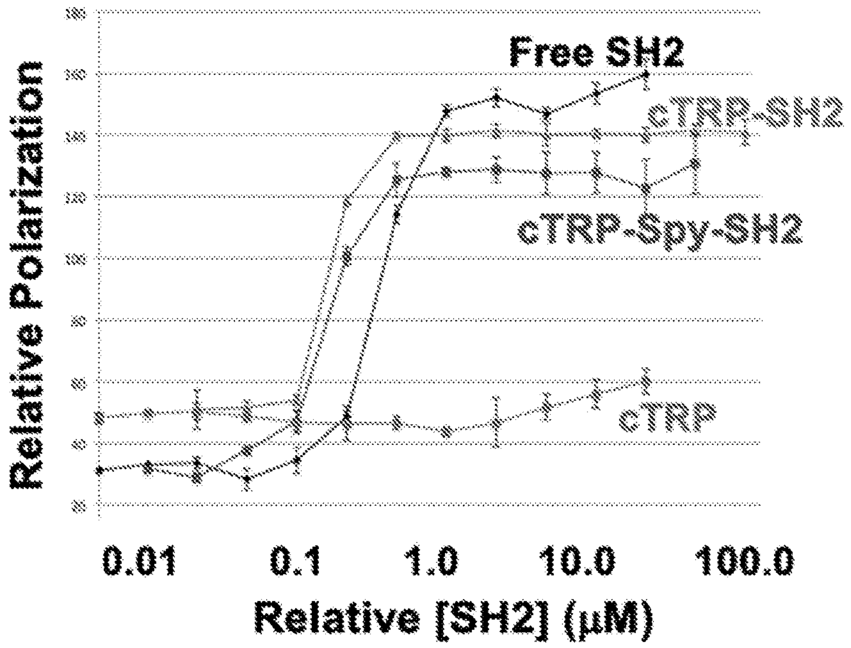

The fusion proteins described above were expressed and purified at levels comparable to the underlying cTRP protein itself and could be concentrated to 10+ mg/mL without obvious loss or aggregation of material (FIG. 9A; left and top right panels). Initial tests of the protein ligation function of the cTRP-Spycatcher fusion protein FIG. 6B), via incubation with a 'spytagged' Nck2 SH2 domain, demonstrated that the Spycatcher domains could be fully loaded with the cargo protein in a 15 minute incubation at room temperature (FIG. 9A; bottom right panel), similar to the kinetics reported for the free Spycatcher domain. Zakeri et al., Proc Natl Acad Sci USA 109, E690-697 (2012).

Phosphopeptide binding by three constructs was examined: the free SH2 domain, the cTRP harboring four direct fusions of the same SH2 domain, and the cTRP harboring four covalently captured copies of the SH2 by Spycatcher at the same four positions. Binding measurements were also performed on undecorated cTRP scaffolds (lacking SH2 domains) to test for nonspecific binding. The experiments were performed in solution (using fluorescence polarization with a labeled peptide ligand) and on a surface (using Biacore Surface Plasmon Resonance, with biotin-labeled peptide captured on a streptavidin chip).

In the solution-based peptide binding experiment (FIG. 9B), the constructs were all observed to bind peptide in a saturable manner, with KD values of 200 to 500 nM (0.2 to 0.5 μM), which is similar to previously reported values for the same SH2 domain/peptide combination. Frese et al., J Biol Chem 281, 18236-18245 (2006).

The cTRP scaffold on its own did not display significant peptide binding. Although the differences in estimated KD values for the three binding proteins are small (no more than 2- to 3-fold), the specific binding activity of the cTRP-displayed SH2 domains appears slightly higher than the isolated SH2 domain.

Figure 9C:
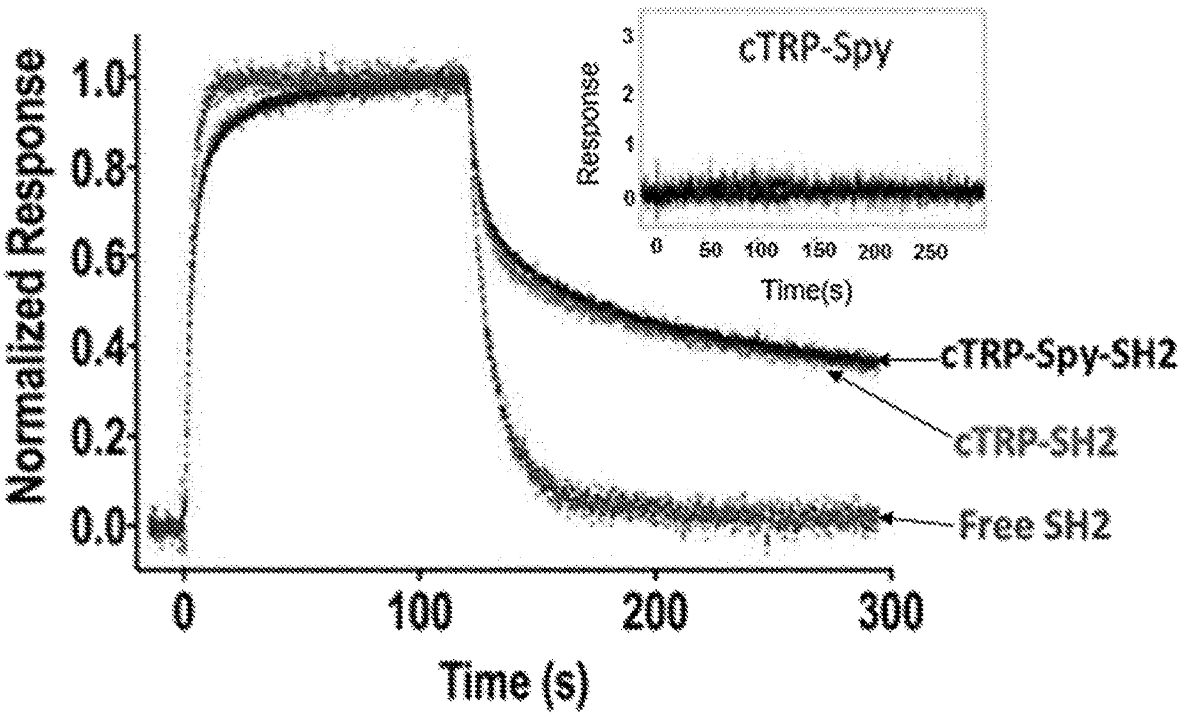

In surface-based binding experiments against the same peptide target, superimposable binding kinetics was observed for both the cTRP-SH2 and cTRP-Spy-SH2 fusions, both of which present four copies of the SH2 domain around the surface of the cTRP nanoparticle (FIG. 9C). Both constructs display a significant avidity effect, manifested in a considerably slower off-rate. The difference in off-rates between free SH2 domains versus a cTRP array of SH2 domains increases significantly when the density of captured peptides on the chip is increased (FIG. 10).

Figure 11A:
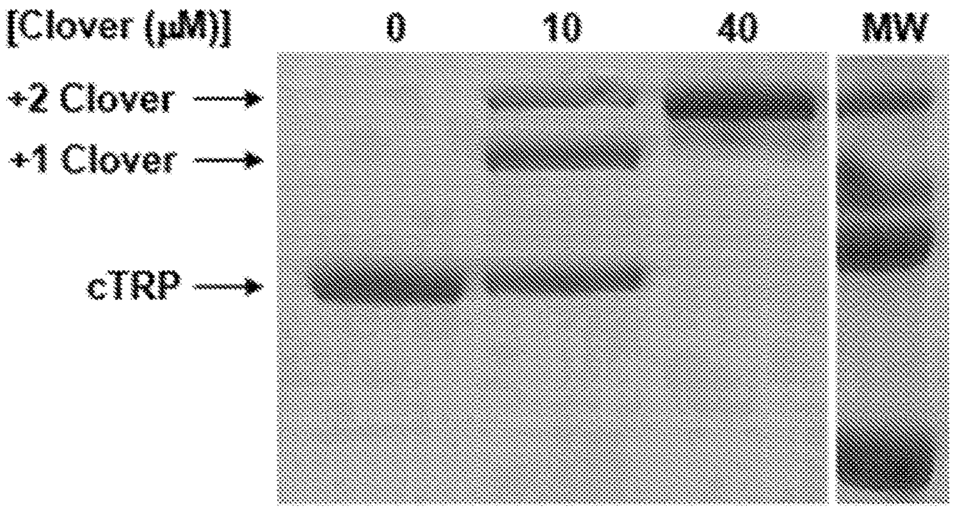
FIGS. 11A-11C. Functional characterization of additional cTRP constructs.
Figure 11B:
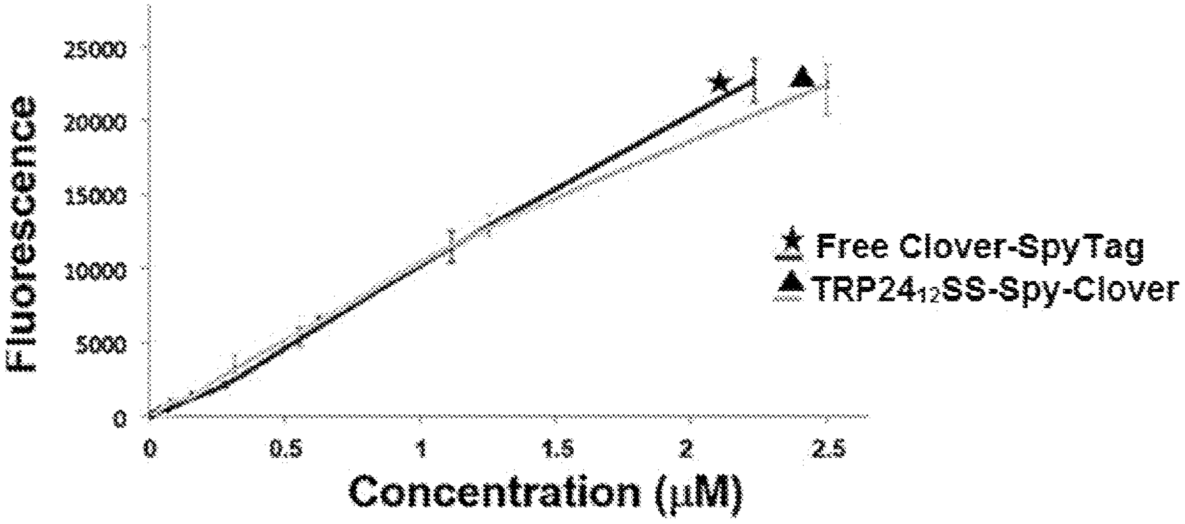

In a separate experiment to further test the Spycatcher domain, the cTRP was covalently coupled to four copies of a tagged 'Clover' variant of GFP (FIG. 11A). The covalent capture of that cargo was observed to proceed similarly to capture of tagged SH2. Subsequent examination of the 'cTRP-Spy-Clover' fusion demonstrated that the overall fluorescent signal from the individual fused proteins was equivalent (on a per-molecule basis) to the signal from free GFP protein (FIG. 11B).

Figure 11C:
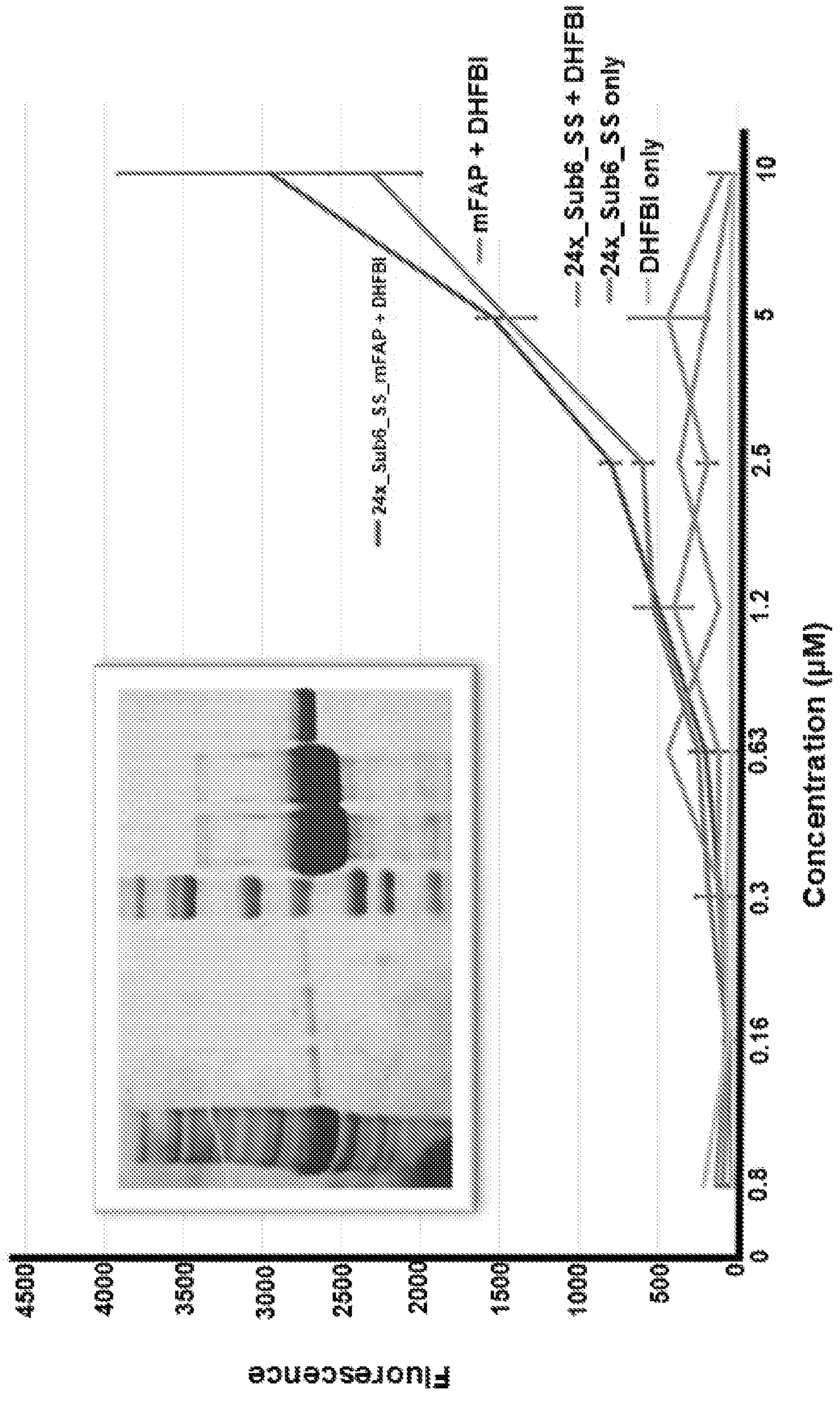

Incorporation of cTRP nanoparticles with functional cargo fused to multiple positions around its opposite ('bottom') face was next tested by inserting copies of a de novo engineered fluorescence-activating protein ('mFAP') into four evenly spaced loops between every 6 repeats (FIGS. 6C and 11C). Similar to constructs harboring inserted protein domains around its top surface, this protein was expressed at very high levels and displayed excellent solution properties upon purification. Biochemical analyses demonstrated that the protein displayed functional behavior similar to the free protein (Dou et al., Nature 561, 485-491 (2018)), with comparable fluorescent signals and strengths induced only upon addition and binding of exogenous DHFBI fluorophore, leading to excitation and emission maxima at 450 and 510 nm, respectively.

Figure 7C:
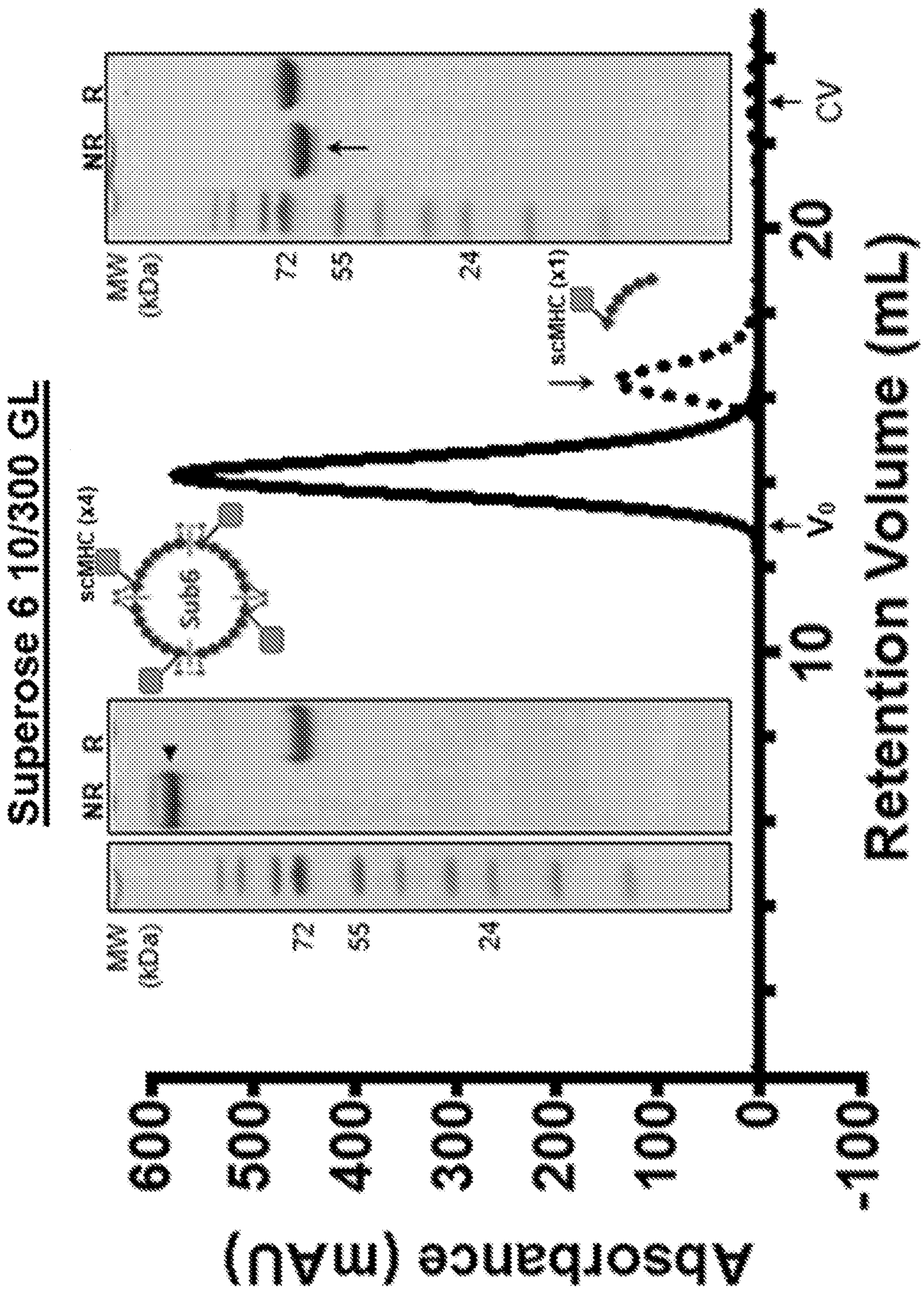
Figure 7D:
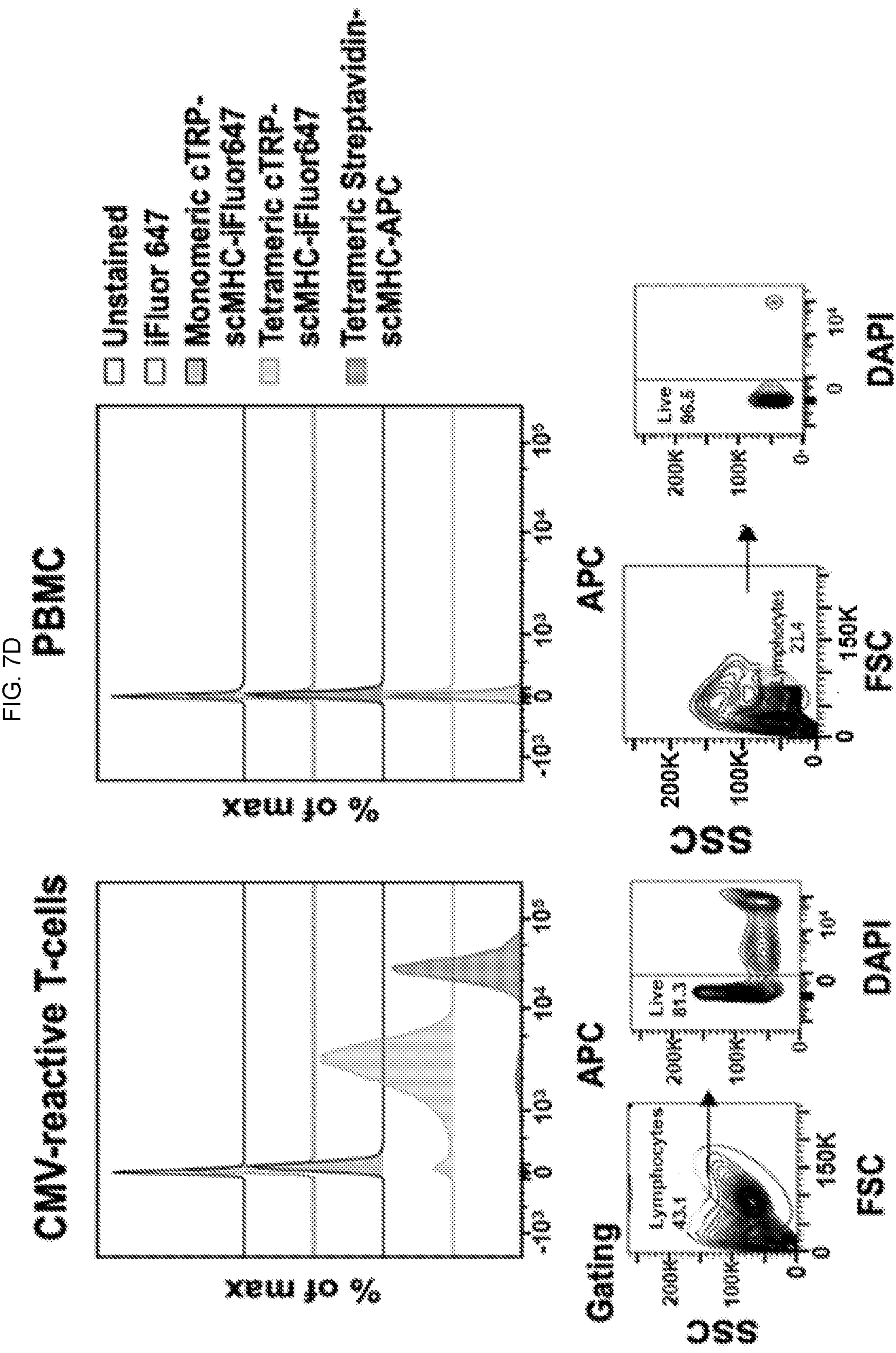
Figure 7E:
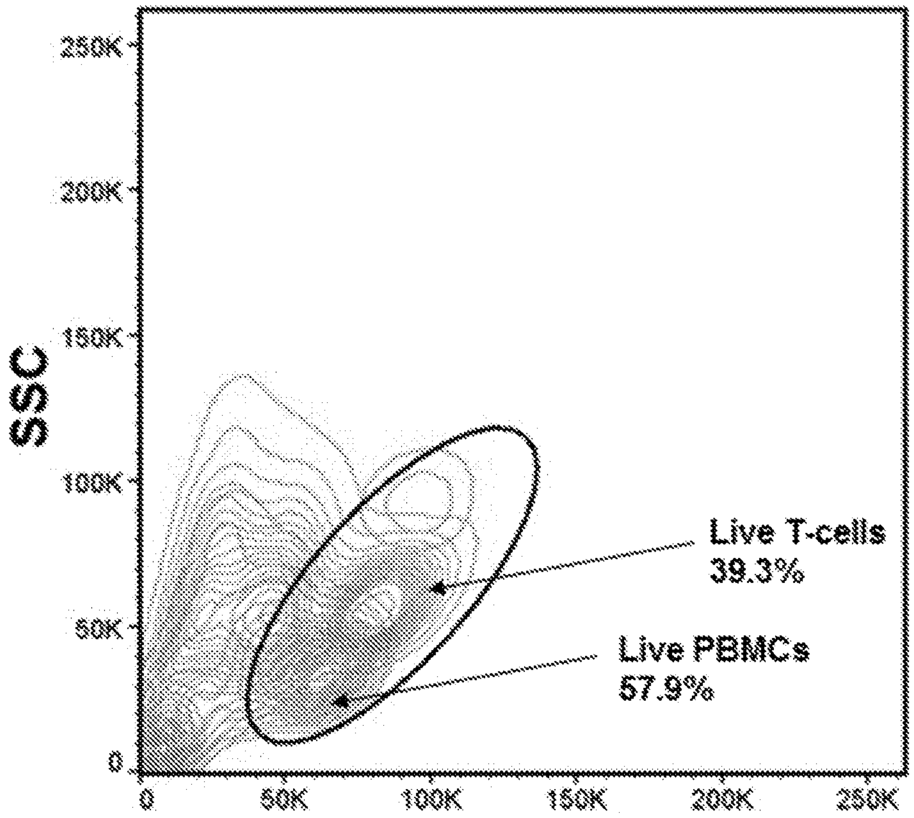
Figure 7F:
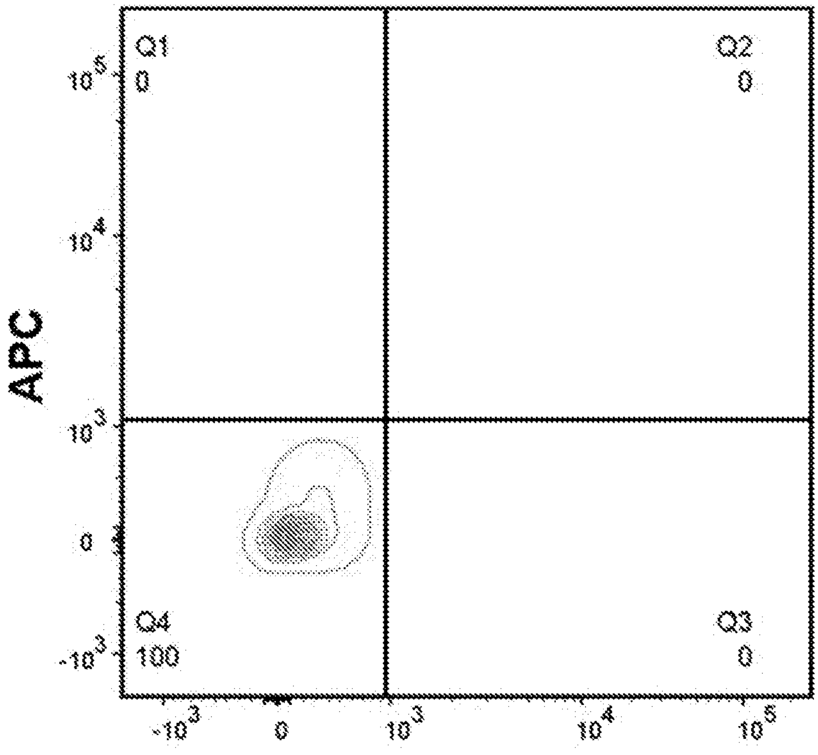
Figures 7G, 7H:
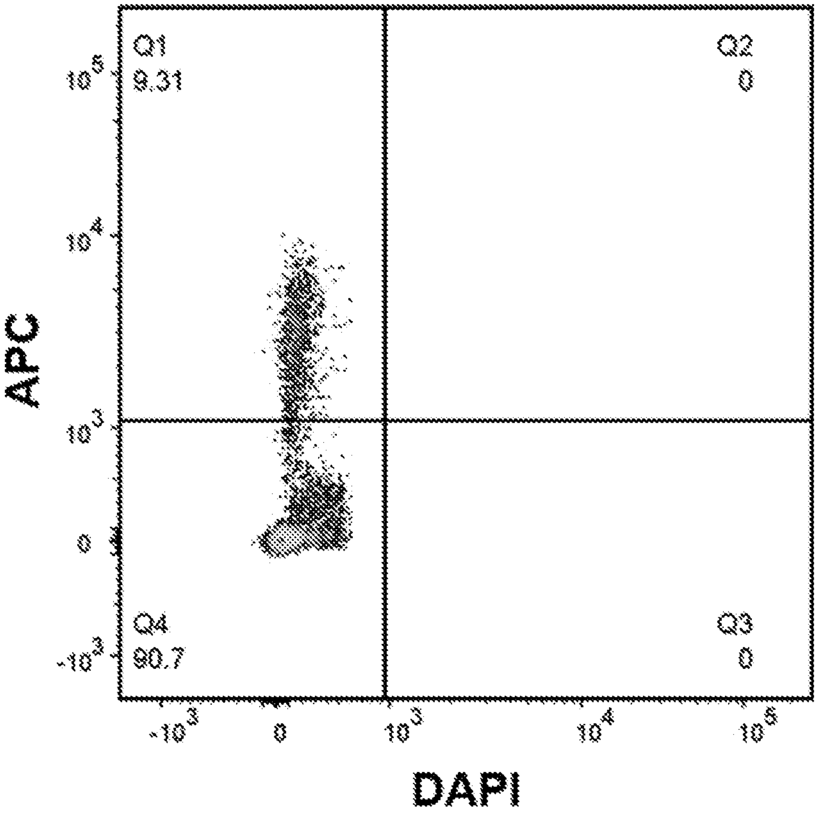

Display and characterization of a eukaryotic protein construct on a cTRP scaffold from human cells. The constructs described above were all capable of folding and expression in bacterial cells, both as isolated proteins and also as cTRP-fusions. Because many functional protein constructs of interest are of eukaryotic origin and generally cannot be easily generated in bacterial expression systems, the ability of the cTRP system to be expressed from a human cell line and to contain a protein known to require a eukaryotic (human) expression platform for proper folding was tested. For that purpose, a direct fusion of a single-chain MHC trimer ('scMHC'—a construct consisting of an antigenic peptide, a platform protein domain and β-microglobulin domain arranged on a single polypeptide (Yu et al., J Immunol 168, 3145-3149 (2002))) at four positions around the cTRP scaffold (FIGS. 7A-7D) was created. This construct (corresponding to fusion of an scMHC construct to each of four separate N-termini within a 'cTRP24_sub6SS' tetrameric assemblage) was expressed and secreted from HEK 293-F cells, using a lentiviral-based protein expression system that was described previously. Bandaranayake et al., Nucleic Acids Res. 31, e143 (2011). Expression of the cTRP-scMHC resulted in a yield of 100 mg per liter of conditioned culture media and subsequent purification using Ni-NTA affinity chromatography yielded a fully assembled tetramer harboring internal disulfide bonds that could be reduced to generate a shift in electrophoretic mobility (FIG. 7C).

The activity of the resulting construct was tested in a flow cytometric analysis in which a CMV-reactive cytotoxic T-cell line (CTL) was stained with the 24x-cTRP-scMHC tetramer. In parallel experiments, the same cells were stained with either (i) a streptavidin-conjugated tetramer of the same scMHC construct (a positive control), (ii) an unassembled cTRP24-scMHC monomer (to evaluate the avidity gain promoted by tetramerization of the cTRP-scMHC construct) and (iii) no reagent or with secondary antibody only (both serving as negative controls). The same experiments were repeated using a T-cell population isolated from a CMV-negative human peripheral blood population (PBMCs) as a further set of control experiments.

In these experiments (FIG. 7D) the monomeric cTRP-scMHC produced a very small fluorescent staining signal over the unstained cells, while the tetrameric cTRP-scMHC (and the streptavidin-conjugated scMHC tetramers) stained the vast majority of cells in the samples with equivalent efficiencies at comparable protein concentrations. In a similar experiment using a CMV-negative T-cell population, all constructs were observed to be non-reactive.

To further demonstrate the utility of self-assembling cTRPs, a series of T-cell 'superagonists' were designed to use as protein reagents to mimic immunological synapse interactions in vitro that are important during the process of T-cell differentiation and expansion (Chen, et al., Nat Rev Immunol 13, 227-242 (2013)). Several agonistic antibodies exist against a variety of human T-cell co-stimulatory receptors (examples include the anti-CD28 antibody TGN1412 [Theralizumab], anti-CD27 antibody 1F5 [Varlilumab], and anti-CD3 antibody OKT3 [Muromonab]). Bivalent reagents often work poorly in solution and as a result are often conjugated to beads (e.g. Dynabeads® Human T-Activator CD3/CD28) or aggregated on tissue culture plates in order to drive robust T-cell expansion. Soluble, multimeric proteins that agonize co-stimulatory receptors and thereby induce canonical signaling pathways can serve as an alternative to typical culture systems, especially if they could be (i) easily expressed and purified, (ii) added directly to tissue culture medium at low concentrations, (iii) be easily washed away or inactivated and (iv) enable large scale suspension or bioreactor expansion of human T-cells.

Figure 12A:
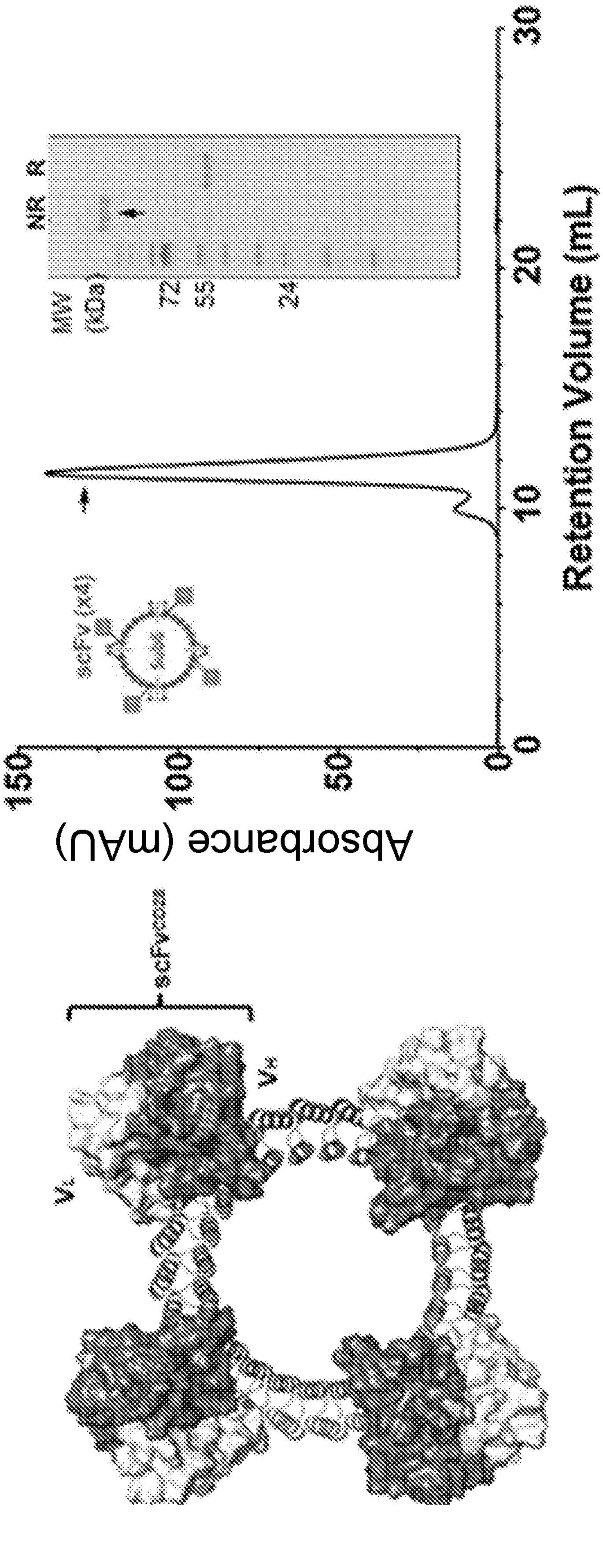
FIGS. 12A-12C. Functional characterization of a cTRP24$_6$SS construct harboring an N-terminal single chain Fv (scFv) specific for the T-cell co-stimulatory receptor CD28.
Figure 12B:
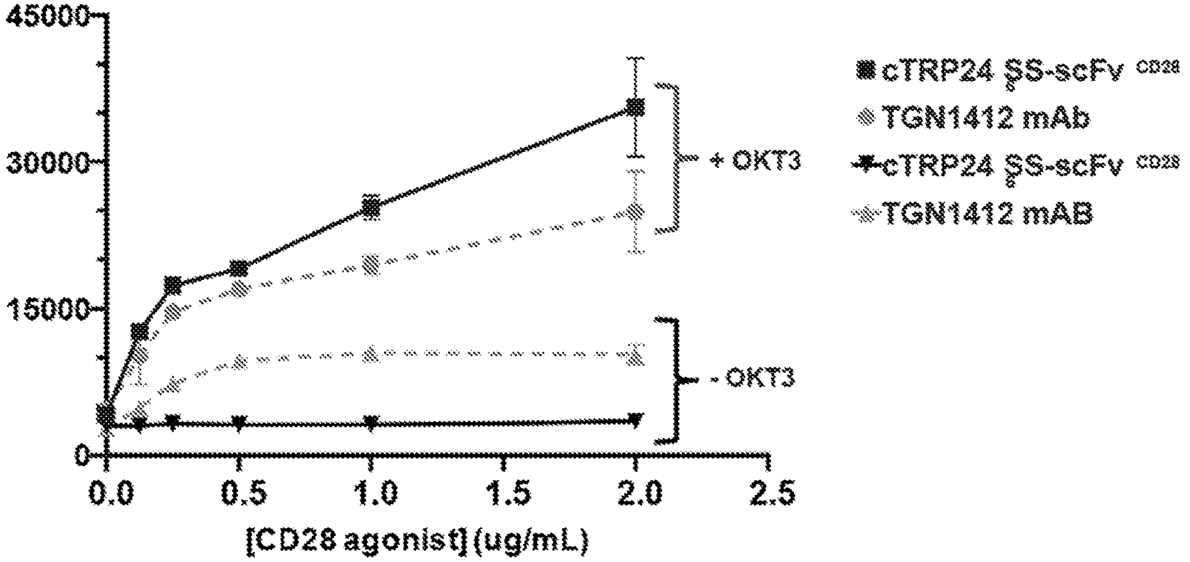
Figure 12C:
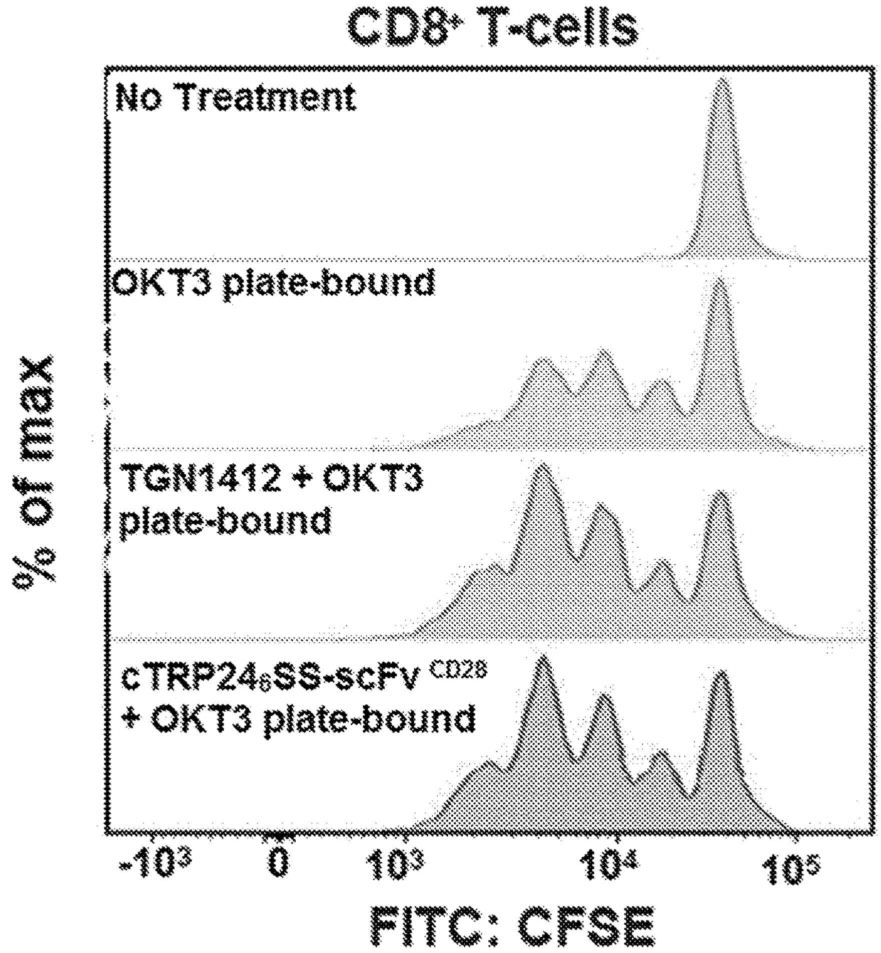

To achieve these goals, a CD28 agonist cTRP construct was created (cTRP$24_6$SS-scFv$^{CD28}$) using the variable region (as a single chain Fv) of the CD28-specific antibody TGN1412. The scFv was successfully displayed in a tetrameric arrangement and easily purified from conditioned media (FIG. 12A). The functionality of the molecule was verified using a NF-κB Jurkat reporter line in the presence of plate-immobilized OKT3 (FIG. 12B). The proliferation capacity of CFSE labelled human CD8+ T-cells in vitro was next assessed. The addition of soluble cTRP$24_6$SS-scFv$^{CD28}$ enhanced OKT3-induced proliferation to a similar extent as the soluble superagonistic TGN1412 mAb (FIG. 12C). These combined results show that cTRP$24_6$SS-scFv$^{CD28}$ is active when combined with OKT3 and demonstrate that displaying scFvs as cTRP24 multimeric arrangements provide a robust way to generate soluble receptor agonists.

Figure 13A:
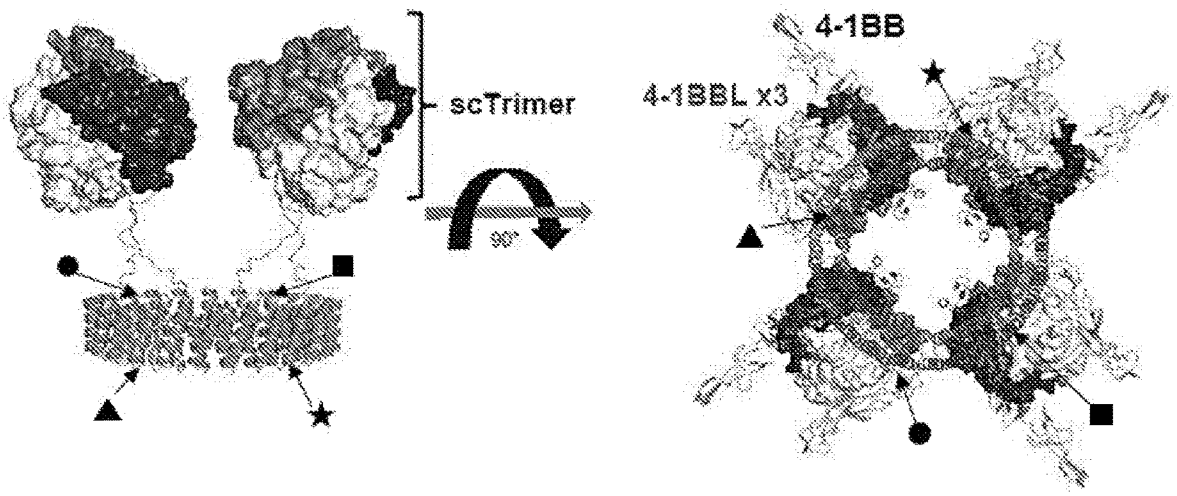
FIGS. 13A-13D. Functional characterization of cTRP24$_6$SS constructs harboring single chain trimers of tumor necrosis factor receptor (TNFR) ligands targeting T-cell co-stimulatory receptors 4-1BB and OX40.
Figure 13B:
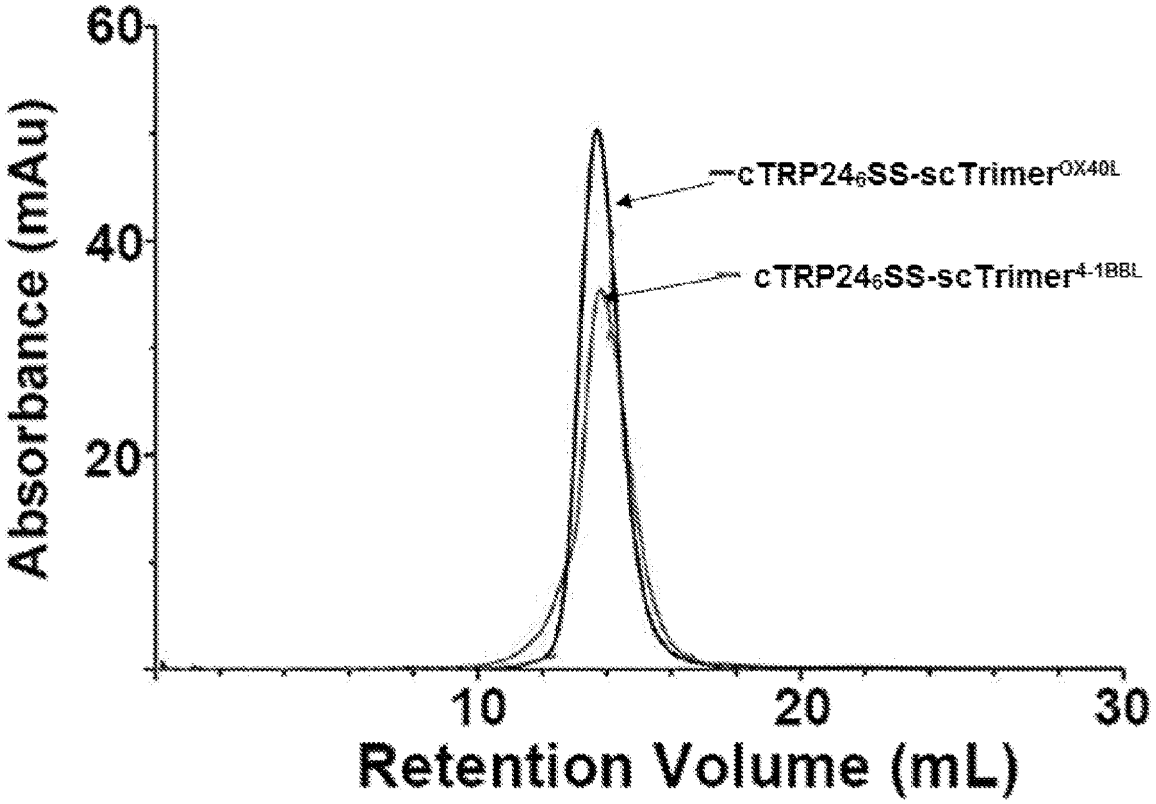
Figure 13C:
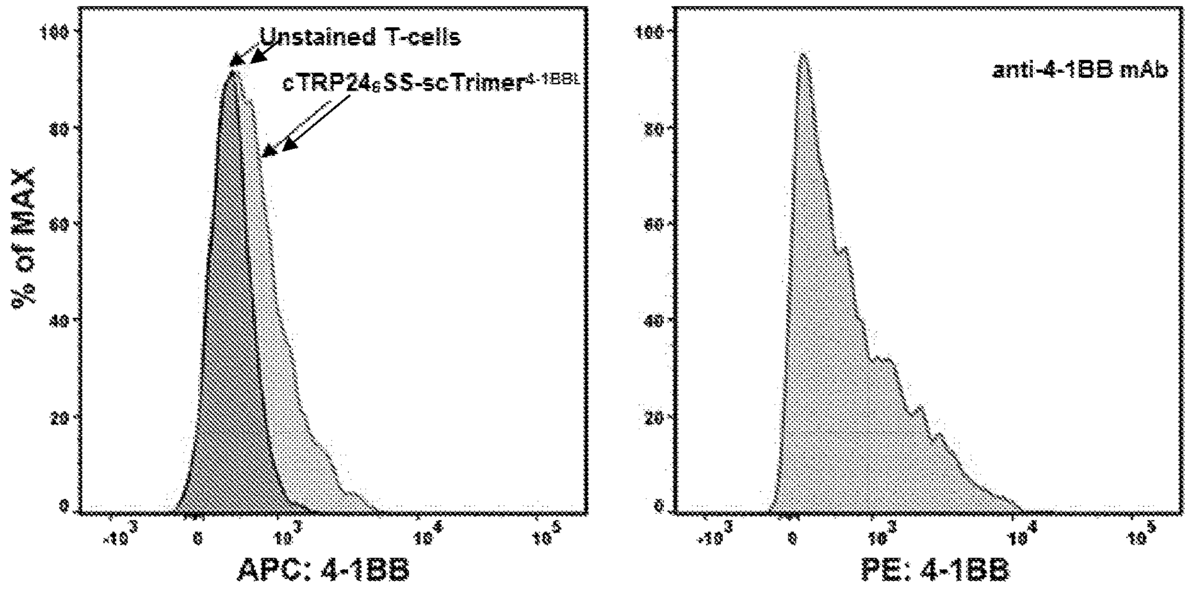
Figure 13D:
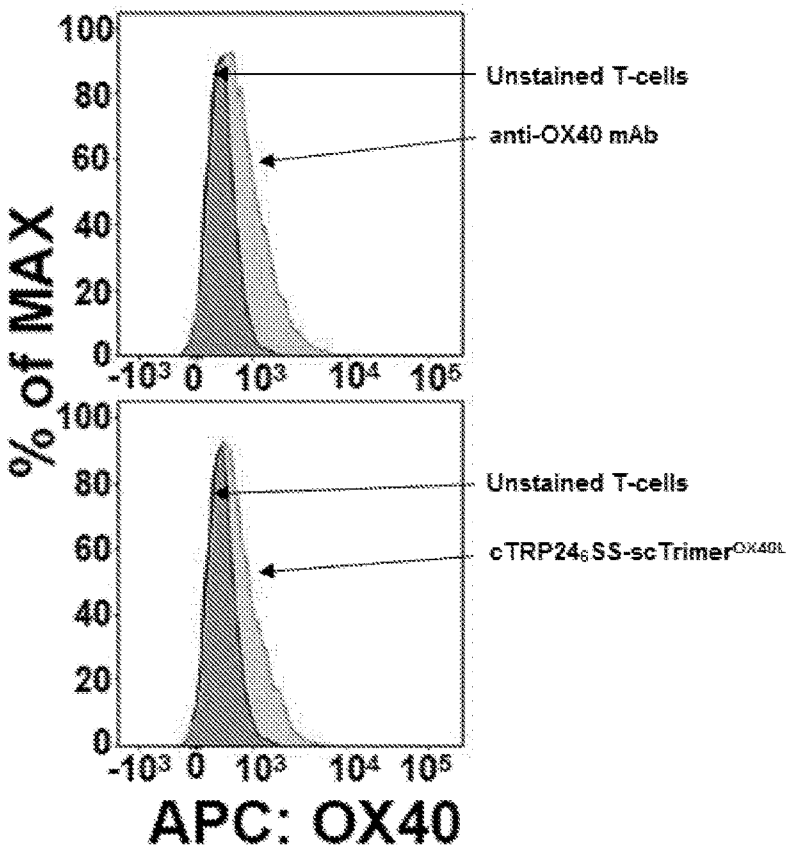

A series of TNF receptor superfamily ligands (4-1BBL and OX4OL) were also designed and expressed as single chain fusions to the cTRP$24_6$SS scaffold, to generate a tool kit of T-cell superagonists (FIGS. 13A, 13B). Both of these tetramers secreted well from 293-F cells and ran as monodispersed, tetrameric proteins by SEC (FIG. 13B). The binding capacity of the OX40L and 4-1BBL tetramers was assessed using CD3/CD28-bead activated CD8+ T-cells four days following activation. Incubation of CD8+ T cells with cTRP$24_6$SS-scFv$^{OX40L}$ and fluorophore labeled anti-His antibody revealed similar OX40 receptor expression as compared to a via anti-OX40 mAb (FIG. 13D). Similar results were observed for cTRP$24_6$SS-scFv$^{4\text{-}1BBL}$ (FIG. 13C). These data show that co-stimulatory receptors, such as CD28, OX40 and 4-1BB, can be effectively bound and triggered by soluble self-assembling cTRP$24_6$SS-ligand expressing superagonists.

Discussion. The experiments described in this Example illustrate that a self-assembling protein scaffold, capable of displaying a wide variety of functional protein domains and cargo, can be generated from a variety of expression systems with straightforward (often single-step) purification protocols; that the resulting constructs display architectures that closely resemble their computational designs, that the constructs are very thermostable and soluble, and that they provide display platforms that facilitate arrangements of functional cargo that benefit from symmetric preorganization and significantly enhanced avidity. Such constructs offer a straightforward approach for the development and application of a wide variety of constructs for use in biotech and industrial processes.

The ability of the cTRP scaffold to be assembled from smaller protein subunits, and to harbor functional protein domains (as well as smaller peptide epitopes) through fusions at the N- or C-termini of each subunit (as well as within individual surface loops at defined positions in each subunit) provides considerable flexibility in the design of functionalized constructs that is tailored to their folded structure. Additionally, the ability of the cTRP scaffold to be expressed and secreted at high levels from a eukaryotic (in this case, human) expression platform enables the creation of nanoparticles harboring functional protein constructs that cannot typically be expressed in a properly folded form from prokaryotic systems.

Methods. Computational Design. The 24-repeat cTRP scaffold was designed using a modified version of the tandem repeat protein design protocol introduced in Doyle et al, Nature 528, 585-588 (2015). This protocol consists of an initial large-scale exploration of cTRP topologies (helix lengths and turn types) compatible with the desired repeat number, followed by a round of focused design simulations targeting a handful of specific topologies. In the first stage helix lengths compatible with a total repeat length between 30 and 40 residues were explored. In the second stage two specific topologies (with inner/outer helix lengths of 13/14 and 14/11 respectively) that emerged as consensus low-energy solutions were the focus. On the order of 100,000 design simulations were conducted in each stage, with each independent run consisting of a fragment-based backbone buildup followed by all-atom sequence design and structure relaxation. Based on the observation of over-packing in previously published designs, the all-atom sequence design calculation was modified to more stringently penalize close contacts. Final designs were selected based on the ability of structure prediction simulations to recapitulate the designed structure when given only the designed sequence, with a final manual inspection to assess surface composition, buried unsatisfied polar residues, and packing quality.

Protein expression and purification from *E. coli*. The SH2 domain of human Nck2 cloned into pGEX-6P1 (Frese et al., J Biol Chem 281, 18236-18245 (2006)) was obtained from the Helmholtz Centre for Infection Research in Germany. SH2 was amplified by PCR, with primers adding Ndel and Xhol sites at the 5' and 3' ends of DNA, and subcloned into linearized pET15HE (described in Lambert & Stoddard, Structure 18(10), 1321-1331 (2010)) using the NEBuilder HiFi DNA Assembly Kit (New England Biolabs). All other genes were synthesized commercially and subcloned into the same pET-15HE bacterial expression vector (GenScript).

Plasmids were transformed into BL21(DE3)-RIL Escherichia coli cells (Agilent Technologies) and plated on LB medium with ampicillin (100 μg $ml^{-1}$). A 10 mL aliquot of LB-ampicillin media was inoculated with a single colony and shaken overnight at 37° C. Overnight cell cultures were added to 1 L volumes of LB-ampicillin, which were then shaken at 37° C. until the cells reached an optical density at 600 nm of 0.6-0.8. The cells were chilled for 20 min at 4° C., then isopropyl-β-d-thiogalactoside (IPTG) was then added to each flask to a final concentration of 0.3 mM to induce protein expression. The flasks were shaken overnight at 16° C., and then pelleted by centrifugation and stored at −20° C. until purification.

Figure 5A:
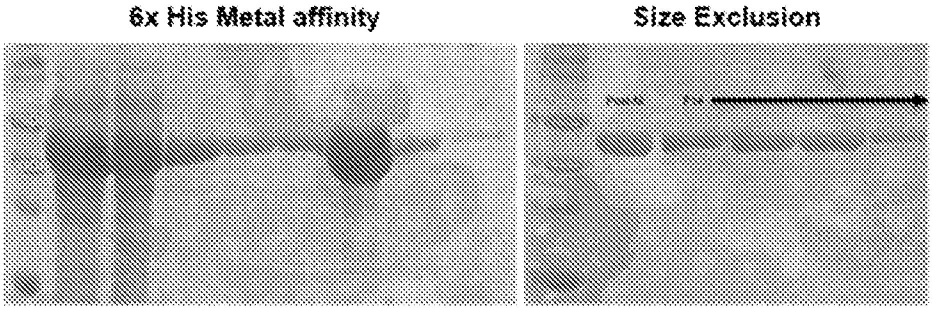
FIGS. 5A, 5B. Typical purifications of cTRP constructs. See Example 1 methods for details of this approach. (FIG.

For protein constructs without disulfide staples and for the free SH2 domain (FIG. 5A), cell pellets from 1 L of cell culture were resuspended in 50 mL of purification buffer (PBS with 20 mM Imidazole pH 8.0). Cells were lysed via sonication and centrifuged to remove cell debris. The supernatant was passed through a 5 μm filter, and then incubated on a rocker platform at 4° C. for 1 h after adding 1 mL of nickel-NTA metal affinity resin (Invitrogen) equilibrated with purification buffer. After loading onto a gravity-fed column, the resin was washed three times with 10 mL of purification buffer, and the protein was eluted from the column by 10-minute incubations with three consecutive aliquots of 5 mL of elution buffer (PBS with 300 mM Imidazole pH 8.0). Fractions containing the eluted protein were pooled, filtered and run over SEC (BioRad ENrich 650) in PBS.

Figure 5B:
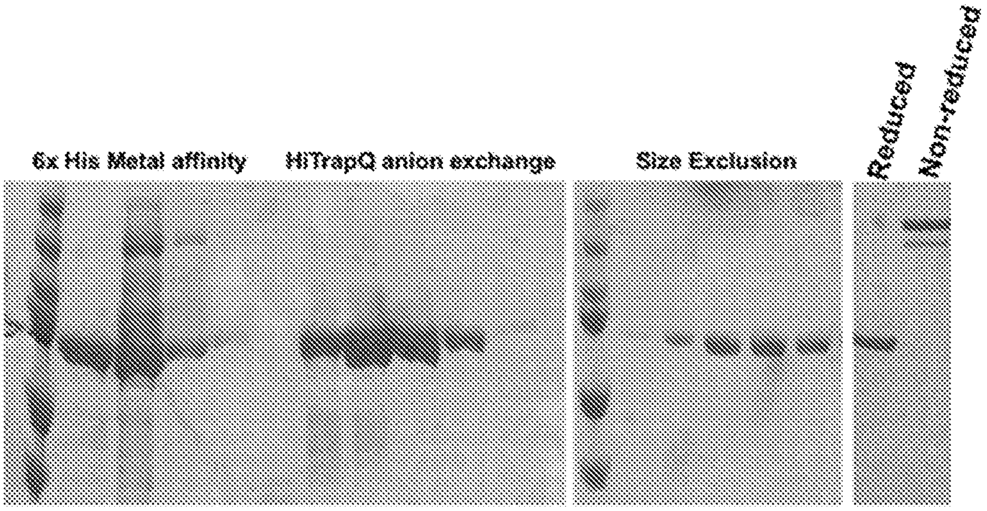
Figure 5C:
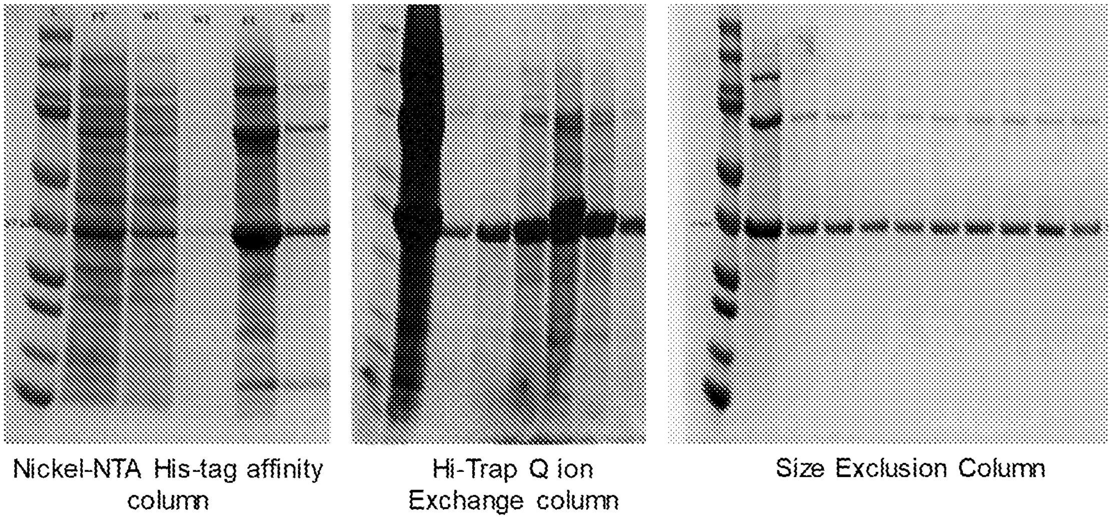
FIGS. 5C-5G. Purification and analysis of t-cTRP_24x$_8$_SS (SEQ ID NO: 119).
Figure 5D:
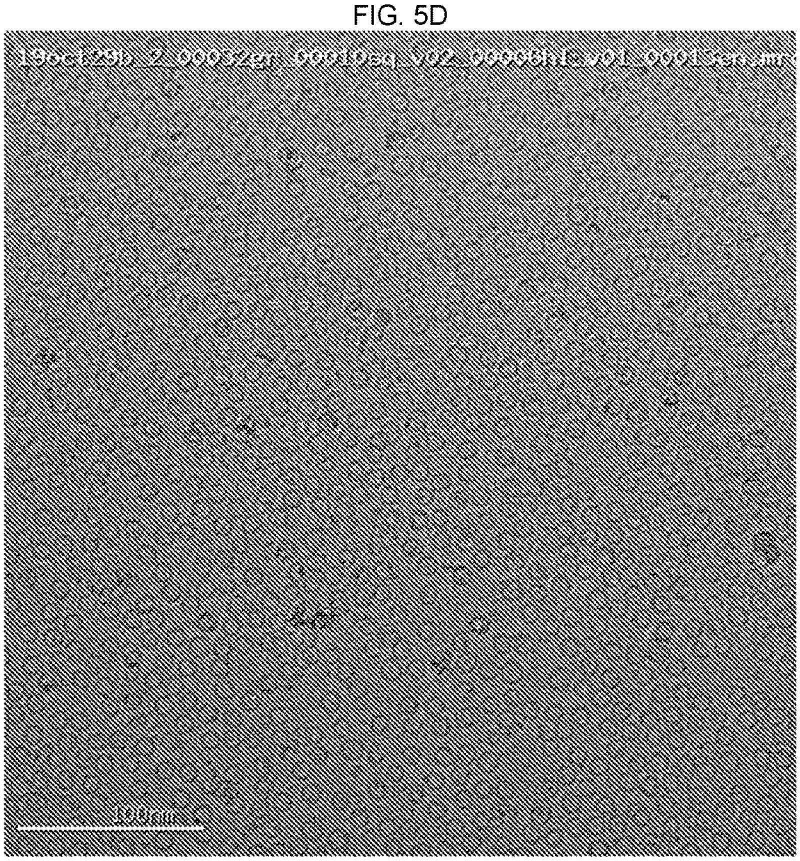
Figure 5E:
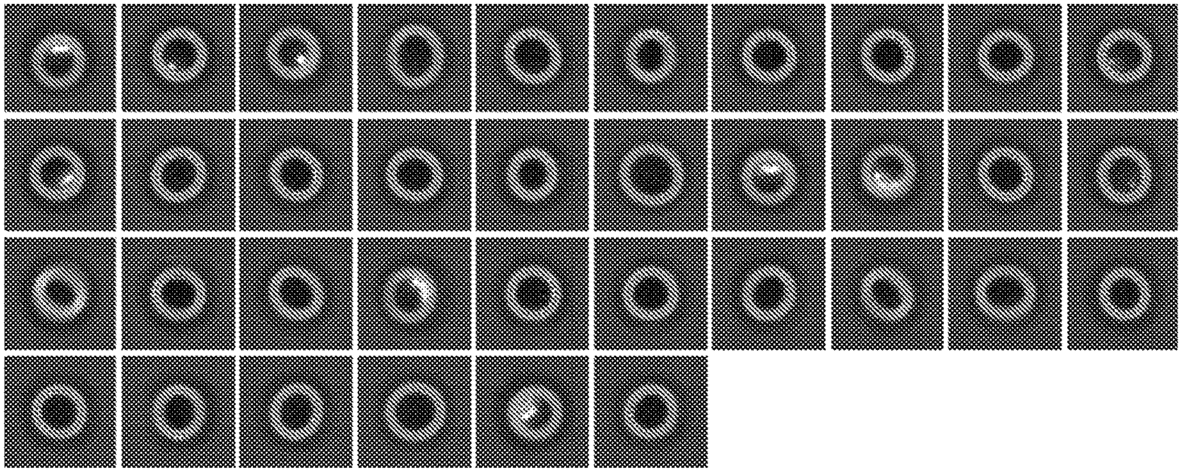
Figure 5F:
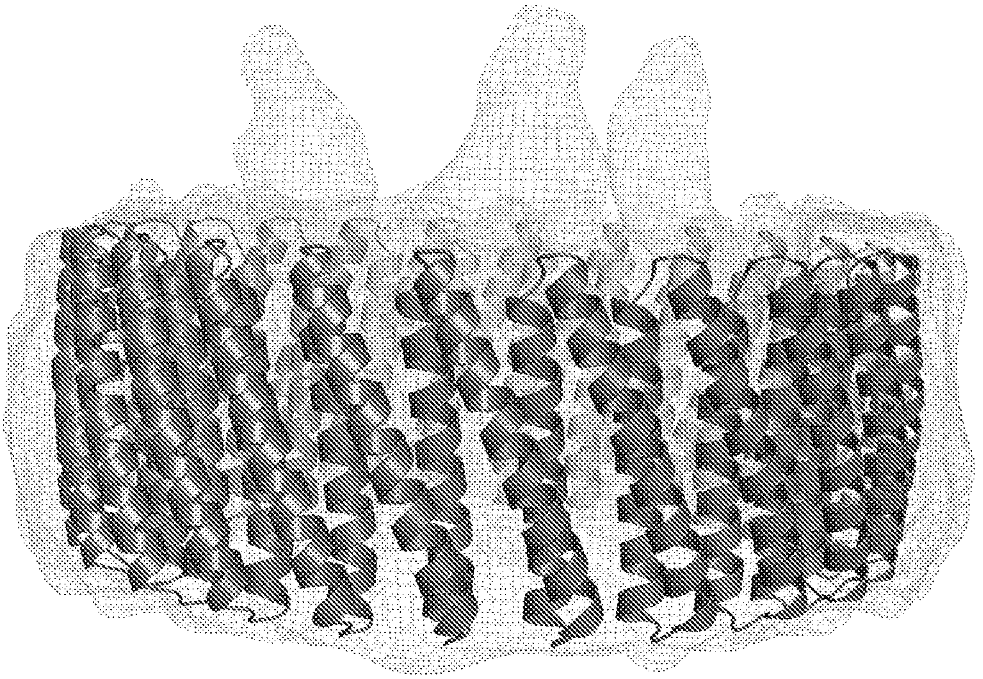
Figure 5G:
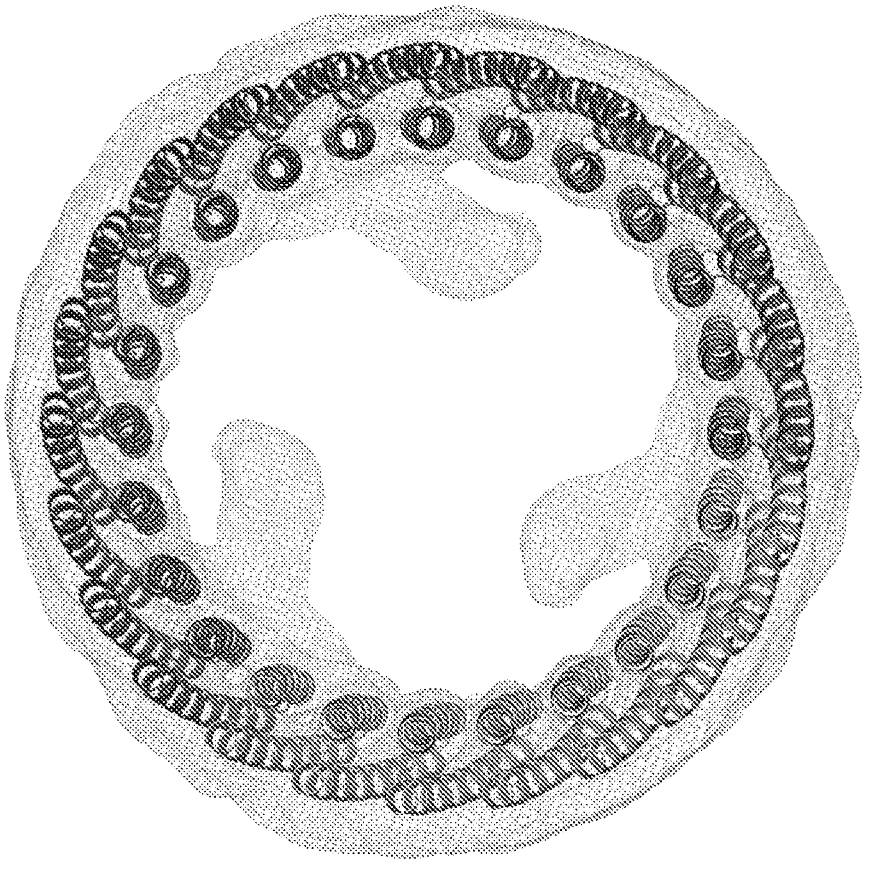
Figure 5H:
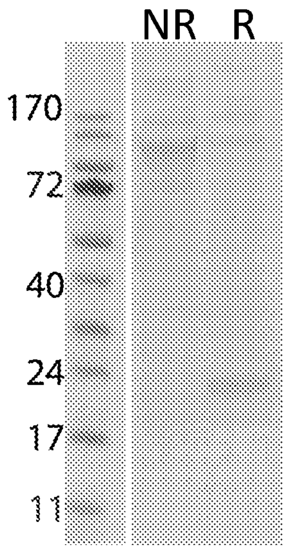
FIGS. 5H, 5I. SDS-PAGE analysis of the secreted protein confirms assembly following secretion from mammalian cells.
Figure 5I:
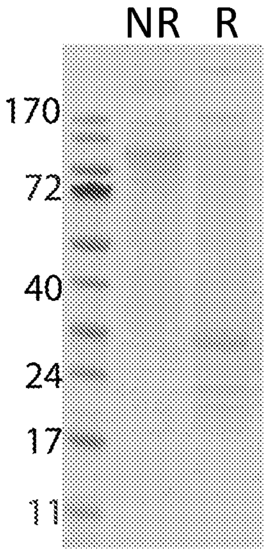

For protein constructs containing disulfide staples (FIG. 5B), cell pellets from 1 L of cell culture were resuspended in 50 mL of purification buffer (400 mM NaCl, 25 mM Tris pH 7.5, 20 mM Imidazole pH 8.0). Cells were lysed via sonication and centrifuged to remove cell debris. The supernatant was passed through a 5 μm filter, and then incubated on a rocker platform at 4° C. for 1 h after adding 1 mL of nickel-NTA metal affinity resin (Invitrogen) equilibrated with purification buffer. After loading onto a gravity-fed column, the resin was washed eight times with 10 mL of purification buffer, and the protein was eluted from the column by 10-minute incubations with three consecutive aliquots of 1.5 mL of elution buffer (300 mM NaCl, 25 mM Tris 7.5, 200 mM Imidazole pH 8.0). Fractions containing the eluted protein were pooled and DTT was added to 5 mM. Pooled fractions were run over a HiTrap Q column (GE Healthcare) at 2 mL/min with a gradient from buffer A (25 mM Tris pH 7.5, 5 mM DTT)+20% buffer B (25 mM Tris pH 7.5, 1 M NaCl, 5 mM DTT) to 100% buffer B over 20 mL. Fractions containing eluted protein were pooled, filtered and run over a SEC sizing column (BioRad ENrich 650) in 150 mM NaCl, 25 mM Tris pH 7.5.

Protein expression and purification from human HEK cells. The 'Daedalus' human cell line expression platform was employed for the production and purification of secreted cTRP-scMHC tetramers, using methods described in Bandaranayake et al., Nucleic Acids Res. 31, e143 (2011). That system makes use of engineered suspension-adapted HEK293 Freestyle cells harboring a ubiquitous chromatin opening ('UCOE') element along with a highly optimized lentiviral transduction protocol to generate cell lines that secrete proteins at high levels. The lentiviral vector contains a cis-linked fluorescent protein reporter driven by an internal ribosome entry site (IRES) that allows for tracking of relative protein expression levels. Expressed proteins can include a C-terminal poly-Histidine affinity purification tag that also can serve as an epitope tag for fluorescent visualization. Expressed mammalian proteins were purified directly from conditioned media using HisTrap FF Crude columns (GE #17528601) and subsequently polished on a Superose 6 10/300 GL SEC column (GE #17517201) using an AKTA pure 25 instrument.

Briefly, the amino acid sequence of the scMHC-cTRP with a C-terminal 6×-His tag was cloned into an optimized lentiviral expression vector harboring a ubiquitous chromatin opening ('UCOE') element along with a cis-linked fluorescent reporter driven by an internal ribosome entry site (IRES) that allows for rapid detection of transduced cells and tracking of relative protein expression levels. Lentivirus was harvested and used to transduce 293 Freestyle cells (Thermo Fisher). The 6×-His tag was used to purify the secreted protein directed from the conditioned media and used as an epitope tag for secondary antibody detection in the subsequent flow cytometry studies.

Circular Dichroism Spectroscopy (CD). Purified recombinant constructs were diluted to between 10-20 μM concentration and dialyzed overnight into 10 mM potassium phosphate buffer at pH 8.0. Circular dichroism (CD) thermal denaturation experiments were performed on a JASCO J-815 CD spectrometer with a Peltier thermostat. Wavelength scans (190-250 nm) were carried out for each construct at 20° C. and 95° C.

Small angle X-ray scattering analyses (SAXS). Proteins were filtered and run over SEC (BioRad ENrich 650) in 150 mM NaCl, Tris pH 7.5, 2% Glycerol. Fractions containing pure protein were concentrated to a low and high range (2 mg/mL and 10 mg/mL respectively) before being collected and averaged on SIBLYS Beamline at the Advanced Light Source, Lawrence Berkeley National Laboratory. Dyer et al., Methods in Molecular Biology 1091, 245-258. FoXS was used to examine the fit to the Rosetta structures.

Negative stain electron microscopy analysis (EM). Negative stained specimens for Transmission Electron Microscopy were prepared using methods previously described. Scarff et al., Variations on Negative Stain Electron Microscopy Methods: Tools for Tackling Challenging Systems. J Vis Exp (2018). Briefly, 4 μL of a cTRP solution at 40 to 50 nM was applied to the surface of a freshly glow-discharged carbon film coated Copper grid held at the tip of an anti-capillary tweezer. The solution was allowed to adsorb for 15-60 seconds. The grid was then washed 3 times by touching the surface of a 20 μL water droplet on the surface of a parafilm strip. Each time, the water attached to the grid was removed by briefly touching the surface of a nearby filter paper. The washing process was repeated twice with 20 μL and 40 μL of 0.7% Uranyl Format (UF). The last droplet of UF was allowed to remain in contact with the grid for 15 to 60 seconds prior to removing the filter paper. The stained grid was air-dried for 5 minutes prior to storage in a grid box. Grids were analyzed by TEM using a JEOL1400 microscope operating at 120 kV. The images were recorded using a GATAN CCD detector at a nominal magnification of 60,000× at the surface of the fluorescent screen.

Solution binding analyses via fluorescence polarization (FP). A 10-residue peptide, Tir10, containing a phosphorylated Tyrosine ('pY') was chemically synthesized with a FITC tag at the 5'-end linked to the peptide with a 7 atom aminohexanoyl spacer, Ahx (GenScript).Tir10: FITC-Ahx-EHI-pY-DEVAAD. Tir10 stock was re-suspended to 5.7 mM in DMSO, then diluted to 0.5 μM in FP Buffer (20 mM HEPES, 150 mM KCl, pH 7.4). Proteins were exchanged into FP Buffer then 2-fold serially diluted from 23 μM to 0.011 μM. Diluted proteins were mixed with Tir10 at a ratio of 9:1 for final concentrations of 20.7-0.01 μM protein and 0.05 μM Tir10, and incubated, shielded from light, at room temperature for 20 minutes. FP values were read at excitation of 485 nm and emission of 525 nm (SpectraMax M5). After subtracting background from the raw perpendicular (S) and parallel (P) measurements, polarization (mP) and anisotropy (r) were calculated with the following equations:

$$mP = \left(\frac{P-S}{P+S}\right) * 1000$$

$$r = \frac{P-S}{P+2S}$$

Surface binding analyses via Surface Plasmon Resonance analyses (SPR). Surface binding analyses via Surface Plasmon Resonance analyses (SPR). SPR experiments were performed at 25° C. on a Biacore T100 instrument (GE Healthcare) with a Series S SA chip using a running buffer of 10 mM HEPES, pH 7.4, 150 mM NaCl, 3 mM EDTA, 0.05% surfactant P20 with 0.1 mg/mL bovine serum albumin. Biotinylated Tir-10_v2 peptide (Biotin-Ahx-EHI-pY-DEVAAD) at 10 ng/mL was injected at 10 μL/minute over a flow cell for 15 or 90 seconds to capture 2 or 14 RUs, respectively. The reference surface was blank streptavidin alone. Analytes were repurified by SEC just prior to use. A buffer blank paired with each 50 nM analyte (concentration based on MW of construct, with no regard to the number of SH2 units) was injected at 50 μL/minute with 2 minutes of association and 3 minutes of dissociation. On the lower density Tir10_v2 surface (FIG. 9C), buffer was allowed to flow at 50 μL/minute for 1 hour after the first tetramer injection to regenerate the surface. Buffer flow alone was insufficient for regeneration of the higher density surface (FIG. 10) so only one tetramer injection was used. Overlay plots of double-referenced data were generated, then normalized for off-rate comparison by dividing each curve by its maximum response in Scrubber2.0b software (BioLogic Software). Maximum binding responses observed on the lower density Tir10_v2 surface were 10, 16 and 22 RUs for free SH2, cTRP-SH2, and cTRP-Spy-SH2, respectively. Responses observed on the higher density Tir10_v2 surface were 80 RUs for free SH2 and 230 RUs for cTRP-Spy-SH2. Figures were made in Prism 7 (GraphPad) for Mac OS X version 7.0c.

Epitope-specific T-cell staining. $0.5\times10^6$ clonal CMVpp65-reactive HLA-A*02$^+$CD8$^+$ T-cells or healthy PBMCs per sample (authenticated using microscopy morphology checks and STR analyses), from an overnight incubation in CTL media [RPMI, 10% heat-inactivated human AB sera, 2% L-glutamine (4 mM), 1% Penicillin/Streptomycin, 0.01% β-mercaptoethanol (0.5 M)] (Warren et al., Blood 91, 2197-2207 (1998)), were spun in 5 mL FACS tubes at 1200 RPM for 10 minutes at 4° C., and washed 1 time with wash buffer (Miltenyi autoMACS running buffer, Miltenyi). The washed cells were resuspended in 100 μL of wash buffer. cTRP- or streptavidin-allophycocyanin (APC) conjugated scMHC constructs were added at 5 μg/mL concentration to each sample, mixed well and incubated on ice in the dark for 30 minutes. 4 mL of wash buffer was added, the cells were spun down at 1200 RPM for ten minutes at 4° C. and resuspended in 100 μL of wash buffer. A secondary labeling antibody (THE™ anti-His tag conjugated with iFluor 647, Genscript #A01802) was added to 4 μg/mL to samples incubated with the cTRP-scMHC conjugates and incubated for a further 30 minutes. The cells were washed with 4 mL of wash buffer, resuspended in 100 μL of wash or DAPI buffer, and then analyzed on an BD™ LSR II flow cytometer (BD Biosciences). Gating strategies were chosen based on their forward and side scatter properties, single parameter histograms, and two-parameter density plots of cell populations.

T-cell isolation, proliferation and activation assays. Human CD8+ T-cells were derived from healthy donor PBMCs and isolated following the instructions of EasySep™ Human Bulk CD8+ T-cell Isolation Kit (STEM CELL #17951). Cells were labelled with CFSE for 10 minutes 37° C. and subsequently quenched with FBS prior to washing. $1\times10^5$ cells were resuspended in CTL media supplemented with 50 U/mL human IL-2 and added to anti-CD3 (OKT3; 5 μg/mL; BioLegend #317347) coated (non-TC treated) flat bottom 96 well plates in the presence or absence of soluble anti-CD28 (TGN1412; 1 μg/mL) or cTRP$_6$SS-scTrimer$^{CD28}$ (1 μg/mL). CFSE dilution was assessed 3 days after activation by flow cytometry. Alternatively, CD8 T-cells were activated with anti-CD3/anti-CD28 beads (ThermoFisher #11131D) for 4 days. Cells were incubated for 30 min at 37° C. with cTRP24$_6$SS-scTrimer$^{OX40L}$ (2 μg/mL) or cTRP24$_6$SS-scTrimer$^{4\text{-}1BBL}$ (2 μg/mL) and subsequently stained at 4° C. using THE anti-His Ab (GenScript; #A00186). Receptor surface expression was assessed using anti-human OX40 (BioLegend #350007; Clone ACT53) and 4-1BB (BioLegend #309803; Clone 4B4-1) mAb.

For the NF-κB luciferase reporter assays, Ultra-LEAF™ Purified anti-human CD3 Antibody (OKT3) was diluted in 1×DPBS to 50 μl and incubated overnight in a non-tissue culture treated round bottom plate (Corning #3788) at 4° C. Contents of the plate were drained as to not disturb the protein monolayer formed in the bottom of each well.

Dilution series of the co-stimulation constructs were prepared in serum free media (X-Vivo #04-744Q) and added to the plate. $10^5$ Jurkat cells transduced with an NF-κB luciferase reporter were added to each well and incubated for 24 hours at 37° C. Data was collected using a Biotek Synergy 2 plate reader with auto-injector dispensing coelenterazine (Nanolight Technology, 303-10) dissolved in propylene glycol and diluted to 0.01 mg/ml in cell media at 25° C.

(x) Closing Paragraphs. As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in the ability of a 24-repeat cTRP to self-assemble with increased stability following expression from a eukaryotic cell type.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A cTRP comprising the sequence of
SEQ ID NO: 121,
SEQ ID NO: 123,
SEQ ID NO: 127,
SEQ ID NO: 129,
SEQ ID NO: 130,
SEQ ID NO: 132,
SEQ ID NO: 140,
SEQ ID NO: 154,
SEQ ID NO: 155,
SEQ ID NO: 195,
SEQ ID NO: 196, or
SEQ ID NO: 252.

2. The cTRP of claim 1, wherein the cTRP lacks an N-terminal signal peptide.

3. The cTRP of claim 1, wherein the cTRP lacks a C-terminal tag.

4. The cTRP of claim 1, wherein the cTRP lacks an N-terminal signal peptide and lacks a C-terminal tag.

5. The cTRP of claim 1, further comprising an N-terminal signal peptide.

6. The cTRP of claim 1, further comprising a C-terminal tag.

7. The cTRP of claim 1, further comprising an N-terminal signal peptide and a C-terminal tag.

8. A nucleotide encoding the cTRP of claim 1.

9. The nucleotide of claim 8, comprising a sequence having at least 98% sequence identity to SEQ ID NO: 120, SEQ ID NO: 122, SEQ ID NO: 126, SEQ ID NO: 128, or SEQ ID NO: 131.

10. The nucleotide of claim 8, comprising SEQ ID NO: 120, SEQ ID NO: 122, SEQ ID NO: 126, SEQ ID NO: 128, or SEQ ID NO: 131.

* * * * *